(12) United States Patent
Kottayil et al.

(10) Patent No.: US 8,628,796 B2
(45) Date of Patent: Jan. 14, 2014

(54) ROOM-TEMPERATURE STABLE DRONABINOL FORMULATIONS

(75) Inventors: S. George Kottayil, Long Grove, IL (US); Zhongyuan Zhu, Vernon Hills, IL (US); Venkat R. Goskonda, Gurnee, IL (US)

(73) Assignee: Insys Therapeutics, Inc., Phoenix, AZ (US)

( * ) Notice: Subject to any disclaimer, the term of this patent is extended or adjusted under 35 U.S.C. 154(b) by 920 days.

(21) Appl. No.: 11/299,183

(22) Filed: Dec. 9, 2005

(65) Prior Publication Data

US 2006/0160888 A1 Jul. 20, 2006

Related U.S. Application Data

(60) Provisional application No. 60/634,474, filed on Dec. 9, 2004.

(51) Int. Cl.
*A61K 9/64* (2006.01)
*A61K 31/35* (2006.01)

(52) U.S. Cl.
USPC .......................................... 424/456; 514/454

(58) Field of Classification Search
USPC .......................................... 424/456; 514/454
See application file for complete search history.

(56) References Cited

U.S. PATENT DOCUMENTS

| | | | |
|---|---|---|---|
| 3,668,224 A | 6/1972 | Petrzilka | |
| 4,933,368 A | 6/1990 | Satzinger et al. | |
| 5,389,375 A | 2/1995 | ElSohly | |
| 5,430,021 A | 7/1995 | Rudnic et al. | |
| 5,447,729 A | 9/1995 | Belenduik et al. | |
| 5,496,811 A | 3/1996 | Aviv et al. | |
| 5,508,037 A | 4/1996 | ElSohly | |
| 5,508,051 A | 4/1996 | Falla | |
| 5,804,592 A * | 9/1998 | Volicer | 514/454 |
| 5,989,583 A | 11/1999 | Amselem | |
| 6,008,383 A | 12/1999 | ElSohly et al. | |
| 6,121,234 A | 9/2000 | Benet et al. | |
| 6,267,985 B1 | 7/2001 | Chen | |
| 6,284,788 B1 | 9/2001 | Mittendorf et al. | |
| 6,294,192 B1 | 9/2001 | Patel et al. | |
| 6,365,416 B1 | 4/2002 | ElSohly et al. | |
| 6,383,513 B1 | 5/2002 | Watts et al. | |
| 6,403,126 B1 | 6/2002 | Webster et al. | |
| 6,451,339 B2 | 9/2002 | Patel et al. | |
| 6,503,532 B1 | 1/2003 | Murty et al. | |
| 6,509,005 B1 | 1/2003 | Peart et al. | |
| 6,623,765 B1 | 9/2003 | Dennis et al. | |
| 6,630,507 B1 | 10/2003 | Hampson et al. | |
| 6,638,537 B2 | 10/2003 | Dennis et al. | |
| 6,703,418 B2 | 3/2004 | Plasse | |
| 6,713,048 B2 | 3/2004 | Peart et al. | |
| 6,720,001 B2 | 4/2004 | Chen et al. | |
| 6,730,330 B2 * | 5/2004 | Whittle et al. | 424/725 |
| 6,730,519 B2 | 5/2004 | ElSohly et al. | |
| 6,747,058 B1 | 6/2004 | Dedhiya et al. | |
| 6,923,988 B2 | 8/2005 | Patel et al. | |
| 6,946,150 B2 | 9/2005 | Whittle | |
| 6,949,256 B2 | 9/2005 | Fonkwe et al. | |
| 6,977,070 B2 | 12/2005 | Dugger, III | |
| 7,025,992 B2 | 4/2006 | Whittle et al. | |
| 7,090,830 B2 | 8/2006 | Hale et al. | |
| 7,186,850 B2 | 3/2007 | Silverberg | |
| 7,321,047 B2 | 1/2008 | Field et al. | |
| 7,323,576 B2 | 1/2008 | Souza et al. | |
| 7,344,736 B2 | 3/2008 | Whittle et al. | |
| 7,358,245 B2 | 4/2008 | Lehmann | |
| 2003/0015196 A1 | 1/2003 | Hodges et al. | |
| 2003/0191180 A1 | 10/2003 | Ross | |
| 2003/0229027 A1 * | 12/2003 | Eissens et al. | 514/23 |
| 2004/0096402 A1 | 5/2004 | Hodges et al. | |
| 2004/0138293 A1 | 7/2004 | Werner et al. | |
| 2004/0143126 A1 | 7/2004 | Webster et al. | |
| 2004/0147767 A1 | 7/2004 | Whittle et al. | |
| 2004/0162336 A1 | 8/2004 | McPhillips | |
| 2004/0192760 A1 | 9/2004 | Whittle et al. | |
| 2004/0198813 A1 | 10/2004 | Dennis et al. | |
| 2004/0229939 A1 | 11/2004 | Chowdhury et al. | |
| 2004/0258622 A1 | 12/2004 | Peart et al. | |
| 2005/0031651 A1 | 2/2005 | Gervais et al. | |
| 2005/0049298 A1 | 3/2005 | Goodwin et al. | |
| 2005/0171361 A1 | 8/2005 | Goodwin et al. | |
| 2005/0266108 A1 | 12/2005 | Flockhart et al. | |
| 2005/0281752 A1 | 12/2005 | Dugger, III | |
| 2006/0068034 A1 | 3/2006 | Whittle | |
| 2006/0094774 A1 | 5/2006 | Duchek | |

(Continued)

FOREIGN PATENT DOCUMENTS

| | | | |
|---|---|---|---|
| EP | 0266 443 A | 5/1988 | |
| WO | 82 03768 A | 11/1982 | |

(Continued)

OTHER PUBLICATIONS

Remington's Pharmaceutical Sciences, 17$^{th}$ edition, pp. 1482-1484 and 1625-1629.*
The Merck Index, 12$^{th}$ edition, p. 3770.*
Remington's Pharmaceutical Sciences, 17$^{th}$ edition, 1985, pp. 1625-1631.*
AU Patent App No. 2005314021 Notice of Acceptance dated Feb. 1, 2010.
Office Action on Canadian Patent App No. 2,589,993 dated Apr. 22, 2009.
Office Action on Canadian Patent App No. 2,589,993 dated Mar. 11, 2010.
Office Action on Israel Patent App No. 183815 dated Nov. 19, 2009.
Office Action of Chinese Patent App No. 200580047957.0 dated Oct. 16, 2009.
Notice of Publication of Chinese Patent App No. 200580047957.0 dated Feb. 27, 2008.

(Continued)

*Primary Examiner* — Renee Claytor
(74) *Attorney, Agent, or Firm* — Wood, Phillips, Katz, Clark & Mortimer

(57) ABSTRACT

A room temperature stable cannabinoid formulation is disclosed. In preferred embodiments, the cannabinoid formulation is dronabinol in an oil-based carrier contained within a hard gelatin capsule.

15 Claims, 2 Drawing Sheets

(56) References Cited

U.S. PATENT DOCUMENTS

| | | |
|---|---|---|
| 2006/0167084 A1 | 7/2006 | Dudley |
| 2006/0258738 A1 | 11/2006 | Dieterich |
| 2006/0264647 A1 | 11/2006 | Field et al. |
| 2007/0020193 A1 | 1/2007 | de Vries et al. |
| 2007/0060639 A1 | 3/2007 | Wermeling |
| 2007/0072938 A1 | 3/2007 | Rose |
| 2007/0072939 A1 | 3/2007 | Kupper |
| 2007/0088077 A1 | 4/2007 | Plasse |
| 2007/0099989 A1 | 5/2007 | Barbato |
| 2007/0104741 A1 | 5/2007 | Murty et al. |

FOREIGN PATENT DOCUMENTS

| | | |
|---|---|---|
| WO | 9736577 | 10/1997 |
| WO | 9932107 | 7/1999 |
| WO | 0103668 | 1/2001 |
| WO | 02064109 | 8/2002 |
| WO | 2005074890 | 8/2005 |

OTHER PUBLICATIONS

AU Patent Office Examination Report SG 200704139-5 dated Jul. 16, 2008.
SG Patent App No. 200704139-5 Certificate of Grant of Patent dated Dec. 31, 2009.
SG Patent App No. 200704139-5 Written Opinion dated Jul. 16, 2008.
SG Patent App No. 200704139-5 Search Report dated Jul. 16, 2008.
International Search Report and Written Opinion on PCT/US07/17620 dated Sep. 17, 2008.
Plasse et al. Dronabinol stimulates appetite and causes weight gain in HIV patients. Int conf AIDS. Jul. 19-24, 1992, vol. 8, No. 122 (abstract No. PuB 7442).
International Search Report and Written Opinion on PCT/US05/44375 dated Oct. 31, 2006.
Office Action on 200701246/(2007070045) dated Jun. 16, 2010.
Office Action on 200701246/27 dated Nov. 10, 2009.
U.S. Appl. No. 11/299,183 Non-Final Office Action dated Mar. 18, 2009.
U.S. Appl. No. 11/299,183 Non-Final Office Action dated Feb. 21, 2008.
U.S. Appl. No. 11/299,183 Final Office Action dated May 11, 2010.
Burnstein et al.; "Synthetic Nonpsychotropic Cannabinoids with Patent Antiinflamatory, Analgesic, and Leukocyte Antiadhesion Activities;" J. Med. Chem. 35, 3135, 1992.
PCT/US2005/044375 International Preliminary Report on Patentability dated Jun. 21, 2007.
PCT/US2008/009623 International Preliminary Report on Patentability dated Feb. 9, 2010.
PCT/US2008/09623 Written Opinion dated Nov. 6, 2008.
Chemical Abstracts vol. 77, 1972, p. 93-94.
Japan Office Action for Application No. 2007-545614 mailed Jan. 18, 2011.
Burnstein et al.; "Synthetic Nonpsychotropic Cannabinoids with Potent Antiinflamatory, Analgesic, and Leukocyte Antiadhesion Activities;" J. Med. Chem. 35, 3135, 1992.
Featured Excipient: Antioxidants. *Int. J. Pharm. Compounding.* 3(1): 52-, Jan./Feb. 1999.
Bradley Morris J. Food, industrial, nutraceutical, and pharmaceutical uses of sesame genetic resources. In: *Trends in New Crops and New Uses.* Editors: Janick J and Whipkey A, 2002.
Ewart T. Cole. Liquid filled and sealed hard gelatin capsules In: *Modified-Release Drug Delivery Technology.* Editors: Rathbone MJ, Hadgraft J, Roberts MS, Publishers Marcel Dekker, 2002.
Shah N., Phuarpradit W., Ahmed H. Liquid filling in hard gelatin capsules: formulation and processing consideration. *American Pharmaceutical Review.* 6(1): 14-21, Spring 2003.
Mattes, R. D.; Shaw, L. M.; Edling-Owens, J., Engleman, K.; and ElSohly, M. A.; Bypassing the first-pass effect for the therapeutic use of cannabinoids; Pharm., Biochem., Behav., 44(3):745-747, 1993.
Mattes, R. D.; Engelman, K.; Shaw, L. M.; and ElSohly, M. A.; Cannabinoids and appetite stimulation, Pharmacol., Biochem., Behav., 49(1):187-195, 1994.
Kato M.J.; Chu A.; Davin L.B.; Lewis N.G.; Biosynthesis of antioxidant lignans in sesamum indicum seeds. *Phytochemisrty.* 47: 583-591, 1998.
Armstrong N.A.; James K.C.; Pugh W.K.L; Drug migration into soft gelatin capsule shells and its effect on in-vitro availability. *J. Pharm. Pharmacol.* 36: 361-365, 1984.
Bauer K.H., Die herstellung von hart- und weichgelatinekapsein. In: *Die Kapsel. Stuttgart: Wissenschaftliche Verlags GmbH.* Editors: Fahrig W, Hofer UH, 58-82, 1983.
Beckstrom-Stenberg SM and Duke JA. "The phytochemical database." Ars-genome.cornell.edu/cgi-bin/WebAce/webace?db=phytochemdb. (Data version Jul. 1994).
Brenneisen, R.; Egli, A.; ElSohly, M. A.; Henn, V.; and Speiss, Y.; The effect of orally and rectally administered delta-9-tetrahydrocannabinol on spasticity: A pilot study with 2 patients; Inter. J. Clin. Pharmacol. and Therapeutics, 34(10):446-452, 1996.
Durr, M., et al. Liquid filled and sealed hard gelatin capsules. *Acta Pharm. Technol.* 29: 245-251, 1983.
Dalby, R. N. and Byron, P. R. (1988) Comparison of output particle size distributions from pressurized aerosols formulated as solutions or suspensions. Pharm. Res. vol. 5 No. 1, Jan. 1988, pp. 36-39.
Hom F.S.; Veresh S.A.; Ebert W.R.; Soft gelatin capsules II: Oxygen permeability study of capsule shells. *J. Pharm. Sci.* 64(5): 851-857, 1975.
Martin A, Bustamante P, and Chun AHC. *Physical Pharmacy.* Fourth ed., Lea & Febiger, 1993.
Mechoulam R. Chemistry of cannabis. *Handbook Exp. Pharmacol.* 55: 119-134, 1981.
Olsen, J. L.; Lodge, J. W.; Shapiro, B. J.; and Tashkin, D. P. (1976) An inhalation aerosol of D9THC. J. Pharmacy and Pharmacol. 28:86.
Sirato-Yasumoto S.; Katsuta M.; Okuyama Y.; Takahashi Y.; and Ide T.; Effect of sesame seeds rich in sesamin and sesamolin on fatty acid oxidation in rat liver. *J. Agr. Food Chem.* 49: 2647-2651, 2001.
Tashkin, D. P.; Reiss, S.; Shapiro, B. J.; Calvarese, B; Olsen, J. L.; and Lodge, J. W.; (1977) Bronchial effects of aerosolized D9THC in healthy and asthmatic subjects. Amer. Rev. of Resp. Disease. 115:57-65.
U.S. Department of Health and Human Services, Food and Drug Administration "*Guidance for Industry: Q1A (R2) Stability Testing of New Drug Substances and Products.*" ICH, Nov. 2003.
Williams, S. J., Hartley, J. P. R. and Graham, J. D. P. (1976) Bronchodilator effect of D9THC administered by aerosol to asthmatic patients. Thorax. 31:720-723.
Remington's Pharmaceutical Sciences, 17th Ed., p. 1637 (1985).
Physicians' Desk Reference 2003 Marinol Package Label.
Handbook of Pharmaceutical Excipients, Shesky, P and Weller, P, 4th Ed., 2003, pp. 35-36, 340-342, 381-403, 535-537.

* cited by examiner

US 8,628,796 B2

ROOM-TEMPERATURE STABLE DRONABINOL FORMULATIONS

This application claims priority from U.S. Provisional Patent Application No. 60/634,474, filed on Dec. 9, 2004, the disclosure of which is hereby incorporated by reference in its entirety.

TECHNICAL FIELD

The present invention relates to formulations of cannabinoids which are stable at room temperature for extended periods of time, e.g., for two years or more. The present invention is further related to oral cannabinoid formulations which rapidly disintegrate when orally administered to human patients. The invention has utility in the fields of pharmaceutical formulation, pharmacology and medicine.

BACKGROUND OF THE INVENTION

Delta-9-Tetrahydrocannabinol (also known as THC, Dronabinol and D9THC) is a naturally occurring compound and is the primary active ingredient in the controlled substance marijuana. Marijuana refers to the dried flowers and leaves of *Cannabis Sativa*, the hemp plant. These parts of the plant contain several compounds called cannabinoids (including Dronabinol), that may help patients with certain disease conditions. Dronabinol has been approved by the Food and Drug Administration (FDA) for the control of nausea and vomiting associated with chemotherapy and, more recently, for appetite stimulation of AIDS patients suffering from wasting syndrome. Synthetic dronabinol has been utilized as a pharmaceutically active ingredient, and cannabis-based medicines using botanical sources of cannibis rather than synthetic THC are also known in the art.

Currently, dronabinol is commercially available in the U.S. as a solution in a soft gelatin capsule under the tradename Marinol® from Unimed Pharmaceuticals, Inc., which is orally administered. Upon oral administration, the gelatin dissolves, releasing the drug. The dronabinol dissolved in sesame oil, is then absorbed during its passage through the gastrointestinal tract. Marinol is indicated for the treatment of: 1) anorexia associated with weight loss in patients with AIDS and 2) nausea and vomiting associated with cancer chemotherapy in patients who have failed to respond adequately to conventional antiemetic treatments. Marinol capsules are sold in 2.5 mg, 5 mg, or 10 mg dosages and formulated with the following inactive ingredients: sesame oil, gelatin, glycerin, (glycerol), methylparaben, propylparaben, and titanium dioxide. The Marinol soft gelatin capsule form of dronabinol is highly unstable at room temperature, and it is recommended that the product be stored at refrigerated (2-8° C.) or cool (8-15° C.) conditions (Marinol package label, Physicians Desk Reference®, ed. 2003). Additionally, Marinol should be packaged in a well-closed container and stored in a cool environment between 8° and 15° C. (46° and 59° F.). At the present time, dronabinol is the only approved cannabinoid drug commercially available.

Other formulations containing dronabinol appear in the art. In 1976, Olsen et al. described a chlorofluorocarbon (CFC) propelled MDI formulation of dronabinol. Olsen, J. L., Lodge, J. W., Shapiro, B. J. and Tashkin, D. P. (1976) An inhalation aerosol of D9THC. J. Pharmacy and Pharmacol. 28:86. However, dronabinol is known to deteriorate during storage, and the stability of the dronabinol in this formulation is suspect. In addition, the ethanol content in this formulation was so high (about 23%) that an aerosol was created with droplets too large to be effectively inhaled. See, Dalby, R. N. and Byron, P. R. (1988) Comparison of output particle size distributions from pressurized aerosols formulated as solutions or suspensions. Pharm. Res. 5:36-39. The dronabinol CFC formulations were tested for use in treating asthma but were shown to be only moderately effective. See, Tashkin, D. P., Reiss, S., Shapiro, B. J., Calvarese, B., Olsen, J. L. and Lidgek, J. W. (1977) Bronchial effects of aerosolized D9THC in healthy and asthmatic subjects. Amer. Rev. of Resp. Disease. 115:57-65; Williams, S. J., Hartley, J. P. R. and Graham, J. D. P. (1976) Bronchodilator effect of D9THC administered by aerosol to asthmatic patients. Thorax. 31:720-723. Moreover, CFC propellants have since been banned so that such a formulation is now useless.

U.S. Pat. No. 6,509,005 describes an aerosol-dispensable pharmaceutical formulation comprising a hydrofluoroalkane propellant, (for example, HFA 227 or HFA 134a) and dronabinol (D9THC), which formulation is said to be stable. The propellant is present in the range of approximately 78 to 100% by weight, and more particularly the propellant is present in the range of approximately 85 to 100% by weight. An organic solvent such as ethanol can be used to assist in solubilizing the dronabinol in the propellant but is stated that it is not required. If a solvent is used, preferably less than 20% by weight will be required, and most preferably less than 15% by weight will be required. The pharmaceutically effective concentration of dronabinol is preferably in the range of 0.05 to 10% by weight.

U.S. Pat. No. 6,747,058 and U.S. Patent Application Publication No. 2004/0162336 describe an aerosolizable formulation for delivery of delta-9-tetrahydrocannabinol in a semi-aqueous solvent, such as 35:10:55 alcohol:water:propylene glycol (v/v), which is said to produce a stable clear solution near the solubility point of the drug.

U.S. Pat. No. 6,383,513 describes a composition for nasal delivery comprising a cannabinoid in a biphasic delivery system, wherein the biphasic delivery system is an oil-in-water emulsion.

U.S. Patent Application Publication No. 2003/0229027 describes a method of preparing a pharmaceutical composition comprising a natural cannabinoid compound such as delta-9-tetrahydrocannabinol which is said to be stabilized which comprises such a compound and a glass of a sugar, a sugar alcohol, a mixture of sugars or a mixture of sugars alcohols. The natural cannabinoid compound is dissolved in an organic solvent that is soluble in water and the sugar, sugar alcohol, mixture of sugars or mixture of sugar alcohols is dissolved in water; the dissolved cannabinoid compound and the dissolved sugar(s) are mixed; and the mixture is then dried by freeze drying, spray drying, vacuum drying, or super critical drying.

U.S. Pat. Nos. 5,508,037 and 5,389,375 describe suppository formulations prepared by admixing a therapeutically effective amount of at least one dronabinol prodrug ester derivative with a suppository base which is said to provide long term stability to the suppository formulation.

Dronabinol has been used as an antiemetic to relieve nausea and vomiting in patients receiving cancer chemotherapy. Additionally, U.S. Pat. No. 6,703,418 describes a method of treating a patient with symptomatic HIV infection to stimulate weight gain in the patient, which comprises administering to the patient a pharmaceutical composition comprising dronabinol in an amount sufficient to cause an increase in weight of the patient.

Despite all of the work outlined above and elsewhere, to date a room temperature stable oral dosage form of a cannabinoid such as dronabinol in a capsule has not been achieved.

OBJECTS AND SUMMARY OF THE INVENTION

It is an object of the present invention to provide a room temperature stable cannabinoid drug product.

It is another object of the present invention to provide a room temperature stable formulation of a cannabinoid such as dronabinol (delta-9 tetrahydrocannabinol) which is orally administrable to mammals.

It is a further object of the invention to provide a room temperature stable formulation of a cannabinoid such as dronabinol which is readily available for absorption in any part of the gastrointestinal tract of mammals, e.g., human subjects or patients.

It is a further object of the invention to provide a room temperature stable formulation of a cannabinoid such as dronabinol which is homogeneous and thermodynamically stable.

It is a further object of the invention to provide a room-temperature stable cannabinoid formulation by utilizing liquid filled hard gelatin technology.

It is a further object of the invention to provide a stabilized cannabinoid formulation where the cannabinoid is contained in a lipophilic medium such as an oil.

It is a further object of the invention to provide a stabilized cannabinoid formulated in a lipophilic medium such as an oil which has no inclusions or additives responsible for the instability of cannabinoid contained therein.

In accordance with these and other objects and features, the present invention is directed in part to a room-temperature stable cannabinoid formulation comprising a hard gelatin capsule containing therapeutically effective amount of a pharmaceutically acceptable cannabinoid in an oil-based carrier.

The invention is further directed to a cannabinoid dosage form, comprising an effective amount of a mixture of pharmaceutically acceptable cannabinoid and a pharmaceutically acceptable oil-based carrier, and a hard gelatin capsule encapsulating the mixture of the cannabinoid and the oil-based carrier.

The invention is further directed in part to a room-temperature stable formulation of a cannabinoid, comprising a therapeutically effective amount of a cannabinoid dispersed in an oil-based carrier contained in a unit dose enclosure, said unit dose enclosure composed of one or more materials which do not react with the cannabinoid or allow substantial permeation of oxygen and which effectively seals the cannabinoid from moisture, such that the cannabinoid in the formulation is protected against unacceptable degradation.

The invention is further directed in part to a formulation of a therapeutically effective amount of an encapsulated cannabinoid and means for stabilizing the cannabinoid.

The invention is further directed in part to a stabilized oral dosage form of a cannabinoid, comprising a mixture of a therapeutically effective amount of a cannabinoid dispersed in an oil-based carrier contained in unit dosage form selected from a hard gelatin capsule, a cellulosic capsule, a starch capsule, and a non-animal based hydrocolloid film-forming composition.

The invention is further directed in part to a stabilized cannabinoid dosage form prepared by utilizing liquid filled hard gelatin technology to obtain a dosage form.

The invention is further directed in part to a stabilized oral dosage form of a cannabinoid, comprising a therapeutically effective amount of a cannabinoid dispersed in an oil-based carrier and encapsulated within a soft gelatin capsule, said oil-based carrier containing an effective amount of a stabilizer for the cannabinoid to provide a room-temperature stable formulation for at least one year.

In further preferred embodiments of the invention where the formulation contains dronabinol as the active ingredient, the dosage form containing ingredients at a level selected from the following during its claimed shelf-life: (i) not less than 90% of the initial dronabinol content; (ii) not greater than about 2% cannabinol; (iii) not greater than about 2% delta-8-THC; and any combination of the foregoing.

In certain preferred embodiments, the present invention provides a cannabinoid formulation (e.g., dronabinol) that is stable at all conditions—refrigerated, cool and room temperature (2-8° C., 25° C./60% RH, 30° C./60% RH). In other words, in certain preferred embodiments, the stabilized cannabinoid formulations may be stored at ambient temperature and humidity, or in a refrigerator, by the patient.

In certain preferred embodiments, the cannabinoid is dronabinol formulated in sesame oil-containing capsules. However, the cannabinoid formulations of the invention may also be in the form of liquids (including suspensions and emulsions), tablets, suppositories, transdermal formulations and sublingual formulations, as well as injectable formulations.

In certain preferred embodiments, the invention is directed to a stabilized oral dosage form of dronabinol, comprising from about 0.05 mg to about 20 mg dronabinol dispersed in sesame oil, the concentration of dronabinol in the sesame oil being from about 1.5 to about 6% by weight, encapsulated in a sealed hard gelatin capsule.

The invention is further directed in part to a method for stabilizing an oral dosage form containing a cannabinoid; comprising incorporating a therapeutically effective amount of a cannabinoid dispersed in an oil-based carrier into a unit dosage form suitable for oral administration, said unit dosage form consisting of a material selected from a hard gelatin capsule, a cellulosic capsule, a starch capsule, and a non-animal based hydrocolloid film-forming composition.

The invention is further directed in part to a method for stabilizing a dosage form containing a cannabinoid as the active pharmaceutical ingredient, comprising encapsulating a therapeutically effective amount of the cannabinoid in a pharmaceutically acceptable oil-based carrier containing an effective amount of one or more anti-oxidants.

The invention is further directed in part to a method for stabilizing a dosage form containing a cannabinoid as the active pharmaceutical ingredient, comprising encapsulating a therapeutically effective amount of the cannabinoid in a pharmaceutically acceptable oil-based carrier containing an amount of one or more organic bases that is effective to stabilize the cannabinoid.

The invention is further directed in part to a method for preparing a stabilized dosage form containing a cannabinoid as the active pharmaceutical ingredient, comprising
mixing a solution of a cannabinoid with an oil-based carrier to obtain a flowable mixture;
filling an appropriately-sized hard gelatin capsule with a quantity of said mixture that contains a desired therapeutically effective amount of said cannabinoid; and
sealing the hard gelatin capsule.

The invention is further directed in part to a method for preparing a stabilized dosage form containing a cannabinoid as the active pharmaceutical ingredient, comprising mixing a solution of a cannabinoid with an oil-based carrier to obtain a flowable mixture; encapsulating a quantity of the mixture containing a desired therapeutically effective amount of said cannabinoid within a non-glycerin based composition composed of one or more materials which do not react with the cannabinoid or allow substantial permeation of oxygen and which effectively seals the cannabinoid from moisture.

In certain preferred embodiments, the formulation contains at least about 80% w/w of the cannabinoid in undegraded form after exposure of the formulation to storage conditions selected from the group consisting of (i) 2-8° C., (ii) 25° C./60% relative humidity (RH) for 6 months; (iii) 30° C./60% relative humidity (RH) for 6 months; (iv) elevated temperature and humidity conditions of 40° C./75% relative humidity (RH) for 6 months; (v) elevated temperature conditions of 55° C. for two weeks; (vi) room temperature (25° C.) for two years; and (vii) any combination thereof.

In certain embodiments, formulations and methods of the invention provide for the active pharmaceutical cannabinoid ingredient remaining within about 90 to about 110 percent of its original amount included in the dosage form for at least 1 year, and preferably at least about 2 years after manufacture.

In certain preferred embodiments, formulations of the invention are homogeneous and thermodynamically stable.

In certain embodiments, the cannabinoid formulations of the invention comprise effective amounts of one or more stabilizers to promote stability of the cannabinoid against unacceptable degradation. The stabilizers may comprise one or more anti-oxidants, one or more organic bases, and/or other stabilizers for cannabinoids known to those skilled in the art.

The invention is further directed in part to a method for stabilizing a dosage form containing a cannabinoid as the active pharmaceutical ingredient, comprising encapsulating a therapeutically effective amount of the cannabinoid in a liquid filled hard gelatin capsule. In certain embodiments, the liquid comprises an oil-based carrier. In certain embodiments, the oil-based carrier further comprises one or more stabilizers for the cannabinoid (e.g, anti-oxidants, organic bases, or both, as set forth more specifically herein).

In certain embodiments, the oil-based carrier is a triglyceride selected from the group consisting of almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; and mixtures thereof.

In certain embodiments, the oil-based carrier is selected from the group consisting of soybean oil, olive oil, cotton seed oil, peanut oil, sesame oil, castor oil, and mixtures of any of the foregoing. In certain preferred embodiments, the oil-based carrier comprises sesame oil (e.g., a Food Grade sesame oil or a NF grade sesame oil).

In certain embodiments wherein the oil-based carrier is sesame oil, the sesame oil contains an effective amount of an anti-oxidant selected from the group consisting of sesamin, sesamol, sesamolin, lecithin and any combination of the foregoing (either already present in the (unpurified) sesame oil or added to purified sesame oil.

In certain embodiments, the oil-based carrier may comprise a semi-solid lipophilic material selected from the group consisting of arachis oil (Groundnut 36); castor oil (Cutina HR); cottonseed oil (Sterotex); palm oil (Softisan 154); soybean oil (Alkosol 407). In certain such embodiments, an effective amount of a viscosity modifier may be included to provide a pharmaceutically acceptable viscosity to the cannabinoid dispersed in the oil-based carrier. Such viscosity modifiers may be, e.g., Aerosil (silicon dioxide); cetostearyl alcohol; cetyl alcohol; stearyl alcohol; Gelucire 33/01; Gelucire 39/01; Gelucire 43/01; glyceryl behenate (Compritol 888 ATO); glyceryl palmitostearate (Precirol AT05); Softisan 100; Softisan 142; Softisan 378; Softisan 649; and mixtures thereof.

The invention is further directed to a dosage form wherein the cannabinoid is dronabinol and does not contain unacceptable levels of dronabinol degradants in the dosage form selected from the group consisting of greater than 2% delta-8 tetrahydrocannabinol (D8THC), greater than 2% cannabinol (CBN), greater than 2% cannabidiol (CBD), and any combination thereof.

In certain preferred embodiments where the stabilizer comprises an organic base, the dosage form may comprise from about 0.001% w/w to about 5% organic base, preferably from about 0.007% w/w to about 2% organic base, by weight. In certain preferred embodiments, the organic base is selected from the group consisting of ethanolamine, methanolamine, meglumine, and any combination of the foregoing.

In certain embodiments where the stabilizer is an anti-oxidant (such as lecithin), the dosage from may comprise from about 0.001% to about 10%, and more preferably from about 0.3% to about 8.25% anti-oxidant, by weight. In other embodiments where the anti-oxidant is L-ascorbic acid-6-palmitate, it may be included in an amount from about 0.001% to about 15%, and preferably from about 0.01% to about 1% by weight.

The anti-oxidant included in the formulations of the invention may further be selected from e.g., butyl hydroxyl anisole (BHA), butyl hydroxyl toluene (BHT), propyl gallate, lecithin, Vitamin E tocopherol, sesamin, sesamol, sesamolin, alpha tocopherol, ascorbic acid, ascorbyl palmitate, fumaric acid, malic acid, sodium ascorbate and sodium metabisulphite, disodium EDTA, and combinations of any of the foregoing.

In certain preferred embodiments, the dosage forms of the invention comprises from about 0.05% to about 90% cannabinoid, preferably from about 0.1% to about 50% cannabinoid, more preferably about 1.5% to about 6% cannabinoid, and most preferably from about 2.5% to about 4.5% cannabinoid by weight.

In certain embodiments wherein the unit dose enclosure is a hard gelatin capsule, the capsule preferably contains from about 85% to about 100% gelatin and from about 1% to about 15% water, by weight.

The invention is further directed to a dosage form which further comprises one or more additional therapeutically active agents. Non-limiting examples of such additional therapeutically active agents include a narcotic analgesic, a non-narcotic analgesic, an anti-emetic, a steroid, and mixtures of any of the foregoing.

In certain embodiments, formulations of the invention include further pharmaceutically acceptable excipients. Non-limiting examples of such pharmaceutically acceptable excipients include solubilizers for said cannabinoid, emulsifiers, absorption enhancers, a surfactants, etc.

In certain preferred embodiments, the cannabinoid formulations include dronabinol as the active pharmaceutical ingredient, preferably in an amount from about 0.05 mg to about 20 mg. In other embodiments, the formulations include from about 2.5 mg to about 20 mg dronabinol.

The term "pharmaceutically acceptable" is defined for purposes of the invention as meaning that a particular ingredient (e.g., pharmaceutical carrier, excipient) is not biologically or otherwise undesirable in an oral dosage form, i.e., the amount of the compound in an orally administered composition or dosage form does not cause any undesirable effects to the formulation or to the patient.

Testing for stability may be conducted, (e.g., for two year stability determination) by placing the dosage forms of the present invention under accelerated storage conditions of elevated temperature and humidity of 40° C./75% relative humidity (RH) for 6 months, and/or placing the dosage forms of the present invention under elevated temperature conditions of 55° C. for two weeks; and/or placing the dosage forms of the present invention in storage at room temperature (25° C.) under ambient relative humidity conditions for two years.

The phrase "does not degrade to an unacceptable extent" and the term "stable" as it applies to the cannabinoid formulations of the invention is meant for purposes of the invention to mean that the formulation contains at least about 80% w/w, and preferably at least about 90% w/w of the cannabinoid in undegraded form after exposure of the formulation to storage conditions selected from the group consisting of (i) 2-8° C., (ii) 25° C./60% relative humidity (RH) for 6 months; (iii) 30° C./60% relative humidity (RH) for 6 months; (iv) 40° C./75% relative humidity (RH) for 6 months; (v) elevated temperature conditions of 55° C. for two weeks; (vi) room temperature (25° C.) for at least one year (and preferably at least about two years); and (vii) any combination thereof. In preferred embodiments, the phrase "does not degrade to an unacceptable extent" means that the active pharmaceutically acceptable cannabinoid ingredient (e.g., dronabinol) contained within the dosage form is maintained preferably between 90-110% of its initial (incorporated) amount during the desired (e.g., labeled) shelf-life of the dosage form (e.g., a minimum of 2 years after the date of manufacture of the dosage form).

For purposes of the invention, the term "dispersed" as it is used to describe the presence of the cannabinoid in the oil-based carrier, is meant to encompass a mixture of the cannabinoid and oil-based carrier in which the cannabinoid is completely or partially dissolved therein, or the cannabinoid is partially or completely in solid particulate form therein.

For purposes of the invention, the term "unacceptable degradation" means degradation of the cannabinoid within the dosage form to an extent which will cause the dosage form to have cannabinoid in the dosage form at a level outside the acceptable ranges set forth herein, and/or which cause the formulation to include cannabinoid degradants at levels which exceed the amounts specified herein, and/or which cause the formulation to not meet its label claim for shelf life. In certain preferred embodiments, the cannabinoid formulations of the invention are deemed stable as per the FDA guidance for two-year expiration dating.

DETAILED DESCRIPTION

Figure 1:
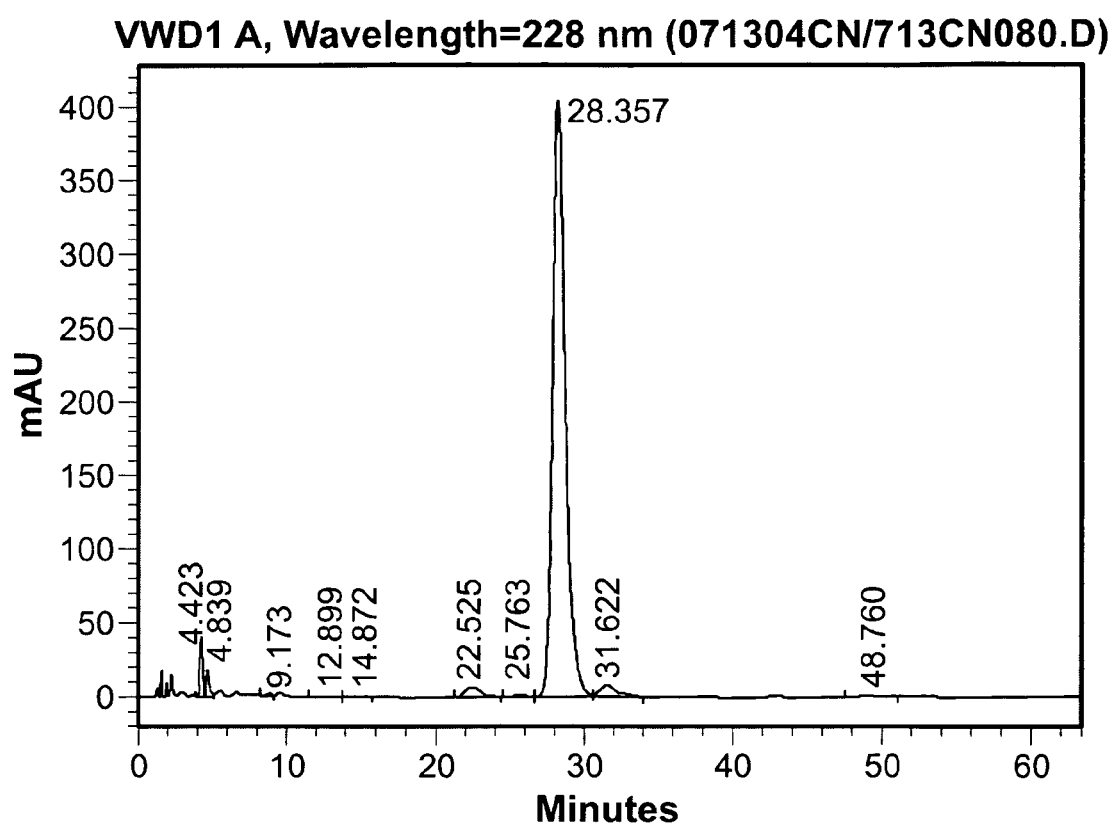
FIG. 1 is a chromatogram of a formulation of 3.03% w/w dronabinol in sesame oil after storage for two weeks at 55° C.

It has been reported that because lipophilic compounds (e.g., such as dronabinol) are highly soluble in glycerol, these compounds migrate into the shell of a soft gelatin capsule, thus inducing instability (Armstrong et al., 1984). The relatively large amount of glycerol present in soft gelatin has been reported to lead to increased permeability of the gelatin shell to oxygen (Cade et al., 1987; Hom et al., 1975). It is also known that Dronabinol readily degrades to cannabinol and cannabidiol in the presence of oxygen (Mechoulam, 1981). Also, the large amount of glycerol in soft gelatin has been reported to lead to increased sensitivity of formulation to heat and humidity (Bauer, 1983). Dronabinol has been reported to rapidly degrade to delta-8-tetrahydrocannabinol when exposed to heat (Mechoulam, 1981). Dronabinol is also believed to rapidly degrade when exposed to humidity or high moisture conditions. Glycerin or glycerol is a major component in the gelatin shell that comprises the soft gelatin capsule. Glycerin functions as a plasticizer in soft gelatin and is therefore vital to the manufacture of soft gelatin capsules. Glycerin makes up approximately 30% of the soft gelatin capsule shell (Ewart T. Cole, 2002).

As demonstrated in the appended examples, dronabinol is highly unstable in the presence of glycerin. In fact, as demonstrated in the appended examples, over one-third of the active ingredient dronabinol is lost to degradation in two weeks at 55° C. when exposed to even small quantities of glycerin (0.002%). In view of the known properties of soft gelatin capsules, it is believed that the manufacturing process of soft gelatin capsules may contribute to the degradation of moisture and glycerol sensitive compounds like dronabinol. In the hard gelatin capsule process, the capsule is pre-fabricated and supplied empty whereas in the soft gelatin capsule process the encapsulation and filling of drug formulation take place simultaneously. The moisture content of gelatin/plasticizer mass at the filling stage can be around 50%, the equilibrium moisture level only being reached after several days of storage on trays. It is conceivable that during this most critical period migration and degradation of moisture sensitive drugs like dronabinol, which are readily soluble in glycerol can occur. The branded dronabinol product (Marinol, which consists of drug in sesame oil encapsulated in soft gelatin capsules) contains a significant amount of glycerol in the soft gelatin shell and is therefore considered by the inventors of the present invention to inherently be an unstable drug product.

The instability of prior art dronabinol formulations has been overcome by virtue of the present invention, which in certain embodiments (i) provides methods and formulations which eliminate the inclusion of glycerin from the capsule shell of dronabinol formulations, e.g., via the encapsulation of the dronabinol formulation into hard gelatin capsules; (ii) significantly reduces the possibility of the dronabinol formulation being exposed to moisture during storage; (iii) provides methods and formulations which include anti-oxidants in effective amounts to substantially prevent or slow the oxidation of the dronabinol in the formulation such that, e.g., the formulation has a shelf-life of at least two years; (iv) provides methods and formulations which include organic bases (amines) in effective amounts to stabilize the dronabinol in the formulation from degradation such that, e.g., the formulation has a shelf-life of at least two years; or any combination of (i)-(iv) above.

Cannabinoids

Although certain sections of this specification provide specific focus on dronabinol, one skilled in the art will appreciate that the present invention is applicable to the class of pharmaceutically acceptable cannabinoids. For purposes of the present invention, the term "cannabinoid" includes naturally occurring and non-natural derivatives of cannabinoids which can be obtained by derivatization of natural cannabinoids and which are unstable like natural cannabinoids. In other words, the cannabinoid used in the formulations of the invention may be natural, semi-synthetic, or synthetic. The cannabinoid may be included in its free form, or in the form of a salt; an acid addition salt of an ester; an amide; an enantiomer; an isomer; a tautomer; a prodrug; a derivative of an active agent of the present invention; different isomeric forms (for example, enantiomers and diastereoisomers), both in pure form and in admixture, including racemic mixtures; enol forms. The term "cannabinoid" is also meant to encompass derivatives that are produced from another compound of similar structure by the replacement of, e.g., substitution of one atom, molecule or group by another. The term "cannabinoid", as used in the present invention, includes, inter alia, delta-8-tetrahydrocannabinol, delta-9-tetrahydrocannabinol, cannabidol, olivetol, cannabinol, cannabigerol, nabilone, delta-9-tetrahydro cannabinotic acid, the non-psychotropic cannabinoid 3-dimethylnepty 11 carboxylic acid homologine 8, delta-8-tetrahydrocannabinol. (J. Med. Chem. 35, 3135, 1992), prodrugs of cannabinoids, as well as pharmaceutically acceptable salts and complexes of cannabinoids. An example of a suitable prodrug is THC-hemisuccinate.

The term "cannabinoid" is further meant to encompass natural cannabinoids, natural cannabinoids that have been purified or modified, and synthetically derived cannabinoids, for example, U.S. Patent Application Publication 2005/0266108, hereby incorporated by reference in its entirety, describes a method of purifying cannabinoids obtained from plant material.

In certain preferred embodiments of the present invention, the active ingredient (cannabinoid) comprises or consists essentially of Delta-9-tetrahydrocannabinol, also known as (and referred to herein as) dronabinol. Dronabinol is naturally-occurring and has been extracted from Cannabis saliva L. (marijuana). It has also been produced chemically as described in U.S. Pat. No. 3,668,224. Dronabinol is a light-yellow resinous oil that is sticky at room temperature, but hardens upon refrigeration. It turns to a flowable liquid when heated at higher temperatures. Dronabinol is insoluble in water and typically formulated in sesame oil. It has a pKa of 10.6 and an octanol-water partition coefficient: 6,000:1 at pH 7. Dronabinol is available in natural (extracted from plant) and synthetic forms. On the other hand, synthetic dronabinol may be utilized and may be synthesized using the starting materials, Olivetol and p-2,8-menthadien-2-ol (PMD).

The term "dronabinol" is further meant to encompass naturally occurring dronabinol, synthetically derived dronabinol, and synthetically modified dronabinol starting with a molecule obtained from a natural source for example, U.S. Patent Application Publication 2005/0171361, hereby incorporated by reference in its entirety, describes a method of extracting delta-9-THC acid from the plant material by chromatography and then synthetically converting it to dronabinol.

The preparation of pharmaceutically acceptable cannabinoids useful in the present invention may be accomplished via any procedure known to those skilled in the art. Generally, in the isolation of THC and other cannabinoid constituents from the natural material (e.g., cannabis), the alcoholic or the petroleum ether or benzene or hexane extract of the plant is separated into neutral and acidic fractions, which are then further purified by repeated column chromatography and/or countercurrent distribution. Various adsorbents have been used in column chromatography, especially silica gel, silicic acid, silicic acid-silver nitrate, florisil, acid washed alumina, and acid washed alumina-silver nitrate. U.S. Pat. Nos. 6,365,416 and 6,730,519 describe improvements wherein Cannabis plant material is extracted with a non-polar organic solvent to provide an extract containing THC and the extract is subjected to fractional distillation under reduced pressure to provide a distillation fraction (distillate) having a high content of THC. The process further comprises subjecting the extract from the plant material to column chromatography prior to fractional distillation. A still further aspect of the process comprises subjecting the distillate from the fractional distillation to column chromatography. Additionally, the process uses high pressure liquid chromatography (HPLC) in the purification of the extract from the plant material. Another method of manufacture for obtaining cannabinoids useful in the present invention includes the method described in U.S. Pat. Nos. 6,730,519 and 6,365,416 (both to Elsohly, et al.), both hereby incorporated by reference in its entirety. Therein, a method for the isolation of delta-9-tetrahydrocannibinol (THC) from, Cannabis plant material is described wherein delta-9-THC Acid and THC are separately obtained including the steps of extracting the Cannabis plant material, chelating delta-9-THC acid on alumina solid support from cannabis extracts rich in the acid washing of non-acid components of the extract with organic solvents and eluting of the delta-9-THC acid with strong polar solvents.

In certain preferred embodiments of the invention, the cannabinoid used in the formulation is esterified. Esterified forms of THC are described in U.S. Pat. No. 4,933,368 and in U.S. Pat. No. 5,389,375. Other useful polar esters are the hemiester of malonic acid and the alaninate ester of alanine. It has been reported, e.g., in U.S. Pat. Nos. 5,508,051 and 5,389,375, that salts of the terminal carboxylic acid group of the ester, for example, the N-methyl glutamine salt as well as the sodium and potassium salts are also useful. The descriptions of U.S. Pat. Nos. 4,933,368; 5,508,037; and 5,389,375, are incorporated herein by reference. These ester compounds are hydrolyzed in the blood stream releasing THC to provide a high degree of bioavailability of THC without regard to patient conditions and anomalies.

Oral THC is known to possess erratic absorption from the gastrointestinal tract, is subject to the first-pass effect resulting in heavy metabolism with production of high levels of 11-OH-THC, and undesirable side effects. The pro-drug THC hemisuccinate (THC-HS) has been formulated in a suppository base as described in U.S. Pat. Nos. 5,508,037 and 5,389,375, both of which are hereby incorporated by reference) in order to avoid this problem. Preliminary clinical investigations show promise for this formulation (Mattes, R. D.; Shaw, L. M.; Edling-Owens, J., Engleman, K.; and ElSohly, M. A.; Bypassing the first-pass effect for the therapeutic use of cannabinoids; Pharm., Biochem., Behav., 44(3):745-747, 1991; Mattes, R. D.; Engelman, K.; Shaw, L. M.; and ElSohly, M. A.; Bypassing the first-pass effect for the therapeutic use of cannabinoids, Pharmacol., Biochem., Behav., 49(1):187-195, 1994; Brenneisen, R.; Egli, A.; ElSohly, M. A.; Henn, V.; and Speiss, Y.; The effect of orally and rectally administered delta-9-tetrahydrocannabinol on spasticity: A pilot study with 2 patients; Inter. J. Clin. Pharmacol. and Therapeutics, 34(10):446-452, 1996; all of which are hereby incorporated by reference).

THC obtained by any means can be esterified by the reaction of THC with an organic acid, an organic acid halide or preferably organic acid anhydride in the presence of 4-amino-substituted pyridine alone or in admixture with an organic amine, or in any other manner known to those skilled in the art. U.S. Pat. No. 6,008,383 (Elsohly, et al.), hereby incorporated by reference, describes a process for converting dronabinol to a variety of ester analogs, which process is said to be economical and efficient. Therein, dronabinol is esterified by reaction with a carboxylic acid, an acid halide or an acid anhydride in the presence of a 4-aminopyridine either alone or in admixture with an organic amine such as a mono-, di-, or tri-alkyl amine.

In certain preferred embodiments, the cannabinoid comprises dronabinol hemisuccinate ester (THC-HS).

Formulations

Cannabinoids in general, and dronabinol specifically, are insoluble in water. The formulations of the present invention therefore preferably include one or more pharmaceutically acceptable oil-based compounds, i.e., triglycerides, as a carrier for the cannabinoid. In certain embodiments, the oil-based compound or compounds are a liquid at room temperature. In certain other embodiments, the oil-based compound or compounds are a semi-solid at room temperature.

Such oil-based compounds are readily available from commercial sources. Examples of suitable oil-based compounds include, but are not limited to, Aceituno oil, Almond oil, Arachis oil, Babassu oil, Blackcurrant seed oil, Borage oil, Buffalo ground oil, Candlenut oil, Canola oil, Lipex 108 (Abitec), Castor oil, Chinese vegetable tallow oil, Cocoa butter, Coconut oil Pureco 76 (Abitec), Coffee seed oil, Corn oil, Cottonseed oil, Crambe oil, Cuphea species oil, Evening primrose oil, Grapeseed oil, Groundnut oil, Hemp seed oil, Illipe butter, Kapok seed oil, Linseed oil, Menhaden oil, Mowrah butter, Mustard seed oil, Oiticica oil, Olive oil, Palm oil, Palm kernel oil, Peanut oil, Poppy seed oil, Rapeseed oil, Rice bran oil, Safflower oil, Sal fat, Sesame oil, Shark liver oil, Shea nut oil, Soybean oil, Stillingia oil, Sunflower oil, Tall oil, Tea seed oil, Tobacco seed oil, Tung oil, (China wood oil), Ucuhuba, Vernonia oil, Wheat germ oil, mixtures of any of the foregoing, and the like. Fractionated triglycerides, modified triglycerides, synthetic triglycerides, and mixtures of triglycerides are also within the scope of the invention.

Lecithin and Components of Lecithin as Carriers for Cannabinoids

In certain embodiments of the invention, lecithin may be used as part or all of the oil-based carrier. Cannabinoids are dispersible (dissolve) in lecithin. Lecithin is a complex mixture of phospholipids, glycolipids, triglycerides, sterols, small quantities of fatty acids, carbohydrates and sphingolipids. The primary phospholipid components of lecithin are: (i) phosphatidylcholine (13-18%); (ii) phosphatidylethonolamine (10-15%); (iii) phosphatidyinositol (10-15%) and (iv) phosphatidicacid (5-12%).

Experiments described herein showed that bases like ethanolamine prevent degradation of dronabinol. It is suggested that components of lecithin, (e.g., phosphatidyl ethanolamine and phosphatidyl choline) that contain an amine functionality help protect dronabinol from degradation. Therefore, lecithin may include both anti-oxidant(s) and organic base(s) which impart stability to the cannabinoid. In addition to lecithin, commercially available phospholipids may also be suitable as oil-based carriers.

Exemplary phospholipids suitable for oral dosage forms include: Phosal® 50 PG; Phosal® 53MCT; Phosal® 75SA, Phospholipon® 80; Phospholipon®80H; Phospholipon®85G; Phospholipon® 90G; Phospholipon® 90H; and Phospholipon® 90NG. Exemplary phospholipids suitable for dermal dosage forms include: Phosal® 50 PG; Phosal® 50SA; Phosal®53MCT; Phosal® 75SA; Phospholipon® 80; Phospholipon® 80H; Phospholipon® 85G; Phospholipon® 90NG; Phospholipon®90G; Phospholipon® 90H; and Phospholipon® 100H. Exemplary phospholipids suitable for parenteral dosage forms include: Phospholipon®90G; Phospholipon®90H; and Phospholipon® 100H. Phosholipids suitable for pulmonary drug formulations include: Phospholipon® 90G; Phospholipon® 9.0H and Phospholipon®.

Preferred triglycerides include vegetable oils, fish oils, animal fats, hydrogenated vegetable oils, partially hydrogenated vegetable oils, medium and long-chain triglycerides, and structured triglycerides. Preferred oils are vegetable oils such as soybean oil, olive oil, cotton seed oil, peanut oil, sesame oil and castor oil, with sesame oil and castor oil being preferred. Vitamin E (tocopherol) can also be used as the oil phase. This material is also an antioxidant and can help to stabilize the chosen cannabinoid (which as a class tend to be prone to oxidation).

In certain preferred embodiments, the oil-based carrier utilized in the formulations of the invention comprises sesame oil or cottonseed oil, most preferably sesame oil. The antioxidant properties of sesame oil have previously been reported in literature (Kato et al., 1998). Sesame oil is a major component of Marinol capsules and comprises over 90% of the finished product. The antioxidant effect of sesame oil has been attributed to the presence of several antioxidant chemicals in sesame oil. They include sesamin, sesamol, sesamolin and lecithin (Bradley Morris, 2002; Sirato-Yasumoto et al., 2001). It is preferred that the sesame oil used in the formulations of the present invention contain one or more of these anti-oxidants.

In certain embodiments, the formulation contains from about 0.05 to about 90% cannabinoid, weight to weight (w/w), with the remainder comprising the oil-based carrier. In preferred embodiments, the formulation contains from about 0.1% to about 50% by weight, and in certain preferred embodiments from about 1.5 to about 6% cannabinoid, by weight, with the remainder comprising the oil-based carrier, and in certain preferred embodiments, the formulation contains from about 2.5% to about 4.5% cannabinoid by weight, with the remainder comprising the oil-based carrier.

In preferred embodiments, the cannabinoid formulations of the invention do not degrade to an unacceptable extent such that the final product (cannabinoid dosage form) has a shelf-life of at least about 2 years. As previously mentioned, this means that the active ingredient (e.g., dronabinol) within the dosage form remains within 90-110% of its initial amount in the dosage form during the desired (e.g., labeled) shelf-life of the dosage form (e.g., a minimum of 2 years after the date of manufacture of the dosage form). In further preferred embodiments, where the dosage form contains dronabinol as the active ingredient, the dosage form will contain not greater than 2% D8THC during the claimed shelf-life of the dosage form. In further preferred embodiments, where the dosage form contains dronabinol, the dosage form will contain not greater than 2% cannabidiol during the claimed shelf-life of the dosage form. In further preferred embodiments, where the dosage form contains dronabinol, the dosage form will contain not greater than 1% exo-THC. In certain especially preferred embodiments where the dosage form contains dronabinol as the active ingredient, the dosage form will contain the following during its claimed shelf-life: (i) not less than 90% of the initial dronabinol content; (ii) not greater than about 2% cannabinol; (iii) not greater than about 2% delta-8-THC; (iv) not greater than 2% cannabidiol; (v) not greater than about 0.5% exo-THC; or any combination of the foregoing. Although exo-THC is not a degradant of dronabinol, it is an impurity formed during the synthesis of dronabinol. These ranges of particular degradants/impurities may be applicable for other cannabinoids, as well.

Hard Gelatin Capsules

In one embodiment, the present invention overcomes the deficiencies of prior art dronabinol oral dosage forms via the utilization of hard gelatin capsules in replacement of the soft gelatin capsules of the prior art. Hard gelatin capsules suitable for liquid filling are identical in composition to hard gelatin capsules used for powders. In contrast to soft gelatin capsule shells, hard gelatin capsule shells do not contain glycerol, and therefore a major cause of instability for the active pharmaceutical ingredient is eliminated. Hard gelatin capsule shells also have a lower moisture content than soft gelatin capsules. The moisture uptake for soft gelatin capsules plasticized with glycerol is considerably higher than that for hard gelatin capsules [Bauer K H, "Die Herstellung von Hart—und Weichgelatinekapseln." In Die Kapsel. W Fahrig and U H Hofer, Eds., Wissenschaftliche Verlags GmbH, Stuttgart, pp. 58-82 (1983)] Therefore, it is believed that the hard gelatin capsule shells used in embodiments of the present invention will have lower moisture content compared to soft gelatin shells. It has been reported that liquid and semi-solid formulations in hard gelatin capsules may improve bioavailability and stability for moisture or oxygen-sensitive drugs (Shah, et al., 2003). Also, by utilizing hard gelatin capsules to encapsulate the cannabinoid (e.g., dronabinol) solution, the need for the plasticizer glycerin is eliminated.

Alternatively, the cannabinoid solutions in oil-based carriers can be incorporated into a soft gelatin capsule, a cellulosic capsule, a starch capsule, and a non-gelatin capsule shell, in any manner known to those skilled in the art. Exemplary non-gelatin capsule shells include hydrocolloid film-forming compositions as described in U.S. Pat. No. 6,949,256, hereby incorporated by reference. As described in U.S. Pat. No. 6,949,256, non-animal based (e.g., non-glycerin containing) compositions may be used to encapsulate oil-based compositions such as those of the present invention. Such non-animal based compositions are described therein as comprising iota carrageenan in an amount from about 1-15%; kappa carrageenan in an amount less than or equal to 50% by weight of the total encapsulation (film-forming) composition; a bulking agent in the ratio of bulking agent:total carrageenan from at least about 1:1 to about 20:1; a plasticizer in an amount from about 10-50%, and water to form 100% by weight of the composition. The kappa carrageenan provides gel strength while the iota carrageenan provides flexibility to the composition. A mixture of kappa carrageenan and a glucomannan such as konjac flour may be used in place of some or all of the kappa karageenan in the composition, as described in U.S. Pat. No. 6,949,256. Furthermore, one skilled in the art will appreciate that it would be possible to substitute other naturally occurring or synthetic gums used in pharmaceuticals and/or food products to achieve similar results. The bulking agent may be, e.g., a modified starch. A useful plasticizer may be, e.g., a combination of sorbitol and maltitol. Briefly, and as discussed in detail in U.S. Pat. No. 6,949,256, capsules utilizing such compositions may be prepared by using a rotary die process in which a molten mass of the composition is fed onto cooled drums to form two spaced sheets or ribbons in a semi-molten state. These sheets are fed around rollers and brought together a convergent angle into the nip of a pair of roller dies that include opposed die cavities. A dosage form (e.g., the cannabinoid dispersed in oil-based carrier) is fed into the wedge-shaped joinder of the sheets such that it is trapped between the sheets inside the die cavities. The sheets are then pressed together and cut in a manner to encapsulate the enclosed formulation.

Alternatively, the cannabinoid solutions in oil-based carriers can be incorporated into a non-reactive container (e.g., a glass vial), in any manner known to those skilled in the art.

It is believed that the cannabinoid formulations encapsulated within hard gelatin capsules in accordance with the present invention are significantly more stable than formulations contained within commercially available soft gelatin capsules (e.g. Marinol). A possible explanation is that the higher moisture content of soft gelatin capsule shells combined with glycerol induces migration of the active ingredient dronabinol, leading to its profound instability (e.g., in the currently available commercialized dronabinol product). Therefore, a major cause of instability of the active pharmaceutical ingredient dronabinol may be eliminated by encapsulating the formulation in hard gelatin capsules. The stability studies set forth in the appended examples are believed to confirm that by utilizing hard gelatin capsules to encapsulate the cannabinoid solution and eliminating the inclusion of glycerin/glycerol, an oral cannabinoid drug product that is stable for at least about two years at room temperature is obtained.

Table 1 provides examples of cannabinoid formulations in accordance with the present invention. As can be ascertained from that table, hard gelatin capsules contain from about 85% to about 100% gelatin and from about 1% to about 15% water.

TABLE 1

Examples of Formulation Composition

| COMPONENT | CONCENTRATION RANGE (W/W) |
|---|---|
| Dronabinol | 1.5-6.0%; 0.05-90% |
| Sesame Oil | 0-100% |
| Sesamin | 0-10% |
| Sesamol | 0-10% |
| Sesamolin | 0-10% |
| Lecithin | 0-10% |
| Capsule Shell | |
| Gelatin | 85-100% |
| Water | 1-15% |

Hard gelatin capsules have been used for many years in the oral delivery of pharmaceutical compounds. Drug formulations in a powdered or granular form are usually filled into a hard gelatin capsule thus providing for a unit dose that effectively masks the bitter taste of some drugs. More recently, new technology has been developed to accurately dose and seal liquids into hard gelatin capsules (Shah et al., 2003).

To prepare liquid filled hard gelatin capsules, basically the hard gelatin capsules are filled with the (compatible) drug/carrier, and then the capsule is sealed, e.g., by spraying a small amount of water/ethanol mixture at the cap and body interface followed by a gentle warming (optional) to fuse the two capsule parts together.

In further embodiments, additional excipients compatible with hard gelatin capsule shells may be incorporated into the liquid drug formulation, if needed, such as known viscosity modifiers for lipophilic liquid vehicles (e.g., Aerosil, Cetostearyl alcohol, Gelucires 33/01, 39/01 and 43/01, glyceryl behenate, glyceryl palmitostearate, Softisans 100, 142, 378 and 649, and stearyl alcohol; and solubilizing agents (surfactants) such as Capryol 90, Gelucire 44/14, 50/13, Cremophor RH 40, Imitor 191.308, 742,780 K, 928 and 988, Labrafil M 1994 CS, M 2125 CS, Lauroglycol 90, PEG MW>4000, Plurol Oleique CC 497, Poloxamer 124 and 188, Softigen 701, 767, Tagat TO, and Tween 80.

Stabilizers

In certain preferred embodiments, the oil-based carrier contains amounts of one or more pharmaceutically acceptable anti-oxidants in an amount effective to stabilize the cannabinoid contained therein such that the cannabinoid does not degrade to an unacceptable extent and the formulation is deemed stable as per the FDA guidance for two-year expiration dating (i) when placed under accelerated storage conditions of elevated temperature and humidity of 40° C./75% relative humidity (RH) for 6 months, and/or (ii) when placed under elevated temperature conditions of 55° C. for two weeks; and/or when stored at room temperature (25° C.) for two years.

In certain preferred embodiments, the oil-based carrier is sesame oil and the formulation contains one or more anti-oxidants (e.g., sesamin, sesamol, sesamolin, lecithin, and any combinations thereof) in an amount effective to stabilize the cannabinoid contained therein (e.g., dronabinol). It is noted that although lecithin is generally recognized as an emollient, emulsifier, and solubilizer, it was observed that lecithin protects cannabinoids much like an anti-oxidant. Lecithin is also referred to as an anti-oxidant in the literature (e.g., Featured Excipient: Antioxidants, 1999 and Bradley Morris, 2002; Sirato-Yasumoto et al., 2001).

In certain preferred embodiments, the formulation contains a total of about 0.001% to about 50% of an anti-oxidant(s) selected from sesamin, sesamol, sesamolin, lecithin, and any combinations thereof. In certain other preferred embodiments, the oil-based carrier in the formulation comprises from about 0.001% to about 10% of an anti-oxidant(s) selected from sesamin, sesamol, sesamolin, lecithin, and any combinations thereof. In other preferred embodiments, the oil-based carrier in the formulation comprises from about 0.01% to about 10% of an anti-oxidant(s) selected from sesamin, sesamol, sesamolin, lecithin, and any combinations thereof.

In other embodiments of the invention, the oil-based carrier does not inherently contain an anti-oxidant such as sesamin, sesamol, sesamolin, or lecithin, and in certain preferred embodiments effective amounts of one or more of these anti-oxidants is added to the formulation in order to stabilize the cannabinoid contained therein.

In further embodiments of the invention, an effective (stabilizing) amount of one or more pharmaceutically acceptable anti-oxidants is added to the oil-based carrier. The term "anti-oxidant" is used herein to describe any compound which is oxidized more easily than the cannabinoid compounds included in the dosage forms of the present invention. Any of the known anti-oxidants may be used, including but not limited to anti-oxidants such as butyl hydroxyl anisole (BHA), butyl hydroxyl toluene (BHT), propyl gallate, lecithin, Vitamin E tocopherol, sesamin, sesamol, sesamolin, alpha tocopherol, ascorbic acid, ascorbyl palmitate, fumaric acid, malic acid, sodium ascorbate and sodium metabisulphite, as well as chelating agents such as disodium EDTA, may also be used to stabilize the cannabinoid formulations of the present invention.

The preparation may also contain anti-oxidant synergists to prevent oxidative degradation. Any of the known anti-oxidant synergists may also be used in effective amounts, for example disodium edetate.

The level of anti-oxidant which may be used will be optimized for each formulation, in order to obtain a stable product (dosage form) having the desired shelf-life. Generally speaking, in embodiments in which an anti-oxidant is included, suitable formulations may include from about 0.001% to about 50% w/w of a pharmaceutically acceptable anti-oxidant(s). For example, in certain preferred embodiments, the amount of lecithin included in the cannabinoid dosage form is in the range from about 0.1 to about 10% w/w, and in certain embodiments more preferably from about 0.3% to about 8.25% w/w. In other preferred embodiments, the amount of L-ascorbic acid-6-palmitate is from about 0.001 to about 1%, w/w, and in certain embodiments more preferably in the range from about 0.01% to about 0.1% w/w. The anti-oxidant preferably prevents the formation of degradants in the dosage form such as those mentioned above, namely delta-8 tetrahydrocannabinol (D8THC), cannabinol (CBN), or cannabidiol (CBD), to unacceptable levels (e.g., as previously specified herein).

In certain other embodiments, the formulation contains one or more of the following stabilizers, lysolecithin; phosphatidylcholine; phosphatidylethanolamine; phosphatidylglycerol; phosphatidic acid; phosphatidylserine; lysophosphatidylcholine; lysophosphatidylethanolamine; lysophosphatidylglycerol; lysophosphatidic acid; lysophosphatidylserine; PEG-phosphatidylethanolamine; PVP-phosphatidylethanolamine; mixtures thereof; and mixtures of any of the foregoing with lecithin.

Organic Bases

In further embodiments of the invention, effective amounts of one or more pharmaceutically acceptable organic bases are added to the cannabinoid and oil-based carrier mixture in order to stabilize the cannabinoid from undesirable levels of degradation. In certain preferred embodiments, the oil-based carrier contains amounts of one or more pharmaceutically acceptable organic bases in an amount effective to stabilize the cannabinoid contained therein such that the cannabinoid does not degrade to an unacceptable extent and the formulation is deemed stable as per the FDA guidance for two-year expiration dating (i) when placed under accelerated storage conditions of elevated temperature and humidity of 40° C./75% relative humidity (RH) for 6 months, and/or (ii) when placed under elevated temperature conditions of 55° C. for two weeks; and/or when stored at room temperature (25° C.) for two years.

Examples of suitable organic bases which may be effectively used in the cannabinoid formulations of the present invention include but are not limited to any pharmaceutically acceptable primary organic amines which are GRAS ingredients (generally regarded as safe), such as methanolamine, ethanolamine, meglumine, other alkylamines (e.g. di-alkyl amines and tri-alkyl amines), and any combination thereof In certain preferred embodiments, the amount of organic base(s) in the cannabinoid/oil-based carrier mixture is from about 0.001% w/w to about 5% w/w, and more preferably from about 0.007% w/w to about 2% w/w.

In other preferred embodiments, the cannabinoid/oil-based carrier mixtures include stabilizing amounts of both one or more anti-oxidants and one or more organic bases.

In further alternative embodiments, the cannabinoid solutions in oil-based carriers can be incorporated into soft gelatin capsules, where sufficient amounts of anti-oxidant(s), organic base(s), or combinations thereof are included therein in order to provide a room temperature stable soft gelatin cannabinoid capsule in accordance with the present invention. In certain preferred embodiments, the cannabinoid is dronabinol.

Soft Gelatin Capsules

In certain embodiments, the liquid formulations of the present invention (e.g., cannabinoid in oil-based carrier) can be stabilized utilizing effective amounts of (i) an anti-oxidant(s); (ii) an organic base; or (iii) a combination of an anti-oxidant and an organic base, such that the liquid formulation can be encapsulated within a soft gelatin capsule and remain stable for a desired period of time (e.g., such that the cannabinoid does not degrade to an unacceptable extent and the formulation is deemed stable as per the FDA guidance for two-year expiration dating (i) when placed under accelerated storage conditions of elevated temperature and humidity of 40° C./75% relative humidity (RH) for 6 months, and/or (ii) when placed under elevated temperature conditions of 55° C. for two weeks; and/or when stored at room temperature (25° C.) for two years).

Additional Ingredients

Formulations of the invention also may include one or more additional excipients incorporated into the formulation, if needed. Exemplary excipients are:

Viscosity modifiers for lipophilic vehicles (e.g., Aerosil, Cetostearyl alcohol, Cetyl alcohol, stearyl alcohol, Gelucires 33/01, 39/01 and 43/01, glyceryl behenate, glyceryl palmitostearate, Softisans 100, 142, 378 and 649, and stearyl alcohol;

Solubilizing agents (e.g., Capryol 90; Cremophor RH40; Labrafil M 1944 CS; Labrafil M 2125 CS; Lauroglycol 90; PEG MW>4000; Plurol Oleique CC 497; poloxamer 124; poloxamer 188; Softigen 701; Softigen 767; Tagat TO; Tween 80; triacetin; triethylcitrate; tributylcitrate; acetyl triethylcitrate; acetyl tributyl citrate; triethylcitrate; ethyl oleate; ethyl caprylate; ethyl butyrate; triacetin; 2-pyrrolidone; 2-piperidone; N-methylpyrrolidone; N-ethylpyrrolidone; N-hydroxyethyl pyrrolidone; N-octylpyrrolidone; N-laurylpyrrolidone; dimethylacetamide; and mixtures thereof);

Surfactants (e.g. Capryol 90; Cremophor RH40; Gelucire 44/14; Gelucire 50/13; Imwitor 91; Imwitor 308; Imwitor 380; Imwitor 742; Imwitor 780K; Imwitor 928; Imwitor 988; Labrafil M 1944 CS; Labrafil M 2125 CS; Lauroglycol 90; Tagat TO; Tween 80; and mixtures thereof); emulsifiers (e.g., Gelucire 44/14; Gelucire 50/13; Imwitor 91; Imwitor 308; Imwitor 380; Imwitor 742; Imwitor 780K; Imwitor 928; Imwitor 988; poloxamer 124; poloxamer 188; Tagat TO; Tween 80; lecithin; lysolecithin; phosphatidylcholine; phosphatidylethanolamine; phosphatidylglycerol; phosphatidic acid; phosphatidylserine; lysophosphatidylcholine; lysophosphatidylethanolamine; lysophosphatidylglycerol; lysophosphatidic acid; lysophosphatidylserine; PEG-phosphatidylethanolamine; PVP-phosphatidylethanolamine; and mixtures thereof); and Absorption enhancers (e.g., Gelucire 44/14; Gelucire 50/13; Tagat TO; Tween 80; and mixtures thereof).

It is recognized that pharmaceutical excipients may perform more than one function, and are therefore characterized as having different uses depending on the particular application. While the use of an excipient in the context of a particular formulation may determine the function of the excipient, the inclusion of any particular excipient into any one or more category as set forth above is not meant to limit the function of that excipient.

Seal Coating

In accordance with the invention, the dosage form may further be coated with a seal coating alone or in addition to another coating. In one embodiment, the seal coating occurs between the core and the enteric coating. The seal coating may comprise a hydrophilic polymer. Examples include but are not limited to hydroxypropylcellulose, hydroxypropylmethylcellulose, methoxypropyl cellulose, hydroxypropylisopropylcellulose, hydroxypropylpentylcellulose, hydroxypropylhexylcellulose and any mixtures thereof. The seal coat may also be a polymer such as polyvinyl alcohol.

The seal coating may be applied by press coating, molding, spraying, dipping and/or air-suspension or air tumbling procedures. A preferred method of applying the seal coating is by pan coating, where the seal coating is applied by spraying it onto the cores accompanied by tumbling in a rotating pan. The seal coating material may be applied to the dosage form as a suspension by employing solvents, e.g., an organic, aqueous, or a mixture of an organic and aqueous solvent. The seal coating material and solvent should be compatible with the encapsulating material of the dosage form, active pharmaceutical ingredient(s), and any other coating. Exemplary solvents suitable in applying the seal coating include aqueous-based solutions, an alcohol, ketone, ester, ether, aliphatic hydrocarbon, halogenated solvents, cycloaliphatic solvents, aromatic, heterocyclic, aqueous solvents, and mixtures thereof. In a preferred embodiment, the seal coating comprises hydroxypropyl cellulose and hydroxypropylmethylcellulose, and is delivered as a suspension using a suitable solvent such as e.g., ethanol or water.

Enteric Coating

The dosage form of the present invention may also be coated with an enteric layer, alone or in addition to another coating. The enteric materials for use in the enteric layer preferably resist the action of gastric fluid preferably allowing for release of the active agent in the intestinal tract.

Suitable enteric coating may comprise cellulose acetate phthalate, polyvinyl acetate phthalate, acrylic resins such as Eudragit L®, shellac, cellulose acetate butyrate, hydroxypropyl methylcellulose phthalate or combinations thereof.

Additional materials suitable for use in the enteric coating include phthalates including cellulose acetyl phthalate, cellulose triacetyl phthalate, cellulose acetate tetrahydrophthalate, cellulose acetate trimellilate, sodium cellulose acetate phthalate, cellulose ester phthalate, cellulose ether phthalate, methylcellulose phthalate, cellulose ester-ether phthalate, hydroxy propyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, and polyvinyl acetate phthalate, may be used as gastroresistant, enterosoluble coatings for the formulations of the present invention. Other enteric coatings may be used as long as they do not readily dissolve or disperse in the gastric juices of the stomach but do dissolve or disperse in the intestinal fluid of the intestines. An acrylic-based film-coating system, commercially available as Acryl-EZE® by Colorcon, West Point, Va., is a preferred enteric coating. Enteric materials are also particularly preferred because they form an impermeable barrier which will not readily dissolve or disperse at the low pH provided by the gastric juices in the stomach. The enteric materials are discussed in Remington's Pharmaceutical Sciences, 17th Ed., page 1637 (1985).

The enteric coating may be applied by press coating, molding, spraying, dipping and/or air-suspension or air tumbling procedures. One method of applying the enteric coating is by pan coating, where the enteric coating is applied by spraying the enteric composition onto the cores accompanied by tumbling in a rotating pan. The enteric coating material may be applied to the cores by employing solvents, including an organic, aqueous or a mixture of an organic and aqueous solvent. The enteric coating material and solvent should be compatible with the encapsulating material of the dosage form, active pharmaceutical ingredient(s), and any other coating. Exemplary solvents suitable in applying the enteric coating include an alcohol, ketone, ester, ether, aliphatic hydrocarbon, halogenated solvents, cycloaliphatic solvents, aromatic, heterocyclic, aqueous solvents, and mixtures thereof.

Controlled Release Coating

In other embodiments of the invention the formulation is coated with a controlled release coating, which is compatible with the other components of the dosage form. The controlled release coating may comprise a hydrophobic controlled release material selected from (i) an alkylcellulose; (ii) an acrylic polymer; or (iii) mixtures thereof. The coating may be applied in the form of an organic or aqueous solution or dispersion.

In certain embodiments, the controlled release coatings include a plasticizer such as those described herein.

In certain embodiments, it is necessary to overcoat the substrate comprising the active pharmaceutical ingredient with an aqueous dispersion of e.g., alkylcellulose or acrylic polymer to obtain a controlled-release formulation. The amount of overcoat may vary depending upon the physical properties of the active pharmaceutical ingredient and the desired release rate, the inclusion of plasticizer in the aqueous dispersion and the manner of incorporation of the same, for example.

Alkylcellulose Polymers

Cellulosic materials and polymers, including alkylcelluloses are controlled release materials suited for coating substrates containing the active pharmaceutical ingredient according to the invention. Simply by way of example, one preferred alkylcellulosic polymer is ethylcellulose, although the artisan will appreciate that other cellulose and/or alkylcellulose polymers may be readily employed, singly or on any combination, as all or part of a hydrophobic coatings according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the controlled release material comprises a pharmaceutically acceptable acrylic polymer, including but not limited to acrylic acid and methacrylic acid copolymers, methyl methacrylate copolymers, ethoxyethyl methacrylates, cynaoethyl methacrylate, poly(acrylic acid), poly(methacrylic acid), methacrylic acid alkylamide copolymer, poly(methyl methacrylate), polymethacrylate, poly(methyl methacrylate)copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm Tech, Inc. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent, however, dosage forms coated with Eudragit RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a controlled-release formulation having a desirable dissolution profile. Desirable controlled-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers in Control Release Coatings

In embodiments of the present invention where the coating comprises an aqueous dispersion of a hydrophobic controlled release material, the inclusion of an effective amount of a plasticizer in the aqueous dispersion of hydrophobic material will further improve the physical properties of the controlled-release coating. For example, because ethylcellulose has a relatively high glass transition temperature and does not form flexible films under normal coating conditions, it is preferable to incorporate a plasticizer into an ethylcellulose coating containing controlled-release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

In certain embodiments, the addition of a small amount of talc to the controlled release coating reduces the tendency of the aqueous dispersion to stick during processing, and acts as a polishing agent.

Additional Drugs

Cannabinoids such as dronabinol may be used alone or in combination with other medications. Those skilled in the art will readily recognize that, for example, in the case of AIDS wasting syndrome, the patient will likely also be taking drugs that combat the AIDS virus. Similarly, those skilled in the art will readily recognize that patients receiving chemotherapy for cancer may also receive other antiemetics, and cancer patients seeking to relieve pain are likely to receive opioids as well as nonsteroidal anti-inflammatory agents. The formulations and methods of the invention may further include one or more additional therapeutically active agents, such as, for example, non-narcotic analgesics such as acetaminophen or aspirin, opioid or opiate analgesics, non-steroidal anti-inflammatory drugs (NSAIDs, for example, non-selective cyclooxygenase inhibitors and COX-2 inhibitors), anti-emetics (for example, ondansetron) and steroids (for example megestrol acetate, oxandrolone, oxymetholone). In certain embodiments of the invention, a second therapeutically active drug including but not limited to the above-mentioned drugs, is incorporated into the oral cannabinoid dosage form. In yet other embodiments, the second therapeutically active drug is separately administered to the patient in conjunction with the oral cannabinoid dosage form. The sequence in which the therapeutic agents are administered is not narrowly critical. "Combination therapy" embraces the administration of the therapeutic agents as described above in further combination with other biologically active ingredients, such as, but not limited to, a pain reliever, such as a steroidal or nonsteroidal anti-inflammatory drug, or an agent for improving stomach motility, for example, and with non-drug therapies, such as, but not limited to, surgery.

The therapeutic compounds that make up the combination therapy may also be administered sequentially, with either therapeutic compound being administered by a regimen calling for two-step administration. Thus, a regimen may call for sequential administration of the therapeutic compounds with spaced-apart administration of the separate, active agents. The time period between the multiple administration steps may range from, for example, a few minutes to several hours to days, depending upon the properties of each therapeutic compound such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval.

The therapeutic compounds of the combined therapy whether administered simultaneously, substantially simultaneously, or sequentially, may involve a regimen calling for administration of one therapeutic compound by oral route and another therapeutic compound by an oral route, a percutaneous route, an intravenous route, an intramuscular route, or by direct absorption through mucous membrane tissues, for example. Whether the therapeutic compounds of the combined therapy are administered orally, rectally, topically, buccally, sublingually, or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

Other additives conventionally used in pharmaceutical compositions can be included, and these additives are well known in the art. Such additives include pharmaceutically acceptable detackifiers, anti-foaming agents, buffering agents, antioxidants, preservatives, chelating agents, viscomodulators, tonicifiers, flavorants, colorants odorants, opacifiers, suspending agents, binders, fillers, plasticizers, lubricants, and mixtures thereof. The amounts of such additives can be readily determined by one skilled in the art, according to the particular properties desired, keeping in mind the possibility that any such additives should preferably not negatively impact the stability of the final formulation.

Route of Administration

The formulations of the present invention are preferably administered orally. However, one skilled in the art will appreciate that the stabilized cannabinoid formulations of the present invention are not limited to administration by the oral route, and can be administered via the nasogastric route, a percutaneous route, an intravenous route, an intramuscular route, or by direct absorption through mucous membrane tissues (e.g., buccally or rectally). Although formulations specifically suited to oral administration are presently preferred, the compositions of the present invention can also be formulated for topical, transdermal, buccal, ocular, pulmonary, vaginal, rectal, transmucosal or parenteral administration, as well as for oral administration. Thus, the dosage form can be a solution, suspension, emulsion, suppository, spray, aerosol, gel, drops, syrup, elixir, or other dosage form, as desired.

Dosage

The dosage range of dronabinol may vary widely from 2.5 mg to 20 mg daily, in single or divided doses, or therapeutically equivalent amounts of one or more other cannabinoids may be utilized (as can be determined by one skilled in the art).

Making the Capsule

In one embodiment of the invention, the cannabinoid formulation is a liquid-filled hard capsule. An essential part of a liquid-filling operation is the ability to effectively seal the capsule. The methods that are available to seal hard gelatin capsules are banding using a gelatin band and sealing using a hydroalcoholic solution. The capsule sealing process uses the principle of lowering of the melting point of gelatin by the application of moisture to the area between the capsule body and cap. One machine for industrially sealing hard gelatin capsules is commercially available and is marketed under the name LEMS™ 30 (Liquid Encapsulation by Microspray). This machine is connected to the output of a capsule-filling machine by means of a conveyor.

Cannabinoid (e.g., dronabinol) hard gelatin room temperature stable capsules can be manufactured using the Capsugel LEMS system and capsule-filling machine (Bosch, Zanazzi etc.). Alternatively, they can also be manufactured by using the banding method to seal the two halves of the hard gelatin capsules (e.g. Shionogi HG capsule banding machine). Further (optional) methodology is known to those skilled in the art, and is set forth in various industry publications. (See, e.g., Cole, E. T., Liquid Filled and Sealed Hard Gelatin Capsules, Capsugel Library (Originally published in Gattefosse Bulletin nr 92 (1992), incorporated herein by reference.

Advantages of the Invention

The branded product Marinol® (Dronabinol solution in soft gelatin capsules) is highly unstable at room temperature. Therefore the manufacturer of Marinol (Unimed Pharmaceuticals Inc.) recommends that the product be stored at refrigerated (2-8° C.) or cool (8-15° C.) conditions (Marinol package label, Physicians Desk Reference®, Ed. 2003). Unlike the branded product Marinol, the present invention provides a cannabinoid (e.g., dronabinol) formulation drug product that is preferably stable at all conditions—refrigerated, cool and room temperature (25° C./60% RH). Factors contributing to the improved stability, particularly at room temperature, of the present invention include: the absence of glycerin (glycerol) in the hard gelatin shell embodiment; low amounts of moisture in the hard gelatin shell embodiment; low permeability of oxygen through the shell of hard gelatin capsules; low sensitivity to heat and humidity of hard gelatin capsules; and the presence of sesamin and/or other antioxidants in the formulation. In certain embodiments, additional factors contributing to improved stability of the cannabinoid dosage forms of the present invention include the addition of effective stabilizing amounts of organic bases (e.g., ethanolamine and meglumine); and/or the addition of additional effective stabilizing amounts of anti-oxidants which may or may not be inherently found in the oil-based carrier (for example, sesamin, lecithin and/or L-ascorbic acid-6-palmitate).

In certain preferred embodiments, the cannabinoid formulations of the present invention may improve the delivery of the cannabinoid with respect to the extent, rate, and/or consistency of absorption from the gastrointestinal tract.

Uses of the Present Invention

The formulations of the present invention are useful in treatment and prevention of a very wide range of disorders, including, for example, nausea, vomiting, anorexia, cachexia, pain, gastrointestinal tract distress (such as heartburn, indigestion, stomachache, sour stomach), inflammatory bowel disease, Crohn's disease, gastritis, irritable bowel syndrome, ulcerative colitis, migraine headaches, postmenstrual syndrome, Alzheimer's dementia, agitation, muscle spasms and other involuntary movement disorders, Parkinson's disease and Parkinsonian-type symptoms, spasticity as result of multiple sclerosis, glaucoma, anxiety disorders. Cannabinoids such as dronabinol have also been reported as showing other biological activities which lend themselves to possible therapeutic applications, such as in the treatment of migraine headaches, spinal cord injury, anxiety, and as an analgesic (e.g., to treat neuropathic pain). Cannabinoids such as dronabinol may be used together with opioid analgesics in a synergistic way to relieve pain; advantages of the combination may include decreased administration of opioids (leading to decreased side effects) and may be opioid-sparing (i.e., allowing for a reduced dose of opioid to achieve an equivalent effect). Dronabinol has also been used in the treatment of cancer cachexia (where the loss of appetite induces malnutrition in cancer patients). It has also been used to treat movement disorders including dystonia, Huntington's disease, Parkinson's disease and Tourette's syndrome; epilepsy, and for appetite stimulation in Alzheimer's disease. The use of cannabinoid formulations prepared in accordance with the present invention is contemplated for any and all of the above uses, and any other use known or which become known to those skilled in the art.

DETAILED DESCRIPTION OF PREFERRED EMBODIMENTS

The following examples illustrate various aspects of the present invention, and are set forth to assist in understanding the invention. These examples should not be construed as specifically limiting the invention described and claimed herein. Variations of the invention, including the substitution of all equivalents now known or later developed, which would be within the purview of those skilled in the art, and changes in formulation or minor changes in experimental design, are considered to fall within the scope of the invention and appended claims.

The following equipment and procedure was used to develop and analyze room temperature stable dronabinol formulations:

Equipment
Agilent 1100 HPLC
Agilent 6890 GC
Maxima™ Digital Mixer (Fischer Scientific)
Isotemp Digital Hot-Plate Stirrer
Glass Beakers
Volumetric Flasks
Ovens
Dissolution/Disintegration Procedure An accurately measured volume (500 mL) of dissolution medium was transferred to each of the 6 cylindrical glass vessels of the USP Dissolution Apparatus 2. The apparatus was equilibrated at 37° C. for 1 hour. One capsule was placed in each vessel and the capsules were allowed to sink to the bottom of the vessel before starting the rotation of the blade. The rotation speed of the blade was maintained at 50 rpm during the disintegration testing. The capsules were observed and the time taken for each capsule shell to rupture was recorded. Rupture of capsule is identified by visual inspection of loss of integrity of the capsule.

EXAMPLE 1

Manufacturing Procedure

Delta-9-tetrahydrocannabinol (dronabinol) is chemically synthesized as per procedures known to those skilled in the art, and is supplied as a light-yellow resinous oil that is sticky at room temperature and hardens upon refrigeration. Chemically synthesized dronabinol is supplied in a round bottom flask with high-vacuum adaptor with a 24/40 o-ring seal joint and bakeable PTFE plug.

Dronabinol in sesame oil is prepared as follows: An oil bath (vacuum pump oil, Fisher CAS #72623-87-1) was heated to 90-95° C. A flask containing dronabinol warmed in the preheated oil bath (approx 10 min) until the dronabinol turned into a flowable liquid. The vacuum adapter of the flask was removed before warming the flask. Dronabinol was transferred to a glass container by using a glass pipette and the exact amount transferred was noted. The actual amount of sesame oil to be added to the mixture to obtain the required concentration of dronabinol was calculated. Sesame oil (Sesame oil NF, RBDW (RBDW=refined, bleached, deodorized and winterized) stored at room temperature was transferred to dronabinol container and the actual amount transferred was noted. The mixture containing dronabinol and sesame oil was again heated in the oil bath for approximately 5 minutes and thereafter mixed well by a vortexer for 5 minutes. The resulting solution was cooled to room temperature and a sample was submitted for analysis.

EXAMPLE 2

Filling Hard Gelatin Capsules

A solvent solution for sealing hard gelatin capsules (1:1 ethanol to DI water) was prepared by mixing equal amounts of alcohol and DI water. The cap from the capsule was removed. 184 µL of formulation (equivalent volume of 165 mg) prepared in accordance with Example 1 was filled in the body of capsule by using DISTRIMAN®, a repetitive pipette. A small lip brush was dipped into the sealing solution and applied to inner walls of the cap. The body was immediately closed with the cap. The filled capsules were dried, transferred to clean glass bottles and stored at different temperature conditions (25° C./60% RH, 40° C./75% RH and 55° C.) for stability studies (see Stability Studies, below in Example 13). The capsules utilized in this procedure were size 3 capsules containing 5 mg Dronabinol in a total of 165 mg solution (providing approximately a 3.03% drug concentration in the capsules).

EXAMPLE 3

Commercial Manufacture

An example of a potentially useful commercial manufacturing procedure is as follows:
1. Weigh required amount of Sesame Oil (e.g., approximately 50% of total batch weight) of Sesame Oil in a clean stainless steel tank.
2. Warm Sesame Oil to approximately 55±5° C. Maintain inert blanket (any noble gas, e.g., nitrogen, helium, argon) during warming the oil to prevent oxidation.
3. Weigh the flask containing dronabinol and note the gross weight. Heat the container under vacuum in a convection oven or oil bath or water bath to approximately 95±5° C. until the raw material melts to an easily flowable liquid. Ensure that the heating is uniform. Record the heating time.
4. Remove the adapter on the flask slowly and transfer dronabinol to preheated Sesame Oil with Stirring. Rinse the raw material flask 2 to 3 times with portions of warm Sesame Oil. Add the rinses to Sesame Oil container. Mix with an appropriate industrial mixer for 10 to 15 minutes. Record the mixing time.
5. Weigh the raw material flask to obtain the tare weight. The difference between the gross and tare weights will be the actual amount transferred into the Sesame Oil.
6. Wash the raw material container with a suitable organic solvent (e.g. methanol, ethanol, dichloromethane). Collect the washings for analysis.
7. Reweigh the raw material container to obtain the weight of the container after washing. Calculate the weight of dronabinol used in formulating approx. 50% dronabinol solution.
8. Conduct an HPLC assay of the 50% dronabinol solution. Determine the exact dilution factor (e.g. 49.85% dronabinol)
9. Calculate the additional amount of Sesame Oil to be added to the mixture to obtain the required concentration of dronabinol (e.g. 12%, 6%, 3%, 1.5% w/w).
10. Add slowly the calculated amount of warm Sesame Oil to the mixture with stirring. Mix well for 15 to 20 minutes with steel spatula or an appropriate blending apparatus.
11. Cool the dronabinol solution to room temperature. Record the cooling time.
12. Submit a sample for analysis.

EXAMPLE 4

Commercial Filling in Hard Gelatin Capsules

An important aspect of a liquid-filling operation is the ability to effectively seal the capsule. The methods that are available to seal hard gelatin capsules are, e.g., banding using a gelatin band and sealing using a hydroalcoholic solution. The capsule sealing process uses the principle of lowering of the melting point of gelatin by the application of moisture to the area between the capsule body and cap. The machine for industrially sealing hard gelatin capsules is commercially available and is marketed under the name LEMS™ 30 (Liquid Encapsulation by Microspray). This machine is connected to the output of a capsule-filling machine by means of a conveyor.

Dronabinol hard gelatin room temperature ("HG RT") capsules may be manufactured using the Capsugel LEMS system and capsule-filling machine (Bosch, Zanazzi etc.). Alternatively, they can also be manufactured by using the banding method to seal the two halves of the hard gelatin capsules (e.g. Shionogi HG capsule banding machine).

EXAMPLE 5

Disintegration Studies

Disintegration studies were conducted on Dronabinol-sesame oil formulation filled hard gelatin capsules prepared in accordance with the methods described below. The formulation tested in Example 5 is a 5 mg capsule of Delta-9-THC (3.03%) in sesame oil, super refined (Croda). The formulation was a total of 165 mg and was encapsulated in size 3 capsules.

The test that is most often associated with the assessment of in-vivo performance is the dissolution test. In developing formulations, dissolution is used as a testing tool to select appropriate excipients for the formulation. The United States Pharmacopeia (USP) requires a dissolution test for the branded product, Marinol, a liquid-filled soft gelatin capsule, which is in reality a disintegration test. In the present study, USP Dissolution apparatus 2 was used for conducting all the disintegration tests. The apparatus is described in section 711 of the USP.

Disintegration Medium:

Water and buffer solutions listed below were used as disintegration media with their pH adjusted to within ±0.05 units of the prescribed value.
1. Nanopure Water
2. Phosphate Buffer (pH 1.2)
3. Acetate Buffer (pH 4.5)
4. Phosphate Buffer (pH 6.8)

Procedure:

An accurately measured volume (500 ml) of dissolution medium was transferred to each of the 6 cylindrical glass vessels of the USP Dissolution Apparatus 2. The apparatus was equilibrated at 37° C. for 1 hour. One capsule was placed in each vessel and the capsules were allowed to sink to the bottom of the vessel before starting the rotation of the blade. The rotation speed of the blade was maintained at 50 rpm during the disintegration testing. The capsules were observed and the time taken for each capsule shell to rupture was recorded. Rupture of capsule is identified by visual inspection of loss of integrity of the capsule.

The disintegration times of six dronabinol USP 5 mg capsules used in Example 5 in Water and pH 1.2, 4.5 and 6.8 Buffer Solutions (as set forth above) are provided in Table 2. All the capsules disintegrated in less than 2 minutes (well within the USP monograph specification of 15 minutes), irrespective of the disintegration medium used. These results indicate that the dronabinol capsules of Example 5 rapidly disintegrate in all the media tested and therefore, dronabinol should be readily available for absorption in any part of the gastro-intestinal tract.

TABLE 2

| | Disintegration Times (Minutes) | | | |
|---|---|---|---|---|
| Sample No. | Water | PH 1.2 | pH 4.5 | pH 6.8 |
| 1 | 1.40 | 1.37 | 0.62 | 0.70 |
| 2 | 1.15 | 0.57 | 0.22 | 0.90 |
| 3 | 1.43 | 0.57 | 0.22 | 0.70 |
| 4 | 0.60 | 0.85 | 1.32 | 0.48 |
| 5 | 0.82 | 0.63 | 0.62 | 0.45 |
| 6 | 1.12 | 0.57 | 1.45 | 0.57 |
| Average | 1.09 | 0.76 | 0.74 | 0.63 |
| Std. Dev. | 0.33 | 0.32 | 0.53 | 0.17 |

The disintegration times for these capsules therefore meet the USP specification of not more than 30 minutes for dronabinol capsules.

EXAMPLE 6

Stability Results—Presence of Moisture

In Example 6, a dronabinol formulation prepared in accordance with Example 1 and containing 5 mg dronabinol 3.03% w/w in sesame oil, super refined (Croda) was prepared. Water was added to the formulation, and the formulation was vortexed for several hours. Thereafter, the formulation was separated from remaining water after centrifugation. Although no measurements/calculations were performed to calculate the amount of water in the formulation, it is believed that the formulation would be saturated with water since it was mixed for several hours. The formulation was stored in amber glass vials at 55° C. for 2 weeks while being tested for stability. The rationale for performing stability studies at 55° C. for 2 weeks was based on the hypothesis that the data obtained would be a good representation of two-year shelf life of the product stored at room temperature.

The results of stability testing of Example 6 are set forth in Table 3 below.

TABLE 3

| CONDITION | FORMULATION # | TOTAL ASSAY % | IMPURITY % | RELATED SUBSTANCES | | |
|---|---|---|---|---|---|---|
| | | | | D8THC % | CBN % | CBD % |
| Zero Time | Example 9-ii* | 93.80 | 6.20 | 0.75 | 1.88 | 0.29 |
| 55° C. (1 week) | Example 9-ii* | 82.16 | 17.84 | 0.72 | 1.86 | 0.23 |
| | Example 6 | 77.67 | 22.33 | 0.49 | 1.92 | 0.09 |
| 55° C. (2 weeks) | Example 9-ii | 67.41 | 32.59 | 1.06 | 4.96 | 4.20 |
| | Example 6 | 62.71 | 37.29 | 0.60 | 2.70 | 0.23 |

*Control

The moisture saturation studies conducted on dronabinol solution in sesame oil indicate significant instability of the active ingredient dronabinol. In particular, the assay showed that the level of active drug fell below 90% of its initial amount within one week of storage at 55° C., with significant amounts of impurities present. The levels of the degradants D8THC, CBN and CBD continued to rise significantly during the storage period. Based on the stability results, it was determined that the formulation of Example 6 lacked sufficient stability, e.g., to obtain a two-year shelf-life. The cause of this lack of stability is hypothesized as being due to the presence of moisture and the lack of sufficient anti-oxidant(s) in the formulation to prevent degradation of the dronabinol in that environment (super-refined sesame oil was found to lack such ingredients; see below).

Extended Stability Results—Presence of Moisture

To confirm whether the presence of moisture and lack of sufficient antioxidants caused a lack of stability and an increase in dronabinol related impurities such as delta-8-THC, CBD and CBN, stability studies at room temperature and at accelerated conditions over an extended period of time were conducted using sesame oil from Arista, Croda and Dipasa.

EXAMPLE 6A

Dronabinol Solution in Sesame Oil Sourced from Arista—Capsules

In Example 6A, dronabinol formulations were prepared in accordance with Example 6, using sesame oil sourced from Arista. The formulation in Example 6A was exposed to moisture in accordance with the process in Example 6. The dronabinol formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Example 6A at 25° C. are set forth in Table 4 below.

TABLE 4

| Moisture 25° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.51 | 3.82 | |
| | 50% | 100.00 | 0.01 | 0.60 | 0.58 | 4.31 | |
| 3 Months | 100% | 89.24 | 0.16 | 0.85 | 0.50 | 11.31 | 7.49 |
| | 50% | 90.36 | 0.15 | 0.88 | 0.49 | 11.48 | 7.17 |
| 6 Months | 100% | 90.19 | 1.11 | 0.99 | 0.49 | 13.56 | 9.74 |
| | 50% | 91.38 | 1.08 | 1.06 | 0.49 | 13.25 | 8.94 |

The results of stability testing of Example 6A 40° C. are set forth in Table 5 below.

TABLE 5

| Moisture 40° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.51 | 3.82 | |
| | 50% | 100.00 | 0.01 | 0.60 | 0.58 | 4.31 | |
| 1 Month | 100% | 90.76 | 0.47 | 0.96 | 0.55 | 10.96 | 7.14 |
| | 50% | 91.93 | 0.56 | 0.79 | 0.55 | 9.96 | 5.65 |
| 2 Months | 100% | 88.36 | 0.37 | 1.10 | 0.65 | 12.46 | 8.64 |
| | 50% | 90.08 | 0.33 | 0.95 | 0.53 | 11.15 | 6.84 |
| 3 Months | 100% | 85.90 | 0.36 | 1.64 | 0.43 | 13.23 | 9.41 |
| | 50% | 88.95 | 0.60 | 1.46 | 0.49 | 12.84 | 8.53 |

The results of stability testing of Example 6A 55° C. are set forth in Table 6 below.

TABLE 6

| Moisture 55° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.51 | 3.82 | |
| | 50% | 100.00 | 0.01 | 0.60 | 0.58 | 4.31 | |
| 1 Week | 100% | 91.00 | 0.06 | 0.58 | 0.50 | 11.15 | 7.33 |
| | 50% | 88.82 | 0.04 | 0.69 | 0.44 | 14.74 | 10.43 |
| 2 Weeks | 100% | 75.08 | 0.01 | 1.05 | 0.46 | 22.54 | 18.72 |
| | 50% | 71.65 | 0.01 | 1.47 | 0.50 | 25.45 | 21.14 |

EXAMPLE 6B

Dronabinol Solution in Sesame Oil Sourced from Croda

In Example 6B, dronabinol formulations were prepared in accordance with Example 6A, using sesame oil sourced from Croda. The formulation in Example 6B was exposed to moisture in accordance with the process in Example 6. The dronabinol formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Example 6B at 25° C. are set forth in Table 7 below:
tested, then tested at 25° C. for 3 and 6 months; 40° C. for 1, 2 and 3 months and at 55° C. for 1 and 2 weeks.

The results of stability testing of Example 6B at 25° C. are set forth in Table 7 below:

TABLE 7

| Moisture 25° C. | | Potency % | CBD % | CBN % | D8-THC % | Total Impurities % | Increase + % |
|---|---|---|---|---|---|---|---|
| Zero | 100% | 100.00 | 0.02 | 0.43 | 0.57 | 5.05 | |
| | 50% | 100.00 | 0.01 | 0.48 | 0.58 | 4.32 | |
| 3 Months | 100% | 88.26 | 0.18 | 0.65 | 0.54 | 12.74 | 7.69 |
| | 50% | 86.98 | 0.20 | 0.60 | 0.54 | 12.60 | 8.28 |
| 6 Months | 100% | 90.33 | 1.38 | 0.80 | 0.51 | 15.08 | 10.03 |
| | 50% | 88.85 | 1.70 | 0.86 | 0.58 | 16.05 | 11.73 |

The results of stability testing of Example 6B at 40° C. are set forth in Table 8 below:

TABLE 8

| Moisture 40° C. | | Potency % | CBD % | CBN % | D8-THC % | Total Impurities % | Increase + % |
|---|---|---|---|---|---|---|---|
| Zero | 100% | 100.00 | 0.02 | 0.43 | 0.57 | 5.05 | |
| | 50% | 100.00 | 0.01 | 0.48 | 0.58 | 4.32 | |
| 1 Month | 100% | 91.91 | 1.06 | 0.72 | 0.57 | 12.77 | 7.72 |
| | 50% | 89.41 | 0.94 | 0.82 | 0.62 | 12.60 | 8.28 |
| 2 Months | 100% | 88.85 | 0.65 | 0.98 | 0.71 | 14.18 | 9.13 |
| | 50% | 86.80 | 0.62 | 0.95 | 0.62 | 13.85 | 9.53 |
| 3 Months | 100% | 84.63 | 0.99 | 1.68 | 0.58 | 16.13 | 11.08 |
| | 50% | 82.81 | 0.95 | 1.54 | 0.56 | 15.92 | 11.60 |

The results of stability testing of Example 6B at 55° C. are set forth in Table 9 below:

TABLE 9

| Moisture 55° C. | | Potency % | CBD % | CBN % | D8-THC % | Total Impurities % | Increase + % |
|---|---|---|---|---|---|---|---|
| Zero | 100% | 100.00 | 0.02 | 0.43 | 0.57 | 5.05 | |
| | 50% | 100.00 | 0.01 | 0.48 | 0.58 | 4.32 | |
| 1 Week | 100% | 87.71 | 0.08 | 0.58 | 0.57 | 15.20 | 10.15 |
| | 50% | 87.30 | 0.05 | 0.54 | 0.56 | 16.86 | 12.54 |
| 2 Weeks | 100% | 21.81 | 0.11 | 2.99 | 0.53 | 70.45 | 65.40 |
| | 50% | 69.85 | 0.22 | 1.31 | 0.57 | 31.44 | 27.12 |

EXAMPLE 6C

Sourced from Dipasa

In Example 6C, dronabinol formulations were prepared in accordance with Example 6, using sesame oil sourced from Dipasa. The formulation in Example 6C was exposed to moisture in accordance with the process in Example 6. The dronabinol formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Example 6C of 25° C. are set forth in Table 10 below:

TABLE 10

| Moisture 25° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.60 | 4.11 | |
| | 50% | 100.00 | 0.01 | 0.52 | 0.55 | 3.89 | |
| 3 Months | 100% | 92.95 | 0.06 | 0.64 | 0.51 | 6.08 | 1.97 |
| | 50% | 96.01 | 0.07 | 0.67 | 0.56 | 5.98 | 2.09 |
| 6 Months | 100% | 94.18 | 0.42 | 0.88 | 0.52 | 8.67 | 4.56 |
| | 50% | 96.03 | 0.40 | 0.85 | 0.56 | 8.59 | 4.70 |

The results of stability of Example 6C at 40° C. are set forth in Table 11 below:

TABLE 11

| Moisture 40° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.60 | 4.11 | |
| | 50% | 100.00 | 0.01 | 0.52 | 0.55 | 3.89 | |
| 1 Month | 100% | 94.43 | 0.19 | 0.68 | 0.59 | 7.30 | 3.19 |
| | 50% | 94.40 | 0.22 | 0.80 | 0.61 | 8.50 | 4.61 |
| 2 Months | 100% | 88.61 | 0.19 | 0.94 | 0.58 | 10.81 | 6.70 |
| | 50% | 90.03 | 0.20 | 1.11 | 0.57 | 11.68 | 7.79 |
| 3 Months | 100% | 86.34 | 0.22 | 1.62 | 0.53 | 12.78 | 8.67 |
| | 50% | 88.03 | 0.22 | 1.79 | 0.54 | 13.80 | 9.91 |

The results of stability of Example 6C at 50° C. as set forth in Table 12 below:

TABLE 12

| Moisture 55° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.60 | 4.11 | |
| | 50% | 100.00 | 0.01 | 0.52 | 0.55 | 3.89 | |
| 1 Week | 100% | 95.76 | 0.03 | 0.62 | 0.54 | 6.62 | 2.51 |
| | 50% | 98.81 | 0.02 | 0.73 | 0.55 | 7.00 | 3.11 |
| 2 Weeks | 100% | 93.01 | 0.01 | 0.77 | 0.60 | 9.38 | 5.27 |
| | 50% | 93.75 | 0.01 | 1.12 | 0.56 | 9.52 | 5.63 |

EXAMPLE 6D

In Example 6D, dronabinol formulations were prepared in accordance with Example 6, using sesame oil sourced from Arista. The formulation in Example 6D was exposed to moisture in accordance with the process in Example 6. The formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability of Example 6D at 25° C. as set forth in Table 13 below:

TABLE 13

| Moisture 25° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.51 | 3.82 | |
| | 50% | 100.00 | 0.01 | 0.60 | 0.58 | 4.31 | |
| 3 Months | 100% | 94.96 | 0.24 | 0.52 | 0.47 | 5.51 | 1.69 |
| | 50% | 95.67 | 0.15 | 0.54 | 0.48 | 5.34 | 1.03 |
| 6 Months | 100% | 97.86 | 0.31 | 0.60 | 0.54 | 7.85 | 4.03 |
| | 50% | 97.85 | 0.25 | 0.61 | 0.54 | 7.90 | 3.59 |

The results of stability of Example 6D at 40° C. as set forth in Table 14 below:

TABLE 14

| Moisture 40° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.51 | 3.82 | |
| | 50% | 100.00 | 0.01 | 0.60 | 0.58 | 4.31 | |
| 1 Month | 100% | 90.14 | 0.63 | 0.60 | 0.55 | 11.93 | 8.11 |
| | 50% | 95.28 | 0.07 | 0.47 | 0.55 | 6.32 | 2.01 |

TABLE 14-continued

| Moisture 40° C. | | Potency % | CBD % | CBN % | D8-THC % | Total Impurities % | Increase + % |
|---|---|---|---|---|---|---|---|
| 2 Months | 100% | 80.52 | 1.01 | 1.03 | 0.56 | 18.47 | 14.65 |
| | 50% | 91.10 | 0.34 | 0.59 | 0.57 | 10.33 | 6.02 |
| 3 Months | 100% | 73.36 | 1.15 | 1.83 | 0.52 | 24.85 | 21.03 |
| | 50% | 86.45 | 1.33 | 1.08 | 0.53 | 17.82 | 13.51 |

The results of stability of Example 6D at 55° C. as set forth in Table 15 below:

TABLE 15

| Moisture 55° C. | | Potency % | CBD % | CBN % | D8-THC % | Total Impurities % | Increase + % |
|---|---|---|---|---|---|---|---|
| Zero | 100% | 100.00 | 0.02 | 0.54 | 0.51 | 3.82 | |
| | 50% | 100.00 | 0.01 | 0.60 | 0.58 | 4.31 | |
| 1 Week | 100% | 91.00 | 0.06 | 0.58 | 0.50 | 11.15 | 7.33 |
| | 50% | 88.82 | 0.04 | 0.69 | 0.44 | 14.74 | 10.43 |
| 2 Weeks | 100% | 75.08 | 0.01 | 1.05 | 0.46 | 22.54 | 18.72 |
| | 50% | 71.65 | 0.01 | 1.47 | 0.50 | 25.45 | 21.14 |

EXAMPLE 6E

In Example 6E, dronabinol formulations were prepared in accordance with Example 6, using sesame oil sourced from Croda. The formulation in Example 6E was exposed to moisture in accordance with the process in Example 6. The formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability of Example 6E at 25° C. as set forth in Table 16 below:

TABLE 16

| Moisture 25° C. | | Potency % | CBD % | CBN % | D8-THC % | Total Impurities % | Increase + % |
|---|---|---|---|---|---|---|---|
| Zero | 100% | 100.00 | 0.02 | 0.43 | 0.57 | 5.05 | |
| | 50% | 100.00 | 0.01 | 0.48 | 0.58 | 4.32 | |
| 3 Months | 100% | 59.35 | 5.07 | 1.25 | 0.52 | 39.37 | 34.32 |
| | 50% | 75.87 | 3.25 | 0.84 | 0.52 | 25.17 | 20.85 |
| 6 Months | 100% | 47.17 | 5.48 | 2.13 | 0.64 | 50.49 | 45.44 |
| | 50% | 67.70 | 3.75 | 1.23 | 0.62 | 32.62 | 28.30 |

The results of stability of Example 6E at 40° C. as set forth in Table 17 below:

TABLE 17

| Moisture 40° C. | | Potency % | CBD % | CBN % | D8-THC % | Total Impurities % | Increase + % |
|---|---|---|---|---|---|---|---|
| Zero | 100% | 100.00 | 0.02 | 0.43 | 0.57 | 5.05 | |
| | 50% | 100.00 | 0.01 | 0.48 | 0.58 | 4.32 | |
| 1 Month | 100% | 31.99 | 6.67 | 3.01 | 0.59 | 62.69 | 57.64 |
| | 50% | 84.75 | 2.40 | 0.62 | 0.58 | 17.83 | 13.51 |
| 2 Months | 100% | 22.90 | 5.35 | 3.72 | 0.62 | 66.06 | 61.01 |
| | 50% | 74.41 | 3.52 | 1.12 | 0.56 | 24.48 | 20.16 |

TABLE 17-continued

| Moisture 40° C. | Potency % | CBD % | CBN % | D8-THC % | Total Impurities % | Increase + % |
|---|---|---|---|---|---|---|
| 3 Months | 100% | 16.93 | 4.18 | 6.54 | 1.06 | 72.54 | 67.49 |
| | 50% | 64.95 | 3.62 | 1.41 | 0.54 | 30.28 | 25.96 |

The results of stability of Example 6E at 55° C. as set forth in Table 18 below:

TABLE 18

| Moisture 55° C. | Potency % | CBD % | CBN % | D8-THC % | Total Impurities % | Increase + % |
|---|---|---|---|---|---|---|
| Zero | 100% | 100.00 | 0.02 | 0.43 | 0.57 | 5.05 | |
| | 50% | 100.00 | 0.01 | 0.48 | 0.58 | 4.32 | |
| 1 Week | 100% | 87.71 | 0.08 | 0.58 | 0.57 | 15.20 | 10.15 |
| | 50% | 87.30 | 0.05 | 0.54 | 0.56 | 16.86 | 12.54 |
| 2 Weeks | 100% | 21.81 | 0.11 | 2.99 | 0.53 | 70.45 | 65.40 |
| | 50% | 69.85 | 0.22 | 1.31 | 0.57 | 31.44 | 27.12 |

EXAMPLE 6F

In Example 6F, dronabinol formulations were prepared in accordance with Example 6, using sesame oil sourced from Dipasa. The formulation in Example 6F was exposed to moisture in accordance with the process in Example 6. The formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability of Example 6F at 25° C. as set forth in Table 19 below:

TABLE 19

| Moisture 25° C. | Potency % | CBD % | CBN % | D8-THC % | Total Impurities % | Increase + % |
|---|---|---|---|---|---|---|
| Zero | 100% | 100.00 | 0.02 | 0.54 | 0.60 | 4.11 | |
| | 50% | 100.00 | 0.01 | 0.52 | 0.55 | 3.89 | |
| 3 Months | 100% | 91.32 | 0.23 | 0.60 | 0.53 | 6.30 | 2.19 |
| | 50% | 95.43 | 0.28 | 0.71 | 0.53 | 6.06 | 2.17 |
| 6 Months | 100% | 93.79 | 0.29 | 0.76 | 0.55 | 10.24 | 6.13 |
| | 50% | 96.77 | 0.32 | 0.96 | 0.56 | 8.80 | 4.91 |

The results of stability of Example 6F at 40° C. as set forth in Table 20 below:

TABLE 20

| Moisture 40° C. | Potency % | CBD % | CBN % | D8-THC % | Total Impurities % | Increase + % |
|---|---|---|---|---|---|---|
| Zero | 100% | 100.00 | 0.02 | 0.54 | 0.60 | 4.11 | |
| | 50% | 100.00 | 0.01 | 0.52 | 0.55 | 3.89 | |
| 1 Month | 100% | 92.81 | 0.14 | 0.54 | 0.59 | 7.78 | 3.67 |
| | 50% | 94.40 | 0.12 | 0.70 | 0.60 | 7.24 | 3.35 |
| 2 Months | 100% | 86.15 | 0.43 | 0.79 | 0.60 | 13.86 | 9.75 |
| | 50% | 91.50 | 0.33 | 1.11 | 0.62 | 10.35 | 6.46 |
| 3 Months | 100% | 81.13 | 0.69 | 1.58 | 0.54 | 20.90 | 16.79 |
| | 50% | 91.88 | 0.36 | 1.88 | 0.58 | 14.48 | 10.59 |

The results of stability of Example 6F at 55° C. as set forth in Table 21 below:

TABLE 21

| Moisture 55° C. | Potency % | CBD % | CBN % | D8-THC % | Total Impurities % | Increase + % |
|---|---|---|---|---|---|---|
| Zero | 100% | 100.00 | 0.02 | 0.54 | 0.60 | 4.11 | |
| | 50% | 100.00 | 0.01 | 0.52 | 0.55 | 3.89 | |
| 1 Week | 100% | 95.76 | 0.03 | 0.62 | 0.54 | 6.62 | 2.51 |
| | 50% | 98.81 | 0.02 | 0.73 | 0.55 | 7.00 | 3.11 |

As can be seen, the dronabinol formulations are generally unstable in the presence of moisture. However, the dronabinol formulation utilizing sesame oil sourced from Dipasa is resistant to some extent from degradation due to the presence of moisture. This stability can be attributed to the presence of high levels of the antioxidant lecithin in sesame oil sourced from Dipasa.

EXAMPLE 7

Stability Results—Addition of Glycerin/Glycerol

In Example 7, the effect of added glycerin in dronabinol formulated in a sesame oil solution was evaluated. In each of Examples 7i-7v, the specified amount of glycerin was added to the formulation prepared in accordance with Example 1. The formulations were stored in HPLC amber glass vials.

Example 7-i contains 5 mg dronabinol solution (3.03% w/w) and 1% (w/v) glycerin in sesame oil, super refined NF (by Croda).

Example 7-ii contains 5 mg dronabinol solution (3.03% w/w) and 0.2% (w/v) glycerin in sesame oil, super refined NF (by Croda).

Example 7-iii contains 5 mg dronabinol solution (3.03% w/w) and 0.1% (w/v) glycerin in sesame oil, super refined NF (by Croda).

Example 7-iv contains 5 mg dronabinol solution (3.03% w/w) and 0.02% (w/v) glycerin in sesame oil, super refined NF (by Croda).

Example 7-v contains 5 mg dronabinol solution (3.03% w/w) and 0.002% (w/v) glycerin in sesame oil, super refined NF (by Croda).

As set forth above, the formulations tested in Example 7 each include 5 mg dronabinol (3.03%) in sesame oil, the formulation having a total of 165 mg per sample was transferred to amber glass vials for storage. Comparison Example 9-ii is a formulation prepared in the same manner as Examples 7-i-7v, except there was no added glycerin in Example 9-ii.

A summary of the compositions of Examples 7-i-7v is set forth in Table 22 below:

TABLE 22

| | Composition | | |
|---|---|---|---|
| Formulation | Dronabinol | Sesame Oil | Other Ingredients |
| Example 7-i | 3.03% w/w | QS | Glycerin (1%) |
| Example 7-ii | 3.03% w/w | QS | Glycerin (0.2%) |
| Example 7-iii | 3.03% w/w | QS | Glycerin (0.1%) |
| Example 7-iv | 3.03% w/w | QS | Glycerin (0.02%) |
| Example 7-v | 3.03% w/w | QS | Glycerin (0.002%) |

The formulations of Example 7 were then subjected to stability studies under conditions of 55° C. for one week and 55° C. for two weeks, respectively. The results are provided in Table 23 below:

THC, CBD, and CBN, stability studies at room temperature and at accelerated conditions over an extended period of time were conducted using sesame oil from Arista, Croda and Dipasa.

TABLE 23

| CONDITION | FORMULATION # | ASSAY % | TOTAL IMPURITY % | RELATED SUBSTANCES | | |
|---|---|---|---|---|---|---|
| | | | | D8THC % | CBN % | CBD % |
| Zero Time | Example 9-ii* (no added Glycerin) | 93.80 | 6.20 | 0.75 | 1.88 | 0.29 |
| 55° C. (1 week) | Example 9-ii* (no glycerin added) | 82.16 | 17.84 | 0.72 | 1.86 | 0.23 |
| | Example 7-i (1% Glycerin) | 80.84 | 19.16 | 0.56 | 1.87 | 0.13 |
| | Example 7-ii (0.2% Glycerin) | 77.64 | 22.36 | 0.72 | 1.77 | 0.14 |
| | Example 7-iii (0.1% Glycerin) | 77.57 | 22.43 | 0.56 | 1.73 | 0.12 |
| | Example 7-iv (0.02% Glycerin) | 80.57 | 19.43 | 0.47 | 1.60 | 0.16 |
| | Example 7-v (0.002% Glycerin) | 79.55 | 20.45 | 0.58 | 1.40 | 0.19 |
| 55° C. (2 weeks) | Example 9-ii (no glycerin added) | 67.41 | 32.59 | 1.06 | 4.96 | 0.29 |
| | Example 7-i (1% Glycerin) | 61.35 | 38.65 | 0.16 | 2.98 | 0.76 |
| | Example 7-ii (0.2% Glycerin) | 63.54 | 36.46 | 0.16 | 2.87 | 0.72 |
| | Example 7-iii (0.1% Glycerin) | 62.71 | 37.29 | 0.19 | 2.96 | 0.79 |
| | Example 7-iv (0.02% Glycerin) | 64.04 | 35.96 | 0.18 | 2.84 | 0.88 |
| | Example 7-v (0.002% Glycerin) | 66.02 | 33.98 | 0.17 | 2.79 | 0.77 |

*Control

Based on the results set forth in Table 23, it is clear that dronabinol is highly unstable in the presence of glycerin. In fact, over a third of the active ingredient dronabinol is lost to degradation in two weeks at 55° C. when exposed to even small quantities of glycerin (0.002%).

Extended Stability Results—Addition of Glycerin/Glycerol

To confirm whether the addition of varying amounts of glycerin in dronabinol formulations caused a lack of stability and increase in dronabinol related impurities such as delta-8-

EXAMPLE 7A

Dronabinol Solution in Sesame Oil Sourced from Arista, with Varying Amounts of Glycerin Added In Example 7A, the effect of added varying amounts of glycerin in dronabinol formulations using sesame oil sourced from Arista was evaluated. In each of Examples 7A-i-7A-v, the specified amount of glycerin added was prepared in accordance with Example 7. The formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Examples 7A-i-7A-v at 25° C. are set forth in Table 24 below.

TABLE 24

| | Glycerin | | | | | Total Impurities | |
|---|---|---|---|---|---|---|---|
| | 25° C. | Potency % | CBD % | CBN % | D8-THC % | % | Increase + % |
| Zero | (7A-i) 1% | 100.00 | 0.02 | 0.65 | 0.56 | 3.90 | |
| | (7A-ii) 0.2% | 100.00 | 0.01 | 0.51 | 0.52 | 3.70 | |
| | (7A-iii) 0.1% | 100.00 | 0.02 | 0.63 | 0.58 | 3.81 | |
| | (7A-iv) 0.02% | 100.00 | 0.01 | 0.59 | 0.49 | 3.96 | |
| | (7A-v) 0.002% | 100.00 | 0.02 | 0.54 | 0.52 | 3.95 | |
| 3 Months | (7A-i) 1% | 89.05 | 0.12 | 0.70 | 0.44 | 10.91 | 7.01 |
| | (7A-ii) 0.2% | 88.70 | 0.18 | 0.77 | 0.45 | 11.20 | 7.50 |
| | (7A-iii) 0.1% | 92.12 | 0.11 | 0.76 | 0.50 | 11.07 | 7.26 |
| | (7A-iv) 0.02% | 90.44 | 0.21 | 0.81 | 0.49 | 11.26 | 7.30 |

TABLE 24-continued

| Glycerin | | | | | | Total Impurities | |
|---|---|---|---|---|---|---|---|
| | 25° C. | Potency % | CBD % | CBN % | D8-THC % | % | Increase + % |
| | (7A-v) 0.002% | 91.13 | 0.17 | 0.82 | 0.48 | 11.08 | 7.13 |
| 6 Months | (7A-i) 1% | 91.25 | 1.14 | 0.82 | 0.48 | 12.17 | 8.27 |
| | (7A-ii) 0.2% | 90.91 | 1.10 | 0.95 | 0.47 | 12.71 | 9.01 |
| | (7A-iii) 0.1% | 92.97 | 1.07 | 1.00 | 0.48 | 12.68 | 8.87 |
| | (7A-iv) 0.02% | 91.41 | 0.21 | 0.81 | 0.49 | 11.26 | 7.30 |
| | (7A-v) 0.002% | 92.36 | 1.07 | 1.12 | 0.51 | 13.34 | 9.39 |

The results of stability testing of Examples 7A-i-7A-v at 40° C. are set forth in Table 25 below.

TABLE 25

| Glycerin | | | | | | Total Impurities | |
|---|---|---|---|---|---|---|---|
| | 40° C. | Potency % | CBD % | CBN % | D8-THC % | % | Increase + % |
| Zero | (7A-i) 1% | 100.00 | 0.02 | 0.65 | 0.56 | 3.90 | |
| | (7A-ii) 0.2% | 100.00 | 0.01 | 0.51 | 0.52 | 3.70 | |
| | (7A-iii) 0.1% | 100.00 | 0.02 | 0.63 | 0.58 | 3.81 | |
| | (7A-iv) 0.02% | 100.00 | 0.01 | 0.59 | 0.49 | 3.96 | |
| | (7A-v) 0.002% | 100.00 | 0.02 | 0.54 | 0.52 | 3.95 | |
| 1 Month | (7A-i) 1% | 90.27 | 0.64 | 0.77 | 0.53 | 9.93 | 6.03 |
| | (7A-ii) 0.2% | 106.03 | 0.57 | 0.79 | 0.53 | 9.88 | 6.18 |
| | (7A-iii) 0.1% | 92.63 | 0.53 | 0.83 | 0.52 | 9.88 | 6.07 |
| | (7A-iv) 0.02% | 91.00 | 0.51 | 0.83 | 0.52 | 9.74 | 5.78 |
| | (7A-v) 0.002% | 91.94 | 0.49 | 0.93 | 0.51 | 10.26 | 6.31 |
| 2 Months | (7A-i) 1% | 88.22 | 0.35 | 1.04 | 0.46 | 10.89 | 6.99 |
| | (7A-ii) 0.2% | 88.08 | 0.32 | 1.07 | 0.80 | 11.77 | 8.07 |
| | (7A-iii) 0.1% | 92.00 | 0.29 | 1.23 | 0.96 | 12.56 | 8.75 |
| | (7A-iv) 0.02% | 89.81 | 0.26 | 1.13 | 0.54 | 11.81 | 7.85 |
| | (7A-v) 0.002% | 89.34 | 0.28 | 1.17 | 0.53 | 11.75 | 7.80 |
| 3 Months | (7A-i) 1% | 86.71 | 0.42 | 1.49 | 0.45 | 12.45 | 8.55 |
| | (7A-ii) 0.2% | 86.78 | 0.37 | 1.63 | 0.47 | 13.03 | 9.33 |
| | (7A-iii) 0.1% | 88.38 | 0.38 | 1.63 | 0.47 | 13.07 | 9.26 |
| | (7A-iv) 0.02% | 88.10 | 0.35 | 1.61 | 0.51 | 12.85 | 8.89 |
| | (7A-v) 0.002% | 87.64 | 0.34 | 1.81 | 0.46 | 13.87 | 9.92 |

The results of stability testing of Examples 7A-i-7A-v at 55° C. are set forth in Table 26 below.

TABLE 26

| Glycerin | | | | | | Total Impurities | |
|---|---|---|---|---|---|---|---|
| | 55° C. | Potency % | CBD % | CBN % | D8-THC % | % | Increase + % |
| Zero | (7A-i) 1% | 100.00 | 0.02 | 0.65 | 0.56 | 3.90 | |
| | (7A-ii) 0.2% | 100.00 | 0.01 | 0.51 | 0.52 | 3.70 | |
| | (7A-iii) 0.1% | 100.00 | 0.02 | 0.63 | 0.58 | 3.81 | |
| | (7A-iv) 0.02% | 100.00 | 0.01 | 0.59 | 0.49 | 3.96 | |
| | (7A-v) 0.002% | 100.00 | 0.02 | 0.54 | 0.52 | 3.95 | |
| 1 Week | (7A-i) 1% | 86.50 | 0.01 | 0.79 | 0.48 | 15.02 | 11.12 |
| | (7A-ii) 0.2% | 92.73 | 0.01 | 0.72 | 0.51 | 13.58 | 9.88 |
| | (7A-iii) 0.1% | 90.61 | 0.01 | 0.79 | 0.52 | 12.90 | 9.09 |
| | (7A-iv) 0.02% | 88.88 | 0.02 | 0.71 | 0.49 | 15.10 | 11.14 |
| | (7A-v) 0.002% | 88.77 | 0.02 | 0.80 | 0.49 | 16.67 | 12.72 |
| 2 Weeks | (7A-i) 1% | 42.43 | 0.06 | 3.04 | 0.48 | 48.24 | 44.34 |
| | (7A-ii) 0.2% | 46.43 | 0.04 | 2.66 | 0.45 | 44.57 | 40.87 |
| | (7A-iii) 0.1% | 42.78 | 0.04 | 3.14 | 0.58 | 48.10 | 44.29 |

TABLE 26-continued

| Glycerin | | | | | Total Impurities | |
|---|---|---|---|---|---|---|
| 55° C. | Potency % | CBD % | CBN % | D8-THC % | % | Increase + % |
| (7A-iv) 0.02% | 38.99 | 0.03 | 3.01 | 0.48 | 51.96 | 48.00 |
| (7A-v) 0.002% | 37.79 | 0.04 | 3.08 | 0.44 | 52.66 | 48.71 |

EXAMPLE 7B

Dronabinol Solution in Sesame Oil Sourced from Croda, with Varying Amounts of Glycerin Added In Example 7B, the effect of added varying amounts glycerin in dronabinol formulation using sesame oil sourced from Croda was evaluated. In each of Examples 7B-i-7B-v, the specified amount of glycerin added was prepared in accordance with Example 7. The formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Examples 7B-i-7B-v at 25° C. are set forth in Table 27 below.

TABLE 27

| | Glycerin | | | | | Total Impurities | |
|---|---|---|---|---|---|---|---|
| | 25° C. | Potency % | CBD % | CBN % | D8-THC % | % | Increase + % |
| Zero | (7B-i) 1% | 100.00 | 0.03 | 0.50 | 0.59 | 3.79 | |
| | (7B-ii) 0.2% | 100.00 | 0.01 | 0.49 | 0.61 | 4.09 | |
| | (7B-iii) 0.1% | 100.00 | 0.01 | 0.47 | 0.60 | 4.00 | |
| | (7B-iv) 0.02% | 100.00 | 0.02 | 0.50 | 0.60 | 3.90 | |
| | (7B-v) 0.002% | 100.00 | 0.02 | 0.49 | 0.60 | 4.12 | |
| 3 Months | (7B-i) 1% | 85.70 | 0.15 | 0.53 | 0.55 | 12.54 | 8.75 |
| | (7B-ii) 0.2% | 87.57 | 0.19 | 0.60 | 0.55 | 12.55 | 8.46 |
| | (7B-iii) 0.1% | 87.43 | 0.21 | 0.61 | 0.55 | 12.73 | 8.73 |
| | (7B-iv) 0.02% | 87.37 | 0.29 | 0.58 | 0.55 | 12.27 | 8.37 |
| | (7B-v) 0.002% | 88.13 | 0.30 | 0.59 | 0.56 | 12.84 | 8.72 |
| 6 Months | (7B-i) 1% | 88.20 | 1.35 | 0.64 | 0.55 | 13.77 | 9.98 |
| | (7B-ii) 0.2% | 88.72 | 1.56 | 0.72 | 0.60 | 15.15 | 11.06 |
| | (7B-iii) 0.1% | 88.16 | 1.34 | 0.75 | 0.55 | 14.45 | 10.45 |
| | (7B-iv) 0.02% | 88.21 | 1.37 | 0.74 | 0.53 | 13.81 | 9.91 |
| | (7B-v) 0.002% | 88.65 | 1.30 | 0.79 | 0.53 | 14.79 | 10.67 |

The results of stability testing of Examples 7B-i-7B-v at 40° C. are set forth in Table 28 below.

TABLE 28

| | Glycerin | | | | | Total Impurities | |
|---|---|---|---|---|---|---|---|
| | 40° C. | Potency % | CBD % | CBN % | D8-THC % | % | Increase + % |
| Zero | (7B-i) 1% | 100.00 | 0.03 | 0.50 | 0.59 | 3.79 | |
| | (7B-ii) 0.2% | 100.00 | 0.01 | 0.49 | 0.61 | 4.09 | |
| | (7B-iii) 0.1% | 100.00 | 0.01 | 0.47 | 0.60 | 4.00 | |
| | (7B-iv) 0.02% | 100.00 | 0.02 | 0.50 | 0.60 | 3.90 | |
| | (7B-v) 0.002% | 100.00 | 0.02 | 0.49 | 0.60 | 4.12 | |
| 1 Month | (7B-i) 1% | 88.51 | 1.15 | 0.60 | 0.61 | 12.28 | 8.49 |
| | (7B-ii) 0.2% | 89.51 | 1.02 | 0.71 | 0.59 | 12.26 | 8.17 |
| | (7B-iii) 0.1% | 90.14 | 0.98 | 0.66 | 0.58 | 11.88 | 7.88 |

TABLE 28-continued

| Glycerin 40° C. | | Potency % | CBD % | CBN % | D8-THC % | Total Impurities % | Increase + % |
|---|---|---|---|---|---|---|---|
| | (7B-iv) 0.02% | 88.81 | 0.97 | 0.72 | 0.57 | 12.07 | 8.17 |
| | (7B-v) 0.002% | 90.06 | 1.08 | 0.71 | 0.58 | 12.18 | 8.06 |
| 2 Months | (7B-i) 1% | 85.59 | 0.82 | 0.73 | 0.60 | 13.32 | 9.53 |
| | (7B-ii) 0.2% | 85.39 | 0.67 | 0.90 | 0.81 | 13.25 | 9.16 |
| | (7B-iii) 0.1% | 86.54 | 0.67 | 0.86 | 0.59 | 13.29 | 9.29 |
| | (7B-iv) 0.02% | 86.16 | 0.65 | 0.88 | 0.62 | 13.49 | 9.59 |
| | (7B-v) 0.002% | 87.71 | 0.59 | 0.96 | 0.60 | 13.75 | 9.63 |
| 3 Months | (7B-i) 1% | 83.33 | 1.12 | 1.23 | 0.57 | 14.70 | 10.91 |
| | (7B-ii) 0.2% | 84.36 | 1.00 | 1.48 | 0.59 | 15.38 | 11.29 |
| | (7B-iii) 0.1% | 83.95 | 0.89 | 1.47 | 0.56 | 14.86 | 10.86 |
| | (7B-iv) 0.02% | 84.81 | 1.00 | 1.39 | 0.60 | 14.73 | 10.83 |
| | (7B-v) 0.002% | 84.53 | 0.86 | 1.77 | 0.57 | 15.30 | 11.18 |

The results of stability testing of Examples 7B-i-7B-v at 55° C. are set forth in Table 29 below.

TABLE 29

| Glycerin 55° C. | | Potency % | CBD % | CBN % | D8-THC % | Total Impurities % | Increase + % |
|---|---|---|---|---|---|---|---|
| Zero | (7B-i) 1% | 100.00 | 0.03 | 0.50 | 0.59 | 3.79 | |
| | (7B-ii) 0.2% | 100.00 | 0.01 | 0.49 | 0.61 | 4.09 | |
| | (7B-iii) 0.1% | 100.00 | 0.01 | 0.47 | 0.60 | 4.00 | |
| | (7B-iv) 0.02% | 100.00 | 0.02 | 0.50 | 0.60 | 3.90 | |
| | (7B-v) 0.002% | 100.00 | 0.02 | 0.49 | 0.60 | 4.12 | |
| 1 Week | (7B-i) 1% | 84.97 | 0.01 | 0.75 | 0.56 | 15.42 | 11.63 |
| | (7B-ii) 0.2% | 86.55 | 0.05 | 0.71 | 0.57 | 18.20 | 14.11 |
| | (7B-iii) 0.1% | 84.25 | 0.10 | 0.76 | 0.52 | 20.65 | 16.63 |
| | (7B-iv) 0.02% | 86.91 | 0.08 | 0.66 | 0.55 | 17.86 | 13.96 |
| | (7B-v) 0.002% | 84.44 | 0.11 | 0.76 | 0.53 | 20.93 | 16.81 |
| 2 Weeks | (7B-i) 1% | 67.98 | 0.01 | 1.78 | 0.55 | 24.93 | 21.14 |
| | (7B-ii) 0.2% | 26.76 | 0.18 | 2.76 | 0.71 | 65.03 | 60.94 |
| | (7B-iii) 0.1% | 65.98 | 0.19 | 1.42 | 0.54 | 33.00 | 29.00 |
| | (7B-iv) 0.02% | 21.93 | 0.34 | 3.26 | 0.64 | 71.79 | 67.89 |
| | (7B-v) 0.002% | 19.08 | 0.14 | 3.66 | 0.67 | 72.97 | 68.85 |

EXAMPLE 7C

Dronabinol Solution in Sesame Oil Sourced from Dipasa, with Varying Amounts of Glycerin Added In Example 7C, the effect of added varying amounts glycerin in dronabinol formulation using sesame oil sourced from Dipasa was evaluated. In each of Examples 7C-i-7C-v, the specified amount of glycerin added was prepared in accordance with Example 7. The formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Examples 7C-i-7C-v at 25° C. are set forth in Table 30 below.

TABLE 30

| Glycerin 25° C. | | Potency % | CBD % | CBN % | D8-THC % | Total Impurities % | Increase + % |
|---|---|---|---|---|---|---|---|
| Zero | (7C-i) 1% | 100.00 | 0.03 | 0.56 | 0.63 | 3.99 | |
| | (7C-ii) 0.2% | 100.00 | 0.01 | 0.66 | 0.57 | 3.99 | |

TABLE 30-continued

| Glycerin | | | | | | Total Impurities | |
|---|---|---|---|---|---|---|---|
| 25° C. | | Potency % | CBD % | CBN % | D8-THC % | % | Increase + % |
| | (7C-iii) 0.1% | 100.00 | 0.01 | 0.55 | 0.60 | 4.04 | |
| | (7C-iv) 0.02% | 100.00 | 0.03 | 0.54 | 0.57 | 4.05 | |
| | (7C-v) 0.002% | 100.00 | 0.01 | 0.54 | 0.56 | 3.89 | |
| 3 Months | (7C-i) 1% | 94.52 | 0.02 | 0.70 | 0.55 | 5.87 | 1.88 |
| | (7C-ii) 0.2% | 96.88 | 0.04 | 0.64 | 0.50 | 6.22 | 2.23 |
| | (7C-iii) 0.1% | 96.09 | 0.04 | 0.61 | 0.54 | 5.93 | 1.89 |
| | (7C-iv) 0.02% | 95.47 | 0.06 | 0.62 | 0.53 | 6.23 | 2.18 |
| | (7C-v) 0.002% | 95.37 | 0.05 | 0.61 | 0.54 | 5.93 | 2.04 |
| 6 Months | (7C-i) 1% | 96.79 | 0.39 | 0.83 | 0.54 | 8.54 | 4.55 |
| | (7C-ii) 0.2% | 97.04 | 0.48 | 0.80 | 0.56 | 8.91 | 4.92 |
| | (7C-iii) 0.1% | 97.85 | 0.40 | 0.79 | 0.53 | 8.52 | 4.48 |
| | (7C-iv) 0.02% | 96.52 | 0.41 | 0.90 | 0.55 | 8.80 | 4.75 |
| | (7C-v) 0.002% | 96.69 | 0.37 | 0.75 | 0.59 | 8.47 | 4.58 |

The results of stability testing of Examples 7C-i-7C-v at 40° C. are set forth in Table 31 below.

TABLE 31

| Glycerin | | | | | | Total Impurities | |
|---|---|---|---|---|---|---|---|
| 40° C. | | Potency % | CBD % | CBN % | D8-THC % | % | Increase + % |
| Zero | (7C-i) 1% | 100.00 | 0.03 | 0.56 | 0.63 | 3.99 | |
| | (7C-ii) 0.2% | 100.00 | 0.01 | 0.66 | 0.57 | 3.99 | |
| | (7C-iii) 0.1% | 100.00 | 0.01 | 0.55 | 0.60 | 4.04 | |
| | (7C-iv) 0.02% | 100.00 | 0.03 | 0.54 | 0.57 | 4.05 | |
| | (7C-v) 0.002% | 100.00 | 0.01 | 0.54 | 0.56 | 3.89 | |
| 1 Month | (7C-i) 1% | 94.94 | 0.24 | 0.67 | 0.59 | 7.38 | 3.39 |
| | (7C-ii) 0.2% | 94.94 | 0.20 | 0.71 | 0.57 | 7.81 | 3.82 |
| | (7C-iii) 0.1% | 96.35 | 0.19 | 0.68 | 0.57 | 6.98 | 2.94 |
| | (7C-iv) 0.02% | 95.18 | 0.23 | 0.79 | 0.57 | 8.30 | 4.25 |
| | (7C-v) 0.002% | 93.71 | 0.23 | 0.82 | 0.57 | 8.65 | 4.76 |
| 2 Months | (7C-i) 1% | 90.09 | 0.25 | 0.99 | 0.60 | 11.08 | 7.09 |
| | (7C-ii) 0.2% | 91.06 | 0.21 | 1.03 | 0.62 | 11.06 | 7.07 |
| | (7C-iii) 0.1% | 95.29 | 0.23 | 0.94 | 0.58 | 10.84 | 6.80 |
| | (7C-iv) 0.02% | 90.14 | 0.18 | 1.14 | 0.57 | 11.67 | 7.62 |
| | (7C-v) 0.002% | 90.40 | 0.15 | 1.11 | 0.59 | 11.22 | 7.33 |
| 3 Months | (7C-i) 1% | 87.89 | 0.26 | 1.53 | 0.53 | 12.48 | 8.49 |
| | (7C-ii) 0.2% | 90.10 | 0.26 | 1.61 | 0.53 | 12.64 | 8.65 |
| | (7C-iii) 0.1% | 89.44 | 0.38 | 1.61 | 0.56 | 12.87 | 8.83 |
| | (7C-iv) 0.02% | 88.31 | 0.35 | 1.67 | 0.54 | 13.07 | 9.02 |
| | (7C-v) 0.002% | 88.82 | 0.22 | 1.57 | 0.56 | 12.50 | 8.61 |

The results of stability testing of Examples 7C-i-7C-v at 55° C. are set forth in Table 32 below.

TABLE 32

| Glycerin | | | | | | Total Impurities | |
|---|---|---|---|---|---|---|---|
| 55° C. | | Potency % | CBD % | CBN % | D8-THC % | % | Increase + % |
| Zero | (7C-i) 1% | 100.00 | 0.03 | 0.56 | 0.63 | 3.99 | |
| | (7C-ii) 0.2% | 100.00 | 0.01 | 0.66 | 0.57 | 3.99 | |
| | (7C-iii) 0.1% | 100.00 | 0.01 | 0.55 | 0.60 | 4.04 | |

TABLE 32-continued

| Glycerin 55° C. | | Potency % | CBD % | CBN % | D8-THC % | Total Impurities % | Increase + % |
|---|---|---|---|---|---|---|---|
| | (7C-iv) 0.02% | 100.00 | 0.03 | 0.54 | 0.57 | 4.05 | |
| | (7C-v) 0.002% | 100.00 | 0.01 | 0.54 | 0.56 | 3.89 | |
| 1 Week | (7C-i) 1% | 96.81 | 0.02 | 0.72 | 0.53 | 6.99 | 3.00 |
| | (7C-ii) 0.2% | 98.85 | 0.04 | 0.75 | 0.55 | 7.23 | 3.24 |
| | (7C-iii) 0.1% | 98.53 | 0.03 | 0.80 | 0.55 | 7.32 | 3.28 |
| | (7C-iv) 0.02% | 97.55 | 0.04 | 0.82 | 0.58 | 7.83 | 3.78 |
| | (7C-v) 0.002% | 96.92 | 0.04 | 0.54 | 0.56 | 7.88 | 3.99 |
| 2 Weeks | (7C-i) 1% | 93.18 | 0.01 | 0.99 | 0.60 | 9.38 | 5.39 |
| | (7C-ii) 0.2% | 92.04 | 0.01 | 1.09 | 0.53 | 9.64 | 5.65 |
| | (7C-iii) 0.1% | 92.80 | 0.01 | 1.12 | 0.57 | 10.48 | 6.44 |
| | (7C-iv) 0.02% | 91.55 | 0.01 | 1.20 | 0.57 | 10.75 | 6.70 |
| | (7C-v) 0.002% | 89.74 | 0.01 | 1.31 | 0.52 | 11.18 | 7.29 |

EXAMPLE 7D

Dronabinol Solution in Sesame Oil Sourced from Arista, with Varying Amounts of Glycerin Added In Example 7D, the effect of added varying amounts glycerin in dronabinol formulation using sesame oil sourced from Arista was evaluated. In each of Examples 7D-i-7D-v, the specified amount of glycerin added was prepared in accordance with Example 7. The formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Examples 7D-i-7D-v at 25° C. are set forth in Table 33 below.

TABLE 33

| Glycerin 25° C. | | Potency % | CBD % | CBN % | D8-THC % | Total Impurities % | Increase + % |
|---|---|---|---|---|---|---|---|
| Zero | (7D-i) 1% | 100.00 | 0.02 | 0.65 | 0.56 | 3.90 | |
| | (7D-ii) 0.2% | 100.00 | 0.01 | 0.51 | 0.52 | 3.70 | |
| | (7D-iii) 0.1% | 100.00 | 0.02 | 0.63 | 0.58 | 3.81 | |
| | (7D-iv) 0.02% | 100.00 | 0.01 | 0.59 | 0.49 | 3.96 | |
| | (7D-v) 0.002% | 100.00 | 0.02 | 0.54 | 0.52 | 3.95 | |
| 3 Months | (7D-i) 1% | 86.82 | 1.22 | 0.95 | 0.47 | 12.02 | 8.12 |
| | (7D-ii) 0.2% | 46.83 | 6.13 | 2.56 | 0.60 | 46.56 | 42.86 |
| | (7D-iii) 0.1% | 87.07 | 1.52 | 1.03 | 0.49 | 14.56 | 10.75 |
| | (7D-iv) 0.02% | 59.19 | 4.64 | 1.78 | 0.69 | 36.18 | 32.22 |
| | (7D-v) 0.002% | 85.32 | 1.28 | 0.87 | 0.55 | 16.58 | 12.63 |
| 6 Months | (7D-i) 1% | 87.53 | 0.79 | 1.38 | 0.53 | 15.46 | 11.56 |
| | (7D-ii) 0.2% | 39.88 | 3.54 | 4.54 | 0.52 | 54.18 | 50.48 |
| | (7D-iii) 0.1% | 86.05 | 0.89 | 1.53 | 0.52 | 17.78 | 13.97 |
| | (7D-iv) 0.02% | 55.62 | 2.09 | 2.93 | 0.64 | 42.49 | 38.53 |
| | (7D-v) 0.002% | 86.58 | 0.83 | 1.08 | 0.56 | 17.89 | 13.94 |

The results of stability testing of Examples 7D-i-7D-v at 40° C. are set forth in Table 34 below.

TABLE 34

| Glycerin 40° C. | | Potency % | CBD % | CBN % | D8-THC % | Total Impurities % | Increase + % |
|---|---|---|---|---|---|---|---|
| Zero | (7D-i) 1% | 100.00 | 0.02 | 0.65 | 0.56 | 3.90 | |
| | (7D-ii) 0.2% | 100.00 | 0.01 | 0.51 | 0.52 | 3.70 | |
| | (7D-iii) 0.1% | 100.00 | 0.02 | 0.63 | 0.58 | 3.81 | |
| | (7D-iv) 0.02% | 100.00 | 0.01 | 0.59 | 0.49 | 3.96 | |
| | (7D-v) 0.002% | 100.00 | 0.02 | 0.54 | 0.52 | 3.95 | |
| 1 Month | (7D-i) 1% | 76.38 | 2.55 | 1.06 | 0.54 | 23.03 | 19.13 |
| | (7D-ii) 0.2% | 81.48 | 1.33 | 0.89 | 0.52 | 19.15 | 15.45 |
| | (7D-iii) 0.1% | 84.52 | 2.07 | 0.86 | 0.53 | 19.16 | 15.35 |
| | (7D-iv) 0.02% | 52.70 | 3.96 | 1.75 | 0.55 | 39.11 | 35.15 |
| | (7D-v) 0.002% | 50.42 | 4.35 | 1.96 | 0.58 | 43.47 | 39.52 |
| 2 Months | (7D-i) 1% | 64.72 | 3.15 | 1.76 | 0.51 | 29.80 | 25.90 |
| | (7D-ii) 0.2% | 70.28 | 1.29 | 1.43 | 0.62 | 25.47 | 21.77 |
| | (7D-iii) 0.1% | 72.15 | 2.59 | 1.29 | 0.54 | 23.77 | 19.96 |
| | (7D-iv) 0.02% | 45.57 | 3.31 | 3.04 | 0.60 | 44.34 | 40.38 |
| | (7D-v) 0.002% | 41.69 | 2.83 | 3.28 | 0.62 | 48.44 | 44.49 |
| 3 Months | (7D-i) 1% | 50.17 | 3.34 | 3.39 | 0.62 | 39.21 | 35.31 |
| | (7D-ii) 0.2% | 62.28 | 1.60 | 2.69 | 0.55 | 31.48 | 27.78 |
| | (7D-iii) 0.1% | 63.00 | 3.08 | 2.41 | 0.57 | 29.94 | 26.13 |
| | (7D-iv) 0.02% | 37.61 | 3.27 | 5.02 | 0.68 | 51.80 | 47.84 |
| | (7D-v) 0.002% | 34.82 | 5.44 | 5.35 | 0.73 | 54.47 | 50.52 |

The results of stability testing of Examples 7D-i-7D-v at 55° C. are set forth in Table 35 below.

TABLE 35

| Glycerin 55° C. | | Potency % | CBD % | CBN % | D8-THC % | Total Impurities % | Increase + % |
|---|---|---|---|---|---|---|---|
| Zero | (7D-i) 1% | 100.00 | 0.02 | 0.65 | 0.56 | 3.90 | |
| | (7D-ii) 0.2% | 100.00 | 0.01 | 0.51 | 0.52 | 3.70 | |
| | (7D-iii) 0.1% | 100.00 | 0.02 | 0.63 | 0.58 | 3.81 | |
| | (7D-iv) 0.02% | 100.00 | 0.01 | 0.59 | 0.49 | 3.96 | |
| | (7D-v) 0.002% | 100.00 | 0.02 | 0.54 | 0.52 | 3.95 | |
| 1 Week | (7D-i) 1% | 86.50 | 0.01 | 0.79 | 0.48 | 15.02 | 11.12 |
| | (7D-ii) 0.2% | 92.73 | 0.01 | 0.72 | 0.51 | 13.58 | 9.88 |
| | (7D-iii) 0.1% | 90.61 | 0.01 | 0.79 | 0.52 | 12.90 | 9.09 |
| | (7D-iv) 0.02% | 88.88 | 0.02 | 0.71 | 0.49 | 15.10 | 11.14 |
| | (7D-v) 0.002% | 88.77 | 0.02 | 0.80 | 0.49 | 16.67 | 12.72 |
| 2 Weeks | (7D-i) 1% | 42.43 | 0.06 | 3.04 | 0.48 | 48.24 | 44.34 |
| | (7D-ii) 0.2% | 46.43 | 0.04 | 2.66 | 0.45 | 44.57 | 40.87 |
| | (7D-iii) 0.1% | 42.78 | 0.04 | 3.14 | 0.58 | 48.10 | 44.29 |
| | (7D-iv) 0.02% | 38.99 | 0.03 | 3.01 | 0.48 | 51.96 | 48.00 |
| | (7D-v) 0.002% | 37.79 | 0.04 | 3.08 | 0.44 | 52.66 | 48.71 |

EXAMPLE 7E

Dronabinol Solution in Sesame Oil Sourced from Croda, with Varying Amounts of Glycerin Added In Example 7E, the effect of added varying amounts glycerin in dronabinol formulation using sesame oil sourced from Croda was evaluated. In each of Examples 7E-i-7E-v, the specified amount of glycerin added was prepared in accordance with Example 7. The formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Examples 7E-i-7E-v at 25° C. are set forth in Table 36 below.

TABLE 36

| | Glycerin 25° C. | Potency % | CBD % | CBN % | D8-THC % | Total Impurities % | Increase + % |
|---|---|---|---|---|---|---|---|
| Zero | (7E-i) 1% | 100.00 | 0.03 | 0.50 | 0.59 | 3.79 | |
| | (7E-ii) 0.2% | 100.00 | 0.01 | 0.49 | 0.61 | 4.09 | |
| | (7E-iii) 0.1% | 100.00 | 0..01 | 0.47 | 0.60 | 4.00 | |
| | (7E-iv) 0.02% | 100.00 | 0.02 | 0.50 | 0.60 | 3.90 | |
| | (7E-v) 0.002% | 100.00 | 0.02 | 0.49 | 0.60 | 4.12 | |
| 3 Months | (7E-i) 1% | 70.63 | 4.29 | 1.04 | 0.53 | 28.37 | 24.58 |
| | (7E-ii) 0.2% | 68.17 | 4.50 | 1.19 | 0.52 | 31.50 | 27.41 |
| | (7E-iii) 0.1% | 71.77 | 3.91 | 1.01 | 0.53 | 27.43 | 23.43 |
| | (7E-iv) 0.02% | 60.35 | 4.64 | 1.26 | 0.57 | 36.57 | 32.67 |
| | (7E-v) 0.002% | 53.20 | 5.40 | 1.37 | 0.58 | 42.71 | 38.59 |
| 6 Months | (7E-i) 1% | 63.43 | 4.19 | 1.42 | 0.65 | 33.77 | 29.98 |
| | (7E-ii) 0.2% | 58.49 | 4.63 | 1.54 | 0.60 | 38.65 | 34.56 |
| | (7E-iii) 0.1% | 63.93 | 5.32 | 1.48 | 0.62 | 36.21 | 32.21 |
| | (7E-iv) 0.02% | 53.03 | 4.39 | 1.55 | 0.65 | 42.48 | 38.58 |
| | (7E-v) 0.002% | 45.00 | 4.59 | 1.80 | 0.63 | 48.57 | 44.45 |

The results of stability testing of Examples 7E-i-7E-v at 40° C. are set forth in Table 37 below.

TABLE 37

| | Glycerin 40° C. | Potency % | CBD % | CBN % | D8-THC % | Total Impurities % | Increase + % |
|---|---|---|---|---|---|---|---|
| Zero | (7E-i) 1% | 100.00 | 0.03 | 0.50 | 0.59 | 3.79 | |
| | (7E-ii) 0.2% | 100.00 | 0.01 | 0.49 | 0.61 | 4.09 | |
| | (7E-iii) 0.1% | 100.00 | 0..01 | 0.47 | 0.60 | 4.00 | |
| | (7E-iv) 0.02% | 100.00 | 0.02 | 0.50 | 0.60 | 3.90 | |
| | (7E-v) 0.002% | 100.00 | 0.02 | 0.49 | 0.60 | 4.12 | |
| 1 Month | (7E-i) 1% | 48.72 | 5.38 | 1.74 | 0.64 | 47.55 | 43.76 |
| | (7E-ii) 0.2% | 82.25 | 2.53 | 0.70 | 0.56 | 19.99 | 15.90 |
| | (7E-iii) 0.1% | 26.31 | 6.36 | 2.29 | 0.50 | 66.51 | 62.51 |
| | (7E-iv) 0.02% | 71.91 | 3.89 | 0.97 | 0.54 | 29.67 | 25.77 |
| | (7E-v) 0.002% | 84.93 | 1.97 | 0.66 | 0.54 | 17.91 | 13.79 |
| 2 Months | (7E-i) 1% | 37.99 | 4.44 | 2.73 | 0.61 | 48.50 | 44.71 |
| | (7E-ii) 0.2% | 70.50 | 3.45 | 0.98 | 0.56 | 25.86 | 21.77 |
| | (7E-iii) 0.1% | 18.12 | 5.13 | 4.06 | 0.62 | 73.09 | 69.09 |
| | (7E-iv) 0.02% | 59.49 | 4.38 | 1.37 | 0.55 | 34.19 | 30.29 |
| | (7E-v) 0.002% | 74.54 | 2.69 | 0.87 | 0.61 | 22.82 | 18.70 |
| 3 Months | (7E-i) 1% | 27.98 | 4.07 | 5.18 | 0.94 | 57.62 | 53.83 |
| | (7E-ii) 0.2% | 59.94 | 3.81 | 1.80 | 0.58 | 32.85 | 28.76 |
| | (7E-iii) 0.1% | 13.43 | 5.45 | 7.33 | 1.12 | 76.80 | 72.80 |
| | (7E-iv) 0.02% | 49.87 | 4.41 | 2.48 | 0.57 | 38.93 | 35.03 |
| | (7E-v) 0.002% | 66.48 | 3.26 | 1.48 | 0.54 | 28.45 | 24.33 |

The results of stability testing of Examples 7E-i-7E-v at 55° C. are set forth in Table 38 below.

TABLE 38

| Glycerin 55° C. | | Potency % | CBD % | CBN % | D8-THC % | Total Impurities % | Increase + % |
|---|---|---|---|---|---|---|---|
| Zero | (7E-i) 1% | 100.00 | 0.03 | 0.50 | 0.59 | 3.79 | |
| | (7E-ii) 0.2% | 100.00 | 0.01 | 0.49 | 0.61 | 4.09 | |
| | (7E-iii) 0.1% | 100.00 | 0..01 | 0.47 | 0.60 | 4.00 | |
| | (7E-iv) 0.02% | 100.00 | 0.02 | 0.50 | 0.60 | 3.90 | |
| | (7E-v) 0.002% | 100.00 | 0.02 | 0.49 | 0.60 | 4.12 | |
| 1 Week | (7E-i) 1% | 84.97 | 0.01 | 0.75 | 0.56 | 15.42 | 11.63 |
| | (7E-ii) 0.2% | 86.55 | 0.05 | 0.71 | 0.57 | 18.20 | 14.11 |
| | (7E-iii) 0.1% | 84.25 | 0.10 | 0.76 | 0.52 | 20.65 | 16.63 |
| | (7E-iv) 0.02% | 86.91 | 0.08 | 0.66 | 0.55 | 17.86 | 13.96 |
| | (7E-v) 0.002% | 84.44 | 0.11 | 0.76 | 0.53 | 20.93 | 16.81 |
| 2 Weeks | (7E-i) 1% | 67.98 | 0.01 | 1.78 | 0.55 | 24.93 | 21.14 |
| | (7E-ii) 0.2% | 26.76 | 0.18 | 2.76 | 0.71 | 65.03 | 60.94 |
| | (7E-iii) 0.1% | 65.98 | 0.19 | 1.42 | 0.54 | 33.00 | 29.00 |
| | (7E-iv) 0.02% | 21.93 | 0.34 | 3.26 | 0.64 | 71.79 | 67.89 |
| | (7E-v) 0.002% | 19.08 | 0.14 | 3.66 | 0.67 | 72.97 | 68.85 |

EXAMPLE 7F

Dronabinol Solution in Sesame Oil Sourced from Dipasa, with Varying Amounts of Glycerin Added In Example 7F, the effect of added varying amounts glycerin in dronabinol formulation using sesame oil sourced from Dipasa was evaluated. In each of Examples 7F-i-7F-v, the specified amount of glycerin added was prepared in accordance with Example 7. The formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Examples 7F-i-7F-v at 25° C. are set forth in Table 39 below.

TABLE 39

| Glycerin 25° C. | | Potency % | CBD % | CBN % | D8-THC % | Total Impurities % | Increase + % |
|---|---|---|---|---|---|---|---|
| Zero | (7F-i) 1% | 100.00 | 0.03 | 0.56 | 0.63 | 3.99 | |
| | (7F-ii) 0.2% | 100.00 | 0.01 | 0.66 | 0.57 | 3.99 | |
| | (7F-iii) 0.1% | 100.00 | 0.01 | 0.55 | 0.60 | 4.04 | |
| | (7F-iv) 0.02% | 100.00 | 0.03 | 0.54 | 0.57 | 4.05 | |
| | (7F-v) 0.002% | 100.00 | 0.01 | 0.54 | 0.56 | 3.89 | |
| 3 Months | (7F-i) 1% | 94.38 | 0.34 | 0.69 | 0.53 | 9.98 | 5.99 |
| | (7F-ii) 0.2% | 94.84 | 0.31 | 0.70 | 0.52 | 6.11 | 2.12 |
| | (7F-iii) 0.1% | 95.13 | 0.26 | 0.71 | 0.52 | 5.95 | 1.91 |
| | (7F-iv) 0.02% | 95.21 | 0.25 | 0.70 | 0.53 | 7.22 | 3.17 |
| | (7F-v) 0.002% | 95.13 | 0.26 | 0.73 | 0.62 | 7.36 | 3.47 |
| 6 Months | (7F-i) 1% | 96.00 | 0.29 | 0.93 | 0.57 | 8.56 | 4.57 |
| | (7F-ii) 0.2% | 96.56 | 0.27 | 0.94 | 0.55 | 8.54 | 4.55 |
| | (7F-iii) 0.1% | 97.72 | 0.28 | 0.93 | 0.55 | 8.77 | 4.73 |
| | (7F-iv) 0.02% | 96.81 | 0.32 | 0.93 | 0.55 | 8.96 | 4.91 |
| | (7F-v) 0.002% | 96.66 | 0.29 | 0.93 | 0.54 | 8.94 | 5.05 |

The results of stability testing of Examples 7F-i-7F-v at 40° C. are set forth in Table 40 below.

TABLE 40

| Glycerin 40° C. | | Potency % | CBD % | CBN % | D8-THC % | Total Impurities % | Increase + % |
|---|---|---|---|---|---|---|---|
| Zero | (7F-i) 1% | 100.00 | 0.03 | 0.56 | 0.63 | 3.99 | |
| | (7F-ii) 0.2% | 100.00 | 0.01 | 0.66 | 0.57 | 3.99 | |
| | (7F-iii) 0.1% | 100.00 | 0.01 | 0.55 | 0.60 | 4.04 | |
| | (7F-iv) 0.02% | 100.00 | 0.03 | 0.54 | 0.57 | 4.05 | |
| | (7F-v) 0.002% | 100.00 | 0.01 | 0.54 | 0.56 | 3.89 | |
| 1 Month | (7F-i) 1% | 93.29 | 0.16 | 0.71 | 0.57 | 7.27 | 3.28 |
| | (7F-ii) 0.2% | 95.22 | 0.16 | 0.72 | 0.58 | 7.39 | 3.40 |
| | (7F-iii) 0.1% | 96.08 | 0.13 | 0.71 | 0.56 | 7.26 | 3.22 |
| | (7F-iv) 0.02% | 97.10 | 0.13 | 0.72 | 0.57 | 7.28 | 3.23 |
| | (7F-v) 0.002% | 97.38 | 0.16 | 0.73 | 0.56 | 7.28 | 3.39 |
| 2 Months | (7F-i) 1% | 90.45 | 0.26 | 1.05 | 0.61 | 10.59 | 6.60 |
| | (7F-ii) 0.2% | 92.16 | 0.25 | 1.08 | 0.56 | 10.37 | 6.38 |
| | (7F-iii) 0.1% | 91.19 | 0.44 | 1.03 | 0.55 | 11.00 | 6.96 |
| | (7F-iv) 0.02% | 90.74 | 0.23 | 1.05 | 0.56 | 10.82 | 6.77 |
| | (7F-v) 0.002% | 90.76 | 0.23 | 1.06 | 0.57 | 10.71 | 6.82 |
| 3 Months | (7F-i) 1% | 85.37 | 0.32 | 1.77 | 0.59 | 14.68 | 10.69 |
| | (7F-ii) 0.2% | 87.97 | 0.34 | 1.83 | 0.55 | 13.84 | 9.85 |
| | (7F-iii) 0.1% | 88.24 | 0.41 | 1.73 | 0.58 | 13.91 | 9.87 |
| | (7F-iv) 0.02% | 86.30 | 0.42 | 1.75 | 0.56 | 14.61 | 10.56 |
| | (7F-v) 0.002% | 86.80 | 0.58 | 1.75 | 0.54 | 14.97 | 11.08 |

The results of stability testing of Examples 7F-i-7F-v at 55° C. are set forth in Table 41 below.

TABLE 41

| Glycerin 55° C. | | Potency % | CBD % | CBN % | D8-THC % | Total Impurities % | Increase + % |
|---|---|---|---|---|---|---|---|
| Zero | (7F-i) 1% | 100.00 | 0.03 | 0.56 | 0.63 | 3.99 | |
| | (7F-ii) 0.2% | 100.00 | 0.01 | 0.66 | 0.57 | 3.99 | |
| | (7F-iii) 0.1% | 100.00 | 0.01 | 0.55 | 0.60 | 4.04 | |
| | (7F-iv) 0.02% | 100.00 | 0.03 | 0.54 | 0.57 | 4.05 | |
| | (7F-v) 0.002% | 100.00 | 0.01 | 0.54 | 0.56 | 3.89 | |
| 1 Week | (7F-i) 1% | 96.81 | 0.02 | 0.72 | 0.53 | 6.99 | 3.00 |
| | (7F-ii) 0.2% | 98.85 | 0.04 | 0.75 | 0.55 | 7.23 | 3.24 |
| | (7F-iii) 0.1% | 98.53 | 0.03 | 0.80 | 0.55 | 7.32 | 3.28 |
| | (7F-iv) 0.02% | 97.55 | 0.04 | 0.82 | 0.58 | 7.83 | 3.78 |
| | (7F-v) 0.002% | 96.92 | 0.04 | 0.54 | 0.56 | 7.88 | 3.99 |
| 2 Weeks | (7F-i) 1% | 93.18 | 0.01 | 0.99 | 0.60 | 9.38 | 5.39 |
| | (7F-ii) 0.2% | 92.04 | 0.01 | 1.09 | 0.53 | 9.64 | 5.65 |
| | (7F-iii) 0.1% | 92.80 | 0.01 | 1.12 | 0.57 | 10.48 | 6.44 |
| | (7F-iv) 0.02% | 91.55 | 0.01 | 1.20 | 0.57 | 10.75 | 6.70 |
| | (7F-v) 0.002% | 89.74 | 0.01 | 1.31 | 0.52 | 11.18 | 7.29 |

As can be seen from the results above, the addition of glycerin makes dronabinol highly unstable. The amount of dronabinol chemically degraded is proportional to the glycerin concentration added. Dronabinol degradation continued with increase in storage period. However, dronabinol in sesame oil sourced from Dipasa is highly resistant to degradation induced by glycerin. This stability is believed to be due to the high antioxidant content in sesame oil sourced from Dipasa, most notably lecithin.

EXAMPLE 8

Stability Studies

The International Conference on Harmonisation (ICH) of Technical Requirements for Registration of Pharmaceuticals for Human Use (ICH) has adopted scientific standards for stability testing. These standards are the basis of regulatory guidances published by the FDA (Guidance for Industry, Q1A). The purpose of stability tests is to provide evidence on how the quality and safety of the product varies with time. As per the FDA guidance, a finished product is assigned a tentative two-year expiration dating at room temperature (25° C.) if the product is stable for 6 months at accelerated testing conditions, 40° C. (15° C. above the designated long-term storage temperature). In Example 8, a dronabinol formulation in sesame oil (super-refined, from Croda) was prepared in accordance with Example 1, and packaged in a round, amber glass bottle, which are stored at elevated temperature and humidity levels, 40° C./75% relative humidity (RH) to demonstrate stability of the formulation at room temperature. The formulation was also tested at 2-8° C., 25° C./60% relative humidity and 30° C./60% relative humidity.

The concentrations of dronabinol and the impurities/degradants [D8THC, Cannabidiol (CDN) and Cannabidiol (CBD)] are determined by using the compendial (USP) HPLC method after storage for pre-determined time periods and conditions as set forth in Table 42. The results of the stability testing of Example 8 are set forth in Table 42 below.

TABLE 42

| Condition | Time (Months) | Assay (HPLC) | Related Substances (GC) | | | Dissolution Test |
| --- | --- | --- | --- | --- | --- | --- |
| | | | Delta-8-THC | CBN | CBD | |
| Initial | 0 | 101.40% | 0.90% | 1.30% | 0.20% | NMT 5 min |
| 2-8° C. | 1 | 98.40% | 0.90% | 0.70% | ND | NMT 2 min |
| | 2 | 98.30% | 0.70% | 1.00% | ND | NMT 1 min |
| | 3 | 99.80% | 0.70% | 1.00% | ND | NMT 1 min |
| | 6 | 101.30% | 1.10% | 1.00% | ND | NMT 1 min |
| 25° C./60% RH | 1 | 99.00% | 0.70% | 0.70% | ND | NMT 2 min |
| | 2 | 98.40% | 0.70% | 1.10% | ND | NMT 1 min |
| | 3 | 98.60% | 0.70% | 1.10% | ND | NMT 1 min |
| | 6 | 96.40% | 1.20% | 1.20% | ND | NMT 1 min |
| 30° C./60% RH | 1 | 98.50% | 0.90% | 0.60% | ND | NMT 3 min |
| | 2 | 97.00% | 0.70% | 1.20% | ND | NMT 1 min |
| | 3 | 98.50% | 0.70% | 1.00% | ND | NMT 2 min |
| | 6 | 98.20% | 1.30% | 1.20% | ND | NMT 3 min |
| 40° C./75% RH | 0.5 | 100.00% | 0.60% | 0.80% | ND | NMT 3 min |
| | 1 | 97.00% | 1.00% | 0.70% | ND | NMT 4 min |
| | 2 | 96.90% | 0.70% | 1.20% | ND | NMT 1 min |
| | 3 | 92.80% | 0.80% | 1.40% | ND | NMT 1 min |
| | 6 | 94.00% | 1.40% | 1.70% | ND | NMT 3 min |

ND = not detected
NMT = not more than
GC = gas chromatography

The above stability studies are believed to demonstrate that by removing glycerin/glycerol, a dronabinol oral drug product that is stable for two years at room temperature is obtained.

It is hypothesized that hard gelatin capsule shells do not contain glycerol and therefore a major cause of instability for the active pharmaceutical ingredient dronabinol is eliminated (as compared to the reference standard product, Marinol, which is encapsulated in soft gelatin capsules). Also, by utilizing hard gelatin capsules to encapsulate dronabinol solution, the need for plasticizer (glycerin) is eliminated.

EXAMPLE 9

Effect of Different Brands of Sesame Oil on Stability

In order to study of the effect of the type and source of sesame oil on the stability of the active ingredient dronabinol, different sources of sesame oil were obtained from the following vendors: Super Refined NF grade from Croda; NF grade from Arista & Dipasa; and food grade from Columbus. Formulations of active ingredient (dronabinol) in varying amounts and sesame oil were prepared according the method described in Example 1.

Example 9-i is a 5 mg dronabinol (3.03% w/w) solution in sesame oil, NF (by Arista).

Example 9-ii is a 5 mg dronabinol (3.03% w/w) solution in sesame oil (super refined NF, by Croda).

Example 9-iii is a 10 mg dronabinol (6.06% w/w) solution in sesame oil, NF (from Dipasa).

Example 9-iv is a 10 mg dronabinol (6.06% w/w) solution in food grade sesame oil (obtained from Columbus).

A summary of the compositions of Examples 9-i-9-iv is set forth in Table 43 below:

TABLE 43

| | Composition | | |
| --- | --- | --- | --- |
| Formulation No. | Dronabinol | Sesame Oil | Other Ingredients |
| Example 9-i (Arista) | 3.03% w/w | QS | — |
| Example 9-ii (Croda) | 3.03% w/w | QS | — |
| Example 9-iii (Dipasa) | 6.06% w/w | QS | — |
| Example 9-iv (Columbus) | 6.06% w/w | QS | — |

The formulations were stored in amber glass vials at 55° C. while being tested for stability under elevated temperature conditions (initially ("zero time"), 55° for one week and two weeks, respectively). The results shown are presented in Table 44.

TABLE 44

| CONDITION | FORMULATION # | ASSAY % | TOTAL IMPURITY % | RELATED SUBSTANCES | | |
|---|---|---|---|---|---|---|
| | | | | D8THC % | CBN % | CBD % |
| Zero Time | Example 9-i (Arista) | 96.59 | 3.41 | 0.48 | 0.51 | — |
| | Example 9-ii (Croda) | 93.80 | 6.20 | 0.75 | 1.88 | 0.29 |
| | Example 9-iii (Dipasa) | 94.60 | 3.78 | 0.42 | 0.60 | 0.09 |
| | Example 9-iv (Columbus) | 94.97 | 3.35 | 0.44 | 0.49 | 0.02 |
| 55° C. (1 week) | Example 9-i (Arista) | 94.50 | 5.50 | 0.46 | 0.64 | 0.30 |
| | Example 9-ii (Croda) | 82.16 | 17.84 | 0.72 | 1.86 | 0.23 |
| | Example 9-iii (Dipasa) | 94.29 | 5.71 | 0.42 | 1.11 | 0.20 |
| | Example 9-iv (Columbus) | 87.55 | 12.45 | 0.51 | 1.83 | 0.48 |
| 55° C. (2 weeks) | Example 9-i (Arista) | 92.75 | 7.25 | 0.52 | 0.64 | 0.58 |
| | Example 9-ii (Croda) | 67.41 | 32.59 | 1.06 | 4.96 | 0.29 |
| | Example 9-iii (Dipasa) | 92.92 | 7.08 | 0.52 | 1.54 | 0.05 |
| | Example 9-iv (Columbus) | 71.32 | 28.68 | 0.60 | 3.78 | 0.27 |

Based on the results set forth in Table 44 above, the type (and source) of sesame oil used plays a major role in stabilizing the active ingredient dronabinol. Dronabinol formulations prepared from NF grade sesame oil sourced from Dipasa showed increased stability when compared to similar formulations prepared from NF grade sourced sesame oil from Croda and Arista and food grade sesame oil sourced from Columbus.

Extended Stability Results—Effect of Different Brands of Sesame Oil on Stability It was believed that the source of sesame oil used in the dronabinol formulation is important to the stability of the formulation. To confirm whether the lack of sufficient antioxidants in certain brands of sesame oil caused a lack of stability and an increase in dronabinol related impurities such as delta-8-THC, CBD and CBN, stability studies at room temperature and at accelerated conditions over an extended period of time were conducted using sesame oil from Arista, Croda and Dipasa.

EXAMPLE 9A

Effect of Arista Brand Sesame Oil on Stability

In Example 9A, the effect of the Arista brand of sesame oil used in the dronabinol formulation was evaluated. The formulation was prepared in accordance with the method described for Example 9-i. The formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Examples 9A at 25° C. are set forth in Table 45 below.

TABLE 45

| Control 25° C. | Potency % | CBD % | CBN % | D8-THC % | Total Impurities % | Increase + % |
|---|---|---|---|---|---|---|
| Zero | 100.00 | 0.08 | 0.50 | 0.57 | 4.36 | |
| 3 Months | 91.72 | 0.31 | 0.84 | 0.49 | 11.16 | 6.80 |
| 6 Months | 92.71 | 1.01 | 1.16 | 0.47 | 11.16 | 6.80 |

The results of stability testing of Examples 9A at 40° C. are set forth in Table 46 below.

TABLE 46

| Control 40° C. | Potency % | CBD % | CBN % | D8-THC % | Total Impurities % | Increase + % |
|---|---|---|---|---|---|---|
| Zero | 100.00 | 0.08 | 0.50 | 0.57 | 4.36 | |
| 1 Month | 95.18 | 0.59 | 0.74 | 0.48 | 9.86 | 5.50 |
| 2 Months | 93.22 | 0.43 | 0.88 | 0.52 | 10.41 | 6.05 |
| 3 Months | 91.36 | 0.53 | 1.16 | 0.51 | 10.98 | 6.62 |

The results of stability testing of Examples 9A at 55° C. are set forth in Table 47 below.

TABLE 47

| Control 55° C. | Potency % | CBD % | CBN % | D8-THC % | Total Impurities % | Increase + % |
|---|---|---|---|---|---|---|
| Zero | 100.00 | 0.08 | 0.50 | 0.57 | 4.36 | |
| 1 Week | 90.42 | 0.08 | 0.68 | 0.48 | 13.06 | 8.70 |
| 2 Weeks | 44.67 | 0.02 | 2.63 | 0.56 | 47.45 | 43.09 |

EXAMPLE 9B

Effect of Croda Brand Sesame Oil on Stability

In Example 9B, the effect of the Croda brand of sesame oil used in the dronabinol formulation was evaluated. The formulation was prepared in accordance with the method described for Example 9-ii. The formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Examples 9B at 25° C. are set forth in Table 48 below.

TABLE 48

| Control | | CBD | CBN | | Total Impurities | |
|---|---|---|---|---|---|---|
| 25° C. | Potency % | % | % | D8-THC % | % | Increase + % |
| Zero | 100.00 | 0.08 | 0.46 | 0.59 | 4.13 | |
| 3 Months | 87.36 | 0.32 | 0.62 | 0.62 | 13.61 | 9.48 |
| 6 Months | 91.63 | 1.33 | 0.78 | 0.49 | 14.87 | 10.74 |

The results of stability testing of Examples 9B at 40° C. are set forth in Table 49 below.

TABLE 49

| Control | | CBD | CBN | | Total Impurities | |
|---|---|---|---|---|---|---|
| 40° C. | Potency % | % | % | D8-THC % | % | Increase + % |
| Zero | 100.00 | 0.08 | 0.46 | 0.59 | 4.13 | |
| 1 Month | 91.25 | 0.97 | 0.62 | 0.53 | 12.18 | 8.05 |
| 2 Months | 87.59 | 0.81 | 0.71 | 0.57 | 13.03 | 8.90 |
| 3 Months | 87.62 | 1.02 | 0.90 | 0.56 | 13.78 | 9.65 |

The results of stability testing of Examples 9B at 55° C. are set forth in Table 50 below.

TABLE 50

| Control | | CBD | CBN | | Total Impurities | |
|---|---|---|---|---|---|---|
| 55° C. | Potency % | % | % | D8-THC % | % | Increase + % |
| Zero | 100.00 | 0.08 | 0.46 | 0.59 | 4.13 | |
| 1 Week | 85.53 | 0.09 | 0.69 | 0.51 | 15.38 | 11.25 |
| 2 Weeks | 38.10 | 0.20 | 2.72 | 0.57 | 57.40 | 53.27 |

EXAMPLE 9C

Effect of Dipasa Brand Sesame Oil on Stability

In Example 9C, the effect of the Dipasa brand of sesame oil used in the dronabinol formulation was evaluated. The formulation was prepared in accordance with the method described for Example 9-iii, with a dronabinol concentration of 3.03%. The formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Examples 9C at 25° C. are set forth in Table 51 below.

TABLE 51

| Control | | CBD | CBN | | Total Impurities | |
|---|---|---|---|---|---|---|
| 25° C. | Potency % | % | % | D8-THC % | % | Increase + % |
| Zero | 100.00 | 0.02 | 0.51 | 0.57 | 3.96 | |
| 3 Months | 95.72 | 0.05 | 0.68 | 0.45 | 5.41 | 1.45 |
| 6 Months | 98.00 | 0.38 | 0.76 | 0.55 | 8.49 | 4.53 |

The results of stability testing of Examples 9C at 40° C. are set forth in Table 52 below.

TABLE 52

| Control | | CBD | CBN | | Total Impurities | |
|---|---|---|---|---|---|---|
| 40° C. | Potency % | % | % | D8-THC % | % | Increase + % |
| Zero | 100.00 | 0.02 | 0.51 | 0.57 | 3.96 | |
| 1 Month | 97.56 | 0.16 | 0.67 | 0.55 | 6.63 | 2.67 |
| 2 Months | 92.49 | 0.20 | 0.96 | 0.56 | 10.15 | 6.19 |
| 3 Months | 90.02 | 0.41 | 1.50 | 0.53 | 12.29 | 8.33 |

The results of stability testing of Examples 9C at 55° C. are set forth in Table 53 below.

TABLE 53

| Control | | CBD | CBN | | Total Impurities | |
|---|---|---|---|---|---|---|
| 55° C. | Potency % | % | % | D8-THC % | % | Increase + % |
| Zero | 100.00 | 0.02 | 0.51 | 0.57 | 3.96 | |
| 1 Week | 97.60 | 0.11 | 0.82 | 0.54 | 6.94 | 2.98 |
| 2 Weeks | 96.17 | 0.12 | 1.14 | 0.54 | 9.45 | 5.49 |

EXAMPLE 9D

Effect of Arista Brand Sesame Oil on Stability—Vials

In Example 9D, the effect of the Arista brand of sesame oil used in the dronabinol formulation was evaluated. The formulation was prepared in accordance with the method described for Example 9-i. The formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability testing of Examples 9D at 25° C. are set forth in Table 54 below.

TABLE 54

| Control | | CBD | CBN | | Total Impurities | |
|---|---|---|---|---|---|---|
| 25° C. | Potency % | % | % | D8-THC % | % | Increase + % |
| Zero | 100.00 | 0.08 | 0.50 | 0.57 | 4.36 | |
| 3 Months | 96.92 | 0.25 | 0.55 | 0.55 | 6.91 | 2.55 |
| 6 Months | 99.65 | 0.14 | 0.60 | 0.51 | 7.49 | 3.13 |

The results of stability testing of Examples 9D at 40° C. are set forth in Table 55 below.

TABLE 55

| Control | | | | D8- | Total Impurities | |
|---|---|---|---|---|---|---|
| 40° C. | Potency % | CBD % | CBN % | THC % | % | Increase + % |
| Zero | 100.00 | 0.08 | 0.50 | 0.57 | 4.36 | |
| 1 Month | 98.42 | 0.06 | 0.51 | 0.49 | 5.79 | 1.43 |
| 2 Months | 95.26 | 0.10 | 0.59 | 0.49 | 9.50 | 5.14 |
| 3 Months | 90.41 | 0.64 | 0.90 | 0.49 | 13.67 | 9.31 |

The results of stability testing of Examples 9D at 55° C. are set forth in Table 56 below.

TABLE 56

| Control | | | | D8- | Total Impurities | |
|---|---|---|---|---|---|---|
| 55° C. | Potency % | CBD % | CBN % | THC % | % | Increase + % |
| Zero | 100.00 | 0.08 | 0.50 | 0.57 | 4.36 | |
| 1 Week | 90.42 | 0.08 | 0.68 | 0.48 | 13.06 | 8.70 |
| 2 Weeks | 44.67 | 0.02 | 2.63 | 0.56 | 47.45 | 43.09 |

EXAMPLE 9E

Effect of Croda Brand Sesame Oil on Stability—Vials

In Example 9E, the effect of the Croda brand of sesame oil used in the dronabinol formulation was evaluated. The formulation was prepared in accordance with the method described for Example 9-ii. The formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability testing of Examples 9E at 25° C. are set forth in Table 57 below.

TABLE 57

| Control | | | | D8- | Total Impurities | |
|---|---|---|---|---|---|---|
| 25° C. | Potency % | CBD % | CBN % | THC % | % | Increase + % |
| Zero | 100.00 | 0.08 | 0.46 | 0.59 | 4.13 | |
| 3 Months | 71.55 | 3.62 | 1.26 | 0.56 | 28.72 | 24.59 |
| 6 Months | 61.65 | 4.36 | 1.96 | 0.68 | 40.12 | 35.99 |

The results of stability testing of Examples 9E at 40° C. are set forth in Table 58 below.

TABLE 58

| Control | | | | D8- | Total Impurities | |
|---|---|---|---|---|---|---|
| 40° C. | Potency % | CBD % | CBN % | THC % | % | Increase + % |
| Zero | 100.00 | 0.08 | 0.46 | 0.59 | 4.13 | |
| 1 Month | 80.41 | 3.21 | 0.98 | 0.52 | 23.01 | 18.88 |
| 2 Months | 71.75 | 3.76 | 1.14 | 0.48 | 28.08 | 23.95 |
| 3 Months | 60.30 | 4.21 | 1.94 | 0.58 | 34.99 | 30.86 |

The results of stability testing of Examples 9E at 55° C. are set forth in Table 59 below.

TABLE 59

| Control | | | | D8- | Total Impurities | |
|---|---|---|---|---|---|---|
| 55° C. | Potency % | CBD % | CBN % | THC % | % | Increase + % |
| Zero | 100.00 | 0.08 | 0.46 | 0.59 | 4.13 | |
| 1 Week | 85.53 | 0.09 | 0.69 | 0.51 | 15.38 | 11.25 |
| 2 Weeks | 38.10 | 0.20 | 2.72 | 0.57 | 57.40 | 53.27 |

EXAMPLE 9F

Effect of Dipasa Brand Sesame Oil on Stability—Vials

In Example 9F, the effect of the Dipasa brand of sesame oil used in the dronabinol formulation was evaluated. The formulation was prepared in accordance with the method described for Example 9-iii. The formulation was then used to fill amber glass vials. The formulation within the vials was then tested at 25° C. for 3 and 6 months; 40° C. for 1, 2 and 3 months and at 55° C. for 1 and 2 weeks.

The results of stability testing of Examples 9F at 25° C. are set forth in Table 60 below.

TABLE 60

| Control | | | | D8- | Total Impurities | |
|---|---|---|---|---|---|---|
| 25° C. | Potency % | CBD % | CBN % | THC % | % | Increase + % |
| Zero | 100.00 | 0.02 | 0.51 | 0.57 | 3.96 | |
| 3 Months | 96.39 | 0.25 | 0.70 | 0.60 | 7.26 | 3.30 |
| 6 Months | 98.27 | 0.23 | 0.92 | 0.60 | 8.41 | 4.45 |

The results of stability testing of Examples 9F at 40° C. are set forth in Table 61 below.

TABLE 61

| Control | | | | D8- | Total Impurities | |
|---|---|---|---|---|---|---|
| 40° C. | Potency % | CBD % | CBN % | THC % | % | Increase + % |
| Zero | 100.00 | 0.02 | 0.51 | 0.57 | 3.96 | |
| 1 Month | 96.49 | 0.12 | 0.75 | 0.53 | 6.50 | 2.54 |
| 2 Months | 92.98 | 0.22 | 1.07 | 0.55 | 10.22 | 6.26 |
| 3 Months | 88.64 | 0.43 | 1.70 | 0.55 | 14.19 | 10.23 |

The results of stability testing of Examples 9F at 55° C. are set forth in Table 62 below.

TABLE 62

| Control | | | | D8- | Total Impurities | |
|---|---|---|---|---|---|---|
| 55° C. | Potency % | CBD % | CBN % | THC % | % | Increase + % |
| Zero | 100.00 | 0.02 | 0.51 | 0.57 | 3.96 | |
| 1 Week | 97.60 | 0.11 | 0.82 | 0.54 | 6.94 | 2.98 |
| 2 Weeks | 96.17 | 0.12 | 1.14 | 0.54 | 9.45 | 5.49 |

Based on the results set forth in above tables, it is clear that the source of sesame oil plays a vital role towards the stability of dronabinol formulations. Formulations containing NF grade sesame oil from Arista and Dipasa showed greater stability than super refined sesame oil from Croda.

EXAMPLE 10

HPLC Analysis of Formulation 9-iii

In Example 10, the dronabinol solution of Example 9-iii was further analyzed. In Example 10a, the formulation of Example 9-iii was stored at 55° C. for two weeks and then subjected to HPLC analysis. The results are provided in FIG. 1.

Chromatograms obtained by the High Performance Liquid Chromatography (HPLC) analysis of dronabinol drug product stability samples show a peak at approximately 4.4 minutes which corresponds to sesamin, a major anti-oxidant in sesame oil (FIG. 1).

Figure 2:
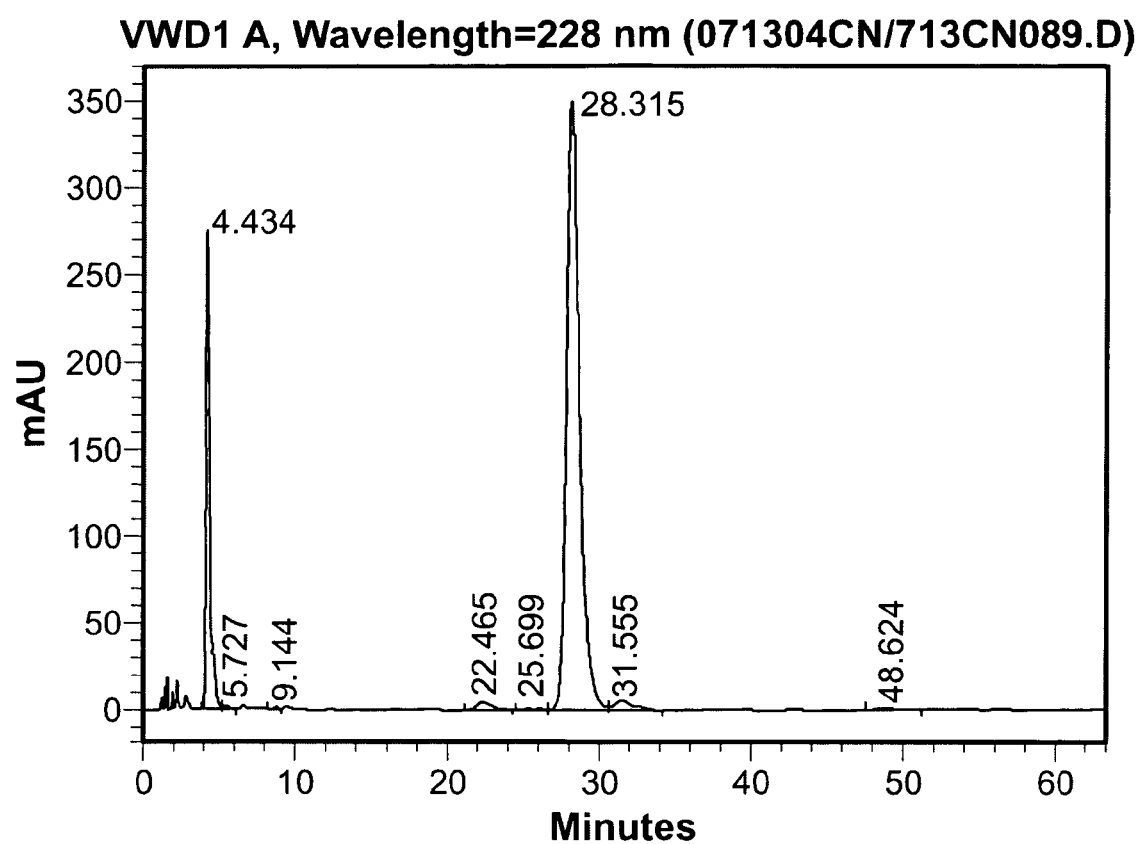
FIG. 2 is a chromatogram of a formulation of 3.03% w/w dronabinol in sesame oil spiked with 1% w/w sesamin after storage for two weeks at 55° C.

This presence of sesamin was confirmed by spiking the sample solution with sesamin. In particular, in Example 10b, the formulation of Example 9-iii was spiked with 1% w/w sesamin (purity: >95%) obtained from Industrial Research Ltd., Lower Hutt, New Zealand. The formulation of Example 10b was stored at 55° C. for two weeks and then subjected to HPLC analysis. The results are provided in FIG. 2.

Most impurities including all the sesame oil anti-oxidants are removed during the purification of NF grade to super refined NF grade sesame oil (Super Refined Oils PN-25, Croda Inc., Data Sheet, hereby incorporated by reference). Therefore, the instability of dronabinol formulations prepared using super refined sesame oil sourced from Croda may be attributed to the absence of anti-oxidants, sesamin in specific. The specifications of the sesame oil obtained from various vendors (Arista, Dipasa, Croda, Columbus) revealed that sesamin was present only in Food and NF grade sesame oils but not in the super refined sesame oil sourced from Croda.

EXAMPLE 11

Stability Results—Addition of Free Fatty Acid(s)

The instability of dronabinol formulations prepared using food grade sesame oil led us to investigate further the effects of other impurities in sesame oil (including free fatty acid on dronabinol formulations). Sesame oil contains one or more free fatty acids, of which myristic acid is prominent (Beckstrom-Sternberg et al., 1994). In order to examine whether the presence of acids oxidize dronabinol, the effect of added fatty acid in dronabinol formulated as a sesame oil solution was evaluated. In Example 11, the specified amount of fatty acid was added to formulations prepared in accordance with Example 1.

Example 11-i is a solution of 5 mg dronabinol (3.03%) and 0.5% myristic acid in sesame oil, NF (by Arista).

Example 11-ii is a solution of 5 mg dronabinol (3.03%) and 0.1% myristic acid in sesame oil, NF (by Arista).

Example 11-iii is a solution of 5 mg dronabinol (3.03%) and 0.05% myristic acid in sesame oil, NF (by Arista).

Example 11-iv is a solution of 5 mg dronabinol (3.03%) and 0.007% myristic acid in sesame oil, NF (by Arista).

Example 11-v is a solution of 5 mg dronabinol (3.03%) and 0.5% myristic acid in sesame oil, super refined NF (by Croda).

Example 11-vi is a solution of 5 mg dronabinol (3.03%) and 0.1% myristic acid in sesame oil, super refined NF (by Croda).

Example 11-vii is a solution of 5 mg dronabinol (3.03%) and 0.05% myristic acid in sesame oil, super refined NF (by Croda).

Example 11-viii is a solution of 5 mg dronabinol (3.03%) and 0.007% myristic acid in sesame oil, super refined NF (by Croda).

A summary of the compositions of Examples 11-i-11-viii is set forth in Table 63 below:

TABLE 63

| | Composition | | |
|---|---|---|---|
| Formulation No. | Dronabinol | Sesame Oil | Other Ingredients |
| Example 11-i | 3.03% w/w | QS | Myristic Acid (0.5%) |
| Example 11-ii | 3.03% w/w | QS | Myristic Acid (0.1%) |
| Example 11-iii | 3.03% w/w | QS | Myristic Acid (0.05%) |
| Example 11-iv | 3.03% w/w | QS | Myristic Acid (0.007%) |
| Example 11-v | 3.03% w/w | QS | Myristic Acid (0.5%) |
| Example 11-vi | 3.03% w/w | QS | Myristic Acid (0.1%) |
| Example 11-vii | 3.03% w/w | QS | Myristic Acid (0.05%) |
| Example 11-viii | 3.03% w/w | QS | Myristic Acid (0.007%) |

The formulations were tested for stability while stored in amber glass vials at 55° C. for one week (Table 64) and two weeks (Table 65), respectively.

TABLE 64

| FORMULATION* # | TOTAL ASSAY % | IMPURITY % | RELATED SUBSTANCES | | |
|---|---|---|---|---|---|
| | | | D8THC % | CBN % | CBD % |
| Example 11-i (A + mysristic 0.5%) | 92.15 | 7.85 | 0.55 | 1.81 | 0.27 |
| Example 11-iii (A + mysristic 0.05%) | 92.83 | 7.17 | 0.48 | 1.38 | 0.31 |
| Example 11-vi (C + mysristic 0.1%) | 81.82 | 18.18 | 0.52 | 4.77 | 2.50 |
| Example 11-viii (C + mysristic 0.007%) | 86.33 | 13.67 | 0.57 | 2.15 | 2.16 |

*A = Arista, C = Croda

TABLE 65

| FORMULATION* # | TOTAL ASSAY % | IMPURITY % | RELATED SUBSTANCES | | |
|---|---|---|---|---|---|
| | | | D8THC % | CBN % | CBD % |
| Example 11-i (A + mysristic 0.5%) | 88.96 | 11.04 | 0.71 | 3.30 | 0.27 |
| Example 11-iii (A + mysristic 0.05%) | 90.51 | 9.49 | 0.55 | 2.35 | 0.09 |
| Example 11-vi (C + mysristic 0.1%) | 68.61 | 31.39 | 0.91 | 8.26 | 0.18 |
| Example 11-viii (C + mysristic 0.007%) | 78.81 | 21.19 | 0.71 | 3.46 | 0.52 |

*A = Arista, C = Croda

As can be seen from the results set forth in Tables 64 and 65, the addition of myristic acid to dronabinol formulation resulted in degradation of the active ingredient dronabinol. The results may also be explained in whole or in part by the fact that the super-refined sesame oil from Croda has no sesamin.

Extended Stability Results—Addition of Free Fatty Acid(s)

To confirm whether the addition of the free fatty acid myristic acid on dronabinol formulations caused a lack of stability and an increase in dronabinol related impurities such as delta-8-THC, CBD and CBN, stability studies at room temperature and at accelerated conditions over an extended period of time were conducted using sesame oil from Arista, Croda and Dipasa.

EXAMPLE 11A

Dronabinol Solution in Sesame Oil Sourced from Arista—Capsules

In Example 11A, dronabinol formulations 11A-i and 11A-ii were prepared in accordance with Examples 11-i and 11-ii using sesame oil sourced from Arista. Formulation 11A-i contained 0.5% myristic acid and formulation 11A-ii contained 0.1% myristic acid. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 11A-i-ii at 25° C. are set forth in Table 66 below.

TABLE 66

| | Myristic acid | | | | | Total Impurities | |
|---|---|---|---|---|---|---|---|
| | 25° C. | Potency % | CBD % | CBN % | D8-THC % | % | Increase + % |
| Zero | 11A-i 0.5% | 100.00 | 0.03 | 0.52 | 0.50 | 3.95 | |
| | 11A-ii 0.1% | 100.00 | 0.02 | 0.49 | 0.51 | 3.91 | |
| 3 | 11A-i 0.5% | 94.03 | 0.29 | 0.78 | 0.50 | 5.25 | 1.30 |
| Months | 11A-ii 0.1% | 88.57 | 0.18 | 1.14 | 0.50 | 10.68 | 6.77 |
| 6 | 11A-i 0.5% | 94.86 | 0.32 | 1.14 | 0.50 | 6.95 | 3.00 |
| Months | 11A-ii 0.1% | 88.32 | 0.93 | 1.58 | 0.57 | 12.19 | 8.28 |

The results of stability testing of Example 11A-i-ii at 40° C. are set forth in Table 67 below.

TABLE 67

| | Myristic acid | | | | | Total Impurities | |
|---|---|---|---|---|---|---|---|
| | 40° C. | Potency % | CBD % | CBN % | D8-THC % | % | Increase + % |
| Zero | 11A-i 0.5% | 100.00 | 0.03 | 0.52 | 0.50 | 3.95 | |
| | 11A-ii 0.1% | 100.00 | 0.02 | 0.49 | 0.51 | 3.91 | |
| 1 | 11A-i 0.5% | 90.98 | 0.18 | 1.83 | 0.49 | 10.36 | 6.41 |
| Month | 11A-ii 0.1% | 88.24 | 0.32 | 1.37 | 0.48 | 10.56 | 6.65 |
| 2 | 11A-i 0.5% | 88.26 | 0.13 | 1.94 | 0.51 | 11.72 | 7.77 |
| Months | 11A-ii 0.1% | 86.99 | 0.22 | 1.61 | 0.42 | 11.70 | 7.79 |
| 3 | 11A-i 0.5% | 86.96 | 0.28 | 2.36 | 0.45 | 12.74 | 8.79 |
| Months | 11A-ii 0.1% | 84.92 | 0.35 | 1.98 | 0.50 | 12.40 | 8.49 |

The results of stability testing of Example 11A-i-ii at 55° C. are set forth in Table 68 below.

TABLE 68

| | Myristic acid | | | | | Total Impurities | |
|---|---|---|---|---|---|---|---|
| | 55° C. | Potency % | CBD % | CBN % | D8-THC % | % | Increase + % |
| Zero | 11A-i 0.5% | 100.00 | 0.03 | 0.52 | 0.50 | 3.95 | |
| | 11A-ii 0.1% | 100.00 | 0.02 | 0.49 | 0.51 | 3.91 | |
| 1 | 11A-i 0.5% | 91.53 | 0.03 | 1.53 | 0.59 | 10.33 | 6.38 |
| Week | 11A-ii 0.1% | 87.94 | 0.01 | 0.92 | 0.49 | 13.11 | 9.20 |
| 2 | 11A-i 0.5% | 88.83 | 0.01 | 2.10 | 0.55 | 12.76 | 8.81 |
| Weeks | 11A-ii 0.1% | 71.58 | 0.03 | 2.16 | 0.58 | 23.69 | 19.78 |

EXAMPLE 11B

Dronabinol Solution in Sesame Oil Sourced from Croda—Capsules

In Example 11B, dronabinol formulations 11B-i and 11B-ii were prepared in accordance with Examples 11-v and 11-vi using sesame oil sourced from Croda. Formulation 11B-i contained 0.5% myristic acid and formulation 11A-ii contained 0.1% myristic acid. The dronabinol formulations were then used to fill hard gelatin capsules in accordance with Example 2. The formulations within the capsules, were initially tested, then tested at 25° C. for 3 and 6 months; 40° C. for 1, 2 and 3 months and at 55° C. for 1 and 2 weeks.

The results of stability testing of Example 11B-i-ii at 25° C. are set forth in Table 69 below.

TABLE 69

| | Myristic acid | | | | | Total Impurities | |
|---|---|---|---|---|---|---|---|
| | 25° C. | Potency % | CBD % | CBN % | D8-THC % | % | Increase + % |
| Zero | 11B-i 0.5% | 100.00 | 0.03 | 0.48 | 0.65 | 5.69 | |
| | 11B-ii 0.1% | 100.00 | 0.02 | 0.46 | 0.62 | 2.29 | |

TABLE 69-continued

| Myristic acid | | | | | | Total Impurities | |
|---|---|---|---|---|---|---|---|
| | 25° C. | Potency % | CBD % | CBN % | D8-THC % | % | Increase + % |
| 3 | 11B-i 0.5% | 89.16 | 0.17 | 1.93 | 0.56 | 11.08 | 5.39 |
| Months | 11B-ii 0.1% | 89.25 | 0.21 | 0.99 | 0.55 | 12.56 | 7.27 |
| 6 | 11B-i 0.5% | 91.12 | 0.65 | 2.24 | 0.67 | 12.29 | 6.60 |
| Months | 11B-ii 0.1% | 91.66 | 1.34 | 1.44 | 0.53 | 14.19 | 8.90 |

The results of stability testing of Example 11B-i-ii at 40° C. are set forth in Table 70 below.

TABLE 70

| Myristic acid | | | | | | Total Impurities | |
|---|---|---|---|---|---|---|---|
| | 40° C. | Potency % | CBD % | CBN % | D8-THC % | % | Increase + % |
| Zero | 11B-i 0.5% | 100.00 | 0.03 | 0.48 | 0.65 | 5.69 | |
| | 11B-ii 0.1% | 100.00 | 0.02 | 0.46 | 0.62 | 2.29 | |
| 1 | 11B-i 0.5% | 62.73 | 1.00 | 8.49 | 0.97 | 31.26 | 25.57 |
| Month | 11B-ii 0.1% | 91.93 | 0.84 | 1.16 | 0.60 | 12.04 | 6.75 |
| 2 | 11B-i 0.5% | 88.49 | 0.21 | 2.21 | 0.57 | 12.51 | 6.82 |
| Months | 11B-ii 0.1% | 87.83 | 0.49 | 1.45 | 0.62 | 13.49 | 8.20 |
| 3 | 11B-i 0.5% | 85.11 | 0.34 | 2.82 | 0.58 | 15.11 | 9.42 |
| Months | 11B-ii 0.1% | 86.43 | 0.53 | 2.08 | 0.58 | 14.70 | 9.41 |

The results of stability testing of Example 11B-i-ii at 55° C. are set forth in Table 71 below.

TABLE 71

| Myristic acid | | | | | | Total Impurities | |
|---|---|---|---|---|---|---|---|
| | 55° C. | Potency % | CBD % | CBN % | D8-THC % | % | Increase + % |
| Zero | 11B-i 0.5% | 100.00 | 0.03 | 0.48 | 0.65 | 5.69 | |
| | 11B-ii 0.1% | 100.00 | 0.02 | 0.46 | 0.62 | 2.29 | |
| 1 | 11B-i 0.5% | 87.77 | 0.01 | 1.99 | 0.63 | 14.67 | 8.98 |
| Week | 11B-ii 0.1% | 85.94 | 0.03 | 0.96 | 0.52 | 17.11 | 11.82 |
| 2 | 11B-i 0.5% | 46.26 | 0.05 | 10.13 | 1.16 | 45.43 | 39.74 |
| Weeks | 11B-ii 0.1% | 33.85 | 0.09 | 5.57 | 0.65 | 57.47 | 52.18 |

EXAMPLE 11C

Dronabinol Solution in Sesame Oil Sourced from Dipasa—Capsules

In Example 11C, dronabinol formulations 11C-i and 11C-ii were prepared in accordance with Examples 11B-i and 11B-ii using sesame oil sourced from Dipasa. Formulation 11C-i contained 0.5% myristic acid and formulation 11C-ii contained 0.1% myristic acid. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 11C-i-ii at 25° C. are set forth in Table 72 below.

TABLE 72

| Myristic acid | | | | | | Total Impurities | |
|---|---|---|---|---|---|---|---|
| | 25° C. | Potency % | CBD % | CBN % | D8-THC % | % | Increase + % |
| Zero | 11C-i 0.5% | 100.00 | 0.06 | 0.53 | 0.54 | 3.81 | |
| | 11C-ii 0.1% | 100.00 | 0.02 | 0.56 | 0.60 | 3.96 | |
| 3 | 11C-i 0.5% | 92.81 | 0.05 | 0.89 | 0.53 | 5.80 | 1.99 |
| Months | 11C-ii 0.1% | 93.55 | 0.05 | 0.70 | 0.55 | 6.11 | 2.15 |
| 6 | 11C-i 0.5% | 94.79 | 0.29 | 1.20 | 0.56 | 7.10 | 3.29 |
| Months | 11C-ii 0.1% | 93.80 | 0.43 | 0.98 | 0.52 | 7.90 | 3.94 |

The results of stability testing of Example 11C-i-ii at 40° C. are set forth in Table 73 below.

TABLE 73

| Myristic acid 40° C. | | Potency % | CBD % | CBN % | D8-THC % | Total Impurities % | Increase + % |
|---|---|---|---|---|---|---|---|
| Zero | 11C-i 0.5% | 100.00 | 0.06 | 0.53 | 0.54 | 3.81 | |
| | 11C-ii 0.1% | 100.00 | 0.02 | 0.56 | 0.60 | 3.96 | |
| 1 Month | 11C-i 0.5% | 92.08 | 0.18 | 1.29 | 0.54 | 9.05 | 5.24 |
| | 11C-ii 0.1% | 92.91 | 0.22 | 0.86 | 0.62 | 8.06 | 4.10 |
| 2 Months | 11C-i 0.5% | 88.81 | 0.09 | 1.65 | 0.56 | 10.53 | 6.72 |
| | 11C-ii 0.1% | 88.46 | 0.14 | 1.31 | 0.51 | 10.53 | 6.57 |
| 3 Months | 11C-i 0.5% | 87.23 | 0.19 | 2.10 | 0.55 | 12.07 | 8.26 |
| | 11C-ii 0.1% | 87.21 | 0.25 | 1.71 | 0.53 | 12.17 | 8.21 |

The results of stability testing of Example 11C-i-ii at 55° C. are set forth in Table 74 below.

TABLE 74

| Myristic acid 55° C. | | Potency % | CBD % | CBN % | D8-THC % | Total Impurities % | Increase + % |
|---|---|---|---|---|---|---|---|
| Zero | 11C-i 0.5% | 100.00 | 0.06 | 0.53 | 0.54 | 3.81 | |
| | 11C-ii 0.1% | 100.00 | 0.02 | 0.56 | 0.60 | 3.96 | |
| 1 Week | 11C-i 0.5% | 97.34 | 0.01 | 0.81 | 0.59 | 6.29 | 2.48 |
| | 11C-ii 0.1% | 96.34 | 0.02 | 0.73 | 0.54 | 6.53 | 2.57 |
| 2 Weeks | 11C-i 0.5% | 93.76 | 0.01 | 1.32 | 0.59 | 8.81 | 5.00 |
| | 11C-ii 0.1% | 91.41 | 0.01 | 1.17 | 0.51 | 9.05 | 5.09 |

EXAMPLE 11D

Dronabinol Solution in Sesame Oil Sourced from Arista—Vials

In Example 11D, dronabinol formulations 11D-i and 11D-ii were prepared in accordance with Examples 11A-i and 11A-ii using sesame oil sourced from Arista. Formulation 11A-i contained 0.5% myristic acid and formulation 11A-ii contained 0.1% myristic acid. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 11D-i-ii at 25° C. are set forth in Table 75 below.

TABLE 75

| Myristic acid 25° C. | | Potency % | CBD % | CBN % | D8-THC % | Total Impurities % | Increase + % |
|---|---|---|---|---|---|---|---|
| Zero | 11D-i 0.5% | 100.00 | 0.03 | 0.52 | 0.50 | 3.95 | |
| | 11D-ii 0.1% | 100.00 | 0.02 | 0.49 | 0.51 | 3.91 | |
| 3 Months | 11D-i 0.5% | 94.69 | 0.25 | 0.73 | 0.48 | 5.44 | 1.49 |
| | 11D-ii 0.1% | 92.42 | 0.32 | 0.56 | 0.48 | 5.61 | 1.70 |
| 6 Months | 11D-i 0.5% | 97.08 | 0.30 | 1.14 | 0.50 | 7.22 | 3.27 |
| | 11D-ii 0.1% | 94.41 | 0.38 | 0.82 | 0.46 | 8.08 | 4.17 |

The results of stability testing of Example 11D-i-ii at 40° C. are set forth in Table 76 below.

TABLE 76

| Myristic acid 40° C. | | Potency % | CBD % | CBN % | D8-THC % | Total Impurities % | Increase + % |
|---|---|---|---|---|---|---|---|
| Zero | 11D-i 0.5% | 100.00 | 0.03 | 0.52 | 0.50 | 3.95 | |
| | 11D-ii 0.1% | 100.00 | 0.02 | 0.49 | 0.51 | 3.91 | |
| 1 Month | 11D-i 0.5% | 94.98 | 0.16 | 0.72 | 0.53 | 6.21 | 2.26 |
| | 11D-ii 0.1% | 93.33 | 0.16 | 0.53 | 0.55 | 6.33 | 2.42 |
| 2 Months | 11D-i 0.5% | 91.54 | 0.32 | 1.12 | 0.47 | 8.02 | 4.07 |
| | 11D-ii 0.1% | 89.55 | 0.42 | 0.75 | 0.54 | 9.37 | 5.46 |
| 3 Months | 11D-i 0.5% | 88.57 | 0.36 | 2.00 | 0.50 | 12.95 | 9.00 |
| | 11D-ii 0.1% | 85.47 | 0.54 | 1.35 | 0.52 | 14.98 | 11.07 |

The results of stability testing of Example 11D-i-ii at 55° C. are set forth in Table 77 below.

TABLE 77

| Myristic acid 55° C. | | Potency % | CBD % | CBN % | THC % | D8-% | Total Impurities Increase + % |
|---|---|---|---|---|---|---|---|
| Zero | 11D-i 0.5% | 100.00 | 0.03 | 0.52 | 0.50 | 3.95 | |
| | 11D-ii 0.1% | 100.00 | 0.02 | 0.49 | 0.51 | 3.91 | |
| 1 Week | 11D-i 0.5% | 91.53 | 0.03 | 1.53 | 0.59 | 10.33 | 6.38 |
| | 11D-ii 0.1% | 87.94 | 0.01 | 0.92 | 0.49 | 13.11 | 9.20 |
| 2 Weeks | 11D-i 0.5% | 88.83 | 0.01 | 2.10 | 0.55 | 12.76 | 8.81 |
| | 11D-ii 0.1% | 71.58 | 0.03 | 2.16 | 0.58 | 23.69 | 19.78 |

EXAMPLE 11E

Dronabinol Solution in Sesame Oil Sourced from Croda—Vials

In Example 11E, dronabinol formulations 11E-i and 11E-ii were prepared in accordance with Examples 11B-i and 11B-ii using sesame oil sourced from Croda. Formulation 11E-i contained 0.5% myristic acid and formulation 11E-ii contained 0.1% myristic acid. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 11E-i-ii at 25° C. are set forth in Table 78 below.

TABLE 78

| Myristic acid 25° C. | | Potency % | CBD % | CBN % | THC % | D8-% | Total Impurities Increase + % |
|---|---|---|---|---|---|---|---|
| Zero | 11E-i 0.5% | 100.00 | 0.03 | 0.48 | 0.65 | 5.69 | |
| | 11E-ii 0.1% | 100.00 | 0.02 | 0.46 | 0.62 | 2.29 | |
| 3 Months | 11E-i 0.5% | 80.55 | 2.17 | 2.98 | 0.61 | 17.38 | 11.69 |
| | 11E-ii 0.1% | 81.10 | 3.13 | 1.26 | 0.52 | 19.40 | 14.11 |
| 6 Months | 11E-i 0.5% | 73.95 | 1.48 | 6.08 | 0.78 | 24.05 | 18.36 |
| | 11E-ii 0.1% | 74.74 | 3.36 | 2.78 | 0.53 | 24.73 | 19.44 |

The results of stability testing of Example 11E-i-ii at 40° C. are set forth in Table 79 below.

TABLE 79

| Myristic acid 40° C. | | Potency % | CBD % | CBN % | THC % | D8-% | Total Impurities Increase + % |
|---|---|---|---|---|---|---|---|
| Zero | 11E-i 0.5% | 100.00 | 0.03 | 0.48 | 0.65 | 5.69 | |
| | 11E-ii 0.1% | 100.00 | 0.02 | 0.46 | 0.62 | 2.29 | |
| 1 Month | 11E-i 0.5% | 86.99 | 1.07 | 2.12 | 0.59 | 14.05 | 8.36 |
| | 11E-ii 0.1% | 75.78 | 3.06 | 1.74 | 0.56 | 24.01 | 18.72 |
| 2 Months | 11E-i 0.5% | 74.43 | 1.22 | 4.09 | 0.68 | 20.17 | 14.48 |
| | 11E-ii 0.1% | 61.23 | 3.47 | 3.52 | 0.63 | 30.90 | 25.61 |
| 3 Months | 11E-i 0.5% | 66.67 | 1.13 | 6.94 | 0.69 | 28.15 | 22.46 |
| | 11E-ii 0.1% | 54.34 | 2.95 | 5.83 | 0.74 | 36.97 | 31.68 |

The results of stability testing of Example 11E-i-ii at 55° C. are set forth in Table 80 below.

TABLE 80

| Myristic acid 55° C. | | Potency % | CBD % | CBN % | THC % | D8-% | Total Impurities Increase + % |
|---|---|---|---|---|---|---|---|
| Zero | 11E-i 0.5% | 100.00 | 0.03 | 0.48 | 0.65 | 5.69 | |
| | 11E-ii 0.1% | 100.00 | 0.02 | 0.46 | 0.62 | 2.29 | |
| 1 Week | 11E-i 0.5% | 87.77 | 0.01 | 1.99 | 0.63 | 14.67 | 8.98 |
| | 11E-ii 0.1% | 85.94 | 0.03 | 0.96 | 0.52 | 17.11 | 11.82 |
| 2 Weeks | 11E-i 0.5% | 46.26 | 0.05 | 10.13 | 1.16 | 45.43 | 39.74 |
| | 11E-ii 0.1% | 33.85 | 0.09 | 5.57 | 0.65 | 57.47 | 52.18 |

EXAMPLE 11F

Dronabinol Solution in Sesame Oil Sourced from Dipasa—Vials

In Example 11F, dronabinol formulations 11F-i and 11F-ii were prepared in accordance with Examples 11C-i and 11C-ii using sesame oil sourced from Dipasa. Formulation 11F-i contained 0.5% myristic acid and formulation 11F-ii contained 0.1% myristic acid. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 11F-i-ii at 25° C. are set forth in Table 81 below.

TABLE 81

| Myristic acid 25° C. | | Potency % | CBD % | CBN % | THC % | D8-% | Total Impurities Increase + % |
|---|---|---|---|---|---|---|---|
| Zero | 11F-i 0.5% | 100.00 | 0.06 | 0.53 | 0.54 | 3.81 | |
| | 11F-ii 0.1% | 100.00 | 0.02 | 0.56 | 0.60 | 3.96 | |
| 3 Months | 11F-i 0.5% | 92.80 | 0.21 | 0.82 | 0.52 | 5.56 | 1.75 |
| | 11F-ii 0.1% | 93.41 | 0.23 | 0.74 | 0.53 | 5.55 | 1.59 |
| 6 Months | 11F-i 0.5% | 95.57 | 0.29 | 1.28 | 0.55 | 7.66 | 3.85 |
| | 11F-ii 0.1% | 94.87 | 0.37 | 1.06 | 0.58 | 7.86 | 3.90 |

The results of stability testing of Example 11F-i-ii at 40° C. are set forth in Table 82 below.

TABLE 82

| Myristic acid 40° C. | | Potency % | CBD % | CBN % | THC % | D8-% | Total Impurities Increase + % |
|---|---|---|---|---|---|---|---|
| Zero | 11F-i 0.5% | 100.00 | 0.06 | 0.53 | 0.54 | 3.81 | |
| | 11F-ii 0.1% | 100.00 | 0.02 | 0.56 | 0.60 | 3.96 | |
| 1 Month | 11F-i 0.5% | 94.33 | 0.14 | 0.86 | 0.61 | 6.78 | 2.97 |
| | 11F-ii 0.1% | 94.02 | 0.14 | 0.74 | 0.60 | 6.34 | 2.38 |
| 2 Months | 11F-i 0.5% | 89.60 | 0.26 | 1.47 | 0.62 | 9.75 | 5.94 |
| | 11F-ii 0.1% | 89.94 | 0.39 | 1.24 | 0.64 | 10.12 | 6.16 |
| 3 Months | 11F-i 0.5% | 86.61 | 0.34 | 2.45 | 0.55 | 14.47 | 10.66 |
| | 11F-ii 0.1% | 86.26 | 0.50 | 2.01 | 0.56 | 15.46 | 11.50 |

The results of stability testing of Example 11F-i-ii at 55° C. are set forth in Table 83 below.

TABLE 83

| | Myristic acid 55° C. | Potency % | CBD % | CBN % | D8-THC % | Total Impurities Increase + % |
|---|---|---|---|---|---|---|
| Zero | 11F-i 0.5% | 100.00 | 0.06 | 0.53 | 0.54 | 3.81 |
| | 11F-ii 0.1% | 100.00 | 0.02 | 0.56 | 0.60 | 3.96 |
| 1 Week | 11F-i 0.5% | 97.34 | 0.01 | 0.81 | 0.59 | 6.29 | 2.48 |
| | 11F-ii 0.1% | 96.34 | 0.02 | 0.73 | 0.54 | 6.53 | 2.57 |
| 2 Weeks | 11F-i 0.5% | 93.76 | 0.01 | 1.32 | 0.59 | 8.81 | 5.00 |
| | 11F-ii 0.1% | 91.41 | 0.01 | 1.17 | 0.51 | 9.05 | 5.09 |

As can be seen from the above results, myristic acid imparts instability to dronabinol formulation at all temperature conditions studied. However, dronabinol in sesame oil sourced from Dipasa is resistant to degradation from exposure to myristic acid to some extent. This stability can be attributed to the presence of high levels of the antioxidant lecithin in sesame oil sourced from Dipasa.

EXAMPLE 12

Stability Results—Presence of Base(s)

In Example 12, the effect of added bases in dronabinol formulated as a sesame oil solution was evaluated. In each of Examples 12-i-12-xiv, the specified amount of base was added to the formulation prepared in accordance with Example 1.

Example 12-i is a solution of dronabinol (3.03% w/w) and 2% (w/v) ethanolamine in sesame oil, NF (by Arista).

Example 12-ii is a solution of dronabinol (3.03% w/w) and 1% (w/v) ethanolamine in sesame oil, NF (by Arista).

Example 12-iii is a solution of dronabinol (3.03% w/w) and 0.5% (w/v) ethanolamine in sesame oil, NF (by Arista).

Example 12-iv is a solution of dronabinol (3.03% w/w) and 0.1% (w/v) ethanolamine in sesame oil, NF (by Arista).

Example 12-v is a solution of dronabinol (3.03% w/w) and 0.05% (w/v) ethanolamine in sesame oil, NF (by Arista).

Example 12-vi is a solution of dronabinol (3.03% w/w) and 0.07% (w/v) ethanolamine in sesame oil, NF (by Arista).

Example 12-vii is a solution of dronabinol (3.03% w/w) and 2% (w/v) ethanolamine in sesame oil, super refined NF (by Croda).

Example 12-viii is solution of dronabinol (3.03% w/w) and 1% (w/v) ethanolamine in sesame oil, super refined NF (by Croda).

Example 12-ix is a solution of dronabinol (3.03% w/w) and 0.5% (w/v) ethanolamine in sesame oil, super refined NF (by Croda).

Example 12-x is a solution of dronabinol (3.03% w/w) and 0.1% (w/v) ethanolamine in sesame oil, super refined NF (by Croda).

Example 12-xi is a solution of dronabinol (3.03% w/w) and 0.05% (w/v) ethanolamine in sesame oil, super refined NF (by Croda).

Example 12-xii is a solution of dronabinol (3.03% w/w) and 0.07% (w/v) ethanolamine in sesame oil, super refined NF (by Croda).

Example 12-xiii is a solution of dronabinol (3.03% w/w) and 0.01% (w/v) meglumine in sesame oil, NF (by Arista).

Example 12-xiv is a solution of dronabinol (3.03% w/w) and 0.1% (w/v) ethanolamine in sesame oil, NF (by Arista).

A summary of the compositions of Examples 12i-12iv is set forth in Table 84 below:

TABLE 84

| | Composition | | |
|---|---|---|---|
| Formulation No. | Dronabinol | Sesame Oil | Other Ingredients |
| Example 12-i | 3.03% w/w | QS | Ethanolamine (2%) |
| Example 12-ii | 3.03% w/w | QS | Ethanolamine (1%) |
| Example 12-iii | 3.03% w/w | QS | Ethanolamine (0.5%) |
| Example 12-iv | 3.03% w/w | QS | Ethanolamine (0.1%) |
| Example 12-v | 3.03% w/w | QS | Ethanolamine (0.05%) |
| Example 12-vi | 3.03% w/w | QS | Ethanolamine (0.07%) |
| Example 12-vii | 3.03% w/w | QS | Ethanolamine (2%) |
| Example 12-viii | 3.03% w/w | QS | Ethanolamine (1%) |
| Example 12-ix | 3.03% w/w | QS | Ethanolamine (0.5%) |
| Example 12-x | 3.03% w/w | QS | Ethanolamine (0.1%) |
| Example 12-xi | 3.03% w/w | QS | Ethanolamine (0.05%) |
| Example 12-xii | 3.03% w/w | QS | Ethanolamine (0.07%) |
| Example 12-xiii | 3.03% w/w | QS | meglumine (0.01%) |
| Example 12-xiv | 3.03% w/w | QS | Ethanolamine (0.1%) |

The formulations were stored in amber glass vials at 55° C. and placed under accelerated stability conditions at 55° C. The results of the stability study after one week are presented in Table 85 and after two weeks are presented in Table 86.

Table 85: Stability of Dronabinol Formulations in the Presence of Bases at 55° C., 1 week

TABLE 85

| FORMULATION* # | ASSAY % | TOTAL IMPURITY % | RELATED SUBSTANCES | | |
|---|---|---|---|---|---|
| | | | D8THC % | CBN % | CBD % |
| Example 12-i (A + EA 2%) | 91.97 | 8.03 | 0.59 | 1.30 | 0.55 |
| Example 12-iii (A + EA 0.5%) | 94.58 | 5.42 | 0.43 | 1.21 | 0.32 |
| Example 12-v (A + EA 0.05%) | 93.82 | 6.18 | 0.43 | 1.20 | 0.15 |
| Example 12-xiii (A + Meglumine 0.01%) | 95.14 | 4.86 | 0.35 | 0.64 | 0.49 |
| Example 12-xiv (A + EA 0.1%) | 95.01 | 4.99 | 0.56 | 0.86 | 0.35 |
| Example 12-viii (C + EA 1%) | 94.56 | 5.44 | 0.45 | 1.23 | 0.48 |
| Example 12-xj (C + EA 0.1%) | 94.65 | 5.35 | 0.50 | 1.22 | 0.12 |
| Example 12-xii (C + EA 0.007%) | 94.09 | 5.95 | 0.47 | 1.24 | 0.25 |

*A = Arista, C = Croda, EA = Ethanolamine

Table 86: Stability of Dronabinol Formulations in the Presence of Bases at 55° C., 2 weeks

TABLE 86

| FORMULATION* # | ASSAY % | TOTAL IMPURITY % | RELATED SUBSTANCES | | |
|---|---|---|---|---|---|
| | | | D8THC % | CBN % | CBD % |
| Example 12-i (A + EA 2%) | 91.16 | 8.84 | 0.51 | 2.00 | 0.67 |
| Example 12-iii (A + EA 0.5%) | 93.88 | 6.12 | 0.47 | 1.57 | 0.31 |
| Example 12-v (A + EA 0.05%) | 92.07 | 7.93 | 0.46 | 1.87 | 0.10 |
| Example 12-xiii (A + Meglumine 0.01%) | 92.17 | 7.83 | 0.48 | 1.30 | 0.42 |
| Example 12-xiv (A + EA 1%) | 91.63 | 8.37 | 0.56 | 2.28 | 0.17 |
| Example 12-viii (C + EA 1%) | 93.53 | 6.47 | 0.53 | 1.70 | 0.65 |

TABLE 86-continued

| FORMULATION* # | ASSAY % | TOTAL IMPURITY % | RELATED SUBSTANCES | | |
|---|---|---|---|---|---|
| | | | D8THC % | CBN % | CBD % |
| Example 12-x (C + EA 0.1%) | 92.68 | 7.32 | 0.54 | 1.51 | 0.13 |
| Example 12-xii (C + EA 0.007%) | 91.49 | 8.51 | 0.47 | 1.78 | 0.06 |

*A = Arista, C = Croda, EA = Ethanolamine

A significant improvement in the stability of dronabinol formulations was observed for all the bases (amines) studied.

Extended Stability Results—Addition of Base(s)

To confirm whether the addition of the organic bases monoethanolamine or meglumine to the dronabinol formulations created more stabile formulations, stability studies at room temperature and at accelerated conditions over an extended period of time were conducted using sesame oil from Arista, Croda and Dipasa.

EXAMPLE 12A

Dronabinol Solution in Sesame Oil Sourced from Arista—Capsules

In Example 12A, dronabinol formulations 12A-i, 12A-ii and 12A-iii were prepared in accordance with Examples 12-ii, 12-iii and 12-iv, respectively using sesame oil sourced from Arista. Formulation 12A-i contained 1% monoethanolamine, formulation 12A-ii contained 0.5% monoethanolamine and 12A-iii contained 0.01% monoethanolamine. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 12A-i-iii at 25° C. are set forth in Table 87 below.

TABLE 87

| Monoethanolamine | | Potency % | CBD % | CBN % | D8-THC % | Total Impurities | |
|---|---|---|---|---|---|---|---|
| | 25° C. | | | | | % | Increase + % |
| Zero | 12A-i 1% | 100.00 | 0.02 | 0.72 | 0.52 | 4.90 | |
| | 12A-ii 0.5% | 100.00 | 0.01 | 0.58 | 0.49 | 4.14 | |
| | 12A-iii 0.01% | 100.00 | 0.02 | 0.50 | 0.54 | 3.71 | |
| 3 Months | 12A-i 1% | 97.48 | 0.11 | 0.81 | 0.51 | 5.13 | 0.23 |
| | 12A-ii 0.5% | 96.11 | 0.20 | 0.71 | 0.47 | 5.16 | 1.02 |
| | 12A-iii 0.01% | 90.67 | 0.65 | 0.67 | 0.43 | 10.23 | 6.52 |
| 6 Months | 12A-i 1% | 99.48 | 0.14 | 0.93 | 0.52 | 5.65 | 0.75 |
| | 12A-ii 0.5% | 100.72 | 0.19 | 0.85 | 0.51 | 5.85 | 1.71 |
| | 12A-iii 0.01% | 91.63 | 1.04 | 0.87 | 0.51 | 12.50 | 8.79 |

The results of stability testing of Example 12A-i-iii at 40° C. are set forth in Table 88 below.

TABLE 88

| Monoethanolamine | | | | | | Total Impurities | |
|---|---|---|---|---|---|---|---|
| | 40° C. | Potency % | CBD % | CBN % | D8-THC % | % | Increase + % |
| Zero | 12A-i 1% | 100.00 | 0.02 | 0.72 | 0.52 | 4.90 | |
| | 12A-ii 0.5% | 100.00 | 0.01 | 0.58 | 0.49 | 4.14 | |
| | 12A-iii 0.01% | 100.00 | 0.02 | 0.50 | 0.54 | 3.71 | |
| 1 Month | 12A-i 1% | 98.57 | 0.13 | 0.70 | 0.51 | 5.19 | 0.29 |
| | 12A-ii 0.5% | 98.53 | 0.24 | 0.75 | 0.48 | 5.71 | 1.57 |
| | 12A-iii 0.01% | 91.50 | 0.66 | 0.68 | 0.48 | 10.49 | 6.78 |
| 2 Months | 12A-i 1% | 96.11 | 0.08 | 0.97 | 0.50 | 5.23 | 0.33 |
| | 12A-ii 0.5% | 97.47 | 0.16 | 1.05 | 0.49 | 5.91 | 1.77 |
| | 12A-iii 0.01% | 90.79 | 0.40 | 0.78 | 0.48 | 10.84 | 7.13 |
| 3 Months | 12A-i 1% | 96.30 | 0.17 | 1.39 | 0.47 | 4.96 | 0.06 |
| | 12A-ii 0.5% | 94.76 | 0.24 | 1.32 | 0.39 | 5.75 | 1.61 |
| | 12A-iii 0.01% | 89.19 | 0.66 | 0.99 | 0.44 | 11.40 | 7.69 |

The results of stability testing of Example 12A-i-iii at 55° C. are set forth in Table 89 below.

TABLE 89

| Monoethanolamine | | | | | | Total Impurities | |
|---|---|---|---|---|---|---|---|
| | 55° C. | Potency % | CBD % | CBN % | D8-THC % | % | Increase + % |
| Zero | 12A-i 1% | 100.00 | 0.02 | 0.72 | 0.52 | 4.90 | |
| | 12A-ii 0.5% | 100.00 | 0.01 | 0.58 | 0.49 | 4.14 | |
| | 12A-iii 0.01% | 100.00 | 0.02 | 0.50 | 0.54 | 3.71 | |
| 1 Week | 12A-i 1% | 98.76 | 0.01 | 1.01 | 0.55 | 6.61 | 1.71 |
| | 12A-ii 0.5% | 96.97 | 0.01 | 0.88 | 0.53 | 6.15 | 2.01 |
| | 12A-iii 0.01% | 97.85 | 0.02 | 0.50 | 0.51 | 6.14 | 2.43 |
| 2 Weeks | 12A-i 1% | 96.66 | 0.01 | 1.38 | 0.52 | 7.32 | 2.42 |
| | 12A-ii 0.5% | 97.17 | 0.01 | 1.17 | 0.53 | 7.23 | 3.09 |
| | 12A-iii 0.01% | 97.56 | 0.01 | 0.53 | 0.51 | 7.77 | 4.06 |

EXAMPLE 12B

Dronabinol Solution in Sesame Oil Sourced from Croda—Capsules

In Example 12B, dronabinol formulations 12B-i, 12B-ii and 12B-iii were prepared in accordance with Examples 12-viii, 12-ix and 12-x, respectively using sesame oil sourced from Croda. Formulation 12B-i contained 1% monoethanolamine, formulation 12B-ii contained 0.5% monoethanolamine and 12B-iii contained 0.01% monoethanolamine. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 12B-i-iii at 25° C. are set forth in Table 90 below.

TABLE 90

| Monoethanolamine | | | | | | Total Impurities | |
|---|---|---|---|---|---|---|---|
| | 25° C. | Potency % | CBD % | CBN % | D8-THC % | % | Increase + % |
| Zero | 12B-i 1% | 100.00 | 0.01 | 0.60 | 0.53 | 6.71 | |
| | 12B-ii 0.5% | 100.00 | 0.03 | 0.55 | 0.58 | 5.35 | |
| | 12B-iii 0.01% | 100.00 | 0.01 | 0.44 | 0.58 | 3.99 | |
| 3 Months | 12B-i 1% | 93.45 | 0.25 | 0.78 | 0.58 | 6.36 | −0.35 |
| | 12B-ii 0.5% | 91.37 | 0.41 | 0.89 | 0.53 | 6.36 | 1.01 |
| | 12B-iii 0.01% | 89.10 | 0.65 | 0.55 | 0.49 | 12.83 | 8.84 |
| 6 Months | 12B-i 1% | 98.56 | 0.08 | 0.93 | 0.59 | 6.50 | −0.21 |
| | 12B-ii 0.5% | 98.51 | 0.18 | 1.18 | 0.57 | 6.62 | 1.27 |
| | 12B-iii 0.01% | 96.84 | 0.36 | 0.75 | 0.55 | 6.87 | 3.07 |

The results of stability testing of Example 12B-i-iii at 40° C. are set forth in Table 91 below.

TABLE 91

| Monoethanolamine | | Potency % | CBD % | CBN % | D8-THC % | Total Impurities | |
|---|---|---|---|---|---|---|---|
| 40° C. | | | | | | % | Increase + % |
| Zero | 12B-i 1% | 100.00 | 0.01 | 0.60 | 0.53 | 6.71 | |
| | 12B-ii 0.5% | 100.00 | 0.03 | 0.55 | 0.58 | 5.35 | |
| | 12B-iii 0.01% | 100.00 | 0.01 | 0.44 | 0.58 | 3.99 | |
| 1 Month | 12B-i 1% | 96.77 | 0.19 | 0.81 | 0.57 | 6.46 | −0.25 |
| | 12B-ii 0.5% | 96.45 | 0.36 | 1.02 | 0.55 | 7.24 | 1.89 |
| | 12B-iii 0.01% | 90.39 | 0.91 | 0.60 | 0.56 | 12.34 | 8.35 |
| 2 Months | 12B-i 1% | 94.28 | 0.14 | 1.05 | 0.54 | 6.38 | −0.33 |
| | 12B-ii 0.5% | 93.34 | 0.15 | 1.41 | 0.52 | 7.40 | 2.05 |
| | 12B-iii 0.01% | 87.54 | 0.56 | 0.64 | 0.54 | 12.64 | 8.65 |
| 3 Months | 12B-i 1% | 94.00 | 0.46 | 1.44 | 0.52 | 6.47 | −0.24 |
| | 12B-ii 0.5% | 93.05 | 0.30 | 1.75 | 0.47 | 7.69 | 2.34 |
| | 12B-iii 0.01% | 85.61 | 0.91 | 0.85 | 0.54 | 14.32 | 10.33 |

The results of stability testing of Example 12B-i-iii at 55° C. are set forth in Table 92 below.

TABLE 92

| Monoethanolamine | | Potency % | CBD % | CBN % | D8-THC % | Total Impurities | |
|---|---|---|---|---|---|---|---|
| 55° C. | | | | | | % | Increase + % |
| Zero | 12B-i 1% | 100.00 | 0.01 | 0.60 | 0.53 | 6.71 | |
| | 12B-ii 0.5% | 100.00 | 0.03 | 0.55 | 0.58 | 5.35 | |
| | 12B-iii 0.01% | 100.00 | 0.01 | 0.44 | 0.58 | 3.99 | |
| 1 Week | 12B-i 1% | 96.00 | 0.01 | 0.94 | 0.58 | 7.79 | 1.08 |
| | 12B-ii 0.5% | 97.27 | 0.07 | 0.99 | 0.57 | 7.30 | 1.95 |
| | 12B-iii 0.01% | 91.46 | 0.03 | 0.48 | 0.54 | 14.81 | 10.82 |
| 2 Weeks | 12B-i 1% | 92.98 | 0.01 | 1.55 | 0.60 | 8.43 | 1.72 |
| | 12B-ii 0.5% | 99.09 | 0.01 | 1.45 | 0.58 | 7.71 | 2.36 |
| | 12B-iii 0.01% | 31.14 | 0.08 | 2.79 | 0.56 | 63.47 | 59.48 |

EXAMPLE 12C

Dronabinol Solution in Sesame Oil Sourced from Dipasa—Capsules

In Example 12C, dronabinol formulations 12C-i, 12C-ii and 12C-iii were prepared in accordance with Examples 12B-i-iii respectively using sesame oil sourced from Dipasa. Formulation 12C-i contained 1% monoethanolamine, formulation 12C-ii contained 0.5% monoethanolamine and 12C-iii contained 0.01% monoethanolamine. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 12C-i-iii at 25° C. are set forth in Table 93 below.

TABLE 93

| Monoethanolamine | | Potency % | CBD % | CBN % | D8-THC % | Total Impurities | |
|---|---|---|---|---|---|---|---|
| 25° C. | | | | | | % | Increase + % |
| Zero | 12C-i 1% | 100.00 | 0.02 | 0.72 | 0.56 | 5.45 | |
| | 12C-ii 0.5% | 100.00 | 0.02 | 0.61 | 0.54 | 4.31 | |
| | 12C-iii 0.01% | 100.00 | 0.03 | 0.53 | 0.58 | 3.80 | |

TABLE 93-continued

| Monoethanolamine | | Potency % | CBD % | CBN % | D8-THC % | Total Impurities | |
|---|---|---|---|---|---|---|---|
| 25° C. | | | | | | % | Increase + % |
| 3 Months | 12C-i 1% | 94.00 | 0.22 | 0.87 | 0.56 | 5.44 | −0.01 |
| | 12C-ii 0.5% | 94.33 | 0.08 | 0.84 | 0.52 | 5.17 | 0.86 |
| | 12C-iii 0.01% | 94.26 | 0.18 | 0.61 | 0.50 | 4.88 | 1.08 |
| 6 Months | 12C-i 1% | 97.99 | 0.16 | 0.97 | 0.55 | 5.99 | 0.54 |
| | 12C-ii 0.5% | 98.95 | 0.12 | 1.05 | 0.53 | 5.43 | 1.12 |
| | 12C-iii 0.01% | 96.84 | 0.36 | 0.75 | 0.55 | 6.87 | 3.07 |

The results of stability testing of Example 12C-i-iii at 40° C. are set forth in Table 94 below.

TABLE 94

| Monoethanolamine | | Potency % | CBD % | CBN % | D8-THC % | Total Impurities | |
|---|---|---|---|---|---|---|---|
| 40° C. | | | | | | % | Increase + % |
| Zero | 12C-i 1% | 100.00 | 0.02 | 0.72 | 0.56 | 5.45 | |
| | 12C-ii 0.5% | 100.00 | 0.02 | 0.61 | 0.54 | 4.31 | |
| | 12C-iii 0.01% | 100.00 | 0.03 | 0.53 | 0.58 | 3.80 | |
| 1 Month | 12C-i 1% | 95.73 | 0.13 | 0.76 | 0.51 | 5.29 | −0.16 |
| | 12C-ii 0.5% | 96.70 | 0.16 | 0.87 | 0.52 | 5.38 | 1.07 |
| | 12C-iii 0.01% | 95.42 | 0.29 | 0.61 | 0.54 | 6.74 | 2.94 |
| 2 Months | 12C-i 1% | 94.07 | 0.06 | 0.91 | 0.57 | 5.32 | −0.13 |
| | 12C-ii 0.5% | 94.47 | 0.10 | 1.16 | 0.53 | 5.55 | 1.24 |
| | 12C-iii 0.01% | 91.05 | 0.16 | 0.82 | 0.55 | 9.25 | 5.45 |
| 3 Months | 12C-i 1% | 93.60 | 0.28 | 1.24 | 0.47 | 5.45 | 0.00 |
| | 12C-ii 0.5% | 93.68 | 0.13 | 1.47 | 0.52 | 6.21 | 1.90 |
| | 12C-iii 0.01% | 90.49 | 0.33 | 1.19 | 0.56 | 10.39 | 6.59 |

The results of stability testing of Example 12C-i-iii at 55° C. are set forth in Table 95 below.

TABLE 95

| Monoethanolamine | | Potency % | CBD % | CBN % | D8-THC % | Total Impurities | |
|---|---|---|---|---|---|---|---|
| 55° C. | | | | | | % | Increase + % |
| Zero | 12C-i 1% | 100.00 | 0.02 | 0.72 | 0.56 | 5.45 | |
| | 12C-ii 0.5% | 100.00 | 0.02 | 0.61 | 0.54 | 4.31 | |
| | 12C-iii 0.01% | 100.00 | 0.03 | 0.53 | 0.58 | 3.80 | |
| 1 Week | 12C-i 1% | 95.67 | 0.01 | 0.95 | 0.55 | 6.86 | 1.41 |
| | 12C-ii 0.5% | 97.38 | 0.05 | 0.93 | 0.55 | 6.03 | 1.72 |
| | 12C-iii 0.01% | 97.08 | 0.01 | 0.56 | 0.54 | 6.57 | 2.77 |
| 2 Weeks | 12C-i 1% | 94.76 | 0.01 | 0.51 | 0.52 | 6.85 | 1.40 |
| | 12C-ii 0.5% | 97.43 | 0.02 | 1.35 | 0.54 | 6.96 | 2.65 |
| | 12C-iii 0.01% | 97.56 | 0.01 | 0.73 | 0.54 | 8.48 | 4.68 |

EXAMPLE 12D

Dronabinol Solution in Sesame Oil Sourced from Arista—Vials

In Example 12D, dronabinol formulations 12D-i, 12D-ii and 12D-iii were prepared in accordance with Examples 12A-i, 12A-ii and 12A-iii, respectively using sesame oil sourced from Arista. Formulation 12A-i contained 1% monoethanolamine, formulation 12A-ii contained 0.5% monoethanolamine and 12A-iii contained 0.01% monoethanolamine. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 12D-i-iii at 25° C. are set forth in Table 96 below.

TABLE 96

| | Monoethanolamine 25° C. | Potency % | CBD % | CBN % | D8-THC % | Total Impurities % | Increase + % |
|---|---|---|---|---|---|---|---|
| Zero | 12D-i 1% | 100.00 | 0.02 | 0.72 | 0.52 | 4.90 | |
| | 12D-ii 0.5% | 100.00 | 0.01 | 0.58 | 0.49 | 4.14 | |
| | 12D-iii 0.01% | 100.00 | 0.02 | 0.50 | 0.54 | 3.71 | |
| 3 Months | 12D-i 1% | 95.09 | 0.10 | 1.07 | 0.50 | 5.98 | 1.08 |
| | 12D-ii 0.5% | 95.26 | 0.34 | 0.86 | 0.48 | 5.53 | 1.39 |
| | 12D-iii 0.01% | 95.34 | 0.12 | 0.52 | 0.48 | 4.83 | 1.12 |
| 6 Months | 12D-i 1% | 99.49 | 0.06 | 1.48 | 0.51 | 6.62 | 1.72 |
| | 12D-ii 0.5% | 99.30 | 0.13 | 1.09 | 0.52 | 6.23 | 2.09 |
| | 12D-iii 0.01% | 98.65 | 0.16 | 0.59 | 0.48 | 6.22 | 2.51 |

The results of stability testing of Example 12D-i-iii at 40° C. are set forth in Table 97 below.

TABLE 97

| | Monoethanolamine 40° C. | Potency % | CBD % | CBN % | D8-THC % | Total Impurities % | Increase + % |
|---|---|---|---|---|---|---|---|
| Zero | 12D-i 1% | 100.00 | 0.02 | 0.72 | 0.52 | 4.90 | |
| | 12D-ii 0.5% | 100.00 | 0.01 | 0.58 | 0.49 | 4.14 | |
| | 12D-iii 0.01% | 100.00 | 0.02 | 0.50 | 0.54 | 3.71 | |
| 1 Month | 12D-i 1% | 95.67 | 0.16 | 1.11 | 0.56 | 6.13 | 1.23 |
| | 12D-ii 0.5% | 97.85 | 0.17 | 0.82 | 0.54 | 5.55 | 1.41 |
| | 12D-iii 0.01% | 95.46 | 0.08 | 0.46 | 0.54 | 5.62 | 1.91 |
| 2 Months | 12D-i 1% | 93.49 | 0.09 | 1.31 | 0.58 | 6.21 | 1.31 |
| | 12D-ii 0.5% | 93.65 | 0.16 | 1.04 | 0.54 | 6.30 | 2.16 |
| | 12D-iii 0.01% | 93.46 | 0.17 | 0.53 | 0.55 | 7.51 | 3.80 |
| 3 Months | 12D-i 1% | 93.40 | 0.48 | 2.03 | 0.45 | 7.92 | 3.02 |
| | 12D-ii 0.5% | 92.64 | 0.15 | 1.70 | 0.50 | 8.23 | 4.09 |
| | 12D-iii 0.01% | 91.13 | 0.27 | 0.76 | 0.47 | 10.43 | 6.72 |

The results of stability testing of Example 12D-i-iii at 55° C. are set forth in Table 98 below.

TABLE 98

| | Monoethanolamine | | | | | Total Impurities | |
|---|---|---|---|---|---|---|---|
| | 55° C. | Potency % | CBD % | CBN % | D8-THC % | % | Increase + % |
| Zero | 12D-i 1% | 100.00 | 0.02 | 0.72 | 0.52 | 4.90 | |
| | 12D-ii 0.5% | 100.00 | 0.01 | 0.58 | 0.49 | 4.14 | |
| | 12D-iii 0.01% | 100.00 | 0.02 | 0.50 | 0.54 | 3.71 | |
| 1 Week | 12D-i 1% | 98.76 | 0.01 | 1.01 | 0.55 | 6.61 | 1.71 |
| | 12D-ii 0.5% | 96.97 | 0.01 | 0.88 | 0.53 | 6.15 | 2.01 |
| | 12D-iii 0.01% | 97.85 | 0.02 | 0.50 | 0.51 | 6.14 | 2.43 |
| 2 Weeks | 12D-i 1% | 96.66 | 0.01 | 1.38 | 0.52 | 7.32 | 2.42 |
| | 12D-ii 0.5% | 97.17 | 0.01 | 1.17 | 0.53 | 7.23 | 3.09 |
| | 12D-iii 0.01% | 97.56 | 0.01 | 0.53 | 0.51 | 7.77 | 4.06 |

EXAMPLE 12E

Dronabinol Solution in Sesame Oil Sourced from Croda—Vials

In Example 12E, dronabinol formulations 12E-i, 12E-ii and 12E-iii were prepared in accordance with Examples 12B-i, 12B-ii and 12B-iii, respectively using sesame oil sourced from Croda. Formulation 12E-i contained 1% monoethanolamine, formulation 12E-ii contained 0.5% monoethanolamine and 12E-iii contained 0.01% monoethanolamine. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 12E-i-iii at 25° C. are set forth in Table 99 below.

TABLE 99

| | Monoethanolamine | | | | | Total Impurities | |
|---|---|---|---|---|---|---|---|
| | 25° C. | Potency % | CBD % | CBN % | D8-THC % | % | Increase + % |
| Zero | 12E-i 1% | 100.00 | 0.01 | 0.60 | 0.53 | 6.71 | |
| | 12E-ii 0.5% | 100.00 | 0.03 | 0.55 | 0.58 | 5.35 | |
| | 12E-iii 0.01% | 100.00 | 0.01 | 0.44 | 0.58 | 3.99 | |
| 3 Months | 12E-i 1% | 93.38 | 0.08 | 1.02 | 0.54 | 6.94 | 0.23 |
| | 12E-ii 0.5% | 94.64 | 0.27 | 0.94 | 0.54 | 6.26 | 0.91 |
| | 12E-iii 0.01% | 95.25 | 0.14 | 0.48 | 0.52 | 5.30 | 1.31 |
| 6 Months | 12E-i 1% | 97.78 | 0.03 | 1.40 | 0.57 | 7.43 | 0.72 |
| | 12E-ii 0.5% | 99.21 | 0.05 | 1.27 | 0.56 | 6.67 | 1.32 |
| | 12E-iii 0.01% | 97.81 | 0.16 | 0.51 | 0.54 | 6.97 | 2.98 |

The results of stability testing of Example 12E-i-iii at 40° C. are set forth in Table 100 below.

TABLE 100

| | Monoethanolamine | | | | | Total Impurities | |
|---|---|---|---|---|---|---|---|
| | 40° C. | Potency % | CBD % | CBN % | D8-THC % | % | Increase + % |
| Zero | 12E-i 1% | 100.00 | 0.01 | 0.60 | 0.53 | 6.71 | |
| | 12E-ii 0.5% | 100.00 | 0.03 | 0.55 | 0.58 | 5.35 | |
| | 12E-iii 0.01% | 100.00 | 0.01 | 0.44 | 0.58 | 3.99 | |
| 1 Month | 12E-i 1% | 95.45 | 0.16 | 1.37 | 0.62 | 7.12 | 0.41 |
| | 12E-ii 0.5% | 98.70 | 0.09 | 0.87 | 0.61 | 5.74 | 0.39 |

TABLE 100-continued

| Monoethanolamine | | | | | | Total Impurities | |
|---|---|---|---|---|---|---|---|
| | 40° C. | Potency % | CBD % | CBN % | D8-THC % | % | Increase + % |
| | 12E-iii 0.01% | 85.86 | 0.57 | 0.54 | 0.58 | 16.05 | 12.06 |
| 2 Months | 12E-i 1% | 93.25 | 0.11 | 1.26 | 0.58 | 7.52 | 0.81 |
| | 12E-ii 0.5% | 91.93 | 0.17 | 1.21 | 0.71 | 7.90 | 2.55 |
| | 12E-iii 0.01% | 70.93 | 1.27 | 0.93 | 0.54 | 26.35 | 22.36 |
| 3 Months | 12E-i 1% | 92.64 | 0.49 | 2.11 | 0.56 | 8.80 | 2.09 |
| | 12E-ii 0.5% | 93.61 | 0.06 | 1.73 | 0.52 | 7.28 | 1.93 |
| | 12E-iii 0.01% | 61.88 | 1.48 | 1.66 | 0.57 | 34.77 | 30.78 |

The results of stability testing of Example 12E-i-iii at 55° C. are set forth in Table 101 below.

TABLE 101

| Monoethanolamine | | | | | | Total Impurities | |
|---|---|---|---|---|---|---|---|
| | 55° C. | Potency % | CBD % | CBN % | D8-THC % | % | Increase + % |
| Zero | 12E-i 1% | 100.00 | 0.01 | 0.60 | 0.53 | 6.71 | |
| | 12E-ii 0.5% | 100.00 | 0.03 | 0.55 | 0.58 | 5.35 | |
| | 12E-iii 0.01% | 100.00 | 0.01 | 0.44 | 0.58 | 3.99 | |
| 1 Week | 12E-i 1% | 96.00 | 0.01 | 0.94 | 0.58 | 7.79 | 1.08 |
| | 12E-ii 0.5% | 97.27 | 0.07 | 0.99 | 0.57 | 7.30 | 1.95 |
| | 12E-iii 0.01% | 91.46 | 0.03 | 0.48 | 0.54 | 14.81 | 10.82 |
| 2 Weeks | 12E-i 1% | 92.98 | 0.01 | 1.55 | 0.60 | 8.43 | 1.72 |
| | 12E-ii 0.5% | 99.09 | 0.01 | 1.45 | 0.58 | 7.71 | 2.36 |
| | 12E-iii 0.01% | 31.14 | 0.08 | 2.79 | 0.56 | 63.47 | 59.48 |

EXAMPLE 12F

Dronabinol Solution in Sesame Oil Sourced from Dipasa—Vials

In Example 12F, dronabinol formulations 12F-i, 12F-ii and 12F-iii were prepared in accordance with Examples 12C-i, 12C-ii and 12C-iii respectively using sesame oil sourced from Dipasa. Formulation 12F-i contained 1% monoethanolamine, formulation 12F-ii contained 0.5% monoethanolamine and 12F-iii contained 0.01% monoethanolamine. The dronabinol formulations were then used to fill amber glass vials. The formulations within the glass vials were initially tested, then tested at 25° C. for 3 and 6 months; 40° C. for 1, 2 and 3 months and at 55° C. for 1 and 2 weeks.

The results of stability testing of Example 12F-i-iii at 25° C. are set forth in Table 102 below.

TABLE 102

| Monoethanolamine | | | | | | Total Impurities | |
|---|---|---|---|---|---|---|---|
| | 25° C. | Potency % | CBD % | CBN % | D8-THC % | % | Increase + % |
| Zero | 12F-i 1% | 100.00 | 0.02 | 0.72 | 0.56 | 5.45 | |
| | 12F-ii 0.5% | 100.00 | 0.02 | 0.61 | 0.54 | 4.31 | |
| | 12F-iii 0.01% | 100.00 | 0.03 | 0.53 | 0.58 | 3.80 | |
| 3 Months | 12F-i 1% | 93.57 | 0.15 | 0.96 | 0.52 | 5.96 | 0.51 |
| | 12F-ii 0.5% | 93.74 | 0.12 | 0.85 | 0.51 | 5.33 | 1.02 |
| | 12F-iii 0.01% | 93.39 | 0.15 | 0.61 | 0.52 | 5.10 | 1.30 |
| 6 Months | 12F-i 1% | 100.19 | 0.08 | 1.28 | 0.55 | 6.55 | 1.10 |
| | 12F-ii 0.5% | 98.39 | 0.08 | 1.12 | 0.54 | 5.87 | 1.56 |
| | 12F-iii 0.01% | 97.06 | 0.19 | 0.74 | 0.52 | 7.25 | 3.45 |

The results of stability testing of Example 12F-i-iii at 40° C. are set forth in Table 103 below.

TABLE 103

| Monoethanolamine | | Potency % | CBD % | CBN % | D8-THC % | Total Impurities % | Increase + % |
|---|---|---|---|---|---|---|---|
| | 40° C. | | | | | | |
| Zero | 12F-i 1% | 100.00 | 0.02 | 0.72 | 0.56 | 5.45 | |
| | 12F-ii 0.5% | 100.00 | 0.02 | 0.61 | 0.54 | 4.31 | |
| | 12F-iii 0.01% | 100.00 | 0.03 | 0.53 | 0.58 | 3.80 | |
| 1 Month | 12F-i 1% | 94.59 | 0.22 | 1.33 | 0.61 | 6.92 | 1.47 |
| | 12F-ii 0.5% | 93.58 | 0.19 | 0.82 | 0.30 | 5.05 | 0.74 |
| | 12F-iii 0.01% | 96.17 | 0.13 | 0.54 | 0.60 | 6.25 | 2.45 |
| 2 Months | 12F-i 1% | 93.13 | 0.08 | 1.26 | 0.58 | 6.92 | 1.47 |
| | 12F-ii 0.5% | 91.69 | 0.09 | 1.12 | 0.63 | 5.94 | 1.63 |
| | 12F-iii 0.01% | 92.28 | 0.24 | 0.73 | 0.58 | 8.15 | 4.35 |
| 3 Months | 12F-i 1% | 91.51 | 0.47 | 2.02 | 0.55 | 9.15 | 3.70 |
| | 12F-ii 0.5% | 92.52 | 0.09 | 1.72 | 0.50 | 7.25 | 2.94 |
| | 12F-iii 0.01% | 89.34 | 0.41 | 1.15 | 0.52 | 12.31 | 8.51 |

The results of stability testing of Example 12F-i-iii at 55° C. are set forth in Table 104 below.

TABLE 104

| Monoethanolamine | | Potency % | CBD % | CBN % | D8-THC % | Total Impurities % | Increase + % |
|---|---|---|---|---|---|---|---|
| | 55° C. | | | | | | |
| Zero | 12F-i 1% | 100.00 | 0.02 | 0.72 | 0.56 | 5.45 | |
| | 12F-ii 0.5% | 100.00 | 0.02 | 0.61 | 0.54 | 4.31 | |
| | 12F-iii 0.01% | 100.00 | 0.03 | 0.53 | 0.58 | 3.80 | |
| 1 Week | 12F-i 1% | 95.67 | 0.01 | 0.95 | 0.55 | 6.86 | 1.41 |
| | 12F-ii 0.5% | 97.38 | 0.05 | 0.93 | 0.55 | 6.03 | 1.72 |
| | 12F-iii 0.01% | 97.08 | 0.01 | 0.56 | 0.54 | 6.57 | 2.77 |
| 2 Weeks | 12F-i 1% | 94.76 | 0.01 | 0.51 | 0.52 | 6.85 | 1.40 |
| | 12F-ii 0.5% | 97.43 | 0.02 | 1.35 | 0.54 | 6.96 | 2.65 |
| | 12F-iii 0.01% | 97.56 | 0.01 | 0.73 | 0.54 | 8.48 | 4.68 |

EXAMPLE 12G

Dronabinol Solution in Sesame Oil Sourced from Arista—Capsules

In Example 12G, a dronabinol formulation was prepared in accordance with Examples 12-xiii using sesame oil sourced from Arista, containing 0.1% meglumine. The dronabinol formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Example 12G at 25° C. are set forth in Table 105 below.

TABLE 105

| Meglumine | | Potency % | CBD % | CBN % | D8-THC % | Total Impurities % | Increase + % |
|---|---|---|---|---|---|---|---|
| | 25° C. | | | | | | |
| Zero | 0.1% | 100.00 | 0.05 | 0.50 | 0.54 | 4.78 | |
| 3 Months | 0.1% | 90.70 | 0.40 | 0.57 | 0.48 | 9.57 | 4.79 |
| 6 Months | 0.1% | 92.35 | 0.65 | 0.64 | 0.51 | 11.19 | 6.41 |

The results of stability testing of Example 12G at 40° C. are set forth in Table 106 below.

TABLE 106

| Meglumine 40° C. | | Potency % | CBD % | CBN % | D8-THC % | Total Impurities % | Increase + % |
|---|---|---|---|---|---|---|---|
| Zero | 0.1% | 100.00 | 0.05 | 0.50 | 0.54 | 4.78 | |
| 1 Month | 0.1% | 92.30 | 0.50 | 0.55 | 0.47 | 9.21 | 4.43 |
| 2 Months | 0.1% | 89.12 | 0.40 | 0.65 | 0.52 | 10.84 | 6.06 |
| 3 Months | 0.1% | 87.11 | 0.78 | 0.87 | 0.45 | 11.67 | 6.89 |

The results of stability testing of Example 12G at 55° C. are set forth in Table 107 below.

TABLE 107

| Meglumine 55° C. | | Potency % | CBD % | CBN % | D8-THC % | Total Impurities % | Increase + % |
|---|---|---|---|---|---|---|---|
| Zero | 0.1% | 100.00 | 0.05 | 0.50 | 0.54 | 4.78 | |
| 1 Week | 0.1% | 98.13 | 0.02 | 0.48 | 0.52 | 4.71 | −0.07 |
| 2 Weeks | 0.1% | 96.55 | 0.01 | 0.47 | 0.54 | 6.27 | 1.49 |

EXAMPLE 12H

Dronabinol Solution in Sesame Oil Sourced from Croda—Capsules

In Example 12H, a dronabinol formulation was prepared in accordance with Examples 12G using sesame oil sourced from Croda, containing 0.1% meglumine. The dronabinol formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Example 12H at 25° C. are set forth in Table 108 below.

TABLE 108

| Meglumine 25° C. | | Potency % | CBD % | CBN % | D8-THC % | Total Impurities % | Increase + % |
|---|---|---|---|---|---|---|---|
| Zero | 0.1% | 100.00 | 0.06 | 0.43 | 0.58 | 4.11 | |
| 3 Months | 0.1% | 88.79 | 0.68 | 0.51 | 0.53 | 11.38 | 7.27 |
| 6 Months | 0.1% | 88.49 | 0.93 | 0.67 | 0.56 | 14.27 | 10.16 |

The results of stability testing of Example 12H at 40° C. are set forth in Table 109 below.

TABLE 109

| Meglumine 40° C. | | Potency % | CBD % | CBN % | D8-THC % | Total Impurities % | Increase + % |
|---|---|---|---|---|---|---|---|
| Zero | 0.1% | 100.00 | 0.06 | 0.43 | 0.58 | 4.11 | |
| 1 Month | 0.1% | 89.79 | 0.74 | 0.46 | 0.52 | 11.09 | 6.98 |
| 2 Months | 0.1% | 85.70 | 0.60 | 0.47 | 0.52 | 12.16 | 8.05 |
| 3 Months | 0.1% | 84.98 | 0.97 | 0.63 | 0.52 | 14.10 | 9.99 |

The results of stability testing of Example 12H at 55° C. are set forth in Table 110 below.

TABLE 110

| Meglumine 55° C. | | Potency % | CBD % | CBN % | D8-THC % | Total Impurities % | Increase + % |
|---|---|---|---|---|---|---|---|
| Zero | 0.1% | 100.00 | 0.06 | 0.43 | 0.58 | 4.11 | |
| 1 Week | 0.1% | 86.96 | 0.03 | 0.55 | 0.53 | 14.35 | 10.24 |
| 2 Weeks | 0.1% | 23.63 | 0.11 | 2.35 | 0.62 | 68.45 | 64.34 |

EXAMPLE 12I

Dronabinol Solution in Sesame Oil Sourced from Dipasa—Capsules

In Example 12I, a dronabinol formulation was prepared in accordance with Example 12G using sesame oil sourced from Dipasa, containing 0.1% meglumine. The dronabinol formulation was then used to fill hard gelatin capsules in accordance with Example 2. The formulation within the capsules was initially tested, then tested at 25° C. for 3 and 6 months; 40° C. for 1, 2 and 3 months and at 55° C. for 1 and 2 weeks.

The results of stability testing of Example 12I at 25° C. are set forth in Table 111 below.

TABLE 111

| Meglumine 25° C. | | Potency % | CBD % | CBN % | D8-THC % | Total Impurities % | Increase + % |
|---|---|---|---|---|---|---|---|
| Zero | 0.1% | 100.00 | 0.01 | 0.51 | 0.54 | 3.84 | |
| 3 Months | 0.1% | 94.91 | 0.08 | 0.55 | 0.52 | 5.19 | 1.35 |
| 6 Months | 0.1% | 99.21 | 0.17 | 0.61 | 0.55 | 6.67 | 2.83 |

The results of stability testing of Example 12I at 40° C. are set forth in Table 112 below.

TABLE 112

| Meglumine 40° C. | | Potency % | CBD % | CBN % | D8-THC % | Total Impurities % | Increase + % |
|---|---|---|---|---|---|---|---|
| Zero | 0.1% | 100.00 | 0.01 | 0.51 | 0.54 | 3.84 | |
| 1 Month | 0.1% | 93.78 | 0.21 | 0.61 | 0.53 | 7.31 | 3.47 |
| 2 Months | 0.1% | 91.71 | 0.11 | 0.75 | 0.54 | 9.13 | 5.29 |
| 3 Months | 0.1% | 88.91 | 0.31 | 1.05 | 0.54 | 10.44 | 6.60 |

The results of stability testing of Example 12I at 55° C. are set forth in Table 113 below.

TABLE 113

| Meglumine 55° C. | Potency % | CBD % | CBN % | D8-THC % | Total Impurities % | Increase + % |
|---|---|---|---|---|---|---|
| Zero | 0.1% | 100.00 | 0.01 | 0.51 | 0.54 | 3.84 |
| 1 Week | 0.1% | 96.96 | 0.02 | 0.52 | 0.56 | 5.00 | 1.16 |
| 2 Weeks | 0.1% | 94.25 | 0.01 | 0.56 | 0.54 | 6.96 | 3.12 |

EXAMPLE 12J

Dronabinol Solution in Sesame Oil Sourced from Arista—Vials

In Example 12J, a dronabinol formulation was prepared in accordance with Example 12G using sesame oil sourced from Arista, containing 0.1% meglumine. The dronabinol formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability testing of Example 12J at 25° C. are set forth in Table 114 below.

TABLE 114

| Meglumine 25° C. | Potency % | CBD % | CBN % | D8-THC % | Total Impurities % | Increase + % |
|---|---|---|---|---|---|---|
| Zero | 0.1% | 100.00 | 0.05 | 0.50 | 0.54 | 4.78 |
| 3 Months | 0.1% | 94.70 | 0.06 | 0.51 | 0.50 | 4.64 | −0.14 |
| 6 Months | 0.1% | 97.71 | 0.09 | 0.53 | 0.49 | 6.01 | 1.23 |

The results of stability testing of Example 12J at 40° C. are set forth in Table 115 below.

TABLE 115

| Meglumine 40° C. | Potency % | CBD % | CBN % | D8-THC % | Total Impurities % | Increase + % |
|---|---|---|---|---|---|---|
| Zero | 0.1% | 100.00 | 0.05 | 0.50 | 0.54 | 4.78 |
| 1 Month | 0.1% | 96.40 | 0.01 | 0.45 | 0.55 | 4.67 | 0.11 |
| 2 Months | 0.1% | 92.86 | 0.10 | 0.46 | 0.57 | 6.66 | 1.88 |
| 3 Months | 0.1% | 92.70 | 0.10 | 0.59 | 0.50 | 8.68 | 3.90 |

The results of stability testing of Example 12J at 55° C. are set forth in Table 116 below.

TABLE 116

| Meglumine 55° C. | Potency % | CBD % | CBN % | D8-THC % | Total Impurities % | Increase + % |
|---|---|---|---|---|---|---|
| Zero | 0.1% | 100.00 | 0.05 | 0.50 | 0.54 | 4.78 |
| 1 Week | 0.1% | 98.13 | 0.02 | 0.48 | 0.52 | 4.71 | −0.07 |
| 2 Weeks | 0.1% | 96.55 | 0.01 | 0.47 | 0.54 | 6.27 | 1.49 |

EXAMPLE 12K

Dronabinol Solution in Sesame Oil Sourced from Croda—Vials

In Example 12K, a dronabinol formulation was prepared in accordance with Example 12G using sesame oil sourced from Croda, containing 0.1% meglumine. The dronabinol formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability testing of Example 12K at 25° C. are set forth in Table 117 below.

TABLE 117

| Meglumine 25° C. | Potency % | CBD % | CBN % | D8-THC % | Total Impurities % | Increase + % |
|---|---|---|---|---|---|---|
| Zero | 0.1% | 100.00 | 0.06 | 0.43 | 0.58 | 4.11 |
| 3 Months | 0.1% | 93.99 | 0.27 | 0.46 | 0.55 | 5.67 | 1.56 |
| 6 Months | 0.1% | 96.45 | 0.12 | 0.47 | 0.54 | 6.99 | 2.88 |

The results of stability testing of Example 12K at 40° C. are set forth in Table 118 below.

TABLE 118

| Meglumine 40° C. | Potency % | CBD % | CBN % | D8-THC % | Total Impurities % | Increase + % |
|---|---|---|---|---|---|---|
| Zero | 0.1% | 100.00 | 0.06 | 0.43 | 0.58 | 4.11 |
| 1 Month | 0.1% | 88.41 | 0.38 | 0.46 | 0.58 | 11.89 | 7.78 |
| 2 Months | 0.1% | 78.10 | 0.57 | 0.54 | 0.64 | 18.28 | 14.17 |
| 3 Months | 0.1% | 74.65 | 0.48 | 0.82 | 0.57 | 21.75 | 17.64 |

The results of stability testing of Example 12K at 55° C. are set forth in Table 119 below.

TABLE 119

| Meglumine 55° C. | Potency % | CBD % | CBN % | D8-THC % | Total Impurities % | Increase + % |
|---|---|---|---|---|---|---|
| Zero | 0.1% | 100.00 | 0.06 | 0.43 | 0.58 | 4.11 |
| 1 Week | 0.1% | 86.96 | 0.03 | 0.55 | 0.53 | 14.35 | 10.24 |
| 2 Weeks | 0.1% | 23.63 | 0.11 | 2.35 | 0.62 | 68.45 | 64.34 |

EXAMPLE 12L

Dronabinol Solution in Sesame Oil Sourced from Dipasa—Vials

In Example 12L, a dronabinol formulation was prepared in accordance with Example 12G using sesame oil sourced from Dipasa, containing 0.1% meglumine. The dronabinol formulation was then used to fill amber glass vials. The formulation within the vials was initially tested, then tested at 25° C. for 3 and 6 months; 40° C. for 1, 2 and 3 months and at 55° C. for 1 and 2 weeks.

The results of stability testing of Example 12L at 25° C. are set forth in Table 120 below.

TABLE 120

| Meglumine 25° C. | Potency % | CBD % | CBN % | D8-THC % | Total Impurities % | Increase + % |
|---|---|---|---|---|---|---|
| Zero | 0.1% | 100.00 | 0.01 | 0.51 | 0.54 | 3.84 | |
| 3 Months | 0.1% | 94.31 | 0.06 | 0.55 | 0.54 | 4.67 | 0.83 |
| 6 Months | 0.1% | 97.44 | 0.10 | 0.57 | 0.54 | 6.19 | 2.35 |

The results of stability testing of Example 12L at 40° C. are set forth in Table 121 below.

TABLE 121

| Meglumine 40° C. | Potency % | CBD % | CBN % | D8-THC % | Total Impurities % | Increase + % |
|---|---|---|---|---|---|---|
| Zero | 0.1% | 100.00 | 0.01 | 0.51 | 0.54 | 3.84 | |
| 1 Month | 0.1% | 93.37 | 0.05 | 0.48 | 0.59 | 5.54 | 1.70 |
| 2 Months | 0.1% | 91.71 | 0.04 | 0.55 | 0.60 | 6.90 | 3.06 |
| 3 Months | 0.1% | 90.02 | 0.10 | 0.78 | 0.54 | 9.03 | 5.19 |

The results of stability testing of Example 12L at 55° C. are set forth in Table 122 below.

TABLE 122

| Meglumine 55° C. | Potency % | CBD % | CBN % | D8-THC % | Total Impurities % | Increase + % |
|---|---|---|---|---|---|---|
| Zero | 0.1% | 100.00 | 0.01 | 0.51 | 0.54 | 3.84 | |
| 1 Week | 0.1% | 96.96 | 0.02 | 0.52 | 0.56 | 5.00 | 1.16 |
| 2 Weeks | 0.1% | 94.25 | 0.01 | 0.56 | 0.54 | 6.96 | 3.12 |

As can be seen from the above results, the addition of organic bases monoethanolamine or meglumine imparts stability to dronabinol formulations particularly at the higher concentrations. However, monoethanolamine is superior to meglumine in stabilizing dronabinol formulations at all conditions studied.

EXAMPLE 13

Stability Results—Presence of Anti-Oxidants

As previously mentioned, the antioxidant effect of sesame oil has been attributed to the presence of several antioxidant chemicals in sesame oil, including sesamin, sesamol, sesamolin and lecithin. In Example 13, the effect of added antioxidant in hard gelatin capsules of Dronabinol formulated as a sesame oil solution was evaluated. In each of Examples 13a-13l, the specified amount of anti-oxidant was added to the formulation prepared in accordance with Examples 1 and 2 (except for Example 13j, which was not encapsulated). Well-known anti-oxidants (Featured Excipient: Antioxidants, 1999) d-α-tocopherol, butyl hydroxyl anisole (BHA), butyl hydroxyl toluene (BHT), L-ascorbic acid-6-palmitate, lecithin and propyl gallate were added to Dronabinol sesame oil formulation.

Example 13-i is a 5 mg capsule of dronabinol (3.03% w/w) and 0.001% tocopherol (w/w) in sesame oil, super refined NF (by Croda).

Example 13-ii is a 5 mg capsule of dronabinol (3.03% w/w) and 0.05% (w/w) tocopherol in sesame oil, super refined NF (by Croda).

Example 13-iii is a 5 mg capsule of dronabinol (3.03% w/w) and 0.001% butyl hydroxy anisole (BHA) (w/w) in sesame oil, super refined NF (by Croda).

Example 13-iv is a 5 mg capsule of dronabinol (3.03% w/w) and 0.01% butyl hydroxyl anisole (w/w) in sesame oil, super refined NF (by Croda).

Example 13-v is a 5 mg capsule of dronabinol (3.03% w/w) and 0.001% butyl hydroxyl toluene (w/w) in sesame oil, super refined NF (by Croda).

Example 13-vi is a 5 mg capsule of dronabinol (3.03%) and 0.01% butyl hydroxyl toluene in sesame oil, super refined NF (by Croda).

Example 13-vii is a 5 mg capsule of dronabinol (3.03% w/w) and 0.01% L-ascorbic acid-6-palmitate (w/w) in sesame oil, super refined NF (by Croda).

Example 13-viii is a 5 mg capsule of dronabinol (3.03% w/w) and 0.1% L-ascorbic acid-6-palmitate (w/w) in sesame oil, super refined NF (by Croda).

Example 13-ix is a 5 mg capsule of dronabinol (3.03% w/w) and 0.3% lecithin (w/w) in sesame oil, super refined NF (by Croda).

Example 13-x is a solution of dronabinol (3.03% w/w) and 8.25% lecithin (w/w) in sesame oil, super refined NF (by Croda).

Example 13-xi is a 5 mg capsule of dronabinol (3.03% w/w) and 0.001% propyl gallate (w/v) in sesame oil, super refined NF (by Croda).

Example 13-xii is a 5 mg capsule of dronabinol (3.03% w/w) and 0.15% propyl gallate (w/v) in sesame oil, super refined NF (by Croda).

A summary of the compositions of Examples 13-i-13-xii is set forth in Table 123 below:

TABLE 123

| | Composition | | |
|---|---|---|---|
| Formulation No. | Dronabinol | Sesame Oil | Other Ingredients |
| Example 13-i | 5 mg/capsule (3.03%) | QS | Tocopherol (0.001%) |
| Example 13-ii | 5 mg/capsule (3.03%) | QS | Tocopherol (0.05%) |
| Example 13-iii | 5 mg/capsule (3.03%) | QS | BHA (0.001%) |
| Example 13-iv | 5 mg/capsule (3.03%) | QS | BHA (0.01%) |
| Example 13-v | 5 mg/capsule (3.03%) | QS | BHT (0.001%) |
| Example 13-vi | 5 mg/capsule (3.03%) | QS | BHT (0.01%) |
| Example 13-vii | 5 mg/capsule (3.03%) | QS | L-ascorbic acid-6-palmitate (0.01%) |
| Example 13-viii | 5 mg/capsule (3.03%) | QS | L-ascorbic acid-6-palmitate (0.1%) |
| Example 13-ix | 5 mg/capsule (3.03%) | QS | Lecithin (0.3%) |
| Example 13-x | 5 mg/capsule (3.03%) | QS | Lecithin (8.25%) |
| Example 13-xi | 5 mg/capsule (3.03%) | QS | Propyl Gallate (0.001%) |
| Example 13-xii | 5 mg/capsule (3.03%) | QS | Propyl Gallate (0.15%) |

The dronabinol formulations of Examples 13-i-13-xii containing anti-oxidants as set forth above were placed under accelerated stability testing at 55° C. for two weeks. The results of the study are presented in Table 124 (including a comparison to the results of Example 9ii (no anti-oxidant included

TABLE 124

| CONDITION | FORMULATION # | TOTAL ASSAY % | IMPURITY % | RELATED SUBSTANCES D8THC % | CBN % | CBD % |
|---|---|---|---|---|---|---|
| Zero Time | Example 9-ii* (no anti-oxidant added) | 93.80 | 6.20 | 0.75 | 1.88 | 0.29 |
| 55° C. (2 weeks) | Example 9-ii* (no anti-oxidant added) | 67.41 | 32.59 | 1.06 | 4.96 | 0.29 |
| | Example 13-i: A07 Tocopherol (0.001%) | 92.40 | 13.18 | 0.75 | 2.13 | 1.05 |
| | Example 13-ii: A08 Tocopherol (0.05%) | 86.72 | 14.46 | 0.86 | 2.34 | 1.40 |
| | Example 13-iii: A09 BHA (0.001%) | 82.68 | 12.63 | 0.78 | 2.11 | 1.04 |
| | Example 13-iv: A10 BHA (0.01%) | 92.27 | 13.37 | 0.99 | 1.98 | 1.27 |
| | Example 13-v: A11 BHT (0.001%) | 88.54 | 13.58 | 0.82 | 2.13 | 1.11 |
| | Example 13-vi: A12 BHT (0.01%) | 90.66 | 13.40 | 0.89 | 2.15 | 1.10 |
| | Example 13-vii: A13 L-ascorbic acid-6-palmitate (0.01%) | 87.57 | 11.74 | 0.84 | 2.23 | 0.83 |
| | Example 13-viii: A14 L-ascorbic acid-6-palmitate (0.1%) | 93.04 | 8.95 | 0.94 | 2.30 | 0.52 |
| | Example 13-ix: A15 Lecithin (0.3%) | 92.19 | 12.08 | 0.89 | 2.45 | 0.72 |
| | Example 13-x: A16 Lecithin (8.25%) | 94.24 | 9.69 | 0.90 | 3.22 | 0.17 |
| | Example 13-xi: A17 Propyl Gallate (0.001%) | 90.39 | 13.11 | 0.88 | 2.16 | 0.98 |
| | Example 13-xii: A18 Propyl Gallate (0.15%) | 88.66 | 16.98 | 0.86 | 3.59 | 1.10 |

*Control

The results indicated that the addition of Lecithin and L-ascorbic acid-6-palmitate to these dronabinol formulations helps stabilize the active ingredient dronabinol.

Extended Stability Results—Presence of Anti-Oxidants

To further investigate whether the addition of the anti-oxidants lecithin and L-ascorbic acid-6-palmitate to the dronabinol formulations created more stabile formulations, stability studies at room temperature and at accelerated conditions over an extended period of time were conducted using sesame oil from Arista, Croda and Dipasa.

EXAMPLE 13A

Dronabinol Solution in Sesame Oil Sourced from Arista—Capsules

In Example 13A, dronabinol formulations 13A-i, and 13A-ii were prepared in accordance with Examples 13-x and 13-ix, respectively using sesame oil sourced from Arista. Formulation 13A-i contained 8.25% lecithin and formulation 13A-ii contained 0.3% lecithin. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 13A-i-ii at 25° C. are set forth in Table 125 below.

TABLE 125

| Lecithin 25° C. | | Potency % | CBD % | CBN % | D8-THC % | Total Impurities % | Increase + % |
|---|---|---|---|---|---|---|---|
| Zero | 13A-i 8.25% | 100.00 | 0.04 | 0.52 | 0.55 | 4.03 | |
| | 13A-ii 0.3% | 100.00 | 0.01 | 0.49 | 0.53 | 3.67 | |
| 3 Months | 13A-i 8.25% | 97.03 | 0.04 | 0.61 | 0.50 | 4.23 | 0.20 |
| | 13A-ii 0.3% | 96.94 | 0.05 | 0.68 | 0.50 | 4.81 | 1.14 |
| 6 Months | 13A-i 8.25% | 100.47 | 0.04 | 0.72 | 0.53 | 5.56 | 1.53 |
| | 13A-ii 0.3% | 100.23 | 0.08 | 0.73 | 0.43 | 5.51 | 1.84 |

The results of stability testing of Example 13A-i-ii at 40° C. are set forth in Table 126 below.

TABLE 126

| Lecithin 40° C. | | Potency % | CBD % | CBN % | D8-THC % | Total Impurities % | Increase + % |
|---|---|---|---|---|---|---|---|
| Zero | 13A-i 8.25% | 100.00 | 0.04 | 0.52 | 0.55 | 4.03 | |
| | 13A-ii 0.3% | 100.00 | 0.01 | 0.49 | 0.53 | 3.67 | |
| 1 Month | 13A-i 8.25% | 101.18 | 0.01 | 0.70 | 0.50 | 5.16 | 1.13 |
| | 13A-ii 0.3% | 94.92 | 0.06 | 0.88 | 0.50 | 7.72 | 4.05 |
| 2 Months | 13A-i 8.25% | 96.72 | 0.04 | 0.93 | 0.55 | 6.13 | 2.10 |
| | 13A-ii 0.3% | 92.12 | 0.01 | 1.06 | 0.53 | 8.11 | 4.44 |
| 3 Months | 13A-i 8.25% | 93.30 | 0.02 | 1.36 | 0.47 | 7.00 | 2.97 |
| | 13A-ii 0.3% | 93.24 | 0.07 | 1.25 | 0.52 | 8.79 | 5.12 |

The results of stability testing of Example 13A-i-ii at 55° C. are set forth in Table 127 below.

TABLE 127

| Lecithin 55° C. | | Potency % | CBD % | CBN % | D8-THC % | Total Impurities % | Increase + % |
|---|---|---|---|---|---|---|---|
| Zero | 13A-i 8.25% | 100.00 | 0.04 | 0.52 | 0.55 | 4.03 | |
| | 13A-ii 0.3% | 100.00 | 0.01 | 0.49 | 0.53 | 3.67 | |
| 1 Week | 13A-i 8.25% | 98.88 | 0.01 | 0.92 | 0.51 | 5.13 | 1.10 |
| | 13A-ii 0.3% | 99.26 | 0.02 | 0.96 | 0.52 | 5.56 | 1.89 |
| 2 Weeks | 13A-i 8.25% | 96.89 | 0.01 | 1.29 | 0.51 | 6.17 | 2.14 |
| | 13A-ii 0.3% | 95.62 | 0.02 | 1.31 | 0.50 | 6.87 | 3.20 |

EXAMPLE 13B

Dronabinol Solution in Sesame Oil Sourced from Croda—Capsules

In Example 13B, dronabinol formulations 13B-i, and 13B-ii were prepared in accordance with Examples 13-x and 13-ix, respectively using sesame oil sourced from Croda. Formulation 13B-i contained 8.25% lecithin and formulation 13B-ii contained 0.3% lecithin. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 13B-i-ii at 25° C. are set forth in Table 128 below.

TABLE 128

| Lecithin 25° C. | | Potency % | CBD % | CBN % | D8-THC % | Total Impurities % | Increase + % |
|---|---|---|---|---|---|---|---|
| Zero | 13B-i 8.25% | 100.00 | 0.02 | 0.45 | 0.58 | 3.73 | |
| | 13B-ii 0.3% | 100.00 | 0.04 | 0.42 | 0.56 | 3.67 | |
| 3 Months | 13B-i 8.25% | 96.19 | 0.04 | 0.69 | 0.57 | 4.97 | 1.24 |
| | 13B-ii 0.3% | 96.70 | 0.08 | 0.57 | 0.54 | 4.87 | 1.20 |
| 6 Months | 13B-i 8.25% | 97.98 | 0.06 | 0.76 | 0.59 | 6.65 | 2.92 |
| | 13B-ii 0.3% | 98.09 | 0.15 | 0.77 | 0.57 | 7.14 | 3.47 |

The results of stability testing of Example 13B-i-ii at 40° C. are set forth in Table 129 below.

TABLE 129

| | Lecithin | | | | | Total Impurities | |
|---|---|---|---|---|---|---|---|
| | 40° C. | Potency % | CBD % | CBN % | D8-THC % | % | Increase + % |
| Zero | 13B-i 8.25% | 100.00 | 0.02 | 0.45 | 0.58 | 3.73 | |
| | 13B-ii 0.3% | 100.00 | 0.04 | 0.42 | 0.56 | 3.67 | |
| 1 | 13B-i 8.25% | 94.23 | 0.02 | 0.95 | 0.57 | 7.43 | 3.70 |
| Month | 13B-ii 0.3% | 91.53 | 0.06 | 1.16 | 0.55 | 10.47 | 6.80 |
| 2 | 13B-i 8.25% | 89.93 | 0.02 | 1.27 | 0.65 | 9.61 | 5.88 |
| Months | 13B-ii 0.3% | 89.31 | 0.05 | 1.43 | 0.61 | 12.44 | 8.77 |
| 3 | 13B-i 8.25% | 87.62 | 0.02 | 2.01 | 0.56 | 11.07 | 7.34 |
| Months | 13B-ii 0.3% | 86.29 | 0.10 | 2.07 | 0.59 | 13.25 | 9.58 |

The results of stability testing of Example 13B-i-ii at 55° C. are set forth in Table 130 below.

TABLE 130

| | Lecithin | | | | | Total Impurities | |
|---|---|---|---|---|---|---|---|
| | 55° C. | Potency % | CBD % | CBN % | D8-THC % | % | Increase + % |
| Zero | 13B-i 8.25% | 100.00 | 0.02 | 0.45 | 0.58 | 3.73 | |
| | 13B-ii 0.3% | 100.00 | 0.04 | 0.42 | 0.56 | 3.67 | |
| 1 | 13B-i 8.25% | 97.01 | 0.03 | 1.25 | 0.58 | 6.43 | 2.70 |
| Week | 13B-ii 0.3% | 88.98 | 0.13 | 2.51 | 0.58 | 12.47 | 8.80 |
| 2 | 13B-i 8.25% | 92.29 | 0.02 | 1.89 | 0.53 | 8.50 | 4.77 |
| Weeks | 13B-ii 0.3% | 43.06 | 0.16 | 10.13 | 1.19 | 49.26 | 45.59 |

EXAMPLE 13C

Dronabinol Solution in Sesame Oil Sourced from Dipasa—Capsules

In Example 13C, dronabinol formulations 13C-i, and 13C-ii were prepared in accordance with Examples 13-x and 13-ix, respectively using sesame oil sourced from Dipasa. Formulation 13C-i contained 8.25% lecithin and formulation 13C-ii contained 0.3% lecithin. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 13C-i-ii at 25° C. are set forth in Table 131 below.

TABLE 131

| | Lecithin | | | | | Total Impurities | |
|---|---|---|---|---|---|---|---|
| | 25° C. | Potency % | CBD % | CBN % | D8-THC % | % | Increase + % |
| Zero | 13C-i 8.25% | 100.00 | 0.02 | 0.55 | 0.59 | 3.93 | |
| | 13C-ii 0.3% | 100.00 | 0.03 | 0.53 | 0.59 | 3.93 | |
| 3 | 13C-i 8.25% | 96.33 | 0.05 | 0.71 | 0.55 | 4.84 | 0.91 |
| Months | 13C-ii 0.3% | 96.85 | 0.03 | 0.81 | 0.56 | 5.17 | 1.24 |
| 6 | 13C-i 8.25% | 98.70 | 0.04 | 0.97 | 0.50 | 5.56 | 1.63 |
| Months | 13C-ii 0.3% | 98.81 | 0.10 | 0.95 | 0.50 | 6.30 | 2.37 |

The results of stability testing of Example 13C-i-ii at 40° C. are set forth in Table 132 below.

TABLE 132

| | Lecithin | | | | | Total Impurities | |
|---|---|---|---|---|---|---|---|
| | 40° C. | Potency % | CBD % | CBN % | D8-THC % | % | Increase + % |
| Zero | 13C-i 8.25% | 100.00 | 0.02 | 0.55 | 0.59 | 3.93 | |
| | 13C-ii 0.3% | 100.00 | 0.03 | 0.53 | 0.59 | 3.93 | |
| 1 | 13C-i 8.25% | 96.94 | 0.04 | 0.94 | 0.55 | 6.05 | 2.12 |
| Month | 13C-ii 0.3% | 96.81 | 0.06 | 0.84 | 0.52 | 6.96 | 3.03 |
| 2 | 13C-i 8.25% | 94.44 | 0.01 | 1.39 | 0.57 | 7.08 | 3.15 |
| Months | 13C-ii 0.3% | 93.21 | 0.04 | 1.14 | 0.58 | 8.91 | 4.98 |
| 3 | 13C-i 8.25% | 92.31 | 0.03 | 2.13 | 0.56 | 8.53 | 4.60 |
| Months | 13C-ii 0.3% | 90.99 | 0.05 | 1.77 | 0.53 | 10.54 | 6.61 |

The results of stability testing of Example 13C-i-ii at 55° C. are set forth in Table 133 below.

TABLE 133

| | Lecithin | | | | | Total Impurities | |
|---|---|---|---|---|---|---|---|
| | 55° C. | Potency % | CBD % | CBN % | D8-THC % | % | Increase + % |
| Zero | 13C-i 8.25% | 100.00 | 0.02 | 0.55 | 0.59 | 3.93 | |
| | 13C-ii 0.3% | 100.00 | 0.03 | 0.53 | 0.59 | 3.93 | |
| 1 | 13C-i 8.25% | 98.48 | 0.01 | 1.16 | 0.56 | 5.74 | 1.81 |
| Week | 13C-ii 0.3% | 97.97 | 0.04 | 1.42 | 0.55 | 6.70 | 2.77 |
| 2 | 13C-i 8.25% | 94.16 | 0.01 | 1.75 | 0.55 | 7.10 | 3.17 |
| Weeks | 13C-ii 0.3% | 96.66 | 0.05 | 2.27 | 0.52 | 8.73 | 4.80 |

EXAMPLE 13D

Dronabinol Solution in Sesame Oil Sourced from Arista—Vials

In Example 13D, dronabinol formulations 13D-i, and 13D-ii were prepared in accordance with Examples 13-x and 13-ix, respectively using sesame oil sourced from Arista. Formulation 13D-i contained 8.25% lecithin and formulation 13D-ii contained 0.3% lecithin. The dronabinol formulations were then used to amber fill glass vials. The formulations within the vials were initially tested, then tested at 25° C. for 3 and 6 months; 40° C. for 1, 2 and 3 months and at 55° C. for 1 and 2 weeks.

The results of stability testing of Example 13D-i-ii at 25° C. are set forth in Table 134 below.

TABLE 134

| | Lecithin | | | | | Total Impurities | |
|---|---|---|---|---|---|---|---|
| | 25° C. | Potency % | CBD % | CBN % | D8-THC % | % | Increase + % |
| Zero | 13D-i 8.25% | 100.00 | 0.04 | 0.52 | 0.55 | 4.03 | |
| | 13D-ii 0.3% | 100.00 | 0.01 | 0.49 | 0.53 | 3.67 | |
| 3 | 13D-i 8.25% | 97.24 | 0.04 | 0.66 | 0.50 | 4.66 | 0.63 |
| Months | 13D-ii 0.3% | 95.91 | 0.10 | 0.65 | 0.61 | 5.86 | 2.19 |
| 6 | 13D-i 8.25% | 100.94 | 0.01 | 0.83 | 0.52 | 5.26 | 1.23 |
| Months | 13D-ii 0.3% | 100.23 | 0.01 | 0.83 | 0.52 | 5.26 | 1.23 |

The results of stability testing of Example 13D-i-ii at 40° C. are set forth in Table 135 below.

TABLE 135

| | Lecithin | | | | | Total Impurities | |
|---|---|---|---|---|---|---|---|
| | 40° C. | Potency % | CBD % | CBN % | D8-THC % | % | Increase + % |
| Zero | 13D-i 8.25% | 100.00 | 0.04 | 0.52 | 0.55 | 4.03 | |
| | 13D-ii 0.3% | 100.00 | 0.01 | 0.49 | 0.53 | 3.67 | |
| 1 Month | 13D-i 8.25% | 98.34 | 0.01 | 0.74 | 0.50 | 4.71 | 0.68 |
| | 13D-ii 0.3% | 98.39 | 0.02 | 0.77 | 0.50 | 4.90 | 1.23 |
| 2 Months | 13D-i 8.25% | 95.96 | 0.01 | 1.10 | 0.48 | 5.80 | 1.77 |
| | 13D-ii 0.3% | 94.97 | 0.02 | 1.18 | 0.47 | 6.52 | 2.85 |
| 3 Months | 13D-i 8.25% | 94.41 | 0.07 | 1.72 | 0.48 | 8.18 | 4.15 |
| | 13D-ii 0.3% | 93.70 | 0.10 | 1.92 | 0.49 | 8.83 | 5.16 |

The results of stability testing of Example 13D-i-ii at 55° C. are set forth in Table 136 below.

TABLE 136

| | Lecithin | | | | | Total Impurities | |
|---|---|---|---|---|---|---|---|
| | 55° C. | Potency % | CBD % | CBN % | D8-THC % | % | Increase + % |
| Zero | 13D-i 8.25% | 100.00 | 0.04 | 0.52 | 0.55 | 4.03 | |
| | 13D-ii 0.3% | 100.00 | 0.01 | 0.49 | 0.53 | 3.67 | |
| 1 Week | 13D-i 8.25% | 98.88 | 0.01 | 0.92 | 0.51 | 5.13 | 1.10 |
| | 13D-ii 0.3% | 99.26 | 0.02 | 0.96 | 0.52 | 5.56 | 1.89 |
| 2 Weeks | 13D-i 8.25% | 96.89 | 0.01 | 1.29 | 0.51 | 6.17 | 2.14 |
| | 13D-ii 0.3% | 95.62 | 0.02 | 1.31 | 0.50 | 6.87 | 3.20 |

EXAMPLE 13E

Dronabinol Solution in Sesame Oil Sourced from Croda—Vials

In Example 13E, dronabinol formulations 13E-i, and 13E-ii were prepared in accordance with Examples 13-x and 13-ix, respectively using sesame oil sourced from Croda. Formulation 13E-i contained 8.25% lecithin and formulation 13E-ii contained 0.3% lecithin. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 13E-i-ii at 25° C. are set forth in Table 137 below.

TABLE 137

| | Lecithin | | | | | Total Impurities | |
|---|---|---|---|---|---|---|---|
| | 25° C. | Potency % | CBD % | CBN % | D8-THC % | % | Increase + % |
| Zero | 13E-i 8.25% | 100.00 | 0.02 | 0.45 | 0.58 | 3.73 | |
| | 13E-ii 0.3% | 100.00 | 0.04 | 0.42 | 0.56 | 3.67 | |
| 3 Months | 13E-i 8.25% | 95.66 | 0.06 | 0.69 | 0.56 | 5.27 | 1.54 |
| | 13E-ii 0.3% | 95.91 | 0.10 | 0.65 | 0.61 | 5.86 | 2.19 |
| 6 Months | 13E-i 8.25% | 98.93 | 0.03 | 0.91 | 0.58 | 6.29 | 2.56 |
| | 13E-ii 0.3% | 98.55 | 0.08 | 0.92 | 0.59 | 7.34 | 3.67 |

The results of stability testing of Example 13E-i-ii at 40° C. are set forth in Table 138 below.

TABLE 138

| | Lecithin | | | | | Total Impurities | |
|---|---|---|---|---|---|---|---|
| | 40° C. | Potency % | CBD % | CBN % | D8-THC % | % | Increase + % |
| Zero | 13E-i 8.25% | 100.00 | 0.02 | 0.45 | 0.58 | 3.73 | |
| | 13E-ii 0.3% | 100.00 | 0.04 | 0.42 | 0.56 | 3.67 | |
| 1 | 13E-i 8.25% | 97.76 | 0.01 | 0.78 | 0.55 | 5.57 | 1.84 |
| Month | 13E-ii 0.3% | 97.58 | 0.03 | 0.70 | 0.56 | 5.90 | 2.23 |
| 2 | 13E-i 8.25% | 93.74 | 0.02 | 1.19 | 0.57 | 7.24 | 3.51 |
| Months | 13E-ii 0.3% | 92.91 | 0.04 | 1.10 | 0.56 | 8.51 | 4.84 |
| 3 | 13E-i 8.25% | 91.85 | 0.05 | 0.68 | 0.56 | 10.85 | 7.12 |
| Months | 13E-ii 0.3% | 90.95 | 0.15 | 1.85 | 0.56 | 11.35 | 7.68 |

The results of stability testing of Example 13E-i-ii at 55° C. are set forth in Table 139 below.

TABLE 139

| | Lecithin | | | | | Total Impurities | |
|---|---|---|---|---|---|---|---|
| | 55° C. | Potency % | CBD % | CBN % | D8-THC % | % | Increase + % |
| Zero | 13E-i 8.25% | 100.00 | 0.02 | 0.45 | 0.58 | 3.73 | |
| | 13E-ii 0.3% | 100.00 | 0.04 | 0.42 | 0.56 | 3.67 | |
| 1 | 13E-i 8.25% | 97.01 | 0.03 | 1.25 | 0.58 | 6.43 | 2.70 |
| Week | 13E-ii 0.3% | 88.98 | 0.13 | 2.51 | 0.58 | 12.47 | 8.80 |
| 2 | 13E-i 8.25% | 92.29 | 0.02 | 1.89 | 0.53 | 8.50 | 4.77 |
| Weeks | 13E-ii 0.3% | 43.06 | 0.16 | 10.13 | 1.19 | 49.26 | 45.59 |

EXAMPLE 13F

Dronabinol Solution in Sesame Oil Sourced from Dipasa—Vials

In Example 13F, dronabinol formulations 13F-i, and 13F-ii were prepared in accordance with Examples 13-x and 13-ix, respectively using sesame oil sourced from Dipasa. Formulation 13F-i contained 8.25% lecithin and formulation 13F-ii contained 0.3% lecithin. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 13F-i-ii at 25° C. are set forth in Table 140 below.

TABLE 140

| | Lecithin | | | | | Total Impurities | |
|---|---|---|---|---|---|---|---|
| | 25° C. | Potency % | CBD % | CBN % | D8-THC % | % | Increase + % |
| Zero | 13F-i 8.25% | 100.00 | 0.02 | 0.55 | 0.59 | 3.93 | |
| | 13F-ii 0.3% | 100.00 | 0.03 | 0.53 | 0.59 | 3.93 | |
| 3 | 13F-i 8.25% | 96.62 | 0.06 | 0.80 | 0.55 | 5.37 | 1.44 |
| Months | 13F-ii 0.3% | 96.46 | 0.09 | 0.89 | 0.53 | 5.75 | 1.82 |
| 6 | 13F-i 8.25% | 99.94 | 0.02 | 1.08 | 0.56 | 5.82 | 1.89 |
| Months | 13F-ii 0.3% | 100.60 | 0.04 | 1.39 | 0.55 | 6.39 | 2.46 |

The results of stability testing of Example 13F-i-ii at 40° C. are set forth in Table 141 below.

TABLE 141

| | Lecithin | | | | | Total Impurities | |
|---|---|---|---|---|---|---|---|
| | 40° C. | Potency % | CBD % | CBN % | D8-THC % | % | Increase + % |
| Zero | 13F-i 8.25% | 100.00 | 0.02 | 0.55 | 0.59 | 3.93 | |
| | 13F-ii 0.3% | 100.00 | 0.03 | 0.53 | 0.59 | 3.93 | |
| 1 | 13F-i 8.25% | 97.40 | 0.01 | 0.95 | 0.51 | 5.16 | 1.23 |
| Month | 13F-ii 0.3% | 98.37 | 0.03 | 1.10 | 0.52 | 5.69 | 1.76 |
| 2 | 13F-i 8.25% | 93.01 | 0.01 | 1.53 | 0.51 | 6.82 | 2.89 |
| Months | 13F-ii 0.3% | 93.86 | 0.03 | 1.98 | 0.53 | 7.85 | 3.92 |
| 3 | 13F-i 8.25% | 92.48 | 0.12 | 2.53 | 0.52 | 10.97 | 7.04 |
| Months | 13F-ii 0.3% | 91.50 | 0.17 | 3.45 | 0.52 | 11.87 | 7.94 |

The results of stability testing of Example 13F-i-ii at 55° C. are set forth in Table 142 below.

TABLE 142

| | Lecithin | | | | | Total Impurities | |
|---|---|---|---|---|---|---|---|
| | 55° C. | Potency % | CBD % | CBN % | D8-THC % | % | Increase + % |
| Zero | 13F-i 8.25% | 100.00 | 0.02 | 0.55 | 0.59 | 3.93 | |
| | 13F-ii 0.3% | 100.00 | 0.03 | 0.53 | 0.59 | 3.93 | |
| 1 | 13F-i 8.25% | 98.48 | 0.01 | 1.16 | 0.56 | 5.74 | 1.81 |
| Week | 13F-ii 0.3% | 97.97 | 0.04 | 1.42 | 0.55 | 6.70 | 2.77 |
| 2 | 13F-i 8.25% | 94.16 | 0.01 | 1.75 | 0.55 | 7.10 | 3.17 |
| Weeks | 13F-ii 0.3% | 96.66 | 0.05 | 2.27 | 0.52 | 8.73 | 4.80 |

EXAMPLE 13G

Dronabinol Solution in Sesame Oil Sourced from Arista—Capsules

In Example 13G, dronabinol formulations 13G-i, and 13G-ii were prepared in accordance with Examples 13-viii and 13-vii, respectively using sesame oil sourced from Arista. Formulation 13F-i contained 0.1% L-ascorbic acid-6-palmitate and formulation 13G-ii contained 0.1% L-ascorbic acid-6-palmitate. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 13G-i-ii at 25° C. are set forth in Table 143 below.

TABLE 143

| | Ascorbic-palmitate | | | | | Total Impurities | |
|---|---|---|---|---|---|---|---|
| | 25° C. | Potency % | CBD % | CBN % | D8-THC % | % | Increase + % |
| Zero | 13G-i 0.1% | 100.00 | 0.01 | 0.54 | 0.52 | 3.73 | |
| | 13G-ii 0.01% | 100.00 | 0.02 | 0.50 | 0.51 | 3.10 | |
| 3 | 13G-i 0.1% | 97.70 | 0.05 | 0.71 | 0.52 | 4.21 | 0.48 |
| Months | 13G-ii 0.01% | 96.30 | 0.05 | 0.64 | 0.52 | 4.99 | 1.89 |
| 6 | 13G-i 0.1% | 100.53 | 0.09 | 0.71 | 0.54 | 4.79 | 1.06 |
| Months | 13G-ii 0.01% | 97.60 | 0.28 | 0.72 | 0.54 | 7.17 | 4.07 |

The results of stability testing of Example 13G-i-ii at 40° C. are set forth in Table 144 below.

TABLE 144

| Ascorbic-palmitate | | | | | | Total Impurities | |
|---|---|---|---|---|---|---|---|
| | 40° C. | Potency % | CBD % | CBN % | D8-THC % | % | Increase + % |
| Zero | 13G-i 0.1% | 100.00 | 0.01 | 0.54 | 0.52 | 3.73 | |
| | 13G-ii 0.01% | 100.00 | 0.02 | 0.50 | 0.51 | 3.10 | |
| 1 Month | 13G-i 0.1% | 98.35 | 0.02 | 0.63 | 0.52 | 4.33 | 0.60 |
| | 13G-ii 0.01% | 96.00 | 0.16 | 0.72 | 0.50 | 7.21 | 4.11 |
| 2 Months | 13G-i 0.1% | 96.14 | 0.04 | 0.84 | 0.50 | 5.92 | 2.19 |
| | 13G-ii 0.01% | 90.97 | 0.25 | 0.93 | 0.53 | 10.06 | 6.96 |
| 3 Months | 13G-i 0.1% | 93.58 | 0.17 | 1.34 | 0.52 | 8.34 | 4.61 |
| | 13G-ii 0.01% | 88.83 | 0.51 | 1.44 | 0.50 | 12.63 | 9.53 |

The results of stability testing of Example 13G-i-ii at 55° C. are set forth in Table 145 below.

TABLE 145

| Ascorbic-palmitate | | | | | | Total Impurities | |
|---|---|---|---|---|---|---|---|
| | 55° C. | Potency % | CBD % | CBN % | D8-THC % | % | Increase + % |
| Zero | 13G-i 0.1% | 100.00 | 0.01 | 0.54 | 0.52 | 3.73 | |
| | 13G-ii 0.01% | 100.00 | 0.02 | 0.50 | 0.51 | 3.10 | |
| 1 Week | 13G-i 0.1% | 99.29 | 0.04 | 0.71 | 0.51 | 4.30 | 0.57 |
| | 13G-ii 0.01% | 99.17 | 0.05 | 0.62 | 0.49 | 4.59 | 1.49 |
| 2 Weeks | 13G-i 0.1% | 98.19 | 0.01 | 0.88 | 0.53 | 4.69 | 0.96 |
| | 13G-ii 0.01% | 97.17 | 0.01 | 0.73 | 0.51 | 6.60 | 3.50 |

EXAMPLE 13H

Dronabinol Solution in Sesame Oil Sourced from Croda—Capsules

In Example 13H, dronabinol formulations 13H-i, and 13H-ii were prepared in accordance with Examples 13-viii and 13-vii, respectively using sesame oil sourced from Croda. Formulation 13H-i contained 0.1% L-ascorbic acid-6-palmitate and formulation 13H-ii contained 0.1% L-ascorbic acid-6-palmitate. The dronabinol formulations were then used to fill hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 13H-i-ii at 25° C. are set forth in Table 146 below.

TABLE 146

| Ascorbic-palmitate | | | | | | Total Impurities | |
|---|---|---|---|---|---|---|---|
| | 25° C. | Potency % | CBD % | CBN % | D8-THC % | % | Increase + % |
| Zero | 13H-i 0.1% | 100.00 | 0.03 | 0.48 | 0.56 | 3.85 | |
| | 13H-ii 0.01% | 100.00 | 0.02 | 0.56 | 0.60 | 4.31 | |
| 3 Months | 13H-i 0.1% | 97.23 | 0.06 | 0.75 | 0.56 | 5.14 | 1.29 |
| | 13H-ii 0.01% | 93.93 | 0.07 | 0.56 | 0.56 | 6.31 | 2.00 |
| 6 Months | 13H-i 0.1% | 97.66 | 0.20 | 0.90 | 0.60 | 6.91 | 3.06 |
| | 13H-ii 0.01% | 98.02 | 0.39 | 0.66 | 0.55 | 8.55 | 4.24 |

The results of stability testing of Example 13H-i-ii at 40° C. are set forth in Table 147 below.

TABLE 147

| Ascorbic-palmitate | | | | | | Total Impurities | |
|---|---|---|---|---|---|---|---|
| | 40° C. | Potency % | CBD % | CBN % | D8-THC % | % | Increase + % |
| Zero | 13H-i 0.1% | 100.00 | 0.03 | 0.48 | 0.56 | 3.85 | |
| | 13H-ii 0.01% | 100.00 | 0.02 | 0.56 | 0.60 | 4.31 | |
| 1 | 13H-i 0.1% | 96.37 | 0.06 | 0.76 | 0.54 | 5.98 | 2.13 |
| Month | 13H-ii 0.01% | 88.91 | 0.59 | 1.09 | 0.56 | 12.48 | 8.17 |
| 2 | 13H-i 0.1% | 90.81 | 0.21 | 1.09 | 0.60 | 9.76 | 5.91 |
| Months | 13H-ii 0.01% | 86.27 | 0.45 | 1.22 | 0.64 | 13.44 | 9.13 |
| 3 | 13H-i 0.1% | 88.71 | 0.16 | 1.67 | 0.59 | 11.17 | 7.32 |
| Months | 13H-ii 0.01% | 84.36 | 0.75 | 1.63 | 0.57 | 15.03 | 10.72 |

The results of stability testing of Example 13H-i-ii at 55° C. are set forth in Table 148 below.

TABLE 148

| Ascorbic-palmitate | | | | | | Total Impurities | |
|---|---|---|---|---|---|---|---|
| | 55° C. | Potency % | CBD % | CBN % | D8-THC % | % | Increase + % |
| Zero | 13H-i 0.1% | 100.00 | 0.03 | 0.48 | 0.56 | 3.85 | |
| | 13H-ii 0.01% | 100.00 | 0.02 | 0.56 | 0.60 | 4.31 | |
| 1 | 13H-i 0.1% | 95.77 | 0.10 | 0.80 | 0.57 | 6.84 | 2.99 |
| Week | 13H-ii 0.01% | 87.54 | 0.12 | 0.61 | 0.50 | 15.28 | 10.97 |
| 2 | 13H-i 0.1% | 91.07 | 0.01 | 1.05 | 0.56 | 11.52 | 7.67 |
| Weeks | 13H-ii 0.01% | 23.06 | 0.11 | 3.39 | 0.66 | 67.78 | 63.47 |

EXAMPLE 13I

Dronabinol Solution in Sesame Oil Sourced from Dipasa—Capsules

In Example 13I, dronabinol formulations 13I-i, and 13I-ii were prepared in accordance with Examples 13-viii and 13-vii, respectively using sesame oil sourced from Dipasa. Formulation 13I-i contained 0.1% L-ascorbic acid-6-palmitate and formulation 13I-ii contained 0.1% L-ascorbic acid-6-palmitate. The dronabinol formulations were then used to hard gelatin capsules in accordance with Example 2. The formulations within the capsules were initially tested, then tested at 25° C. for 3 and 6 months; 40° C. for 1, 2 and 3 months and at 55° C. for 1 and 2 weeks.

The results of stability testing of Example 13I-i-ii at 25° C. are set forth in Table 149 below.

TABLE 149

| Ascorbic-palmitate | | | | | | Total Impurities | |
|---|---|---|---|---|---|---|---|
| | 25° C. | Potency % | CBD % | CBN % | D8-THC % | % | Increase + % |
| Zero | 13I-i 0.1% | 100.00 | 0.01 | 0.54 | 0.58 | 3.99 | |
| | 13I-ii 0.01% | 100.00 | 0.03 | 0.53 | 0.54 | 3.81 | |
| 3 | 13I-i 0.1% | 96.89 | 0.02 | 0.84 | 0.55 | 4.52 | 0.53 |
| Months | 13I-ii 0.01% | 95.50 | 0.03 | 0.69 | 0.53 | 5.72 | 1.91 |
| 6 | 13I-i 0.1% | 97.83 | 0.13 | 0.94 | 0.56 | 5.79 | 1.80 |
| Months | 13I-ii 0.01% | 98.16 | 0.30 | 0.81 | 0.56 | 7.99 | 4.18 |

The results of stability testing of Example 13I-i-ii at 40° C. are set forth in Table 150 below.

TABLE 150

| Ascorbic-palmitate | | | | | | Total Impurities | |
|---|---|---|---|---|---|---|---|
| | 40° C. | Potency % | CBD % | CBN % | D8-THC % | % | Increase + % |
| Zero | 13I-i 0.1% | 100.00 | 0.01 | 0.54 | 0.58 | 3.99 | |
| | 13I-ii 0.01% | 100.00 | 0.03 | 0.53 | 0.54 | 3.81 | |
| 1 Month | 13I-i 0.1% | 96.31 | 0.05 | 0.85 | 0.56 | 5.52 | 1.53 |
| | 13I-ii 0.01% | 96.26 | 0.12 | 0.76 | 0.56 | 6.89 | 3.08 |
| 2 Months | 13I-i 0.1% | 92.89 | 0.04 | 1.22 | 0.59 | 7.86 | 3.87 |
| | 13I-ii 0.01% | 92.24 | 0.24 | 1.01 | 0.61 | 10.03 | 6.22 |
| 3 Months | 13I-i 0.1% | 89.96 | 0.12 | 1.92 | 0.54 | 10.10 | 6.11 |
| | 13I-ii 0.01% | 89.56 | 0.36 | 1.53 | 0.54 | 12.04 | 8.23 |

The results of stability testing of Example 13I-i-ii at 55° C. are set forth in Table 151 below.

TABLE 151

| Ascorbic-palmitate | | | | | | Total Impurities | |
|---|---|---|---|---|---|---|---|
| | 55° C. | Potency % | CBD % | CBN % | D8-THC % | % | Increase + % |
| Zero | 13I-i 0.1% | 100.00 | 0.01 | 0.54 | 0.58 | 3.99 | |
| | 13I-ii 0.01% | 100.00 | 0.03 | 0.53 | 0.54 | 3.81 | |
| 1 Week | 13I-i 0.1% | 96.37 | 0.05 | 0.92 | 0.58 | 5.31 | 1.32 |
| | 13I-ii 0.01% | 99.37 | 0.06 | 0.67 | 0.61 | 5.70 | 1.89 |
| 2 Weeks | 13I-i 0.1% | 93.81 | 0.01 | 1.45 | 0.52 | 8.07 | 4.08 |
| | 13I-ii 0.01% | 93.68 | 0.01 | 1.04 | 0.50 | 8.40 | 4.59 |

EXAMPLE 13J

Dronabinol Solution in Sesame Oil Sourced from Arista—Vials

In Example 13J, dronabinol formulations 13J-i, and 13J-ii were prepared in accordance with Examples 13-viii and 13-vii, respectively using sesame oil sourced from Arista. Formulation 13J-i contained 0.1% L-ascorbic acid-6-palmitate and formulation 13J-ii contained 0.1% L-ascorbic acid-6-palmitate. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 13J-i-ii at 25° C. are set forth in Table 152 below.

TABLE 152

| Ascorbic-palmitate | | | | | | Total Impurities | |
|---|---|---|---|---|---|---|---|
| | 25° C. | Potency % | CBD % | CBN % | D8-THC % | % | Increase + % |
| Zero | 13J-i 0.1% | 100.00 | 0.01 | 0.54 | 0.52 | 3.73 | |
| | 13J-ii 0.01% | 100.00 | 0.02 | 0.50 | 0.51 | 3.10 | |
| 3 Months | 13J-i 0.1% | 96.55 | 0.12 | 0.76 | 0.49 | 4.84 | 1.11 |
| | 13J-ii 0.01% | 95.51 | 0.15 | 0.68 | 0.52 | 5.49 | 2.39 |
| 6 Months | 13J-i 0.1% | 98.93 | 0.13 | 0.98 | 0.50 | 5.75 | 2.02 |
| | 13J-ii 0.01% | 98.38 | 0.18 | 0.86 | 0.49 | 7.21 | 4.11 |

The results of stability testing of Example 13J-i-ii at 40° C. are set forth in Table 153 below.

TABLE 153

| | Ascorbic-palmitate | | | | | Total Impurities | |
|---|---|---|---|---|---|---|---|
| | 40° C. | Potency % | CBD % | CBN % | D8-THC % | % | Increase + % |
| Zero | 13J-i 0.1% | 100.00 | 0.01 | 0.54 | 0.52 | 3.73 | |
| | 13J-ii 0.01% | 100.00 | 0.02 | 0.50 | 0.51 | 3.10 | |
| 1 | 13J-i 0.1% | 97.70 | −0.04 | 0.76 | 0.50 | 4.36 | 0.63 |
| Month | 13J-ii 0.01% | 97.00 | 0.06 | 0.68 | 0.50 | 5.49 | 2.39 |
| 2 | 13J-i 0.1% | 95.10 | 0.08 | 1.05 | 0.50 | 6.06 | 2.33 |
| Months | 13J-ii 0.01% | 93.36 | 0.11 | 0.86 | 0.49 | 8.35 | 5.25 |
| 3 | 13J-i 0.1% | 91.36 | 0.33 | 1.70 | 0.49 | 9.53 | 5.80 |
| Months | 13J-ii 0.01% | 89.30 | 0.42 | 1.24 | 0.48 | 11.99 | 8.89 |

The results of stability testing of Example 13J-i-ii at 55° C. are set forth in Table 154 below.

TABLE 154

| | Ascorbic-palmitate | | | | | Total Impurities | |
|---|---|---|---|---|---|---|---|
| | 55° C. | Potency % | CBD % | CBN % | D8-THC % | % | Increase + % |
| Zero | 13J-i 0.1% | 100.00 | 0.01 | 0.54 | 0.52 | 3.73 | |
| | 13J-ii 0.01% | 100.00 | 0.02 | 0.50 | 0.51 | 3.10 | |
| 1 | 13J-i 0.1% | 99.29 | 0.04 | 0.71 | 0.51 | 4.30 | 0.57 |
| Week | 13J-ii 0.01% | 99.17 | 0.05 | 0.62 | 0.49 | 4.59 | 1.49 |
| 2 | 13J-i 0.1% | 98.19 | 0.01 | 0.88 | 0.53 | 4.69 | 0.96 |
| Weeks | 13J-ii 0.01% | 97.17 | 0.01 | 0.73 | 0.51 | 6.60 | 3.50 |

EXAMPLE 13K

Dronabinol Solution in Sesame Oil Sourced from Croda—Vials

In Example 13K, dronabinol formulations 13K-i, and 13K-ii were prepared in accordance with Examples 13-viii and 13-vii, respectively using sesame oil sourced from Croda. Formulation 13K-i contained 0.1% L-ascorbic acid-6-palmitate and formulation 13K-ii contained 0.1% L-ascorbic acid-6-palmitate. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 13K-i-ii at 25° C. are set forth in Table 155 below.

TABLE 155

| | Ascorbic-palmitate | | | | | Total Impurities | |
|---|---|---|---|---|---|---|---|
| | 25° C. | Potency % | CBD % | CBN % | D8-THC % | % | Increase + % |
| Zero | 13K-i 0.1% | 100.00 | 0.03 | 0.48 | 0.56 | 3.85 | |
| | 13K-ii 0.01% | 100.00 | 0.02 | 0.56 | 0.60 | 4.31 | |
| 3 | 13K-i 0.1% | 94.37 | 0.23 | 0.63 | 0.57 | 5.77 | 1.92 |
| Months | 13K-ii 0.01% | 92.48 | 0.31 | 0.52 | 0.58 | 6.59 | 2.28 |
| 6 | 13K-i 0.1% | 94.76 | 0.20 | 0.86 | 0.62 | 7.88 | 4.03 |
| Months | 13K-ii 0.01% | 94.19 | 0.26 | 0.61 | 0.58 | 9.40 | 5.09 |

The results of stability testing of Example 13K-i-ii at 40° C. are set forth in Table 156 below.

TABLE 156

| | Ascorbic-palmitate 40° C. | Potency % | CBD % | CBN % | D8-THC % | Total Impurities % | Increase + % |
|---|---|---|---|---|---|---|---|
| Zero | 13K-i 0.1% | 100.00 | 0.03 | 0.48 | 0.56 | 3.85 | |
| | 13K-ii 0.01% | 100.00 | 0.02 | 0.56 | 0.60 | 4.31 | |
| 1 Month | 13K-i 0.1% | 96.31 | 0.11 | 0.66 | 0.55 | 5.79 | 1.94 |
| | 13K-ii 0.01% | 95.48 | 0.14 | 0.50 | 0.54 | 7.66 | 3.35 |
| 2 Months | 13K-i 0.1% | 89.91 | 0.17 | 0.96 | 0.57 | 9.18 | 5.33 |
| | 13K-ii 0.01% | 86.82 | 0.22 | 0.62 | 0.58 | 12.53 | 8.22 |
| 3 Months | 13K-i 0.1% | 86.06 | 0.73 | 1.57 | 0.56 | 14.00 | 10.15 |
| | 13K-ii 0.01% | 82.08 | 0.19 | 0.97 | 0.53 | 17.65 | 13.34 |

The results of stability testing of Example 13K-i-ii at 55° C. are set forth in Table 157 below.

TABLE 157

| | Ascorbic-palmitate 55° C. | Potency % | CBD % | CBN % | D8-THC % | Total Impurities % | Increase + % |
|---|---|---|---|---|---|---|---|
| Zero | 13K-i 0.1% | 100.00 | 0.03 | 0.48 | 0.56 | 3.85 | |
| | 13K-ii 0.01% | 100.00 | 0.02 | 0.56 | 0.60 | 4.31 | |
| 1 Week | 13K-i 0.1% | 95.77 | 0.10 | 0.80 | 0.57 | 6.84 | 2.99 |
| | 13K-ii 0.01% | 87.54 | 0.12 | 0.61 | 0.50 | 15.28 | 10.97 |
| 2 Weeks | 13K-i 0.1% | 91.07 | 0.01 | 1.05 | 0.56 | 11.52 | 7.67 |
| | 13K-ii 0.01% | 23.06 | 0.11 | 3.39 | 0.66 | 67.78 | 63.47 |

EXAMPLE 13L

Dronabinol Solution in Sesame Oil Sourced from Dipasa—Vials

In Example 13L, dronabinol formulations 13L-i, and 13L-ii were prepared in accordance with Examples 13-viii and 13-vii, respectively using sesame oil sourced from Dipasa. Formulation 13L-i contained 0.1% L-ascorbic acid-6-palmitate and formulation 13L-ii contained 0.1% L-ascorbic acid-6-palmitate. The dronabinol formulations were then used to fill amber glass vials. The formulations within the vials were initially tested, then tested at 25° C. for 3 and 6 months; 40° C. for 1, 2 and 3 months and at 55° C. for 1 and 2 weeks.

The results of stability testing of Example 13L-i-ii at 25° C. are set forth in Table 158 below.

TABLE 158

| | Ascorbic-palmitate 25° C. | Potency % | CBD % | CBN % | D8-THC % | Total Impurities % | Increase + % |
|---|---|---|---|---|---|---|---|
| Zero | 13L-i 0.1% | 100.00 | 0.01 | 0.54 | 0.58 | 3.99 | |
| | 13L-ii 0.01% | 100.00 | 0.03 | 0.53 | 0.54 | 3.81 | |
| 3 Months | 13L-i 0.1% | 95.76 | 0.11 | 0.75 | 0.53 | 5.08 | 1.09 |
| | 13L-ii 0.01% | 96.06 | 0.22 | 0.72 | 0.59 | 6.81 | 3.00 |
| 6 Months | 13L-i 0.1% | 98.96 | 0.13 | 1.04 | 0.54 | 6.12 | 2.13 |
| | 13L-ii 0.01% | 96.94 | 0.19 | 0.96 | 0.53 | 8.82 | 5.01 |

The results of stability testing of Example 13L-i-ii at 40° C. are set forth in Table 159 below.

TABLE 159

| Ascorbic-palmitate | | | | | | Total Impurities | |
|---|---|---|---|---|---|---|---|
| | 40° C. | Potency % | CBD % | CBN % | D8-THC % | % | Increase + % |
| Zero | 13L-i 0.1% | 100.00 | 0.01 | 0.54 | 0.58 | 3.99 | |
| | 13L-ii 0.01% | 100.00 | 0.03 | 0.53 | 0.54 | 3.81 | |
| 1 Month | 13L-i 0.1% | 98.21 | 0.03 | 0.77 | 0.53 | 4.50 | 0.51 |
| | 13L-ii 0.01% | 96.57 | 0.15 | 0.76 | 0.54 | 6.97 | 3.16 |
| 2 Months | 13L-i 0.1% | 93.96 | 0.09 | 1.15 | 0.57 | 6.09 | 2.10 |
| | 13L-ii 0.01% | 91.98 | 0.15 | 1.14 | 0.57 | 10.09 | 6.28 |
| 3 Months | 13L-i 0.1% | 89.30 | 0.44 | 2.01 | 0.53 | 11.38 | 7.39 |
| | 13L-ii 0.01% | 87.48 | 0.13 | 1.77 | 0.53 | 15.25 | 11.44 |

The results of stability testing of Example 13L-i-ii at 55° C. are set forth in Table 160 below.

TABLE 160

| Ascorbic-palmitate | | | | | | Total Impurities | |
|---|---|---|---|---|---|---|---|
| | 55° C. | Potency % | CBD % | CBN % | D8-THC % | % | Increase + % |
| Zero | 13L-i 0.1% | 100.00 | 0.01 | 0.54 | 0.58 | 3.99 | |
| | 13L-ii 0.01% | 100.00 | 0.03 | 0.53 | 0.54 | 3.81 | |
| 1 Week | 13L-i 0.1% | 96.37 | 0.05 | 0.92 | 0.58 | 5.31 | 1.32 |
| | 13L-ii 0.01% | 99.37 | 0.06 | 0.67 | 0.61 | 5.70 | 1.89 |
| 2 Weeks | 13L-i 0.1% | 93.81 | 0.01 | 1.45 | 0.52 | 8.07 | 4.08 |
| | 13L-ii 0.01% | 93.68 | 0.01 | 1.04 | 0.50 | 8.40 | 4.59 |

As shown from the results above, the addition of lecithin or L-ascorbic acid-6-palmitate to the dronabinol formulations helps stabilize the formulations. The higher the concentration of anti-oxidants, the better the stability of dronabinol formulations. Irrespective of the source of sesame oil used, lecithin is better at stabilizing dronabinol than L-ascorbic acid. Both anti-oxidants however help in maintaining dronabinol stability.

Extended Stability Results-Combination of Degradants with Lecithin in Dronabinol Formulation In view of the stabilizing property of lecithin shown in the above examples, specifically 13A-F, further studies were performed to evaluate the effect of lecithin with the addition of degradants such as glycerin, moisture and myristic acid to dronabinol formulations stored at different temperature conditions for an extended period of time.

EXAMPLE 14A

Control Dronabinol Solution in Sesame Oil Sourced from Arista

In Example 14A, a dronabinol control formulation was prepared in accordance with Example 1, using sesame oil sourced from Arista. The dronabinol formulation was then used to fill hard gelatin capsules in accordance with Example 2. The formulation within the capsules was initially tested, then tested at 25° C. for 3 and 6 months; 40° C. for 1, 2, 3 and 6 months and at 55° C. for 1 and 2 weeks.

The results of stability testing of Example 14A at 25° C. are set forth in Table 161 below.

TABLE 161

| Control 25° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 3 Months | 94.51 | 0.66 | 0.89 | 0.56 | 11.03 | 6.95 |
| 6 Months | 93.26 | 0.72 | 0.98 | 0.53 | 11.41 | 7.33 |

The results of stability testing of Example 14A at 40° C. are set forth in Table 162 below.

TABLE 162

| Control 40° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 1 Month | 94.87 | 0.76 | 0.80 | 0.51 | 10.31 | 6.23 |
| 2 Months | 94.16 | 0.59 | 1.09 | 0.55 | 11.28 | 7.20 |
| 3 Months | 94.61 | 0.57 | 1.31 | 0.56 | 12.25 | 8.17 |
| 6 Months | 89.15 | 0.06 | 1.90 | 0.57 | 14.64 | 10.56 |

The results of stability testing of Example 14A at 55° C. are set forth in Table 163 below.

TABLE 163

| Control 55° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 1 Week | 88.90 | 0.19 | 0.61 | 0.55 | 14.72 | 10.64 |
| 2 Weeks | 71.45 | 2.67 | 1.54 | 0.60 | 27.11 | 23.03 |

EXAMPLE 14B

Control Dronabinol Solution in Sesame Oil Sourced from Croda

In Example 14B, a dronabinol control formulation was prepared in accordance with Example 1, using sesame oil sourced from Croda. The dronabinol formulation was then used to fill hard gelatin capsules in accordance with Example 2. The formulation within the capsules was initially tested, then tested at 25° C. for 3 and 6 months; 40° C. for 1, 2, 3 and 6 months and at 55° C. for 1 and 2 weeks.

The results of stability testing of Example 14B at 25° C. are set forth in Table 164 below.

TABLE 164

| Control 25° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 3 Months | 91.48 | 1.01 | 0.62 | 0.61 | 12.51 | 6.98 |
| 6 Months | 88.95 | 1.11 | 0.75 | 0.59 | 13.64 | 8.11 |

The results of stability testing of Example 14B at 40° C. are set forth in Table 165 below.

TABLE 165

| Control 40° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 1 Month | 87.89 | 1.22 | 0.67 | 0.53 | 12.01 | 6.48 |
| 2 Months | 90.94 | 0.98 | 0.84 | 0.61 | 12.49 | 6.96 |
| 3 Months | 87.61 | 0.95 | 1.00 | 0.62 | 13.45 | 7.92 |
| 6 Months | 86.92 | 0.61 | 1.25 | 0.49 | 14.63 | 9.10 |

The results of stability testing of Example 14B at 40° C. are set forth in Table 166 below.

TABLE 166

| Control 55° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 1 Week | 81.35 | 0.26 | 0.69 | 0.58 | 21.10 | 15.57 |
| 2 Weeks | 65.26 | 3.41 | 1.31 | 0.66 | 29.70 | 24.17 |

EXAMPLE 14C

Control Dronabinol Solution in Sesame Oil Sourced from Dipasa

In Example 14C, a dronabinol control formulation was prepared in accordance with Example 1, using sesame oil sourced from Dipasa. The dronabinol formulation was then used to fill hard gelatin capsules in accordance with Example 2. The formulation within the capsules was initially tested, then tested at 25° C. for 3 and 6 months; 40° C. for 1, 2, 3 and 6 months and at 55° C. for 1 and 2 weeks.

The results of stability testing of Example 14C at 25° C. are set forth in Table 167 below.

TABLE 167

| Control 25° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 3 Months | 99.70 | 0.12 | 0.61 | 0.56 | 6.46 | 2.47 |
| 6 Months | 97.64 | 0.23 | 0.80 | 0.52 | 8.20 | 4.21 |

The results of stability testing of Example 14C at 40° C. are set forth in Table 168 below.

TABLE 168

| Control 40° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 1 Month | 95.26 | 0.19 | 0.70 | 0.52 | 6.70 | 2.71 |
| 2 Months | 97.65 | 0.30 | 0.93 | 0.53 | 9.63 | 5.64 |
| 3 Months | 95.26 | 0.34 | 1.18 | 0.54 | 11.18 | 7.19 |
| 6 Months | 91.99 | 0.03 | 1.69 | 0.51 | 12.51 | 8.52 |

The results of stability testing of Example 14C at 55° C. are set forth in Table 169 below.

TABLE 169

| Control 55° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 1 Week | 96.16 | 0.05 | 0.76 | 0.58 | 7.13 | 3.14 |
| 2 Weeks | 92.72 | 0.12 | 1.25 | 0.55 | 11.12 | 7.13 |

EXAMPLE 14D

Control Dronabinol Solution in Sesame Oil Sourced from Arista

In Example 14D, a dronabinol control formulation was prepared in accordance with Example 14A, using sesame oil sourced from Arista. The dronabinol formulation was then used to fill amber glass vials. The formulation within the vials was initially tested, then tested at 25° C. for 3 and 6 months; 40° C. for 1, 2, 3 and 6 months and at 55° C. for 1 and 2 weeks.

The results of stability testing of Example 14D at 25° C. are set forth in Table 170 below.

TABLE 170

| Control 25° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 3 Months | 88.57 | 1.54 | 0.77 | 0.52 | 14.79 | 10.71 |
| 6 Months | 71.21 | 2.95 | 1.62 | 0.56 | 27.29 | 23.21 |

The results of stability testing of Example 14D at 40° C. are set forth in Table 171 below.

TABLE 171

| Control 40° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 1 Month | 90.04 | 1.23 | 0.69 | 0.51 | 12.10 | 8.02 |
| 2 Months | 81.90 | 2.27 | 1.27 | 0.50 | 20.62 | 16.54 |
| 3 Months | 65.52 | 2.75 | 2.43 | 0.59 | 31.20 | 27.12 |
| 6 Months | 29.92 | 2.28 | 7.78 | 0.85 | 60.00 | 55.92 |

The results of stability testing of Example 14D at 55° C. are set forth in Table 172 below.

TABLE 172

| Control 55° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 1 Week | 88.90 | 0.19 | 0.61 | 0.55 | 14.72 | 10.64 |
| 2 Weeks | 71.45 | 2.67 | 1.54 | 0.60 | 27.11 | 23.03 |

EXAMPLE 14E

Control Dronabinol Solution in Sesame Oil Sourced from Croda

In Example 14E, a dronabinol control formulation was prepared in accordance with Example 14B, using sesame oil sourced from Croda. The dronabinol formulation was then used to fill amber glass vials. The formulation within the vials was initially tested, then tested at 25° C. for 3 and 6 months; 40° C. for 1, 2, 3 and 6 months and at 55° C. for 1 and 2 weeks.

The results of stability testing of Example 14E at 25° C. are set forth in Table 173 below.

TABLE 173

| Control 25° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 3 Months | 85.10 | 2.07 | 0.75 | 0.58 | 18.41 | 12.88 |
| 6 Months | 69.68 | 3.38 | 1.18 | 0.60 | 30.45 | 24.92 |

The results of stability testing of Example 14E at 40° C. are set forth in Table 174 below.

TABLE 174

| Control 40° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 1 Month | 84.66 | 1.64 | 0.69 | 0.56 | 15.97 | 10.44 |
| 2 Months | 75.78 | 2.82 | 1.17 | 0.58 | 25.65 | 20.12 |
| 3 Months | 59.02 | 3.54 | 1.89 | 0.56 | 36.06 | 30.53 |
| 6 Months | 23.92 | 2.88 | 7.00 | 0.89 | 65.24 | 59.71 |

The results of stability testing of Example 14E at 55° C. are set forth in Table 175 below.

TABLE 175

| Control 55° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 1 Week | 81.35 | 0.26 | 0.69 | 0.58 | 21.10 | 15.57 |
| 2 Weeks | 65.26 | 3.41 | 1.31 | 0.66 | 29.70 | 24.17 |

EXAMPLE 14F

Control Dronabinol Solution in Sesame Oil Sourced from Dipasa

In Example 14F, a dronabinol control formulation was prepared in accordance with Example 14C, using sesame oil sourced from Dipasa. The dronabinol formulation was then used to fill amber glass vials. The formulation within the vials was then tested at 25° C. for 3 and 6 months; 40° C. for 1, 2, 3 and 6 months and at 55° C. for 1 and 2 weeks.

The results of stability testing of Example 14F at 25° C. are set forth in Table 176 below.

TABLE 176

| Control 25° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 3 Months | 99.26 | 0.18 | 0.70 | 0.53 | 6.04 | 2.05 |
| 6 Months | 95.28 | 0.38 | 0.94 | 0.58 | 9.05 | 5.06 |

The results of stability testing of Example 14F at 40° C. are set forth in Table 177 below.

TABLE 177

| Control 40° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 1 Month | 95.74 | 0.23 | 0.81 | 0.51 | 7.12 | 3.13 |
| 2 Months | 95.31 | 0.38 | 1.15 | 0.52 | 10.16 | 6.17 |
| 3 Months | 90.52 | 0.39 | 1.76 | 0.53 | 14.04 | 10.05 |
| 6 Months | 76.78 | 0.65 | 3.53 | 0.54 | 25.94 | 21.95 |

The results of stability testing of Example 14F at 55° C. are set forth in Table 178 below.

TABLE 178

| Control 55° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 1 Week | 96.16 | 0.05 | 0.76 | 0.58 | 7.13 | 3.14 |
| 2 Weeks | 92.72 | 0.12 | 1.25 | 0.55 | 11.12 | 7.13 |

EXAMPLE 14G

Dronabinol Solution in Sesame Oil Sourced from Arista with Lecithin and Different Degradants Added In Example 14G-i-iii, dronabinol formulations were prepared in accordance with Example 14A, using sesame oil sourced from Arista, with 8.25% lecithin added. Formula 14G-i also contained 0.2% glycerin; formula 14G-ii also contained 0.1% myristic acid; and formula 14G-iii contained 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 14G-i-iii at 25° C. are set forth in Table 179 below.

TABLE 179

| | Lecithin 8.25% | | | | | Total Impurities | |
|---|---|---|---|---|---|---|---|
| | 25° C. | Potency % | CBD % | CBN % | D8-THC % | % | Increase + % |
| Zero | 14G-i Glycerin 0.2% | 100.00 | 0.09 | 0.46 | 0.56 | 3.76 | |
| | 14G-ii Myristic acid 0.1% | 100.00 | 0.10 | 0.47 | 0.56 | 3.77 | |
| | 14G-iii Moisture 100% | 100.00 | 0.09 | 0.46 | 0.54 | 3.69 | |
| 3 M | 14G-i Glycerin 0.2% | 100.41 | 0.01 | 0.70 | 0.52 | 5.18 | 1.42 |
| | 14G-ii Myristic acid 0.1% | 100.81 | 0.01 | 0.73 | 0.51 | 5.27 | 1.50 |
| | 14G-iii Moisture 100% | 100.93 | 0.01 | 0.71 | 0.54 | 5.18 | 1.49 |
| 6 M | 14G-i Glycerin 0.2% | 98.62 | 0.01 | 0.83 | 0.49 | 5.45 | 1.69 |
| | 14G-ii Myristic acid 0.1% | 98.34 | 0.01 | 0.99 | 0.53 | 5.59 | 1.82 |
| | 14G-iii Moisture 100% | 99.01 | 0.01 | 0.85 | 0.51 | 5.64 | 1.95 |

The results of stability testing of Example 14G-i-iii at 40° C. are set forth in Table 180 below.

TABLE 180

| | Lecithin 8.25% | | | | | Total Impurities | |
|---|---|---|---|---|---|---|---|
| | 40° C. | Potency % | CBD % | CBN % | D8-THC % | % | Increase + % |
| Zero | 14G-i Glycerin 0.2% | 100.00 | 0.09 | 0.46 | 0.56 | 3.76 | |
| | 14G-ii Myristic acid 0.1% | 100.00 | 0.10 | 0.47 | 0.56 | 3.77 | |
| | 14G-iii Moisture 100% | 100.00 | 0.09 | 0.46 | 0.54 | 3.69 | |
| 1 M | 14G-i Glycerin 0.2% | 95.91 | 0.07 | 0.80 | 0.51 | 5.47 | 1.71 |
| | 14G-ii Myristic acid 0.1% | 96.58 | 0.04 | 0.79 | 0.53 | 5.80 | 2.03 |
| | 14G-iii Moisture 100% | 96.38 | 0.02 | 0.79 | 0.52 | 5.38 | 1.69 |
| 2 M | 14G-i Glycerin 0.2% | 99.79 | 0.02 | 1.12 | 0.53 | 6.39 | 2.63 |
| | 14G-ii Myristic acid 0.1% | 98.30 | 0.01 | 1.07 | 0.52 | 6.43 | 2.66 |
| | 14G-iii Moisture 100% | 98.42 | 0.02 | 1.10 | 0.48 | 6.57 | 2.88 |
| 3 M | 14G-i Glycerin 0.2% | 97.27 | 0.01 | 1.63 | 0.54 | 7.63 | 3.87 |
| | 14G-ii Myristic acid 0.1% | 96.59 | 0.01 | 1.48 | 0.56 | 7.75 | 3.98 |
| | 14G-iii Moisture 100% | 96.72 | 0.01 | 1.43 | 0.53 | 8.06 | 4.37 |
| 6 M | 14G-i Glycerin 0.2% | 93.62 | 0.01 | 2.55 | 0.50 | 9.52 | 5.76 |
| | 14G-ii Myristic acid 0.1% | 93.81 | 0.02 | 2.41 | 0.52 | 9.76 | 5.99 |
| | 14G-iii Moisture 100% | 94.06 | 0.01 | 2.56 | 0.51 | 10.08 | 6.39 |

The results of stability testing of Example 14G-i-iii at 55° C. are set forth in Table 181 below.

TABLE 181

| Lecithin 8.25% | | | | | | Total Impurities | |
|---|---|---|---|---|---|---|---|
| | 55° C. | Potency % | CBD % | CBN % | D8-THC % | % | Increase + % |
| Zero | 14G-i Glycerin 0.2% | 100.00 | 0.09 | 0.46 | 0.56 | 3.76 | |
| | 14G-ii Myristic acid 0.1% | 100.00 | 0.10 | 0.47 | 0.56 | 3.77 | |
| | 14G-iii Moisture 100% | 100.00 | 0.09 | 0.46 | 0.54 | 3.69 | |
| 1 W | 14G-i Glycerin 0.2% | 98.10 | 0.04 | 0.97 | 0.57 | 5.36 | 1.60 |
| | 14G-ii Myristic acid 0.1% | 97.69 | 0.02 | 0.89 | 0.60 | 5.25 | 1.48 |
| | 14G-iii Moisture 100% | 99.09 | 0.02 | 0.78 | 0.72 | 4.86 | 1.17 |
| 2 W | 14G-i Glycerin 0.2% | 96.94 | 0.01 | 1.57 | 0.55 | 6.73 | 2.97 |
| | 14G-ii Myristic acid 0.1% | 97.68 | 0.01 | 1.41 | 0.55 | 6.68 | 2.91 |
| | 14G-iii Moisture 100% | 98.85 | 0.02 | 1.17 | 0.55 | 5.98 | 2.29 |

EXAMPLE 14H

Dronabinol Solution in Sesame Oil Sourced from Croda with Lecithin and Different Degradants Added In Example 14H-i-iii, dronabinol formulations were prepared in accordance with Example 14B, using sesame oil sourced from Croda, with 8.25% lecithin added. Formula 14H-i also contained 0.2% glycerin; formula 14H-ii also contained 0.1% myristic acid; and formula 14H-iii contained 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 14H-i-iii at 25° C. are set forth in Table 182 below.

TABLE 182

| Lecithin 8.25% | | | | | | Total Impurities | |
|---|---|---|---|---|---|---|---|
| | 25° C. | Potency % | CBD % | CBN % | D8-THC % | % | Increase + % |
| Zero | 14H-i Glycerin 0.2% | 100.00 | 0.05 | 0.47 | 0.56 | 3.52 | |
| | 14H-ii Myristic acid 0.1% | 100.00 | 0.02 | 0.47 | 0.58 | 3.43 | |
| | 14H-iii Moisture 100% | 100.00 | 0.01 | 0.47 | 0.57 | 3.37 | |
| 3 M | 14H-i Glycerin 0.2% | 99.26 | 0.02 | 0.67 | 0.55 | 4.99 | 1.47 |
| | 14H-ii Myristic acid 0.1% | 97.69 | 0.01 | 0.68 | 0.56 | 5.24 | 1.81 |
| | 14H-iii Moisture 100% | 99.34 | 0.01 | 0.65 | 0.59 | 5.26 | 1.89 |
| 6 M | 14H-i Glycerin 0.2% | 96.02 | 0.05 | 0.81 | 0.60 | 6.90 | 3.38 |
| | 14H-ii Myristic acid 0.1% | 96.04 | 0.02 | 0.86 | 0.62 | 6.15 | 2.72 |
| | 14H-iii Moisture 100% | 92.84 | 0.06 | 1.10 | 0.59 | 8.45 | 5.08 |

The results of stability testing of Example 14H-i-iii at 40° C. are set forth in Table 183 below.

TABLE 183

| | Lecithin 8.25% | | | | | Total Impurities | |
|---|---|---|---|---|---|---|---|
| | 40° C. | Potency % | CBD % | CBN % | D8-THC % | % | Increase + % |
| Zero | 14H-i Glycerin 0.2% | 100.00 | 0.05 | 0.47 | 0.56 | 3.52 | |
| | 14H-ii Myristic acid 0.1% | 100.00 | 0.02 | 0.47 | 0.58 | 3.43 | |
| | 14H-iii Moisture 100% | 100.00 | 0.01 | 0.47 | 0.57 | 3.37 | |
| 1 M | 14H-i Glycerin 0.2% | 93.05 | 0.12 | 0.82 | 0.55 | 6.41 | 2.89 |
| | 14H-ii Myristic acid 0.1% | 93.65 | 0.03 | 0.79 | 0.59 | 5.80 | 2.37 |
| | 14H-iii Moisture 100% | 89.84 | 0.05 | 1.30 | 0.59 | 8.58 | 5.21 |
| 2 M | 14H-i Glycerin 0.2% | 94.03 | 0.02 | 1.32 | 0.55 | 9.04 | 5.52 |
| | 14H-ii Myristic acid 0.1% | 95.18 | 0.03 | 1.43 | 0.55 | 9.13 | 5.70 |
| | 14H-iii Moisture 100% | 92.78 | 0.06 | 1.62 | 0.55 | 10.00 | 6.63 |
| 3 M | 14H-i Glycerin 0.2% | 93.16 | 0.01 | 1.69 | 0.60 | 10.45 | 6.93 |
| | 14H-ii Myristic acid 0.1% | 90.68 | 0.02 | 1.82 | 0.58 | 10.16 | 6.73 |
| | 14H-iii Moisture 100% | 91.73 | 0.01 | 1.96 | 0.61 | 10.67 | 7.30 |
| 6 M | 14H-i Glycerin 0.2% | 88.53 | 0.01 | 2.81 | 0.56 | 12.62 | 9.10 |
| | 14H-ii Myristic acid 0.1% | 88.78 | 0.03 | 2.89 | 0.56 | 12.34 | 8.91 |
| | 14H-iii Moisture 100% | 88.61 | 0.02 | 3.08 | 0.55 | 12.90 | 9.53 |

The results of stability testing of Example 14H-i-iii at 55° C. are set forth in Table 184 below.

TABLE 184

| | Lecithin 8.25% | | | | | Total Impurities | |
|---|---|---|---|---|---|---|---|
| | 55° C. | Potency % | CBD % | CBN % | D8-THC % | % | Increase + % |
| Zero | 14H-i Glycerin 0.2% | 100.00 | 0.05 | 0.47 | 0.56 | 3.52 | |
| | 14H-ii Myristic acid 0.1% | 100.00 | 0.02 | 0.47 | 0.58 | 3.43 | |
| | 14H-iii Moisture 100% | 100.00 | 0.01 | 0.47 | 0.57 | 3.37 | |
| 1 W | 14H-i Glycerin 0.2% | 90.92 | 0.04 | 2.11 | 0.65 | 8.95 | 5.43 |
| | 14H-ii Myristic acid 0.1% | 88.54 | 0.04 | 1.81 | 0.63 | 8.22 | 4.79 |
| | 14H-iii Moisture 100% | 87.62 | 0.06 | 2.33 | 0.64 | 9.64 | 6.27 |
| 2 W | 14H-i Glycerin 0.2% | 88.34 | 0.01 | 3.63 | 0.61 | 12.60 | 9.08 |
| | 14H-ii Myristic acid 0.1% | 89.17 | 0.02 | 2.82 | 0.61 | 10.56 | 7.13 |
| | 14H-iii Moisture 100% | 79.64 | 0.06 | 5.89 | 0.69 | 18.07 | 14.70 |

EXAMPLE 14I

Dronabinol Solution in Sesame Oil Sourced from Dipasa with Lecithin and Different Degradants Added In Example 14I-i-iii, dronabinol formulations were prepared in accordance with Example 14C, using sesame oil sourced from Croda, with 8.25% lecithin added. Formula 14i-i also contained 0.2% glycerin; formula 14I-ii also contained 0.1% myristic acid; and formula 14I-iii contained 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 14I-i-iii at 25° C. are set forth in Table 185 below.

TABLE 185

| | Lecithin 8.25% | | | | | Total Impurities | |
|---|---|---|---|---|---|---|---|
| | 25° C. | Potency % | CBD % | CBN % | D8-THC % | % | Increase + % |
| Zero | 14I-i Glycerin 0.2% | 100.00 | 0.07 | 0.45 | 0.52 | 3.73 | |
| | 14I-ii Myristic acid 0.1% | 100.00 | 0.07 | 0.44 | 0.55 | 3.66 | |
| | 14I-iii Moisture 100% | 100.00 | 0.09 | 0.43 | 0.54 | 3.66 | |
| 3 M | 14I-i Glycerin 0.2% | 100.44 | 0.01 | 0.68 | 0.52 | 5.38 | 1.65 |
| | 14I-ii Myristic acid 0.1% | 101.36 | 0.01 | 0.71 | 0.50 | 5.16 | 1.50 |
| | 14I-iii Moisture 100% | 100.05 | 0.02 | 0.68 | 0.51 | 5.16 | 1.50 |
| 6 M | 14I-i Glycerin 0.2% | 99.55 | 0.08 | 0.74 | 0.49 | 5.95 | 2.22 |
| | 14I-ii Myristic acid 0.1% | 99.58 | 0.04 | 0.84 | 0.57 | 6.26 | 2.60 |
| | 14I-iii Moisture 100% | 97.88 | 0.04 | 0.78 | 0.49 | 5.76 | 2.10 |

The results of stability testing of Example 14I-i-iii at 40° C. are set forth in Table 186 below.

TABLE 186

| | Lecithin 8.25% | | | | | Total Impurities | |
|---|---|---|---|---|---|---|---|
| | 40° C. | Potency % | CBD % | CBN % | D8-THC % | % | Increase + % |
| Zero | 14I-i Glycerin 0.2% | 100.00 | 0.07 | 0.45 | 0.52 | 3.73 | |
| | 14I-ii Myristic acid 0.1% | 100.00 | 0.07 | 0.44 | 0.55 | 3.66 | |
| | 14I-iii Moisture 100% | 100.00 | 0.09 | 0.43 | 0.54 | 3.66 | |
| 1 M | 14I-i Glycerin 0.2% | 96.96 | 0.03 | 0.73 | 0.52 | 5.11 | 1.38 |
| | 14I-ii Myristic acid 0.1% | 96.62 | 0.03 | 0.74 | 0.51 | 5.04 | 1.38 |
| | 14I-iii Moisture 100% | 96.07 | 0.04 | 0.77 | 0.50 | 5.38 | 1.72 |
| 2 M | 14I-i Glycerin 0.2% | 99.17 | 0.01 | 0.98 | 0.50 | 6.07 | 2.34 |
| | 14I-ii Myristic acid 0.1% | 99.64 | 0.02 | 1.04 | 0.49 | 6.36 | 2.70 |
| | 14I-iii Moisture 100% | 98.35 | 0.08 | 1.01 | 0.47 | 7.11 | 3.45 |
| 3 M | 14I-i Glycerin 0.2% | 96.74 | 0.01 | 1.38 | 0.53 | 7.94 | 4.21 |
| | 14I-ii Myristic acid 0.1% | 97.77 | 0.01 | 1.46 | 0.53 | 8.06 | 4.40 |
| | 14I-iii Moisture 100% | 95.61 | 0.01 | 1.45 | 0.52 | 8.18 | 4.52 |
| 6 M | 14I-i Glycerin 0.2% | 93.05 | 0.02 | 2.43 | 0.49 | 10.83 | 7.10 |
| | 14I-ii Myristic acid 0.1% | 94.10 | 0.01 | 2.81 | 0.52 | 10.92 | 7.26 |
| | 14I-iii Moisture 100% | 92.47 | 0.01 | 2.64 | 0.51 | 11.36 | 7.70 |

The results of stability testing of Example 14I-i-iii at 55° C. are set forth in Table 187 below.

TABLE 187

| | Lecithin 8.25% | | | | | Total Impurities | |
|---|---|---|---|---|---|---|---|
| | 55° C. | Potency % | CBD % | CBN % | D8-THC % | % | Increase + % |
| Zero | 14I-i Glycerin 0.2% | 100.00 | 0.07 | 0.45 | 0.52 | 3.73 | |

TABLE 187-continued

| Lecithin 8.25% | | | | | | Total Impurities | |
|---|---|---|---|---|---|---|---|
| | 55° C. | Potency % | CBD % | CBN % | D8-THC % | % | Increase + % |
| | 14I-ii Myristic acid 0.1% | 100.00 | 0.07 | 0.44 | 0.55 | 3.66 | |
| | 14I-iii Moisture 100% | 100.00 | 0.09 | 0.43 | 0.54 | 3.66 | |
| 1 W | 14I-i Glycerin 0.2% | 95.12 | 0.01 | 0.93 | 0.56 | 5.88 | 2.15 |
| | 14I-ii Myristic acid 0.1% | 99.31 | 0.01 | 0.94 | 0.58 | 1.70 | 5.36 |
| | 14I-iii Moisture 100% | 97.67 | 0.01 | 0.84 | 0.57 | 5.02 | 1.36 |
| 2 W | 14I-i Glycerin 0.2% | 95.55 | 0.01 | 1.85 | 0.51 | 8.15 | 4.42 |
| | 14I-ii Myristic acid 0.1% | 98.94 | 0.02 | 1.58 | 0.54 | 6.82 | 3.16 |
| | 14I-iii Moisture 100% | 96.48 | 0.02 | 1.30 | 0.55 | 6.34 | 2.68 |

EXAMPLE 14J

Dronabinol Solution in Sesame Oil Sourced from Arista with Lecithin and Different Degradants Added In Example 14J-i-iii, dronabinol formulations were prepared in accordance with Example 14G-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 14J-i-iii at 25° C. are set forth in Table 188 below.

TABLE 188

| Lecithin 8.25% | | | | | | Total Impurities | |
|---|---|---|---|---|---|---|---|
| | 25° C. | Potency % | CBD % | CBN % | D8-THC % | % | Increase + % |
| Zero | 14J-i Glycerin 0.2% | 100.00 | 0.09 | 0.46 | 0.56 | 3.76 | |
| | 14J-ii Myristic acid 0.1% | 100.00 | 0.10 | 0.47 | 0.56 | 3.77 | |
| | 14J-iii Moisture 100% | 100.00 | 0.09 | 0.46 | 0.54 | 3.69 | |
| 3 M | 14J-i Glycerin 0.2% | 101.25 | 0.03 | 0.77 | 0.52 | 4.86 | 1.10 |
| | 14J-ii Myristic acid 0.1% | 100.59 | 0.02 | 0.83 | 0.53 | 5.02 | 1.25 |
| | 14J-iii Moisture 100% | 101.32 | 0.03 | 0.80 | 0.54 | 5.01 | 1.32 |
| 6 M | 14J-i Glycerin 0.2% | 98.50 | 0.02 | 0.98 | 0.54 | 5.85 | 2.09 |
| | 14J-ii Myristic acid 0.1% | 98.45 | 0.02 | 1.08 | 0.54 | 6.09 | 2.32 |
| | 14J-iii Moisture 100% | 99.38 | 0.02 | 0.98 | 0.55 | 5.90 | 2.21 |

The results of stability testing of Example 14J-i-iii at 40° C. are set forth in Table 189 below.

TABLE 189

| Lecithin 8.25% | | | | | | Total Impurities | |
|---|---|---|---|---|---|---|---|
| | 40° C. | Potency % | CBD % | CBN % | D8-THC % | % | Increase + % |
| Zero | 14J-i Glycerin 0.2% | 100.00 | 0.09 | 0.46 | 0.56 | 3.76 | |

TABLE 189-continued

| Lecithin 8.25% | | | | | | Total Impurities | |
|---|---|---|---|---|---|---|---|
| | 40° C. | Potency % | CBD % | CBN % | D8-THC % | % | Increase + % |
| | 14J-ii Myristic acid 0.1% | 100.00 | 0.10 | 0.47 | 0.56 | 3.77 | |
| | 14J-iii Moisture 100% | 100.00 | 0.09 | 0.46 | 0.54 | 3.69 | |
| 1 M | 14J-i Glycerin 0.2% | 96.17 | 0.04 | 0.89 | 0.52 | 5.39 | 1.63 |
| | 14J-ii Myristic acid 0.1% | 95.83 | 0.04 | 0.95 | 0.50 | 5.52 | 1.75 |
| | 14J-iii Moisture 100% | 96.93 | 0.03 | 0.92 | 0.54 | 5.15 | 1.46 |
| 2 M | 14J-i Glycerin 0.2% | 99.06 | 0.01 | 1.24 | 0.53 | 6.12 | 2.36 |
| | 14J-ii Myristic acid 0.1% | 97.53 | 0.02 | 1.29 | 0.55 | 6.35 | 2.58 |
| | 14J-iii Moisture 100% | 98.42 | 0.02 | 1.25 | 0.57 | 6.11 | 2.42 |
| 3 M | 14J-i Glycerin 0.2% | 96.23 | 0.02 | 1.79 | 0.53 | 7.78 | 4.02 |
| | 14J-ii Myristic acid 0.1% | 96.52 | 0.02 | 2.00 | 0.53 | 8.24 | 4.47 |
| | 14J-iii Moisture 100% | 96.49 | 0.01 | 1.81 | 0.54 | 7.88 | 4.19 |
| 6 M | 14J-i Glycerin 0.2% | 90.81 | 0.10 | 3.54 | 0.59 | 14.45 | 10.69 |
| | 14J-ii Myristic acid 0.1% | 90.37 | 0.01 | 4.12 | 0.54 | 13.89 | 10.12 |
| | 14J-iii Moisture 100% | 91.84 | 0.05 | 3.69 | 0.58 | 14.82 | 11.13 |

The results of stability testing of Example 14J-i-iii at 55° C. are set forth in Table 190 below.

TABLE 190

| Lecithin 8.25% | | | | | | Total Impurities | |
|---|---|---|---|---|---|---|---|
| | 55° C. | Potency % | CBD % | CBN % | D8-THC % | % | Increase + % |
| Zero | 14J-i Glycerin 0.2% | 100.00 | 0.09 | 0.46 | 0.56 | 3.76 | |
| | 14J-ii Myristic acid 0.1% | 100.00 | 0.10 | 0.47 | 0.56 | 3.77 | |
| | 14J-iii Moisture 100% | 100.00 | 0.09 | 0.46 | 0.54 | 3.69 | |
| 1 W | 14J-i Glycerin 0.2% | 98.10 | 0.04 | 0.97 | 0.57 | 5.36 | 1.60 |
| | 14J-ii Myristic acid 0.1% | 97.69 | 0.02 | 0.89 | 0.60 | 5.25 | 1.48 |
| | 14J-iii Moisture 100% | 99.09 | 0.02 | 0.78 | 0.72 | 4.86 | 1.17 |
| 2 W | 14J-i Glycerin 0.2% | 96.94 | 0.01 | 1.57 | 0.55 | 6.73 | 2.97 |
| | 14J-ii Myristic acid 0.1% | 97.68 | 0.01 | 1.41 | 0.55 | 6.68 | 2.91 |
| | 14J-iii Moisture 100% | 98.85 | 0.02 | 1.17 | 0.55 | 5.98 | 2.29 |

EXAMPLE 14K

Dronabinol Solution in Sesame Oil Sourced from Croda with Lecithin and Different Degradants Added In Example 14K-i-iii, dronabinol formulations were prepared in accordance with Example 14H-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 14K-i-iii at 25° C. are set forth in Table 191 below.

TABLE 191

| | Lecithin 8.25% | | | | | Total Impurities | |
|---|---|---|---|---|---|---|---|
| | 25° C. | Potency % | CBD % | CBN % | D8-THC % | % | Increase + % |
| Zero | 14K-i Glycerin 0.2% | 100.00 | 0.05 | 0.47 | 0.56 | 3.52 | |
| | 14K-ii Myristic acid 0.1% | 100.00 | 0.02 | 0.47 | 0.58 | 3.43 | |
| | 14K-iii Moisture 100% | 100.00 | 0.01 | 0.47 | 0.57 | 3.37 | |
| 3 M | 14K-i Glycerin 0.2% | 99.01 | 0.03 | 0.69 | 0.60 | 4.87 | 1.35 |
| | 14K-ii Myristic acid 0.1% | 99.05 | 0.03 | 0.74 | 0.57 | 4.88 | 1.45 |
| | 14K-iii Moisture 100% | 99.78 | 0.03 | 0.72 | 0.57 | 4.83 | 1.46 |
| 6 M | 14K-i Glycerin 0.2% | 96.79 | 0.03 | 0.95 | 0.60 | 6.47 | 2.95 |
| | 14K-ii Myristic acid 0.1% | 95.85 | 0.03 | 1.00 | 0.59 | 6.43 | 3.00 |
| | 14K-iii Moisture 100% | 98.03 | 0.03 | 0.92 | 0.58 | 6.17 | 2.80 |

The results of stability testing of Example 14K-i-iii at 40° C. are set forth in Table 192 below.

TABLE 192

| | Lecithin 8.25% | | | | | Total Impurities | |
|---|---|---|---|---|---|---|---|
| | 40° C. | Potency % | CBD % | CBN % | D8-THC % | % | Increase + % |
| Zero | 14K-i Glycerin 0.2% | 100.00 | 0.05 | 0.47 | 0.56 | 3.52 | |
| | 14K-ii Myristic acid 0.1% | 100.00 | 0.02 | 0.47 | 0.58 | 3.43 | |
| | 14K-iii Moisture 100% | 100.00 | 0.01 | 0.47 | 0.57 | 3.37 | |
| 1 M | 14K-i Glycerin 0.2% | 94.94 | 0.04 | 0.83 | 0.55 | 5.16 | 1.64 |
| | 14K-ii Myristic acid 0.1% | 93.71 | 0.03 | 0.88 | 0.57 | 5.57 | 2.14 |
| | 14K-iii Moisture 100% | 95.21 | 0.04 | 0.85 | 0.56 | 5.50 | 2.13 |
| 2 M | 14K-i Glycerin 0.2% | 97.03 | 0.01 | 1.24 | 0.60 | 7.25 | 3.73 |
| | 14K-ii Myristic acid 0.1% | 95.80 | 0.02 | 1.36 | 0.61 | 7.19 | 3.76 |
| | 14K-iii Moisture 100% | 95.71 | 0.01 | 1.17 | 0.49 | 6.47 | 3.10 |
| 3 M | 14K-i Glycerin 0.2% | 93.44 | 0.05 | 1.83 | 0.56 | 9.74 | 6.22 |
| | 14K-ii Myristic acid 0.1% | 92.41 | 0.03 | 2.08 | 0.57 | 9.61 | 6.18 |
| | 14K-iii Moisture 100% | 94.02 | 0.02 | 1.88 | 0.59 | 9.32 | 5.95 |
| 6 M | 14K-i Glycerin 0.2% | 85.96 | 0.03 | 3.93 | 0.58 | 15.24 | 11.72 |
| | 14K-ii Myristic acid 0.1% | 84.65 | 0.01 | 4.57 | 0.58 | 16.16 | 12.73 |
| | 14K-iii Moisture 100% | 86.74 | 0.01 | 4.06 | 0.60 | 15.53 | 12.16 |

The results of stability testing of Example 14K-i-iii at 55° C. are set forth in Table 193 below.

TABLE 193

| | Lecithin 8.25% | | | | | Total Impurities | |
|---|---|---|---|---|---|---|---|
| | 55° C. | Potency % | CBD % | CBN % | D8-THC % | % | Increase + % |
| Zero | 14K-i Glycerin 0.2% | 100.00 | 0.05 | 0.47 | 0.56 | 3.52 | |
| | 14K-ii Myristic acid 0.1% | 100.00 | 0.02 | 0.47 | 0.58 | 3.43 | |
| | 14K-iii Moisture 100% | 100.00 | 0.01 | 0.47 | 0.57 | 3.37 | |
| 1 W | 14K-i Glycerin 0.2% | 90.92 | 0.04 | 2.11 | 0.65 | 8.95 | 5.43 |
| | 14K-ii Myristic acid 0.1% | 88.54 | 0.04 | 1.81 | 0.63 | 8.22 | 4.79 |
| | 14K-iii Moisture 100% | 87.62 | 0.06 | 2.33 | 0.64 | 9.64 | 6.27 |
| 2 W | 14K-i Glycerin 0.2% | 88.34 | 0.01 | 3.63 | 0.61 | 12.60 | 9.08 |
| | 14K-ii Myristic acid 0.1% | 89.17 | 0.02 | 2.82 | 0.61 | 10.56 | 7.13 |
| | 14K-iii Moisture 100% | 79.64 | 0.06 | 5.89 | 0.69 | 18.07 | 14.70 |

EXAMPLE 14L

Dronabinol Solution in Sesame Oil Sourced from Dipasa with Lecithin and Different Degradants Added In Example 14L-i-iii, dronabinol formulations were prepared in accordance with Example 14I-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 14L-i-iii at 25° C. are set forth in Table 194 below.

TABLE 194

| | Lecithin 8.25% | | | | | Total Impurities | |
|---|---|---|---|---|---|---|---|
| | 25° C. | Potency % | CBD % | CBN % | D8-THC % | % | Increase + % |
| Zero | 14L-i Glycerin 0.2% | 100.00 | 0.07 | 0.45 | 0.52 | 3.73 | |
| | 14L-ii Myristic acid 0.1% | 100.00 | 0.07 | 0.44 | 0.55 | 3.66 | |
| | 14L-iii Moisture 100% | 100.00 | 0.09 | 0.43 | 0.54 | 3.66 | |
| 3 M | 14L-i Glycerin 0.2% | 102.67 | 0.03 | 0.65 | 0.53 | 4.86 | 1.13 |
| | 14L-ii Myristic acid 0.1% | 101.65 | 0.03 | 0.82 | 0.53 | 4.88 | 1.22 |
| | 14L-iii Moisture 100% | 100.67 | 0.03 | 0.79 | 0.54 | 5.08 | 1.42 |
| 6 M | 14L-i Glycerin 0.2% | 100.52 | 0.04 | 0.80 | 0.51 | 6.40 | 2.67 |
| | 14L-ii Myristic acid 0.1% | 100.33 | 0.05 | 1.11 | 0.53 | 6.51 | 2.85 |
| | 14L-iii Moisture 100% | 97.76 | 0.04 | 1.03 | 0.54 | 6.55 | 2.89 |

The results of stability testing of Example 14L-i-iii at 40° C. are set forth in Table 195 below.

TABLE 195

| | Lecithin 8.25% | | | | | Total Impurities | |
|---|---|---|---|---|---|---|---|
| | 40° C. | Potency % | CBD % | CBN % | D8-THC % | % | Increase + % |
| Zero | 14L-i Glycerin 0.2% | 100.00 | 0.07 | 0.45 | 0.52 | 3.73 | |
| | 14L-ii Myristic acid 0.1% | 100.00 | 0.07 | 0.44 | 0.55 | 3.66 | |
| | 14L-iii Moisture 100% | 100.00 | 0.09 | 0.43 | 0.54 | 3.66 | |
| 1 M | 14L-i Glycerin 0.2% | 98.45 | 0.04 | 0.83 | 0.55 | 5.16 | 1.64 |
| | 14L-ii Myristic acid 0.1% | 96.90 | 0.04 | 0.97 | 0.52 | 5.33 | 1.67 |
| | 14L-iii Moisture 100% | 95.42 | 0.07 | 0.94 | 0.52 | 5.34 | 1.68 |
| 2 M | 14L-i Glycerin 0.2% | 98.90 | 0.01 | 1.13 | 0.52 | 6.90 | 3.17 |
| | 14L-ii Myristic acid 0.1% | 98.75 | 0.01 | 1.46 | 0.54 | 6.63 | 2.97 |
| | 14L-iii Moisture 100% | 97.06 | 0.03 | 1.38 | 0.52 | 6.59 | 2.93 |
| 3 M | 14L-i Glycerin 0.2% | 95.90 | 0.04 | 1.73 | 0.52 | 9.01 | 5.28 |
| | 14L-ii Myristic acid 0.1% | 96.62 | 0.02 | 2.31 | 0.52 | 8.76 | 5.10 |
| | 14L-iii Moisture 100% | 95.46 | 0.02 | 2.15 | 0.52 | 8.71 | 5.05 |
| 6 M | 14L-i Glycerin 0.2% | 89.33 | 0.08 | 3.90 | 0.51 | 16.39 | 12.66 |
| | 14L-ii Myristic acid 0.1% | 89.58 | 0.01 | 4.93 | 0.53 | 15.02 | 11.36 |
| | 14L-iii Moisture 100% | 88.35 | 0.06 | 4.60 | 0.58 | 17.13 | 13.47 |

The results of stability testing of Example 14L-i-iii at 55° C. are set forth in Table 196 below.

TABLE 196

| | Lecithin 8.25% | | | | | Total Impurities | |
|---|---|---|---|---|---|---|---|
| | 55° C. | Potency % | CBD % | CBN % | D8-THC % | % | Increase + % |
| Zero | 14L-i Glycerin 0.2% | 100.00 | 0.07 | 0.45 | 0.52 | 3.73 | |
| | 14L-ii Myristic acid 0.1% | 100.00 | 0.07 | 0.44 | 0.55 | 3.66 | |
| | 14L-iii Moisture 100% | 100.00 | 0.09 | 0.43 | 0.54 | 3.66 | |
| 1 W | 14L-i Glycerin 0.2% | 95.12 | 0.01 | 0.93 | 0.56 | 5.88 | 2.15 |
| | 14L-ii Myristic acid 0.1% | 99.31 | 0.01 | 0.94 | 0.58 | 1.70 | 5.36 |
| | 14L-iii Moisture 100% | 97.67 | 0.01 | 0.84 | 0.57 | 5.02 | 1.36 |
| 2 W | 14L-i Glycerin 0.2% | 95.55 | 0.01 | 1.85 | 0.51 | 8.15 | 4.42 |
| | 14L-ii Myristic acid 0.1% | 98.94 | 0.02 | 1.58 | 0.54 | 6.82 | 3.16 |
| | 14L-iii Moisture 100% | 96.48 | 0.02 | 1.30 | 0.55 | 6.34 | 2.68 |

As seen from the results above, a significant improvement in the stability of dronabinol formulations was observed when lecithin is added. The above results indicate that lecithin imparts stability to dronabinol by preventing degradation induced by excipients such as glycerin, moisture and myristic acid.

Extended Stability Results—Effect of Bases Meglumine and Ethanolamine on Dronabinol Formulation Stability In view of the stabilizing property of free bases meglumine and monoethanolamine shown in the above examples, specifically 12A-K, further studies were performed to evaluate the effect of meglumine and monoethanolamine with the addition of degradants such as glycerin, moisture and myristic acid to dronabinol formulations stored at different temperature conditions for an extended period of time.

EXAMPLE 15A

Control Dronabinol Solution in Sesame Oil Sourced from Arista

In Example 15A, a dronabinol control formulation was prepared in accordance with Example 1, using sesame oil sourced from Arista. The dronabinol formulation was then used to fill hard gelatin capsules in accordance with Example 2. The formulation within the capsules was initially tested, then tested at 25° C. for 3 and 6 months; 40° C. for 1, 2, 3 and 6 months and at 55° C. for 1 and 2 weeks.

The results of stability testing of Example 15A at 25° C. are set forth in Table 197 below.

TABLE 197

| Control 25° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 3 Months | 94.51 | 0.66 | 0.89 | 0.56 | 11.03 | 6.95 |
| 6 Months | 93.26 | 0.72 | 0.98 | 0.53 | 11.41 | 7.33 |

The results of stability testing of Example 15A at 40° C. are set forth in Table 198 below.

TABLE 198

| Control 40° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 1 Month | 94.87 | 0.76 | 0.80 | 0.51 | 10.31 | 6.23 |
| 2 Months | 94.16 | 0.59 | 1.09 | 0.55 | 11.28 | 7.20 |
| 3 Months | 94.61 | 0.57 | 1.31 | 0.56 | 12.25 | 8.17 |
| 6 Months | 89.15 | 0.06 | 1.90 | 0.57 | 14.64 | 10.56 |

The results of stability testing of Example 15A at 55° C. are set forth in Table 199 below.

TABLE 199

| Control 55° C. | Potency % | CBD % | CBN % | D8-THC % | Total Impurities % | Increase + % |
|---|---|---|---|---|---|---|
| Zero | 100.00 | 0.05 | 0.44 | 0.60 | 4.08 | |
| 1 Week | 88.90 | 0.19 | 0.61 | 0.55 | 14.72 | 10.64 |
| 2 Weeks | 71.45 | 2.67 | 1.54 | 0.60 | 27.11 | 23.03 |

EXAMPLE 15B

Control Dronabinol Solution in Sesame Oil Sourced from Croda

In Example 15B, a dronabinol control formulation was prepared in accordance with Example 1, using sesame oil sourced from Croda. The dronabinol formulation was then used to fill hard gelatin capsules in accordance with Example 2. The formulation within the capsules was initially tested, then tested at 25° C. for 3 and 6 months; 40° C. for 1, 2, 3 and 6 months and at 55° C. for 1 and 2 weeks.

The results of stability testing of Example 15B at 25° C. are set forth in Table 200 below.

TABLE 200

| Control 25° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 3 Months | 91.48 | 1.01 | 0.62 | 0.61 | 12.51 | 6.98 |
| 6 Months | 88.95 | 1.11 | 0.75 | 0.59 | 13.64 | 8.11 |

The results of stability testing of Example 15B at 40° C. are set forth in Table 201 below.

TABLE 201

| Control 40° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 1 Month | 87.89 | 1.22 | 0.67 | 0.53 | 12.01 | 6.48 |
| 2 Months | 90.94 | 0.98 | 0.84 | 0.61 | 12.49 | 6.96 |
| 3 Months | 87.61 | 0.95 | 1.00 | 0.62 | 13.45 | 7.92 |
| 6 Months | 86.92 | 0.61 | 1.25 | 0.49 | 14.63 | 9.10 |

The results of stability testing of Example 15B at 55° C. are set forth in Table 202 below.

TABLE 202

| Control 55° C. | Potency % | CBD % | CBN % | D8-THC % | Total Impurities % | Increase + % |
|---|---|---|---|---|---|---|
| Zero | 100.00 | 0.03 | 0.77 | 0.81 | 5.53 | |
| 1 Week | 81.35 | 0.26 | 0.69 | 0.58 | 21.10 | 15.57 |
| 2 Weeks | 65.26 | 3.41 | 1.31 | 0.66 | 29.70 | 24.17 |

EXAMPLE 15C

Control Dronabinol Solution in Sesame Oil Sourced from Dipasa

In Example 15C, a dronabinol control formulation was prepared in accordance with Example 1, using sesame oil sourced from Dipasa. The dronabinol formulation was then used to fill hard gelatin capsules in accordance with Example 2. The formulation within the capsules was initially tested, then tested at 25° C. for 3 and 6 months; 40° C. for 1, 2, 3 and 6 months and at 55° C. for 1 and 2 weeks.

The results of stability testing of Example 15C at 25° C. are set forth in Table 203 below.

TABLE 203

| Control 25° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 3 Months | 99.70 | 0.12 | 0.61 | 0.56 | 6.46 | 2.47 |
| 6 Months | 97.64 | 0.23 | 0.80 | 0.52 | 8.20 | 4.21 |

The results of stability testing of Example 15C at 40° C. are set forth in Table 204 below.

TABLE 204

| Control 40° C. | Potency % | CBD % | CBN % | THC % | D8- % | Total Impurities Increase + % |
|---|---|---|---|---|---|---|
| Zero | 100.00 | 0.02 | 0.44 | 0.55 | 3.99 | |
| 1 Month | 95.26 | 0.19 | 0.70 | 0.52 | 6.70 | 2.71 |
| 2 Months | 97.65 | 0.30 | 0.93 | 0.53 | 9.63 | 5.64 |
| 3 Months | 95.26 | 0.34 | 1.18 | 0.54 | 11.18 | 7.19 |
| 6 Months | 91.99 | 0.03 | 1.69 | 0.51 | 12.51 | 8.52 |

The results of stability testing of Example 15C at 55° C. are set forth in Table 205 below.

TABLE 205

| Control 55° C. | Potency % | CBD % | CBN % | THC % | D8- % | Total Impurities Increase + % |
|---|---|---|---|---|---|---|
| Zero | 100.00 | 0.02 | 0.44 | 0.55 | 3.99 | |
| 1 Week | 96.16 | 0.05 | 0.76 | 0.58 | 7.13 | 3.14 |
| 2 Weeks | 92.72 | 0.12 | 1.25 | 0.55 | 11.12 | 7.13 |

EXAMPLE 15D

Control Dronabinol Solution in Sesame Oil Sourced from Arista

In Example 15D, a dronabinol control formulation was prepared in accordance with Example 15A, using sesame oil sourced from Arista. The dronabinol formulation was then used to fill amber glass vials. The formulation within the vials was initially tested, then tested at 25° C. for 3 and 6 months; 40° C. for 1, 2, 3 and 6 months and at 55° C. for 1 and 2 weeks.

The results of stability testing of Example 15D at 25° C. are set forth in Table 206 below.

TABLE 206

| Control 25° C. | Potency % | CBD % | CBN % | THC % | D8- % | Total Impurities Increase + % |
|---|---|---|---|---|---|---|
| Zero | 100.00 | 0.05 | 0.44 | 0.60 | 4.08 | |
| 3 Months | 88.57 | 1.54 | 0.77 | 0.52 | 14.79 | 10.71 |
| 6 Months | 71.21 | 2.95 | 1.62 | 0.56 | 27.29 | 23.21 |

The results of stability testing of Example 15D at 40° C. are set forth in Table 207 below.

TABLE 207

| Control 40° C. | Potency % | CBD % | CBN % | THC % | D8- % | Total Impurities Increase + % |
|---|---|---|---|---|---|---|
| Zero | 100.00 | 0.05 | 0.44 | 0.60 | 4.08 | |
| 1 Month | 90.04 | 1.23 | 0.69 | 0.51 | 12.10 | 8.02 |
| 2 Months | 81.90 | 2.27 | 1.27 | 0.50 | 20.62 | 16.54 |
| 3 Months | 65.52 | 2.75 | 2.43 | 0.59 | 31.20 | 27.12 |
| 6 Months | 29.92 | 2.28 | 7.78 | 0.85 | 60.00 | 55.92 |

The results of stability testing of Example 15D at 55° C. are set forth in Table 208 below.

TABLE 208

| Control 55° C. | Potency % | CBD % | CBN % | THC % | D8- % | Total Impurities Increase + % |
|---|---|---|---|---|---|---|
| Zero | 100.00 | 0.05 | 0.44 | 0.60 | 4.08 | |
| 1 Week | 88.90 | 0.19 | 0.61 | 0.55 | 14.72 | 10.64 |
| 2 Weeks | 71.45 | 2.67 | 1.54 | 0.60 | 27.11 | 23.03 |

EXAMPLE 15E

Control Dronabinol Solution in Sesame Oil Sourced from Croda

In Example 15E, a dronabinol control formulation was prepared in accordance with Example 15B, using sesame oil sourced from Croda. The dronabinol formulation was then used to fill amber glass vials. The formulation within the vials was initially tested, then tested at 25° C. for 3 and 6 months; 40° C. for 1, 2, 3 and 6 months and at 55° C. for 1 and 2 weeks.

The results of stability testing of Example 15E at 25° C. are set forth in Table 209 below.

TABLE 209

| Control 25° C. | Potency % | CBD % | CBN % | THC % | D8- % | Total Impurities Increase + % |
|---|---|---|---|---|---|---|
| Zero | 100.00 | 0.03 | 0.77 | 0.81 | 5.53 | |
| 3 Months | 85.10 | 2.07 | 0.75 | 0.58 | 18.41 | 12.88 |
| 6 Months | 69.68 | 3.38 | 1.18 | 0.60 | 30.45 | 24.92 |

The results of stability testing of Example 15E at 40° C. are set forth in Table 210 below.

TABLE 210

| Control 40° C. | Potency % | CBD % | CBN % | THC % | D8- % | Total Impurities Increase + % |
|---|---|---|---|---|---|---|
| Zero | 100.00 | 0.03 | 0.77 | 0.81 | 5.53 | |
| 1 Month | 84.66 | 1.64 | 0.69 | 0.56 | 15.97 | 10.44 |
| 2 Months | 75.78 | 2.82 | 1.17 | 0.58 | 25.65 | 20.12 |
| 3 Months | 59.02 | 3.54 | 1.89 | 0.56 | 36.06 | 30.53 |
| 6 Months | 23.92 | 2.88 | 7.00 | 0.89 | 65.24 | 59.71 |

The results of stability testing of Example 15E at 55° C. are set forth in Table 211 below.

TABLE 211

| Control 55° C. | Potency % | CBD % | CBN % | THC % | D8- % | Total Impurities Increase + % |
|---|---|---|---|---|---|---|
| Zero | 100.00 | 0.03 | 0.77 | 0.81 | 5.53 | |
| 1 Week | 81.35 | 0.26 | 0.69 | 0.58 | 21.10 | 15.57 |
| 2 Weeks | 65.26 | 3.41 | 1.31 | 0.66 | 29.70 | 24.17 |

EXAMPLE 15F

Control Dronabinol Solution in Sesame Oil Sourced from Dipasa

In Example 15F, a dronabinol control formulation was prepared in accordance with Example 15C, using sesame oil sourced from Dipasa. The dronabinol formulation was then used to fill amber glass vials. The formulation within the vials was initially tested, then tested at 25° C. for 3 and 6 months; 40° C. for 1, 2, 3 and 6 months and at 55° C. for 1 and 2 weeks.

The results of stability testing of Example 15F at 25° C. are set forth in Table 212 below.

TABLE 212

| Control 25° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 3 Months | 99.26 | 0.18 | 0.70 | 0.53 | 6.04 | 2.05 |
| 6 Months | 95.28 | 0.38 | 0.94 | 0.58 | 9.05 | 5.06 |

The results of stability testing of Example 15F at 40° C. are set forth in Table 213 below.

TABLE 213

| Control 40° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 1 Month | 95.74 | 0.23 | 0.81 | 0.51 | 7.12 | 3.13 |
| 2 Months | 95.31 | 0.38 | 1.15 | 0.52 | 10.16 | 6.17 |
| 3 Months | 90.52 | 0.39 | 1.76 | 0.53 | 14.04 | 10.05 |
| 6 Months | 76.78 | 0.65 | 3.53 | 0.54 | 25.94 | 21.95 |

The results of stability testing of Example 15F at 55° C. are set forth in Table 214 below.

TABLE 214

| Control 55° C. | Potency % | CBD % | CBN % | D8-THC % | Total Impurities % | Increase + % |
|---|---|---|---|---|---|---|
| Zero | 100.00 | 0.02 | 0.44 | 0.55 | 3.99 | |
| 1 Week | 96.16 | 0.05 | 0.76 | 0.58 | 7.13 | 3.14 |
| 2 Weeks | 92.72 | 0.12 | 1.25 | 0.55 | 11.12 | 7.13 |

EXAMPLE 15G

Dronabinol Solution in Sesame Oil Sourced from Arista with Meglumine and Different Degradants Added In Example 15G-i-iii, dronabinol formulations were prepared in accordance with Example 15A, using sesame oil sourced from Arista. Formula 15G-i also contained 1% meglumine and 0.2% glycerin; formula 15G-ii also contained 1% meglumine and 0.1% myristic acid; and formula 14G-iii also contained 0.5% meglumine and 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 15G-i-iii at 25° C. are set forth in Table 215 below.

TABLE 215

| | Meglumine 1% 25° C. | Potency % | CBD % | CBN % | D8-THC % | Total Impurities % | Increase + % |
|---|---|---|---|---|---|---|---|
| Zero | 15G-i Glycerin 0.2% | 100.00 | 0.02 | 0.44 | 0.52 | 3.61 | |
| | 15G-ii Myristic acid 0.1% | 100.00 | 0.03 | 0.44 | 0.54 | 3.66 | |
| | 15G-iii Moisture 100%* | 100.00 | 0.09 | 0.49 | 0.54 | 3.89 | |
| | | 100.00 | 0.04 | 0.43 | 0.54 | 3.48 | |
| 3 M | 15G-i Glycerin 0.2% | 94.65 | 0.25 | 0.61 | 0.52 | 11.02 | 7.41 |
| | 15G-ii Myristic acid 0.1% | 99.42 | 0.03 | 0.52 | 0.52 | 6.06 | 2.40 |
| | 15G-iii Moisture 100%* | 94.86 | 0.52 | 0.57 | 0.55 | 11.06 | 7.17 |
| | | 95.84 | 0.28 | 0.58 | 0.54 | 11.24 | 7.76 |
| 6 M | 15G-i Glycerin 0.2% | 91.34 | 0.31 | 0.68 | 0.53 | 12.97 | 9.36 |
| | 15G-ii Myristic acid 0.1% | 97.18 | 0.06 | 0.60 | 0.52 | 6.87 | 3.21 |
| | 15G-iii Moisture 100%* | 92.37 | 0.79 | 0.66 | 0.49 | 11.66 | 7.77 |
| | | 94.06 | 0.31 | 0.67 | 0.52 | 11.85 | 8.37 |

*meglumine 0.5% mixture

The results of stability testing of Example 15G-i-iii at 40° C. are set forth in Table 216 below.

TABLE 216

| | Meglumine 1% | | | | | Total Impurities | |
|---|---|---|---|---|---|---|---|
| | 40° C. | Potency % | CBD % | CBN % | D8-THC % | % | Increase + % |
| Zero | 15G-i Glycerin 0.2% | 100.00 | 0.02 | 0.44 | 0.52 | 3.61 | |
| | 15G-ii Myristic acid 0.1% | 100.00 | 0.03 | 0.44 | 0.54 | 3.66 | |
| | 15G-iii Moisture 100%* | 100.00 | 0.09 | 0.49 | 0.54 | 3.89 | |
| | | 100.00 | 0.04 | 0.43 | 0.54 | 3.48 | |
| 1 M | 15G-i Glycerin 0.2% | 90.38 | 0.37 | 0.59 | 0.50 | 11.35 | 7.74 |
| | 15G-ii Myristic acid 0.1% | 92.84 | 0.20 | 0.76 | 0.53 | 8.81 | 5.15 |
| | 15G-iii Moisture 100%* | 91.63 | 0.69 | 0.61 | 0.52 | 10.18 | 6.29 |
| | | 93.33 | 0.39 | 0.59 | 0.51 | 10.66 | 7.18 |
| 2 M | 15G-i Glycerin 0.2% | 91.82 | 0.95 | 0.68 | 0.47 | 14.96 | 11.35 |
| | 15G-ii Myristic acid 0.1% | 94.73 | 0.17 | 0.93 | 0.52 | 10.23 | 6.57 |
| | 15G-iii Moisture 100%* | 93.67 | 0.66 | 0.72 | 0.52 | 11.12 | 7.23 |
| | | 94.03 | 0.32 | 0.69 | 0.49 | 11.77 | 8.29 |
| 3 M | 15G-i Glycerin 0.2% | 91.10 | 0.32 | 0.79 | 0.55 | 13.21 | 9.60 |
| | 15G-ii Myristic acid 0.1% | 94.90 | 0.14 | 0.99 | 0.56 | 9.41 | 5.75 |
| | 15G-iii Moisture 100%* | 94.82 | 0.56 | 0.78 | 0.54 | 11.32 | 7.43 |
| | | 95.63 | 0.30 | 0.74 | 0.54 | 12.08 | 8.60 |
| 6 M | 15G-i Glycerin 0.2% | 87.33 | 0.27 | 1.11 | 0.49 | 15.52 | 11.91 |
| | 15G-ii Myristic acid 0.1% | 91.93 | 0.19 | 1.36 | 0.56 | 11.35 | 7.69 |
| | 15G-iii Moisture 100%* | 89.59 | 0.50 | 1.14 | 0.50 | 13.57 | 9.68 |
| | | 90.36 | 0.25 | 1.10 | 0.49 | 14.02 | 10.54 |

*meglumine 0.5% mixture

The results of stability testing of Example 15G-i-iii at 55° C. are set forth in Table 217 below.

TABLE 217

| | Meglumine 1% | | | | | Total Impurities | |
|---|---|---|---|---|---|---|---|
| | 55° C. | Potency % | CBD % | CBN % | D8-THC % | % | Increase + % |
| Zero | 15G-i Glycerin 0.2% | 100.00 | 0.02 | 0.44 | 0.52 | 3.61 | |
| | 15G-ii Myristic acid 0.1% | 100.00 | 0.03 | 0.44 | 0.54 | 3.66 | |
| | 15G-iii Moisture 100%* | 100.00 | 0.09 | 0.49 | 0.54 | 3.89 | |
| | | 100.00 | 0.04 | 0.43 | 0.54 | 3.48 | |
| 1 W | 15G-i Glycerin 0.2% | 91.77 | 0.22 | 0.50 | 0.59 | 11.33 | 7.72 |
| | 15G-ii Myristic acid 0.1% | 92.63 | 0.33 | 0.73 | 0.60 | 10.66 | 7.00 |
| | 15G-iii Moisture 100%* | 93.29 | 0.41 | 0.48 | 0.60 | 8.64 | 4.75 |
| | | 92.84 | 0.25 | 0.50 | 0.59 | 11.35 | 7.87 |
| 2 W | 15G-i Glycerin 0.2% | 90.01 | 0.14 | 0.61 | 0.56 | 12.91 | 9.30 |
| | 15G-ii Myristic acid 0.1% | 91.29 | 0.24 | 1.03 | 0.56 | 12.21 | 8.55 |
| | 15G-iii Moisture 100%* | 86.17 | 1.07 | 0.75 | 0.56 | 15.44 | 11.55 |
| | | 91.65 | 0.16 | 0.59 | 0.52 | 12.98 | 9.50 |

*meglumine 0.5% mixture

EXAMPLE 15H

Dronabinol Solution in Sesame Oil Sourced from Croda with Meglumine and Different Degradants Added In Example 155H-i-iii, dronabinol formulations were prepared in accordance with Example 15B, using sesame oil sourced from Croda. Formula 15H-i also contained 1% meglumine and 0.2% glycerin; formula 15H-ii also contained 1% meglumine and 0.1% myristic acid; and formula 15H-iii also contained 0.5% meglumine and 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 15H-i-iii at 25° C. are set forth in Table 218 below.

TABLE 218

| | Meglumine 1% | | | | | Total Impurities | |
| --- | --- | --- | --- | --- | --- | --- | --- |
| | 25° C. | Potency % | CBD % | CBN % | D8-THC % | % | Increase + % |
| Zero | 15H-i Glycerin 0.2% | 100.00 | 0.01 | 0.46 | 0.56 | 3.27 | |
| | 15H-ii Myristic acid 0.1% | 100.00 | 0.01 | 0.45 | 0.53 | 3.01 | |
| | 15H-iii Moisture 100%* | 100.00 | 0.11 | 0.49 | 0.56 | 3.82 | |
| | | 100.00 | 0.02 | 0.46 | 0.59 | 3.33 | |
| 3 M | 15H-i Glycerin 0.2% | 93.42 | 0.52 | 0.51 | 0.57 | 10.89 | 7.62 |
| | 15H-ii Myristic acid 0.1% | 89.99 | 0.44 | 0.56 | 0.59 | 11.02 | 8.01 |
| | 15H-iii Moisture 100%* | 94.03 | 0.67 | 0.50 | 0.61 | 12.78 | 8.96 |
| | | 93.61 | 0.53 | 0.51 | 0.58 | 11.25 | 7.92 |
| 6 M | 15H-i Glycerin 0.2% | 90.96 | 0.68 | 0.52 | 0.57 | 13.55 | 10.28 |
| | 15H-ii Myristic acid 0.1% | 88.14 | 0.51 | 0.64 | 0.58 | 12.16 | 9.15 |
| | 15H-iii Moisture 100%* | 90.79 | 0.87 | 0.57 | 0.59 | 13.28 | 9.46 |
| | | 90.69 | 0.59 | 0.56 | 0.62 | 13.19 | 9.86 |

*meglumine 0.5% mixture

The results of stability testing of Example 15H-i-iii at 40° C. are set forth in Table 219 below.

TABLE 219

| | Meglumine 1% | | | | | Total Impurities | |
| --- | --- | --- | --- | --- | --- | --- | --- |
| | 40° C. | Potency % | CBD % | CBN % | D8-THC % | % | Increase + % |
| Zero | 15H-i Glycerin 0.2% | 100.00 | 0.01 | 0.46 | 0.56 | 3.27 | |
| | 15H-ii Myristic acid 0.1% | 100.00 | 0.01 | 0.45 | 0.53 | 3.01 | |
| | 15H-iii Moisture 100%* | 100.00 | 0.11 | 0.49 | 0.56 | 3.82 | |
| | | 100.00 | 0.02 | 0.46 | 0.59 | 3.33 | |
| 1 M | 15H-i Glycerin 0.2% | 90.98 | 0.56 | 0.52 | 0.56 | 10.39 | 7.12 |
| | 15H-ii Myristic acid 0.1% | 86.93 | 0.40 | 0.68 | 0.58 | 10.36 | 7.35 |
| | 15H-iii Moisture 100%* | 90.69 | 0.99 | 0.56 | 0.57 | 12.24 | 8.42 |
| | | 89.84 | 0.56 | 0.52 | 0.56 | 10.60 | 7.27 |
| 2 M | 15H-i Glycerin 0.2% | 91.30 | 0.56 | 0.56 | 0.54 | 11.88 | 8.61 |
| | 15H-ii Myristic acid 0.1% | 88.90 | 0.39 | 0.85 | 0.57 | 11.52 | 8.51 |
| | 15H-iii Moisture 100%* | 92.41 | 0.85 | 0.57 | 0.55 | 12.78 | 8.96 |
| | | 91.42 | 0.51 | 0.56 | 0.56 | 11.34 | 8.01 |
| 3 M | 15H-i Glycerin 0.2% | 91.92 | 0.61 | 0.55 | 0.58 | 12.74 | 9.47 |
| | 15H-ii Myristic acid 0.1% | 88.24 | 0.32 | 0.94 | 0.59 | 12.00 | 8.99 |

TABLE 219-continued

| Meglumine 1% | | | | | | Total Impurities | |
|---|---|---|---|---|---|---|---|
| | 40° C. | Potency % | CBD % | CBN % | D8-THC % | % | Increase + % |
| | 15H-iii Moisture 100%* | 92.54 | 0.69 | 0.62 | 0.60 | 12.56 | 8.74 |
| | | 90.70 | 0.44 | 0.57 | 0.61 | 12.34 | 9.01 |
| 6 M | 15H-i Glycerin 0.2% | 88.61 | 0.35 | 0.62 | 0.57 | 13.43 | 10.16 |
| | 15H-ii Myristic acid 0.1% | 84.71 | 0.18 | 1.19 | 0.56 | 13.14 | 10.13 |
| | 15H-iii Moisture 100%* | 88.90 | 0.58 | 0.75 | 0.56 | 14.02 | 10.20 |
| | | 90.36 | 0.25 | 1.10 | 0.49 | 14.02 | 10.54 |

*meglumine 0.5% mixture

The results of stability testing of Example 15H-i-iii at 55° C. are set forth in Table 220 below.

TABLE 220

| Meglumine 1% | | | | | | Total Impurities | |
|---|---|---|---|---|---|---|---|
| | 55° C. | Potency % | CBD % | CBN % | D8-THC % | % | Increase + % |
| Zero | 15H-i Glycerin 0.2% | 100.00 | 0.01 | 0.46 | 0.56 | 3.27 | |
| | 15H-ii Myristic acid 0.1% | 100.00 | 0.01 | 0.45 | 0.53 | 3.01 | |
| | 15H-iii Moisture 100%* | 100.00 | 0.11 | 0.49 | 0.56 | 3.82 | |
| | | 100.00 | 0.02 | 0.46 | 0.59 | 3.33 | |
| 1 W | 15H-i Glycerin 0.2% | 83.45 | 0.90 | 0.47 | 0.61 | 16.19 | 12.92 |
| | 15H-ii Myristic acid 0.1% | 86.65 | 0.45 | 0.65 | 0.64 | 12.53 | 9.52 |
| | 15H-iii Moisture 100%* | 87.92 | 1.25 | 0.50 | 0.55 | 13.24 | 9.42 |
| | | 86.86 | 0.94 | 0.52 | 0.59 | 15.89 | 12.56 |
| 2 W | 15H-i Glycerin 0.2% | 71.10 | 1.85 | 0.68 | 0.59 | 28.07 | 24.80 |
| | 15H-ii Myristic acid 0.1% | 78.00 | 0.50 | 1.27 | 0.63 | 19.09 | 16.08 |
| | 15H-iii Moisture 100%* | 78.81 | 2.50 | 0.67 | 0.59 | 22.93 | 19.11 |
| | | 73.45 | 1.22 | 0.73 | 0.58 | 26.08 | 22.75 |

*meglumine 0.5% mixture

EXAMPLE 15I

Dronabinol Solution in Sesame Oil Sourced from Dipasa with Meglumine and Different Degradants Added In Example 15I-i-iii, dronabinol formulations were prepared in accordance with Example 15C, using sesame oil sourced from Dipasa. Formula 15I-i also contained 1% meglumine and 0.2% glycerin; formula 15I-ii also contained 1% meglumine and 0.1% myristic acid; and formula 15I-iii also contained 0.5% meglumine and 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 15I-i-iii at 25° C. are set forth in Table 221 below.

TABLE 221

| Meglumine 1% | | | | | | Total Impurities | |
|---|---|---|---|---|---|---|---|
| | 25° C. | Potency % | CBD % | CBN % | D8-THC % | % | Increase + % |
| Zero | 15I-i Glycerin 0.2% | 100.00 | 0.02 | 0.43 | 0.54 | 3.68 | |
| | 15I-ii Myristic acid 0.1% | 100.00 | 0.02 | 0.42 | 0.52 | 3.65 | |

TABLE 221-continued

| | Meglumine 1% 25° C. | Potency % | CBD % | CBN % | D8-THC % | Total Impurities % | Increase + % |
|---|---|---|---|---|---|---|---|
| | 15I-iii Moisture 100%* | 100.00 | 0.05 | 0.44 | 0.50 | 3.61 | |
| | | 100.00 | 0.09 | 0.41 | 0.52 | 3.63 | |
| 3 M | 15I-i Glycerin 0.2% | 100.59 | 0.04 | 0.49 | 0.51 | 6.10 | 2.42 |
| | 15I-ii Myristic acid 0.1% | 99.78 | 0.03 | 0.51 | 0.52 | 5.49 | 1.84 |
| | 15I-iii Moisture 100%* | 95.29 | 0.19 | 0.52 | 0.55 | 7.76 | 4.15 |
| | | 99.41 | 0.04 | 0.49 | 0.53 | 5.66 | 2.03 |
| 6 M | 15I-i Glycerin 0.2% | 99.06 | 0.06 | 0.55 | 0.53 | 6.58 | 2.90 |
| | 15I-ii Myristic acid 0.1% | 97.46 | 0.05 | 0.61 | 0.51 | 6.21 | 2.56 |
| | 15I-iii Moisture 100%* | 93.42 | 0.36 | 0.60 | 0.51 | 8.65 | 5.04 |
| | | 98.88 | 0.07 | 0.57 | 0.55 | 6.36 | 2.73 |

*meglumine 0.5% mixture

The results of stability testing of Example 15I-i-iii at 40° C. are set forth in Table 222 below.

TABLE 222

| | Meglumine 1% 40° C. | Potency % | CBD % | CBN % | D8-THC % | Total Impurities % | Increase + % |
|---|---|---|---|---|---|---|---|
| Zero | 15I-i Glycerin 0.2% | 100.00 | 0.02 | 0.43 | 0.54 | 3.68 | |
| | 15I-ii Myristic acid 0.1% | 100.00 | 0.02 | 0.42 | 0.52 | 3.65 | |
| | 15I-iii Moisture 100%* | 100.00 | 0.05 | 0.44 | 0.50 | 3.61 | |
| | | 100.00 | 0.09 | 0.41 | 0.52 | 3.63 | |
| 1 M | 15I-i Glycerin 0.2% | 96.48 | 0.08 | 0.52 | 0.51 | 6.40 | 2.72 |
| | 15I-ii Myristic acid 0.1% | 95.70 | 0.08 | 0.54 | 0.51 | 6.05 | 2.40 |
| | 15I-iii Moisture 100%* | 91.74 | 0.37 | 0.58 | 0.52 | 7.81 | 4.20 |
| | | 96.13 | 0.07 | 0.51 | 0.52 | 6.04 | 2.41 |
| 2 M | 15I-i Glycerin 0.2% | 97.24 | 0.06 | 0.62 | 0.50 | 7.77 | 4.09 |
| | 15I-ii Myristic acid 0.1% | 97.54 | 0.06 | 0.71 | 0.51 | 7.01 | 3.36 |
| | 15I-iii Moisture 100%* | 94.46 | 0.31 | 0.66 | 0.52 | 8.45 | 4.84 |
| | | 97.04 | 0.06 | 0.60 | 0.51 | 7.29 | 3.66 |
| 3 M | 15I-i Glycerin 0.2% | 96.60 | 0.08 | 0.72 | 0.54 | 9.07 | 5.39 |
| | 15I-ii Myristic acid 0.1% | 95.22 | 0.08 | 0.86 | 0.54 | 8.63 | 4.98 |
| | 15I-iii Moisture 100%* | 94.42 | 0.29 | 0.70 | 0.55 | 8.54 | 4.93 |
| | | 95.98 | 0.08 | 0.70 | 0.53 | 8.80 | 5.17 |
| 6 M | 15I-i Glycerin 0.2% | 92.16 | 0.09 | 1.05 | 0.50 | 10.56 | 6.88 |
| | 15I-ii Myristic acid 0.1% | 91.93 | 0.19 | 1.36 | 0.56 | 11.35 | 7.69 |
| | 15I-iii Moisture 100%* | 89.59 | 0.50 | 1.14 | 0.50 | 13.57 | 9.68 |
| | | 90.36 | 0.25 | 1.10 | 0.49 | 14.02 | 10.54 |

*meglumine 0.5% mixture

The results of stability testing of Example 15I-i-iii at 55° C. are set forth in Table 223 below.

TABLE 223

| | Meglumine 1% 55° C. | Potency % | CBD % | CBN % | D8-THC % | Total Impurities % | Increase + % |
|---|---|---|---|---|---|---|---|
| Zero | 15I-i Glycerin 0.2% | 100.00 | 0.02 | 0.43 | 0.54 | 3.68 | |
| | 15I-ii Myristic acid 0.1% | 100.00 | 0.02 | 0.42 | 0.52 | 3.65 | |
| | 15I-iii Moisture 100%* | 100.00 | 0.05 | 0.44 | 0.50 | 3.61 | |
| | | 100.00 | 0.09 | 0.41 | 0.52 | 3.63 | |
| 1 W | 15I-i Glycerin 0.2% | 93.45 | 0.02 | 0.45 | 0.56 | 6.41 | 2.73 |
| | 15I-ii Myristic acid 0.1% | 94.85 | 0.09 | 0.52 | 0.59 | 5.74 | 2.09 |
| | 15I-iii Moisture 100%* | 91.74 | 0.44 | 0.46 | 0.59 | 8.36 | 4.75 |
| | | 99.04 | 0.06 | 0.44 | 0.58 | 5.40 | 1.77 |
| 2 W | 15I-i Glycerin 0.2% | 94.27 | 0.03 | 0.56 | 0.53 | 8.21 | 4.53 |
| | 15I-ii Myristic acid 0.1% | 96.02 | 0.03 | 0.71 | 0.51 | 7.08 | 3.43 |
| | 15I-iii Moisture 100%* | 85.55 | 0.88 | 0.65 | 0.57 | 14.47 | 10.86 |
| | | 97.15 | 0.01 | 0.49 | 0.51 | 6.59 | 2.96 |

*meglumine 0.5% mixture

EXAMPLE 15J

Dronabinol Solution in Sesame Oil Sourced from Arista with Meglumine and Different Degradants Added In Example 15J-i-iii, dronabinol formulations were prepared in accordance with Example 15G-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 15J-i-iii at 25° C. are set forth in Table 224 below.

TABLE 224

| | Meglumine 1% 25° C. | Potency % | CBD % | CBN % | D8-THC % | Total Impurities % | Increase + % |
|---|---|---|---|---|---|---|---|
| Zero | 15J-i Glycerin 0.2% | 100.00 | 0.02 | 0.44 | 0.52 | 3.61 | |
| | 15J-ii Myristic acid 0.1% | 100.00 | 0.03 | 0.44 | 0.54 | 3.66 | |
| | 15J-iii Moisture 100%* | 100.00 | 0.09 | 0.49 | 0.54 | 3.89 | |
| | | 100.00 | 0.04 | 0.43 | 0.54 | 3.48 | |
| 3 M | 15J-i Glycerin 0.2% | 98.85 | 0.09 | 0.53 | 0.51 | 7.10 | 3.49 |
| | 15J-ii Myristic acid 0.1% | 101.15 | 0.10 | 0.53 | 0.51 | 5.30 | 1.64 |
| | 15J-iii Moisture 100%* | 94.21 | 0.94 | 0.57 | 0.53 | 10.43 | 6.54 |
| | | 101.23 | 0.06 | 0.51 | 0.53 | 5.36 | 1.88 |
| 6 M | 15J-i Glycerin 0.2% | 96.89 | 0.07 | 0.55 | 0.52 | 8.29 | 4.68 |
| | 15J-ii Myristic acid 0.1% | 99.23 | 0.12 | 0.57 | 0.53 | 6.49 | 2.83 |
| | 15J-iii Moisture 100%* | 80.16 | 1.97 | 0.83 | 0.52 | 27.01 | 23.12 |
| | | 99.75 | 0.09 | 0.53 | 0.53 | 6.50 | 3.02 |

*meglumine 0.5% mixture

The results of stability testing of Example 15J-i-iii at 40° C. are set forth in Table 225 below.

TABLE 225

| Meglumine 1% | | Potency % | CBD % | CBN % | D8-THC % | Total Impurities % | Increase + % |
|---|---|---|---|---|---|---|---|
| | 40° C. | | | | | | |
| Zero | 15J-i Glycerin 0.2% | 100.00 | 0.02 | 0.44 | 0.52 | 3.61 | |
| | 15J-ii Myristic acid 0.1% | 100.00 | 0.03 | 0.44 | 0.54 | 3.66 | |
| | 15J-iii Moisture 100%* | 100.00 | 0.09 | 0.49 | 0.54 | 3.89 | |
| | | 100.00 | 0.04 | 0.43 | 0.54 | 3.48 | |
| 1 M | 15J-i Glycerin 0.2% | 94.69 | 0.29 | 0.54 | 0.49 | 7.93 | 4.32 |
| | 15J-ii Myristic acid 0.1% | 95.29 | 0.05 | 0.55 | 0.51 | 5.75 | 2.09 |
| | 15J-iii Moisture 100%* | 90.45 | 0.61 | 0.60 | 0.52 | 11.21 | 7.32 |
| | | 94.68 | 0.05 | 0.51 | 0.52 | 6.23 | 2.75 |
| 2 M | 15J-i Glycerin 0.2% | 96.23 | 0.13 | 0.60 | 0.55 | 9.61 | 6.00 |
| | 15J-ii Myristic acid 0.1% | 97.06 | 0.03 | 0.64 | 0.56 | 6.89 | 3.23 |
| | 15J-iii Moisture 100%* | 87.52 | 0.87 | 0.89 | 0.50 | 15.69 | 11.80 |
| | | 98.99 | 0.06 | 0.53 | 0.55 | 7.39 | 3.91 |
| 3 M | 15J-i Glycerin 0.2% | 94.15 | 0.13 | 0.68 | 0.53 | 10.62 | 7.01 |
| | 15J-ii Myristic acid 0.1% | 96.69 | 0.02 | 0.84 | 0.52 | 8.35 | 4.69 |
| | 15J-iii Moisture 100%* | 76.29 | 1.16 | 1.37 | 0.55 | 22.77 | 18.88 |
| | | 97.55 | 0.04 | 0.64 | 0.53 | 9.12 | 5.64 |
| 6 M | 15J-i Glycerin 0.2% | 88.48 | 0.17 | 1.03 | 0.56 | 14.89 | 11.28 |
| | 15J-ii Myristic acid 0.1% | 91.09 | 0.21 | 1.85 | 0.78 | 15.22 | 11.56 |
| | 15J-iii Moisture 100%* | 48.13 | 1.61 | 3.55 | 0.68 | 43.37 | 39.48 |
| | | 90.73 | 0.06 | 0.98 | 0.53 | 13.48 | 10.00 |

*meglumine 0.5% mixture

The results of stability testing of Example 15J-i-iii at 55° C. are set forth in Table 226 below.

TABLE 226

| Meglumine 1% | | Potency % | CBD % | CBN % | D8-THC % | Total Impurities % | Increase + % |
|---|---|---|---|---|---|---|---|
| | 55° C. | | | | | | |
| Zero | 15J-i Glycerin 0.2% | 100.00 | 0.02 | 0.44 | 0.52 | 3.61 | |
| | 15J-ii Myristic acid 0.1% | 100.00 | 0.03 | 0.44 | 0.54 | 3.66 | |
| | 15J-iii Moisture 100%* | 100.00 | 0.09 | 0.49 | 0.54 | 3.89 | |
| | | 100.00 | 0.04 | 0.43 | 0.54 | 3.48 | |
| 1 W | 15J-i Glycerin 0.2% | 91.77 | 0.22 | 0.50 | 0.59 | 11.33 | 7.72 |
| | 15J-ii Myristic acid 0.1% | 92.63 | 0.33 | 0.73 | 0.60 | 10.66 | 7.00 |
| | 15J-iii Moisture 100%* | 93.29 | 0.41 | 0.48 | 0.60 | 8.64 | 4.75 |
| | | 92.84 | 0.25 | 0.50 | 0.59 | 11.35 | 7.87 |
| 2 W | 15J-i Glycerin 0.2% | 90.01 | 0.14 | 0.61 | 0.56 | 12.91 | 9.30 |
| | 15J-ii Myristic acid 0.1% | 91.29 | 0.24 | 1.03 | 0.56 | 12.21 | 8.55 |
| | 15J-iii Moisture 100%* | 86.17 | 1.07 | 0.75 | 0.56 | 15.44 | 11.55 |
| | | 91.65 | 0.16 | 0.59 | 0.52 | 12.98 | 9.50 |

*meglumine 0.5% mixture

EXAMPLE 15K

Dronabinol Solution in Sesame Oil Sourced from Croda with Meglumine and Different Degradants Added In Example 15K-i-iii, dronabinol formulations were prepared in accordance with Example 15H-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 15K-i-iii at 25° C. are set forth in Table 227 below.

TABLE 227

| | Meglumine 1% | | | | | Total Impurities | |
|---|---|---|---|---|---|---|---|
| | 25° C. | Potency % | CBD % | CBN % | D8-THC % | % | Increase + % |
| Zero | 15K-i Glycerin 0.2% | 100.00 | 0.01 | 0.46 | 0.56 | 3.27 | |
| | 15K-ii Myristic acid 0.1% | 100.00 | 0.01 | 0.45 | 0.53 | 3.01 | |
| | 15K-iii Moisture 100%* | 100.00 | 0.11 | 0.49 | 0.56 | 3.82 | |
| | | 100.00 | 0.02 | 0.46 | 0.59 | 3.33 | |
| 3 M | 15K-i Glycerin 0.2% | 90.75 | 0.73 | 0.54 | 0.59 | 12.50 | 9.23 |
| | 15K-ii Myristic acid 0.1% | 91.94 | 0.31 | 0.55 | 0.57 | 8.89 | 5.88 |
| | 15K-iii Moisture 100%* | 89.64 | 2.09 | 0.71 | 0.65 | 15.63 | 11.81 |
| | | 94.32 | 0.34 | 0.53 | 0.58 | 10.59 | 7.26 |
| 6 M | 15K-i Glycerin 0.2% | 78.64 | 1.84 | 0.69 | 0.59 | 24.09 | 20.82 |
| | 15K-ii Myristic acid 0.1% | 89.29 | 0.22 | 0.58 | 0.58 | 11.45 | 8.44 |
| | 15K-iii Moisture 100%* | 72.69 | 2.90 | 0.75 | 0.58 | 28.54 | 24.72 |
| | | 91.50 | 0.44 | 0.58 | 0.55 | 14.26 | 10.93 |

*meglumine 0.5% mixture

The results of stability testing of Example 15K-i-iii at 40° C. are set forth in Table 228 below.

TABLE 228

| | Meglumine 1% | | | | | Total Impurities | |
|---|---|---|---|---|---|---|---|
| | 40° C. | Potency % | CBD % | CBN % | D8-THC % | % | Increase + % |
| Zero | 15K-i Glycerin 0.2% | 100.00 | 0.01 | 0.46 | 0.56 | 3.27 | |
| | 15K-ii Myristic acid 0.1% | 100.00 | 0.01 | 0.45 | 0.53 | 3.01 | |
| | 15K-iii Moisture 100%* | 100.00 | 0.11 | 0.49 | 0.56 | 3.82 | |
| | | 100.00 | 0.02 | 0.46 | 0.59 | 3.33 | |
| 1 M | 15K-i Glycerin 0.2% | 90.51 | 0.65 | 0.54 | 0.54 | 10.99 | 7.72 |
| | 15K-ii Myristic acid 0.1% | 87.95 | 0.63 | 0.62 | 0.58 | 10.51 | 7.50 |
| | 15K-iii Moisture 100%* | 85.62 | 1.26 | 0.56 | 0.56 | 16.64 | 12.82 |
| | | 87.93 | 0.92 | 0.57 | 0.57 | 13.58 | 10.25 |
| 2 M | 15K-i Glycerin 0.2% | 82.69 | 1.03 | 0.67 | 0.64 | 17.19 | 13.92 |
| | 15K-ii Myristic acid 0.1% | 87.62 | 0.30 | 0.75 | 0.57 | 12.31 | 9.30 |
| | 15K-iii Moisture 100%* | 79.89 | 1.84 | 0.73 | 0.55 | 23.38 | 19.56 |
| | | 82.01 | 1.02 | 0.68 | 0.59 | 18.39 | 15.06 |

TABLE 228-continued

| | Meglumine 1% 40° C. | Potency % | CBD % | CBN % | D8-THC % | Total Impurities % | Increase + % |
|---|---|---|---|---|---|---|---|
| 3 M | 15K-i Glycerin 0.2% | 68.38 | 1.56 | 0.98 | 0.59 | 29.97 | 26.70 |
| | 15K-ii Myristic acid 0.1% | 85.69 | 0.26 | 0.94 | 0.58 | 14.45 | 11.44 |
| | 15K-iii Moisture 100%* | 65.11 | 2.18 | 1.15 | 0.60 | 34.06 | 30.24 |
| | | 70.46 | 0.99 | 0.97 | 0.59 | 28.49 | 25.16 |
| 6 M | 15K-i Glycerin 0.2% | 50.72 | 1.00 | 1.80 | 0.73 | 41.84 | 38.57 |
| | 15K-ii Myristic acid 0.1% | 77.22 | 0.25 | 1.66 | 0.59 | 20.82 | 17.81 |
| | 15K-iii Moisture 100%* | 36.15 | 1.50 | 3.71 | 0.75 | 57.00 | 53.18 |
| | | 59.43 | 0.75 | 1.67 | 0.62 | 36.68 | 33.35 |

*meglumine 0.5% mixture

The results of stability testing of Example 15K-i-iii at 55° C. are set forth in Table 229 below.

TABLE 229

| | Meglumine 1% 55° C. | Potency % | CBD % | CBN % | D8-THC % | Total Impurities % | Increase + % |
|---|---|---|---|---|---|---|---|
| Zero | 15K-i Glycerin 0.2% | 100.00 | 0.01 | 0.46 | 0.56 | 3.27 | |
| | 15K-ii Myristic acid 0.1% | 100.00 | 0.01 | 0.45 | 0.53 | 3.01 | |
| | 15K-iii Moisture 100%* | 100.00 | 0.11 | 0.49 | 0.56 | 3.82 | |
| | | 100.00 | 0.02 | 0.46 | 0.59 | 3.33 | |
| 1 W | 15K-i Glycerin 0.2% | 83.45 | 0.90 | 0.47 | 0.61 | 16.19 | 12.92 |
| | 15K-ii Myristic acid 0.1% | 86.65 | 0.45 | 0.65 | 0.64 | 12.53 | 9.52 |
| | 15K-iii Moisture 100%* | 87.92 | 1.25 | 0.50 | 0.55 | 13.24 | 9.42 |
| | | 86.86 | 0.94 | 0.52 | 0.59 | 15.89 | 12.56 |
| 2 W | 15K-i Glycerin 0.2% | 71.10 | 1.85 | 0.68 | 0.59 | 28.07 | 24.80 |
| | 15K-ii Myristic acid 0.1% | 78.00 | 0.50 | 1.27 | 0.63 | 19.09 | 16.08 |
| | 15K-iii Moisture 100%* | 78.81 | 2.50 | 0.67 | 0.59 | 22.93 | 19.11 |
| | | 73.45 | 1.22 | 0.73 | 0.58 | 26.08 | 22.75 |

*meglumine 0.5% mixture

EXAMPLE 15L

Dronabinol Solution in Sesame Oil Sourced from Dipasa with Meglumine and Different Degradants Added In Example 15L-i-iii, dronabinol formulations were prepared in accordance with Example 15I-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 15L-i-iii at 25° C. are set forth in Table 230 below.

TABLE 230

| Meglumine 1% | | Potency % | CBD % | CBN % | D8-THC % | Total Impurities % | Increase + % |
|---|---|---|---|---|---|---|---|
| | 25° C. | | | | | | |
| Zero | 15L-i Glycerin 0.2% | 100.00 | 0.02 | 0.43 | 0.54 | 3.68 | |
| | 15L-ii Myristic acid 0.1% | 100.00 | 0.02 | 0.42 | 0.52 | 3.65 | |
| | 15L-iii Moisture 100%* | 100.00 | 0.05 | 0.44 | 0.50 | 3.61 | |
| | | 100.00 | 0.09 | 0.41 | 0.52 | 3.63 | |
| 3 M | 15L-i Glycerin 0.2% | 99.49 | 0.07 | 0.49 | 0.52 | 5.12 | 1.44 |
| | 15L-ii Myristic acid 0.1% | 100.55 | 0.05 | 0.51 | 0.51 | 5.31 | 1.66 |
| | 15L-iii Moisture 100%* | 94.65 | 0.53 | 0.55 | 0.52 | 7.88 | 4.27 |
| | | 99.80 | 0.05 | 0.49 | 0.51 | 4.86 | 1.23 |
| 6 M | 15L-i Glycerin 0.2% | 96.65 | 0.07 | 0.50 | 0.51 | 6.65 | 2.97 |
| | 15L-ii Myristic acid 0.1% | 98.80 | 0.07 | 0.56 | 0.52 | 6.39 | 2.74 |
| | 15L-iii Moisture 100%* | 85.81 | 1.13 | 0.74 | 0.54 | 13.52 | 9.91 |
| | | 99.45 | 0.07 | 0.52 | 0.53 | 6.14 | 2.51 |

*meglumine 0.5% mixture

The results of stability testing of Example 15L-i-iii at 40° C. are set forth in Table 231 below.

TABLE 231

| Meglumine 1% | | Potency % | CBD % | CBN % | D8-THC % | Total Impurities % | Increase + % |
|---|---|---|---|---|---|---|---|
| | 40° C. | | | | | | |
| Zero | 15L-i Glycerin 0.2% | 100.00 | 0.02 | 0.43 | 0.54 | 3.68 | |
| | 15L-ii Myristic acid 0.1% | 100.00 | 0.02 | 0.42 | 0.52 | 3.65 | |
| | 15L-iii Moisture 100%* | 100.00 | 0.05 | 0.44 | 0.50 | 3.61 | |
| | | 100.00 | 0.09 | 0.41 | 0.52 | 3.63 | |
| 1 M | 15L-i Glycerin 0.2% | 96.18 | 0.16 | 0.51 | 0.53 | 6.00 | 2.32 |
| | 15L-ii Myristic acid 0.1% | 96.75 | 0.18 | 0.55 | 0.51 | 5.88 | 2.23 |
| | 15L-iii Moisture 100%* | 91.57 | 0.54 | 0.59 | 0.52 | 9.24 | 5.63 |
| | | 94.96 | 0.05 | 0.51 | 0.50 | 5.74 | 2.11 |
| 2 M | 15L-i Glycerin 0.2% | 97.76 | 0.11 | 0.55 | 0.51 | 6.92 | 3.24 |
| | 15L-ii Myristic acid 0.1% | 98.57 | 0.12 | 0.75 | 0.50 | 6.55 | 2.90 |
| | 15L-iii Moisture 100%* | 86.87 | 1.21 | 0.94 | 0.44 | 14.27 | 10.66 |
| | | 98.93 | 0.10 | 0.55 | 0.53 | 6.78 | 3.15 |
| 3 M | 15L-i Glycerin 0.2% | 95.42 | 0.01 | 0.65 | 0.52 | 8.18 | 4.50 |
| | 15L-ii Myristic acid 0.1% | 96.53 | 0.12 | 0.92 | 0.59 | 8.42 | 4.77 |
| | 15L-iii Moisture 100%* | 72.19 | 1.61 | 1.55 | 0.56 | 24.33 | 20.72 |
| | | 97.28 | 0.02 | 0.68 | 0.50 | 8.00 | 4.37 |
| 6 M | 15L-i Glycerin 0.2% | 89.68 | 0.12 | 1.06 | 0.59 | 13.79 | 10.11 |
| | 15L-ii Myristic acid 0.1% | 90.82 | 0.13 | 1.65 | 0.58 | 12.50 | 8.85 |
| | 15L-iii Moisture 100%* | 39.64 | 1.54 | 4.95 | 0.70 | 51.32 | 47.71 |
| | | 91.65 | 0.06 | 1.09 | 0.52 | 12.41 | 8.78 |

*meglumine 0.5% mixture

The results of stability testing of Example 15L-i-iii at 55° C. are set forth in Table 232 below.

TABLE 232

| Meglumine 1% | | | | | | Total Impurities | |
|---|---|---|---|---|---|---|---|
| | 55° C. | Potency % | CBD % | CBN % | D8-THC % | % | Increase + % |
| Zero | 15L-i Glycerin 0.2% | 100.00 | 0.02 | 0.43 | 0.54 | 3.68 | |
| | 15L-ii Myristic acid 0.1% | 100.00 | 0.02 | 0.42 | 0.52 | 3.65 | |
| | 15L-iii Moisture 100%* | 100.00 | 0.05 | 0.44 | 0.50 | 3.61 | |
| | | 100.00 | 0.09 | 0.41 | 0.52 | 3.63 | |
| 1 W | 15L-i Glycerin 0.2% | 93.45 | 0.02 | 0.45 | 0.56 | 6.41 | 2.73 |
| | 15L-ii Myristic acid 0.1% | 94.85 | 0.09 | 0.52 | 0.59 | 5.74 | 2.09 |
| | 15L-iii Moisture 100%* | 91.74 | 0.44 | 0.46 | 0.59 | 8.36 | 4.75 |
| | | 99.04 | 0.06 | 0.44 | 0.58 | 5.40 | 1.77 |
| 2 W | 15L-i Glycerin 0.2% | 94.27 | 0.03 | 0.56 | 0.53 | 8.21 | 4.53 |
| | 15L-ii Myristic acid 0.1% | 96.02 | 0.03 | 0.71 | 0.51 | 7.08 | 3.43 |
| | 15L-iii Moisture 100%* | 85.55 | 0.88 | 0.65 | 0.57 | 14.47 | 10.86 |
| | | 97.15 | 0.01 | 0.49 | 0.51 | 6.59 | 2.96 |

*meglumine 0.5% mixture

EXAMPLE 15M

Dronabinol Solution in Sesame Oil Sourced from Arista with Monoethanolamine and Different Degradants Added In Example 15M-i-iii, dronabinol formulations were prepared in accordance with Example 15A, using sesame oil sourced from Arista with 0.5% monoethanolamine added. Formula 15M-i also contained 0.2% glycerin; formula 15M-ii also contained 0.1% myristic acid; and formula 15M-iii also contained 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 15M-i-iii at 25° C. are set forth in Table 233 below.

TABLE 233

| Monoethanolamine 0.5% | | | | | | Total Impurities | |
|---|---|---|---|---|---|---|---|
| | 25° C. | Potency % | CBD % | CBN % | D8-THC % | % | Increase + % |
| Zero | 15M-i Glycerin 0.2% | 100.00 | 0.12 | 0.49 | 0.53 | 4.08 | |
| | 15M-ii Myristic acid 0.1% | 100.00 | 0.22 | 0.71 | 0.52 | 4.21 | |
| | 15M-iii Moisture 100% | 100.00 | 0.16 | 0.49 | 0.56 | 4.23 | |
| 3 M | 15M-i Glycerin 0.2% | 98.45 | 0.26 | 0.83 | 0.54 | 5.95 | 1.87 |
| | 15M-ii Myristic acid 0.1% | 99.31 | 0.29 | 1.11 | 0.55 | 6.33 | 2.12 |
| | 15M-iii Moisture 100% | 95.61 | 0.37 | 0.80 | 0.54 | 11.01 | 6.78 |
| 6 M | 15M-i Glycerin 0.2% | 98.64 | 0.11 | 1.12 | 0.52 | 5.78 | 1.70 |
| | 15M-ii Myristic acid 0.1% | 99.25 | 0.13 | 1.38 | 0.54 | 6.24 | 2.03 |
| | 15M-iii Moisture 100% | 93.82 | 0.57 | 1.12 | 0.54 | 12.55 | 8.32 |

The results of stability testing of Example 15M-i-iii at 40° C. are set forth in Table 234 below.

TABLE 234

| Monoethanolamine 0.5% | | | | | | Total Impurities | |
|---|---|---|---|---|---|---|---|
| | 40° C. | Potency % | CBD % | CBN % | D8-THC % | % | Increase + % |
| Zero | 15M-i Glycerin 0.2% | 100.00 | 0.12 | 0.49 | 0.53 | 4.08 | |
| | 15M-ii Myristic acid 0.1% | 100.00 | 0.22 | 0.71 | 0.52 | 4.21 | |
| | 15M-iii Moisture 100% | 100.00 | 0.16 | 0.49 | 0.56 | 4.23 | |
| 1 M | 15M-i Glycerin 0.2% | 93.90 | 0.14 | 0.92 | 0.54 | 6.50 | 2.42 |
| | 15M-ii Myristic acid 0.1% | 94.33 | 0.27 | 1.20 | 0.53 | 6.89 | 2.68 |
| | 15M-iii Moisture 100% | 91.75 | 0.81 | 0.99 | 0.49 | 11.23 | 7.00 |
| 2 M | 15M-i Glycerin 0.2% | 97.91 | 0.12 | 1.26 | 0.50 | 6.34 | 2.26 |
| | 15M-ii Myristic acid 0.1% | 99.19 | 0.19 | 1.55 | 0.50 | 6.05 | 1.84 |
| | 15M-iii Moisture 100% | 93.03 | 0.62 | 1.39 | 0.55 | 12.32 | 8.09 |
| 3 M | 15M-i Glycerin 0.2% | 97.81 | 0.08 | 1.54 | 0.54 | 6.11 | 2.03 |
| | 15M-ii Myristic acid 0.1% | 98.95 | 0.09 | 1.59 | 0.52 | 5.24 | 1.03 |
| | 15M-iii Moisture 100% | 93.24 | 0.66 | 1.66 | 0.55 | 13.34 | 9.11 |
| 6 M | 15M-i Glycerin 0.2% | 94.67 | 0.03 | 2.04 | 0.50 | 6.49 | 2.41 |
| | 15M-ii Myristic acid 0.1% | 97.22 | 0.01 | 2.05 | 0.47 | 6.57 | 2.36 |
| | 15M-iii Moisture 100% | 89.65 | 0.13 | 2.46 | 0.63 | 15.64 | 11.41 |

The results of stability testing of Example 15M-i-iii at 55° C. are set forth in Table 235 below.

TABLE 235

| Monoethanolamine 0.5% | | | | | | Total Impurities | |
|---|---|---|---|---|---|---|---|
| | 55° C. | Potency % | CBD % | CBN % | D8-THC % | % | Increase + % |
| Zero | 15M-i Glycerin 0.2% | 100.00 | 0.12 | 0.49 | 0.53 | 4.08 | |
| | 15M-ii Myristic acid 0.1% | 100.00 | 0.22 | 0.71 | 0.52 | 4.21 | |
| | 15M-iii Moisture 100% | 100.00 | 0.16 | 0.49 | 0.56 | 4.23 | |
| 1 W | 15M-i Glycerin 0.2% | 96.64 | 0.15 | 0.86 | 0.59 | 5.53 | 1.45 |
| | 15M-ii Myristic acid 0.1% | 97.85 | 0.06 | 1.11 | 0.62 | 5.70 | 1.49 |
| | 15M-iii Moisture 100% | 95.51 | 0.02 | 0.62 | 0.59 | 8.55 | 4.32 |
| 2 W | 15M-i Glycerin 0.2% | 95.94 | 0.23 | 1.18 | 0.54 | 6.72 | 2.64 |
| | 15M-ii Myristic acid 0.1% | 97.85 | 0.32 | 1.57 | 0.52 | 6.87 | 2.66 |
| | 15M-iii Moisture 100% | 94.83 | 0.34 | 0.93 | 0.57 | 10.24 | 6.01 |

EXAMPLE 15N

Dronabinol Solution in Sesame Oil Sourced from Croda with Monoethanolamine and Different Degradants Added In Example 15N-i-iii, dronabinol control formulations were prepared in accordance with Example 15B, using sesame oil sourced from Croda with 0.5% monoethanolamine added. Formula 15N-i also contained 0.2% glycerin; formula 15N-ii also contained 0.1% myristic acid; and formula 15N-iii also contained 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 15N-i-iii at 25° C. are set forth in Table 236 below.

TABLE 236

| Monoethanolamine 0.5% | | | | | | Total Impurities | |
|---|---|---|---|---|---|---|---|
| | 25° C. | Potency % | CBD % | CBN % | D8-THC % | % | Increase + % |
| Zero | 15N-i Glycerin 0.2% | 100.00 | 0.11 | 0.60 | 0.57 | 3.72 | |
| | 15N-ii Myristic acid 0.1% | 100.00 | 0.11 | 0.66 | 0.54 | 4.02 | |
| | 15N-iii Moisture 100% | 100.00 | 0.10 | 0.58 | 0.57 | 3.53 | |
| 3 M | 15N-i Glycerin 0.2% | 98.36 | 0.38 | 0.98 | 0.58 | 6.57 | 2.85 |
| | 15N-ii Myristic acid 0.1% | 97.48 | 0.22 | 1.20 | 0.58 | 6.47 | 2.45 |
| | 15N-iii Moisture 100% | 94.37 | 0.58 | 0.68 | 0.57 | 12.80 | 9.27 |
| 6 M | 15N-i Glycerin 0.2% | 98.21 | 0.11 | 1.20 | 0.59 | 6.31 | 2.59 |
| | 15N-ii Myristic acid 0.1% | 97.15 | 0.05 | 1.49 | 0.56 | 6.16 | 2.14 |
| | 15N-iii Moisture 100% | 90.25 | 0.77 | 0.88 | 0.55 | 14.08 | 10.55 |

The results of stability testing of Example 15N-i-iii at 40° C. are set forth in Table 237 below.

TABLE 237

| Monoethanolamine 0.5% | | | | | | Total Impurities | |
|---|---|---|---|---|---|---|---|
| | 40° C. | Potency % | CBD % | CBN % | D8-THC % | % | Increase + % |
| Zero | 15N-i Glycerin 0.2% | 100.00 | 0.11 | 0.60 | 0.57 | 3.72 | |
| | 15N-ii Myristic acid 0.1% | 100.00 | 0.11 | 0.66 | 0.54 | 4.02 | |
| | 15N-iii Moisture 100% | 100.00 | 0.10 | 0.58 | 0.57 | 3.53 | |
| 1 M | 15N-i Glycerin 0.2% | 93.59 | 0.17 | 1.15 | 0.56 | 6.73 | 3.01 |
| | 15N-ii Myristic acid 0.1% | 93.54 | 0.10 | 1.38 | 0.57 | 6.68 | 2.66 |
| | 15N-iii Moisture 100% | 90.08 | 0.90 | 0.79 | 0.50 | 12.48 | 8.95 |
| 2 M | 15N-i Glycerin 0.2% | 94.96 | 0.16 | 1.49 | 0.57 | 7.26 | 3.54 |
| | 15N-ii Myristic acid 0.1% | 95.56 | 0.11 | 1.70 | 0.58 | 7.22 | 3.20 |
| | 15N-iii Moisture 100% | 90.30 | 0.65 | 0.94 | 0.51 | 12.75 | 9.22 |
| 3 M | 15N-i Glycerin 0.2% | 97.25 | 0.11 | 1.62 | 0.59 | 6.96 | 3.24 |
| | 15N-ii Myristic acid 0.1% | 95.74 | 0.17 | 1.83 | 0.60 | 7.43 | 3.41 |
| | 15N-iii Moisture 100% | 91.70 | 0.72 | 1.25 | 0.54 | 14.07 | 10.54 |
| 6 M | 15N-i Glycerin 0.2% | 94.46 | 0.05 | 2.23 | 0.56 | 8.03 | 4.31 |
| | 15N-ii Myristic acid 0.1% | 94.00 | 0.12 | 2.63 | 0.54 | 8.31 | 4.29 |
| | 15N-iii Moisture 100% | 87.95 | 0.45 | 1.82 | 0.51 | 15.94 | 12.41 |

The results of stability testing of Example 15N-i-iii at 55° C. are set forth in Table 238 below.

TABLE 238

| Monoethanolamine 0.5% | | | | | | Total Impurities | |
|---|---|---|---|---|---|---|---|
| | 55° C. | Potency % | CBD % | CBN % | D8-THC % | % | Increase + % |
| Zero | 15N-i Glycerin 0.2% | 100.00 | 0.11 | 0.60 | 0.57 | 3.72 | |

TABLE 238-continued

| Monoethanolamine 0.5% | | | | | | Total Impurities | |
|---|---|---|---|---|---|---|---|
| | 55° C. | Potency % | CBD % | CBN % | D8-THC % | % | Increase + % |
| | 15N-ii Myristic acid 0.1% | 100.00 | 0.11 | 0.66 | 0.54 | 4.02 | |
| | 15N-iii Moisture 100% | 100.00 | 0.10 | 0.58 | 0.57 | 3.53 | |
| 1 W | 15N-i Glycerin 0.2% | 96.45 | 0.16 | 0.96 | 0.62 | 6.63 | 2.91 |
| | 15N-ii Myristic acid 0.1% | 95.76 | 0.29 | 1.09 | 0.61 | 6.19 | 2.17 |
| | 15N-iii Moisture 100% | 89.20 | 0.08 | 0.61 | 0.64 | 14.06 | 10.53 |
| 2 W | 15N-i Glycerin 0.2% | 94.40 | 0.32 | 1.40 | 0.59 | 7.80 | 4.08 |
| | 15N-ii Myristic acid 0.1% | 95.41 | 0.13 | 1.53 | 0.59 | 7.54 | 3.52 |
| | 15N-iii Moisture 100% | 89.05 | 0.53 | 0.86 | 0.64 | 16.18 | 12.65 |

EXAMPLE 15O

Dronabinol Solution in Sesame Oil Sourced from Dipasa with Monoethanolamine and Different Degradants Added In Example 15O-i-iii, dronabinol formulations were prepared in accordance with Example 15C, using sesame oil sourced from Dipasa with 0.5% monoethanolamine added. Formula 15O-i also contained 0.2% glycerin; formula 15O-ii also contained 0.1% myristic acid; and formula 15O-iii also contained 100% moisture prepared in accordance with Example 6. The dronabinol formulations were then used to fill hard gelatin capsules in accordance with Example 2. The formulations within the capsules were initially tested, then tested at 25° C. for 3 and 6 months; 40° C. for 1, 2, 3 and 6 months and at 55° C. for 1 and 2 weeks.

The results of stability testing of Example 15O-i-iii at 25° C. are set forth in Table 239 below.

TABLE 239

| Monoethanolamine 0.5% | | | | | | Total Impurities | |
|---|---|---|---|---|---|---|---|
| | 25° C. | Potency % | CBD % | CBN % | D8-THC % | % | Increase + % |
| Zero | 15O-i Glycerin 0.2% | 100.00 | 0.17 | 0.48 | 0.49 | 4.13 | |
| | 15O-ii Myristic acid 0.1% | 100.00 | 0.14 | 0.52 | 0.47 | 3.99 | |
| | 15O-iii Moisture 100% | 100.00 | 0.15 | 0.48 | 0.51 | 3.91 | |
| 3 M | 15O-i Glycerin 0.2% | 97.95 | 0.39 | 0.83 | 0.53 | 6.40 | 2.27 |
| | 15O-ii Myristic acid 0.1% | 99.03 | 0.22 | 0.97 | 0.52 | 5.80 | 1.81 |
| | 15O-iii Moisture 100% | 100.67 | 0.13 | 0.60 | 0.55 | 6.38 | 2.47 |
| 6 M | 15O-i Glycerin 0.2% | 97.89 | 0.15 | 1.10 | 0.52 | 5.91 | 1.78 |
| | 15O-ii Myristic acid 0.1% | 98.49 | 0.05 | 1.28 | 0.52 | 6.09 | 2.10 |
| | 15O-iii Moisture 100% | 98.36 | 0.23 | 0.80 | 0.53 | 7.79 | 3.88 |

The results of stability testing of Example 15O-i-iii at 40° C. are set forth in Table 240 below.

TABLE 240

| | Monoethanolamine 0.5% | | | | | Total Impurities | |
|---|---|---|---|---|---|---|---|
| | 40° C. | Potency % | CBD % | CBN % | D8-THC % | % | Increase + % |
| Zero | 15O-i Glycerin 0.2% | 100.00 | 0.17 | 0.48 | 0.49 | 4.13 | |
| | 15O-ii Myristic acid 0.1% | 100.00 | 0.14 | 0.52 | 0.47 | 3.99 | |
| | 15O-iii Moisture 100% | 100.00 | 0.15 | 0.48 | 0.51 | 3.91 | |
| 1 M | 15O-i Glycerin 0.2% | 94.36 | 0.18 | 0.90 | 0.52 | 6.74 | 2.61 |
| | 15O-ii Myristic acid 0.1% | 94.23 | 0.11 | 1.11 | 0.51 | 6.51 | 2.52 |
| | 15O-iii Moisture 100% | 95.61 | 0.40 | 0.68 | 0.51 | 6.97 | 3.06 |
| 2 M | 15O-i Glycerin 0.2% | 97.31 | 0.18 | 1.26 | 0.53 | 6.37 | 2.24 |
| | 15O-ii Myristic acid 0.1% | 97.79 | 0.10 | 1.40 | 0.53 | 6.10 | 2.11 |
| | 15O-iii Moisture 100% | 96.23 | 0.35 | 1.02 | 0.51 | 9.42 | 5.51 |
| 3 M | 15O-i Glycerin 0.2% | 98.17 | 0.26 | 1.27 | 0.49 | 5.71 | 1.58 |
| | 15O-ii Myristic acid 0.1% | 98.05 | 0.16 | 1.31 | 0.51 | 5.55 | 1.56 |
| | 15O-iii Moisture 100% | 95.47 | 0.48 | 1.23 | 0.53 | 10.66 | 6.75 |
| 6 M | 15O-i Glycerin 0.2% | 96.64 | 0.06 | 1.65 | 0.48 | 6.04 | 1.91 |
| | 15O-ii Myristic acid 0.1% | 96.76 | 0.01 | 1.68 | 0.47 | 5.71 | 1.72 |
| | 15O-iii Moisture 100% | 92.33 | 0.11 | 2.00 | 0.50 | 12.58 | 8.67 |

The results of stability testing of Example 15O-i-iii at 55° C. are set forth in Table 241 below.

TABLE 241

| | Monoethanolamine 0.5% | | | | | Total Impurities | |
|---|---|---|---|---|---|---|---|
| | 55° C. | Potency % | CBD % | CBN % | D8-THC % | % | Increase + % |
| Zero | 15O-i Glycerin 0.2% | 100.00 | 0.17 | 0.48 | 0.49 | 4.13 | |
| | 15O-ii Myristic acid 0.1% | 100.00 | 0.14 | 0.52 | 0.47 | 3.99 | |
| | 15O-iii Moisture 100% | 100.00 | 0.15 | 0.48 | 0.51 | 3.91 | |
| 1 W | 15O-i Glycerin 0.2% | 96.03 | 0.17 | 0.77 | 0.28 | 5.96 | 1.83 |
| | 15O-ii Myristic acid 0.1% | 97.71 | 0.16 | 0.98 | 0.57 | 5.82 | 1.83 |
| | 15O-iii Moisture 100% | 96.84 | 0.01 | 0.60 | 0.59 | 6.94 | 3.03 |
| 2 W | 15O-i Glycerin 0.2% | 94.97 | 0.27 | 1.13 | 0.82 | 7.25 | 3.12 |
| | 15O-ii Myristic acid 0.1% | 96.86 | 0.18 | 1.38 | 0.60 | 6.74 | 2.75 |
| | 15O-iii Moisture 100% | 96.28 | 0.18 | 0.91 | 0.53 | 8.37 | 4.46 |

EXAMPLE 15P

Dronabinol Solution in Sesame Oil Sourced from Arista with Monoethanolamine and Different Degradants Added In Example 15P-i-iii, dronabinol formulations were prepared in accordance with Example 15M-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 15P-i-iii at 25° C. are set forth in Table 242 below.

TABLE 242

| Monoethanolamine 0.5% | | | | | | Total Impurities | |
|---|---|---|---|---|---|---|---|
| | 25° C. | Potency % | CBD % | CBN % | D8-THC % | % | Increase + % |
| Zero | 15P-i Glycerin 0.2% | 100.00 | 0.12 | 0.49 | 0.53 | 4.08 | |
| | 15P-ii Myristic acid 0.1% | 100.00 | 0.22 | 0.71 | 0.52 | 4.21 | |
| | 15P-iii Moisture 100% | 100.00 | 0.16 | 0.49 | 0.56 | 4.23 | |
| 3 M | 15P-i Glycerin 0.2% | 99.52 | 0.32 | 0.80 | 0.52 | 5.26 | 1.18 |
| | 15P-ii Myristic acid 0.1% | 101.10 | 0.37 | 0.96 | 0.52 | 5.52 | 1.31 |
| | 15P-iii Moisture 100% | 98.53 | 0.14 | 0.61 | 0.56 | 6.86 | 2.63 |
| 6 M | 15P-i Glycerin 0.2% | 97.19 | 0.04 | 1.08 | 0.54 | 5.35 | 1.27 |
| | 15P-ii Myristic acid 0.1% | 99.58 | 0.03 | 1.20 | 0.51 | 4.85 | 0.64 |
| | 15P-iii Moisture 100% | 96.45 | 0.21 | 0.72 | 0.57 | 8.76 | 4.53 |

The results of stability testing of Example 15P-i-iii at 40° C. are set forth in Table 243 below.

TABLE 243

| Monoethanolamine 0.5% | | | | | | Total Impurities | |
|---|---|---|---|---|---|---|---|
| | 40° C. | Potency % | CBD % | CBN % | D8-THC % | % | Increase + % |
| Zero | 15P-i Glycerin 0.2% | 100.00 | 0.12 | 0.49 | 0.53 | 4.08 | |
| | 15P-ii Myristic acid 0.1% | 100.00 | 0.22 | 0.71 | 0.52 | 4.21 | |
| | 15P-iii Moisture 100% | 100.00 | 0.16 | 0.49 | 0.56 | 4.23 | |
| 1 M | 15P-i Glycerin 0.2% | 94.91 | 0.06 | 0.73 | 0.54 | 5.67 | 1.59 |
| | 15P-ii Myristic acid 0.1% | 96.77 | 0.08 | 1.08 | 0.53 | 6.04 | 1.83 |
| | 15P-iii Moisture 100% | 93.95 | 0.28 | 0.72 | 0.54 | 9.73 | 5.50 |
| 2 M | 15P-i Glycerin 0.2% | 98.91 | 0.05 | 1.11 | 0.52 | 5.17 | 1.09 |
| | 15P-ii Myristic acid 0.1% | 99.74 | 0.07 | 1.52 | 0.49 | 5.17 | 0.96 |
| | 15P-iii Moisture 100% | 94.59 | 0.43 | 1.07 | 0.42 | 10.64 | 6.41 |
| 3 M | 15P-i Glycerin 0.2% | 97.29 | 0.01 | 1.54 | 0.55 | 6.39 | 2.31 |
| | 15P-ii Myristic acid 0.1% | 98.08 | 0.03 | 2.05 | 0.54 | 7.04 | 2.83 |
| | 15P-iii Moisture 100% | 92.40 | 0.25 | 1.40 | 0.52 | 13.24 | 9.01 |
| 6 M | 15P-i Glycerin 0.2% | 92.84 | 0.04 | 2.84 | 0.56 | 9.73 | 5.65 |
| | 15P-ii Myristic acid 0.1% | 92.59 | 0.06 | 3.81 | 0.55 | 11.13 | 6.92 |
| | 15P-iii Moisture 100% | 82.82 | 0.28 | 2.53 | 0.54 | 20.38 | 16.15 |

The results of stability testing of Example 15P-i-iii at 55° C. are set forth in Table 244 below.

TABLE 244

| Monoethanolamine 0.5% | | | | | | Total Impurities | |
|---|---|---|---|---|---|---|---|
| | 55° C. | Potency % | CBD % | CBN % | D8-THC % | % | Increase + % |
| Zero | 15P-i Glycerin 0.2% | 100.00 | 0.12 | 0.49 | 0.53 | 4.08 | |

TABLE 244-continued

| Monoethanolamine 0.5% | | | | | | Total Impurities | |
|---|---|---|---|---|---|---|---|
| | 55° C. | Potency % | CBD % | CBN % | D8-THC % | % | Increase + % |
| | 15P-ii Myristic acid 0.1% | 100.00 | 0.22 | 0.71 | 0.52 | 4.21 | |
| | 15P-iii Moisture 100% | 100.00 | 0.16 | 0.49 | 0.56 | 4.23 | |
| 1 W | 15P-i Glycerin 0.2% | 96.64 | 0.15 | 0.86 | 0.59 | 5.53 | 1.45 |
| | 15P-ii Myristic acid 0.1% | 97.85 | 0.06 | 1.11 | 0.62 | 5.70 | 1.49 |
| | 15P-iii Moisture 100% | 95.51 | 0.02 | 0.62 | 0.59 | 8.55 | 4.32 |
| 2 W | 15P-i Glycerin 0.2% | 95.94 | 0.23 | 1.18 | 0.54 | 6.72 | 2.64 |
| | 15P-ii Myristic acid 0.1% | 97.85 | 0.32 | 1.57 | 0.52 | 6.87 | 2.66 |
| | 15P-iii Moisture 100% | 94.83 | 0.34 | 0.93 | 0.57 | 10.24 | 6.01 |

EXAMPLE 15Q

Dronabinol Solution in Sesame Oil Sourced from Croda with Monoethanolamine and Different Degradants Added In Example 15Q-i-iii, dronabinol formulations were prepared in accordance with Example 15N-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 15Q-i-iii at 25° C. are set forth in Table 245 below.

TABLE 245

| Monoethanolamine 0.5% | | | | | | Total Impurities | |
|---|---|---|---|---|---|---|---|
| | 25° C. | Potency % | CBD % | CBN % | D8-THC % | % | Increase + % |
| Zero | 15Q-i Glycerin 0.2% | 100.00 | 0.11 | 0.60 | 0.57 | 3.72 | |
| | 15Q-ii Myristic acid 0.1% | 100.00 | 0.11 | 0.66 | 0.54 | 4.02 | |
| | 15Q-iii Moisture 100% | 100.00 | 0.10 | 0.58 | 0.57 | 3.53 | |
| 3 M | 15Q-i Glycerin 0.2% | 100.62 | 0.10 | 0.81 | 0.58 | 5.57 | 1.85 |
| | 15Q-ii Myristic acid 0.1% | 99.22 | 0.21 | 0.97 | 0.59 | 5.64 | 1.62 |
| | 15Q-iii Moisture 100% | 90.31 | 0.40 | 0.55 | 0.59 | 13.92 | 10.39 |
| 6 M | 15Q-i Glycerin 0.2% | 97.99 | 0.04 | 1.05 | 0.62 | 5.61 | 1.89 |
| | 15Q-ii Myristic acid 0.1% | 97.90 | 0.03 | 1.19 | 0.56 | 5.43 | 1.41 |
| | 15Q-iii Moisture 100% | 89.80 | 0.39 | 0.77 | 0.50 | 17.32 | 13.79 |

The results of stability testing of Example 15Q-i-iii at 40° C. are set forth in Table 246 below.

TABLE 246

| | Monoethanolamine 0.5% 40° C. | Potency % | CBD % | CBN % | D8-THC % | Total Impurities % | Increase + % |
|---|---|---|---|---|---|---|---|
| Zero | 15Q-i Glycerin 0.2% | 100.00 | 0.11 | 0.60 | 0.57 | 3.72 | |
| | 15Q-ii Myristic acid 0.1% | 100.00 | 0.11 | 0.66 | 0.54 | 4.02 | |
| | 15Q-iii Moisture 100% | 100.00 | 0.10 | 0.58 | 0.57 | 3.53 | |
| 1 M | 15Q-i Glycerin 0.2% | 96.17 | 0.05 | 0.90 | 0.57 | 6.30 | 2.58 |
| | 15Q-ii Myristic acid 0.1% | 95.70 | 0.04 | 1.04 | 0.57 | 6.32 | 2.30 |
| | 15Q-iii Moisture 100% | 85.37 | 0.67 | 0.78 | 0.57 | 18.04 | 14.51 |
| 2 M | 15Q-i Glycerin 0.2% | 98.46 | 0.06 | 1.16 | 0.58 | 5.86 | 2.14 |
| | 15Q-ii Myristic acid 0.1% | 97.66 | 0.04 | 1.42 | 0.57 | 6.26 | 2.24 |
| | 15Q-iii Moisture 100% | 85.46 | 0.81 | 1.14 | 0.53 | 20.45 | 16.92 |
| 3 M | 15Q-i Glycerin 0.2% | 97.24 | 0.01 | 1.53 | 0.59 | 6.82 | 3.10 |
| | 15Q-ii Myristic acid 0.1% | 95.96 | 0.01 | 2.01 | 0.58 | 7.87 | 3.85 |
| | 15Q-iii Moisture 100% | 52.14 | 1.21 | 3.06 | 0.68 | 45.70 | 42.17 |
| 6 M | 15Q-i Glycerin 0.2% | 92.57 | 0.04 | 2.77 | 0.58 | 10.62 | 6.90 |
| | 15Q-ii Myristic acid 0.1% | 89.50 | 0.05 | 4.14 | 0.59 | 13.37 | 9.35 |
| | 15Q-iii Moisture 100% | — | — | — | — | — | — |

The results of stability testing of Example 15Q-i-iii at 55° C. are set forth in Table 247 below.

TABLE 247

| | Monoethanolamine 0.5% 55° C. | Potency % | CBD % | CBN % | D8-THC % | Total Impurities % | Increase + % |
|---|---|---|---|---|---|---|---|
| Zero | 15Q-i Glycerin 0.2% | 100.00 | 0.11 | 0.60 | 0.57 | 3.72 | |
| | 15Q-ii Myristic acid 0.1% | 100.00 | 0.11 | 0.66 | 0.54 | 4.02 | |
| | 15Q-iii Moisture 100% | 100.00 | 0.10 | 0.58 | 0.57 | 3.53 | |
| 1 W | 15Q-i Glycerin 0.2% | 96.45 | 0.16 | 0.96 | 0.62 | 6.63 | 2.91 |
| | 15Q-ii Myristic acid 0.1% | 95.76 | 0.29 | 1.09 | 0.61 | 6.19 | 2.17 |
| | 15Q-iii Moisture 100% | 89.20 | 0.08 | 0.61 | 0.64 | 14.06 | 10.53 |
| 2 W | 15Q-i Glycerin 0.2% | 94.40 | 0.32 | 1.40 | 0.59 | 7.80 | 4.08 |
| | 15Q-ii Myristic acid 0.1% | 95.41 | 0.13 | 1.53 | 0.59 | 7.54 | 3.52 |
| | 15Q-iii Moisture 100% | 89.05 | 0.53 | 0.86 | 0.64 | 16.18 | 12.65 |

EXAMPLE 15R

Dronabinol Solution in Sesame Oil Sourced from Dipasa with Monoethanolamine and Different Degradants Added In Example 15R-i-iii, dronabinol formulations were prepared in accordance with Example 15O-i-iii, respectively. The dronabinol formulations were then used to fill amber glass vials. The formulations within the vials were initially tested, then tested at 25° C. for 3 and 6 months; 40° C. for 1, 2, 3 and 6 months and at 55° C. for 1 and 2 weeks.

The results of stability testing of Example 15R-i-iii at 25° C. are set forth in Table 248 below.

TABLE 248

| | Monoethanolamine 0.5% 25° C. | Potency % | CBD % | CBN % | D8-THC % | Total Impurities % | Increase + % |
|---|---|---|---|---|---|---|---|
| Zero | 15R-i Glycerin 0.2% | 100.00 | 0.17 | 0.48 | 0.49 | 4.13 | |
| | 15R-ii Myristic acid 0.1% | 100.00 | 0.14 | 0.52 | 0.47 | 3.99 | |
| | 15R-iii Moisture 100% | 100.00 | 0.15 | 0.48 | 0.51 | 3.91 | |
| 3 M | 15R-i Glycerin 0.2% | 98.81 | 0.37 | 0.76 | 0.54 | 6.15 | 2.02 |
| | 15R-ii Myristic acid 0.1% | 98.98 | 0.32 | 0.86 | 0.52 | 5.99 | 2.00 |
| | 15R-iii Moisture 100% | 99.92 | 0.18 | 0.57 | 0.53 | 6.55 | 2.64 |
| 6 M | 15R-i Glycerin 0.2% | 97.61 | 0.07 | 1.03 | 0.56 | 5.71 | 1.58 |
| | 15R-ii Myristic acid 0.1% | 98.05 | 0.03 | 1.13 | 0.53 | 5.46 | 1.47 |
| | 15R-iii Moisture 100% | 97.15 | 0.29 | 0.77 | 0.56 | 8.43 | 4.52 |

The results of stability testing of Example 15R-i-iii at 40° C. are set forth in Table 249 below.

TABLE 249

| | Monoethanolamine 0.5% 40° C. | Potency % | CBD % | CBN % | D8-THC % | Total Impurities % | Increase + % |
|---|---|---|---|---|---|---|---|
| Zero | 15R-i Glycerin 0.2% | 100.00 | 0.17 | 0.48 | 0.49 | 4.13 | |
| | 15R-ii Myristic acid 0.1% | 100.00 | 0.14 | 0.52 | 0.47 | 3.99 | |
| | 15R-iii Moisture 100% | 100.00 | 0.15 | 0.48 | 0.51 | 3.91 | |
| 1 M | 15R-i Glycerin 0.2% | 95.66 | 0.13 | 0.68 | 0.53 | 6.42 | 2.29 |
| | 15R-ii Myristic acid 0.1% | 96.09 | 0.09 | 0.98 | 0.53 | 6.50 | 2.51 |
| | 15R-iii Moisture 100% | 94.19 | 0.15 | 0.66 | 0.51 | 8.42 | 4.51 |
| 2 M | 15R-i Glycerin 0.2% | 98.85 | 0.10 | 1.17 | 0.48 | 5.23 | 1.10 |
| | 15R-ii Myristic acid 0.1% | 98.81 | 0.06 | 1.37 | 0.47 | 5.46 | 1.47 |
| | 15R-iii Moisture 100% | 95.45 | 0.42 | 1.13 | 0.42 | 9.52 | 5.61 |
| 3 M | 15R-i Glycerin 0.2% | 97.03 | 0.07 | 1.57 | 0.52 | 6.81 | 2.68 |
| | 15R-ii Myristic acid 0.1% | 96.95 | 0.01 | 1.94 | 0.52 | 7.21 | 3.22 |
| | 15R-iii Moisture 100% | 93.35 | 0.24 | 1.64 | 0.54 | 12.41 | 8.50 |
| 6 M | 15R-i Glycerin 0.2% | 92.11 | 0.07 | 2.98 | 0.53 | 10.57 | 6.44 |
| | 15R-ii Myristic acid 0.1% | 90.40 | 0.08 | 3.90 | 0.55 | 12.37 | 8.38 |
| | 15R-iii Moisture 100% | 82.67 | 0.38 | 2.91 | 0.56 | 21.52 | 17.61 |

The results of stability testing of Example 15R-i-iii at 55° C. are set forth in Table 250 below.

TABLE 250

| Monoethanolamine 0.5% 55° C. | | Potency % | CBD % | CBN % | D8-THC % | Total Impurities % | Increase + % |
|---|---|---|---|---|---|---|---|
| Zero | 15R-i Glycerin 0.2% | 100.00 | 0.17 | 0.48 | 0.49 | 4.13 | |
| | 15R-ii Myristic acid 0.1% | 100.00 | 0.14 | 0.52 | 0.47 | 3.99 | |
| | 15R-iii Moisture 100% | 100.00 | 0.15 | 0.48 | 0.51 | 3.91 | |
| 1 W | 15R-i Glycerin 0.2% | 96.03 | 0.17 | 0.77 | 0.28 | 5.96 | 1.83 |
| | 15R-ii Myristic acid 0.1% | 97.71 | 0.16 | 0.98 | 0.57 | 5.82 | 1.83 |
| | 15R-iii Moisture 100% | 96.84 | 0.01 | 0.60 | 0.59 | 6.94 | 3.03 |
| 2 W | 15R-i Glycerin 0.2% | 94.97 | 0.27 | 1.13 | 0.82 | 7.25 | 3.12 |
| | 15R-ii Myristic acid 0.1% | 96.86 | 0.18 | 1.38 | 0.60 | 6.74 | 2.75 |
| | 15R-iii Moisture 100% | 96.28 | 0.18 | 0.91 | 0.53 | 8.37 | 4.46 |

As see from the results above, the protective effect of the bases meglumine and monoethanolamine was confirmed by the addition of degradants such as glycerin, moisture, and myristic acid to the dronabinol formulation. The results above clearly indicate that the bases meglumine and monoethanolamine protect dronabinol formulations from degradation induced by glycerin, moisture and myristic acid.

CONCLUSION

Many other variations of the present invention will be apparent to those skilled in the art and are meant to be within the scope of the claims appended hereto. The foregoing specification alludes to beliefs, hypothesis and conclusions of the inventor based on his experience in the field, the reports of others (such as those identified in the publications identified herein), and experiments conducted and reported herein, and are provided for purposes of (possible) explanation only and are not meant to limit the invention in any manner whatsoever.

REFERENCES

Armstrong N A, James K C, Pugh W K L. Drug migration into soft gelatin capsule shells and its effect on in-vitro availability. *J. Pharm. Pharmacol.* 36: 361-365, 1984

Bauer K H. Die herstellung von hart—und weichgelatinekapseln. In: *Die Kapsel. Stuttgart: Wissenschaftliche Verlags GmbH.* Editors: Fahrig W, Hofer U H, 58-82, 1983.

Beckstrom-Stenberg S M and Duke J A. "The phytochemical database." Ars-genome.cornell.edu/cgi-bin/WebAce/webace?db=phytochemdb. (Data version July 1994).

Bradley Morris J. Food, industrial, nutraceutical, and pharmaceutical uses of sesame genetic resources. In: *Trends in New Crops and New Uses.* Editors: Janick J and Whipkey A, 2002.

Cade D, Cole E T, Mayer J-Ph, Wittwer F. Liquid filled and sealed hard gelatin capsules. *Acta Pharm. Technol.* 29: 245-251, 1983.

Ewart T. Cole. Liquid-filled and sealed hard gelatin capsule technologies. In: *Modified-Release Drug Delivery Technology.* Editors: Rathbone M J, Hadgraft J, Roberts M S, Publishers Marcel Dekker, 2002.

Featured Excipients: Antioxidants. *Int. J. Pharm. Compounding.* 3(1): 52-, January/February 1999.

Hom F S, Veresh S A, Ebert W R. Soft gelatin capsules. II. Oxygen permeability study of capsule shells. *J. Pharm. Sci.* 64(5): 851-857, 1975.

Kato M J, Chu A, Davin L B. Lewis N G, Biosynthesis of antioxidant lignans in sesamum indicum seeds. *Phytochemistry.* 47: 583-591, 1998.

Martin A, Bustamante P, and Chun A H C. *Physical Pharmacy.* Fourth ed., Lea & Febiger, 1993.

Mechoulam R. Chemistry of cannabis. *Handbook Exp. Pharmacol.* 55: 119-134, 1981.

Physicians Desk Reference®, ed. 2003.

Shah N H, Phuarpradit W, Ahmed H. Liquid filling in hard gelatin capsules: formulations and processing considerations. *American Pharmaceutical Review.* 6(1): 14-21, Spring 2003.

Sirato-Yasumoto S, Katsuta M, Okuyama Y, Takahashi Y, and Ide T. Effect of sesame seeds rich in sesamin and sesamolin on fatty acid oxidation in rat liver. *J. Agr. Food Chem.* 49: 2647-2651, 2001.

U.S. Department of Health and Human Services, Food and Drug Administration "*Guidance for Industry: QIA (R2) Stability Testing of New Drug Substances and Products.*" ICH, November 2003.

All of the above references (patents and non-patent publications) are hereby incorporated by reference.

What is claimed is:

1. A cannabinoid dosage form consisting essentially of:
   synthetic dronabinol in an amount of 0.05 to 20 mg per dose and L-ascorbic acid-6-palmitate in an amount of 0.01% to 1% by weight, both dispersed in sesame oil; and
   a gelatin capsule encapsulating said synthetic dronabinol, said L-ascorbic acid-6-palmitate, and said sesame oil, said dosage form being stable at room temperature for at least one year.

2. The dosage form of claim 1, which contains not less than 90% of the initial dronabinol content upon exposure of the formulation to storage conditions selected from the group consisting of (i) elevated temperature and humidity conditions of 40° C./75% relative humidity (RH) for 6 months; (ii) room temperature (25° C.) for two years; and (iii) any combination thereof.

3. The dosage form of claim 1, wherein the dronabinol does not contain more than 5% dronabinol degradants in the dosage form, the degradants selected from the group consisting of no more than 2% delta-8 tetrahydrocannabinol (D8THC), no more than 2% cannabinol (CBN), no more than 0.2% cannabidiol (CBD), and any combination thereof.

4. The dosage form of claim 1, which contains an effective amount of one or more organic bases to promote stability of the cannabinoid against unacceptable degradation.

5. The dosage form of claim 4, which comprises from 0.001% to 5% organic base, by weight.

6. The dosage form of claim 4, which comprises from 0.005% to 2% organic base, by weight.

7. The dosage form of claim 4, wherein said organic base is selected from the group consisting of ethanolamine, methanolamine, meglumine, and any combination of the foregoing.

8. The dosage form of claim 1, wherein said gelatin capsule is soft or hard.

9. The dosage form of claim 1, which further comprises one or more additional therapeutically active agents.

10. The dosage form of claim 9, wherein said additional therapeutically active agent is selected from a narcotic analgesic, a non-narcotic analgesic, an anti-emetic, a steroid, and mixtures of any of the foregoing.

11. The dosage form of claim 1 which contains dronabinol as the active ingredient, the dosage form containing ingredients at a level selected from the following during its claimed shelf-life as follows: (i) not less than 90% of the initial dronabinol content; (ii) not greater than 2% cannabinol; (iii) not greater than 2% cannabidiol; (iv) not greater than 2% delta-8-THC; and (v) any combination of the foregoing.

12. The dosage form of claim 1, further comprising a pharmaceutical excipient selected from the group consisting of solubilizers; stabilizers; surfactants; emulsifiers, absorption enhancers, and mixtures thereof.

13. The dosage form of claim 1, wherein the gelatin capsule is a capsule having a coating on its surface selected from the group consisting of an enteric coating, a seal coating, or both.

14. The dosage form of claim 13, wherein the gelatin capsule is selected from the group consisting of a starch capsule; a cellulosic capsule; a hydrocolloid film-forming composition comprising a mixture of iota carrageenan, a bulking agent and kappa carrageenan; and a gelatin capsule.

15. A cannabinoid dosage form consisting essentially of:
synthetic dronabinol in an amount of 0.05 mg to 20 mg per unit dose and L-ascorbic acid-6-palmitate in an amount of 0.001% to 1% by weight, both dispersed in sesame oil; and
a gelatin capsule encapsulating said dronabinol, said L-ascorbic acid-6-palmitate, and said sesame oil, said dosage form contains at least about 90% w/w of the synthetic dronabinol in undegraded form after storage at room temperature for at least one year.

* * * * *